(12) United States Patent
Gross et al.

(10) Patent No.: US 10,363,137 B2
(45) Date of Patent: Jul. 30, 2019

(54) IMPLANTATION OF REPAIR DEVICES IN THE HEART

(71) Applicant: Valtech Cardio, Ltd., Or Yehuda (IL)

(72) Inventors: Amir Gross, Tel Aviv-Jaffa (IL); Iftah Beinart, Hod Hasharon (IL); Eran Miller, Moshav Beit Elazari (IL); Oz Cabiri, Hod Hasharon (IL); Eliahu Eliachar, Haifa (IL); Nir Lilach, Kfar Yehoshua (IL); Ram Grossfeld, Haifa (IL); Dmitry Golom, Haifa (IL); Gideon Meyer-Brodnitz, Haifa (IL); Arnon Mosaiuf, Geva Carmel (IL)

(73) Assignee: Valtech Cardio, Ltd., Or Yehuda (IL)

( * ) Notice: Subject to any disclaimer, the term of this patent is extended or adjusted under 35 U.S.C. 154(b) by 0 days.

(21) Appl. No.: 15/983,542

(22) Filed: May 18, 2018

(65) Prior Publication Data

US 2018/0263776 A1   Sep. 20, 2018

Related U.S. Application Data

(63) Continuation of application No. 15/249,957, filed on Aug. 29, 2016, now Pat. No. 9,974,653, which is a
(Continued)

(51) Int. Cl.
*A61F 2/24* (2006.01)
*A61B 17/064* (2006.01)
*A61B 17/00* (2006.01)

(52) U.S. Cl.
CPC .......... *A61F 2/2445* (2013.01); *A61B 17/064* (2013.01); *A61F 2/2466* (2013.01);
(Continued)

(58) Field of Classification Search
CPC ........................................................ A61F 2/24
See application file for complete search history.

(56) References Cited

U.S. PATENT DOCUMENTS

| | | |
|---|---|---|
| 3,604,488 A | 9/1971 | Wishart et al. |
| 3,656,185 A | 4/1972 | Carpentier |

(Continued)

FOREIGN PATENT DOCUMENTS

| | | |
|---|---|---|
| EP | 1034753 A1 | 9/2000 |
| WO | 9205093 A1 | 4/1992 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Matthew W Schall
(74) *Attorney, Agent, or Firm* — Thomas C. Richardson

(57) ABSTRACT

Apparatuses and devices usable for annuloplasty are provided. These can include a plurality of tissue anchors and an annuloplasty structure for placement on a heart valve annulus. The annuloplasty structure can include a plurality of compressible or adjustable subunits, and a plurality of anchor mounts alternately disposed with respect to the plurality of compressible/adjustable subunits. The anchor mounts are coupleable to the tissue anchors and can define a path for passage therethrough of a respective tissue anchor. The apparatuses and devices can be independently adjustable and can be adjustable for treating various sizes of patient annuli. Other embodiments are also described.

20 Claims, 46 Drawing Sheets

Related U.S. Application Data continuation of application No. 15/144,127, filed on May 2, 2016, now Pat. No. 9,872,769, which is a continuation of application No. 14/551,951, filed on Nov. 24, 2014, now Pat. No. 9,351,830, which is a continuation of application No. 12/996,954, filed as application No. PCT/IL2009/000593 on Jun. 15, 2009, now Pat. No. 9,192,472, said application No. 14/551,951 is a continuation-in-part of application No. 11/950,930, filed on Dec. 5, 2007, now Pat. No. 8,926,695.

(60) Provisional application No. 61/132,295, filed on Jun. 16, 2008, provisional application No. 61/001,013, filed on Oct. 29, 2007, provisional application No. 60/902,146, filed on Feb. 16, 2007, provisional application No. 60/873,075, filed on Dec. 5, 2006.

(52) U.S. Cl.
CPC ........... *A61B 2017/00407* (2013.01); *A61B 2017/0647* (2013.01); *A61B 2017/0649* (2013.01); *A61F 2/2448* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |

(56) References Cited

U.S. PATENT DOCUMENTS

| | | |
|---|---|---|
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,562 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |

(56) References Cited

U.S. PATENT DOCUMENTS

| | | |
|---|---|---|
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,645,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0059413 A1 | 3/2004 | Argento |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |

(56) References Cited

U.S. PATENT DOCUMENTS

| | | |
|---|---|---|
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0288044 A1 | 11/2008 | Osborne |
| 2008/0288062 A1 | 11/2008 | Andrieu et al. |

(56) References Cited

U.S. PATENT DOCUMENTS

| | | |
|---|---|---|
| 2008/0300537 A1 | 12/2008 | Bowman |
| 2008/0300629 A1 | 12/2008 | Surti |
| 2009/0028670 A1 | 1/2009 | Garcia et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1* | 1/2011 | Cartledge ........ A61B 17/00234 623/2.11 |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095522 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2014/0081394 A1 | 3/2014 | Keranen et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243659 A1 | 8/2014 | Robinson |
| 2014/0243894 A1 | 8/2014 | Groothuis et al. |
| 2014/0243963 A1 | 8/2014 | Sheps et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0112432 A1 | 4/2015 | Reich et al. |
| 2015/0127097 A1 | 5/2015 | Neumann et al. |
| 2015/0182336 A1 | 7/2015 | Zipory et al. |
| 2015/0272586 A1 | 10/2015 | Herman et al. |

(56) References Cited

U.S. PATENT DOCUMENTS

| | | | |
|---|---|---|---|
| 2015/0272734 | A1 | 10/2015 | Sheps et al. |
| 2015/0282931 | A1 | 10/2015 | Brunnett et al. |
| 2016/0008132 | A1 | 1/2016 | Cabiri et al. |
| 2016/0058557 | A1 | 3/2016 | Reich et al. |
| 2016/0113767 | A1 | 4/2016 | Miller et al. |
| 2016/0120645 | A1 | 5/2016 | Alon |
| 2016/0158008 | A1 | 6/2016 | Miller et al. |
| 2016/0242762 | A1 | 8/2016 | Gilmore et al. |
| 2016/0262755 | A1 | 9/2016 | Zipory et al. |
| 2016/0302917 | A1 | 10/2016 | Schewel |
| 2016/0317302 | A1 | 11/2016 | Madjarov et al. |
| 2016/0361058 | A1 | 12/2016 | Bolduc et al. |
| 2016/0361168 | A1 | 12/2016 | Gross et al. |
| 2016/0361169 | A1 | 12/2016 | Gross et al. |
| 2017/0000609 | A1 | 1/2017 | Gross et al. |
| 2017/0245993 | A1 | 8/2017 | Gross et al. |
| 2018/0049875 | A1 | 2/2018 | Iflah et al. |

FOREIGN PATENT DOCUMENTS

| | | | |
|---|---|---|---|
| WO | 9846149 | A1 | 10/1998 |
| WO | 02085250 | A3 | 2/2003 |
| WO | 03047467 | A1 | 6/2003 |
| WO | 2010000454 | A1 | 1/2010 |
| WO | 2012176195 | A3 | 3/2013 |
| WO | 2014064964 | A1 | 5/2014 |

OTHER PUBLICATIONS

Ahmadi, A., G. Spillner, and Th Johannesson. "Hemodynamic changes following experimental production and correction of acute mitral regurgitation with an adjustable ring prosthesis," The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriforrn Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success—midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

Odell JA et al., "Early Results o4yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

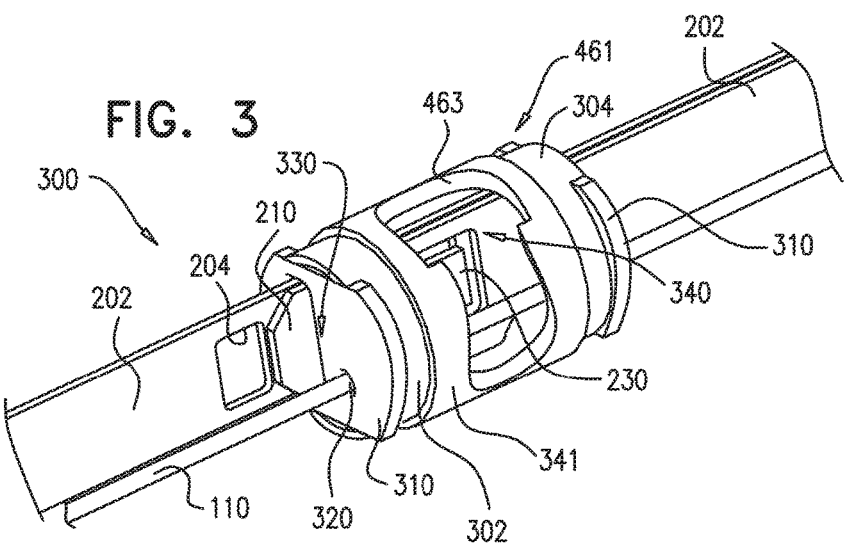
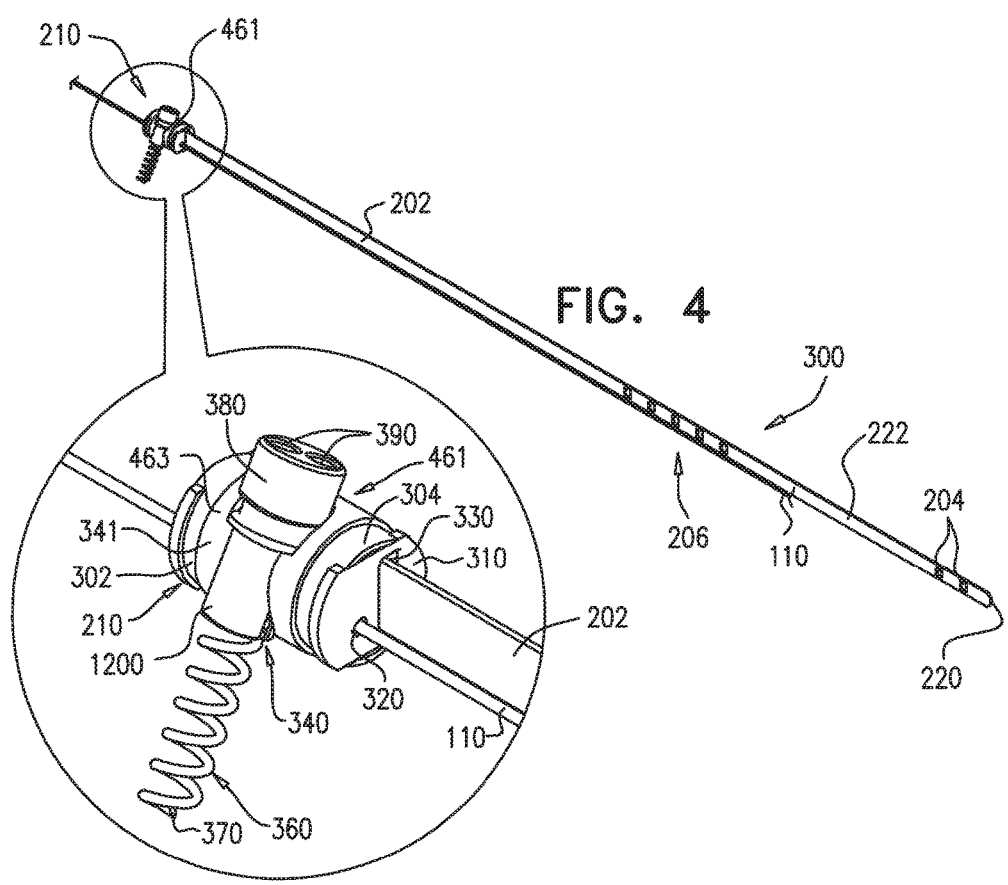

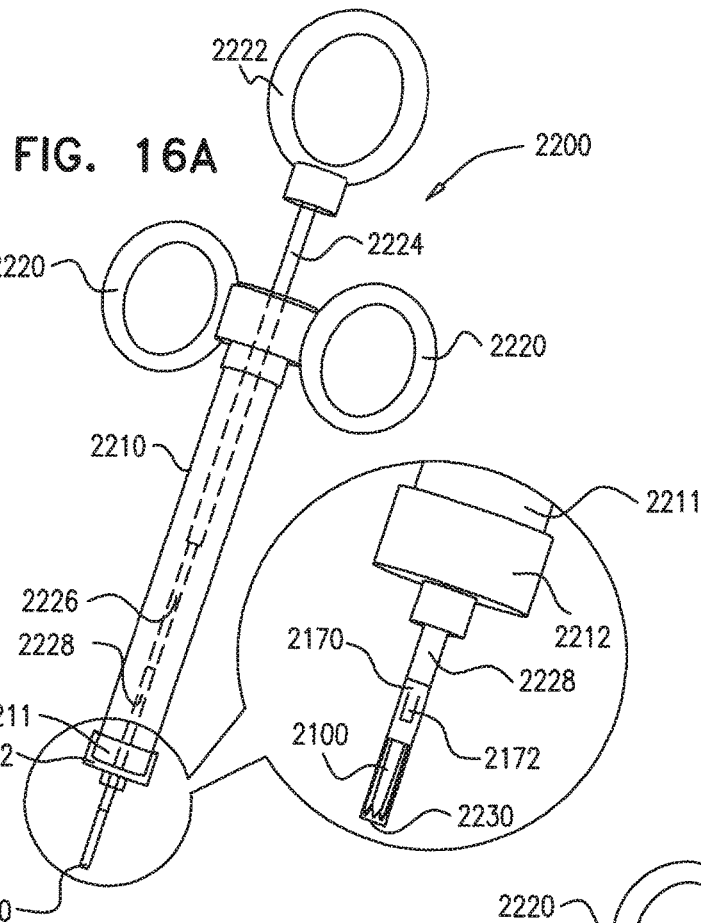
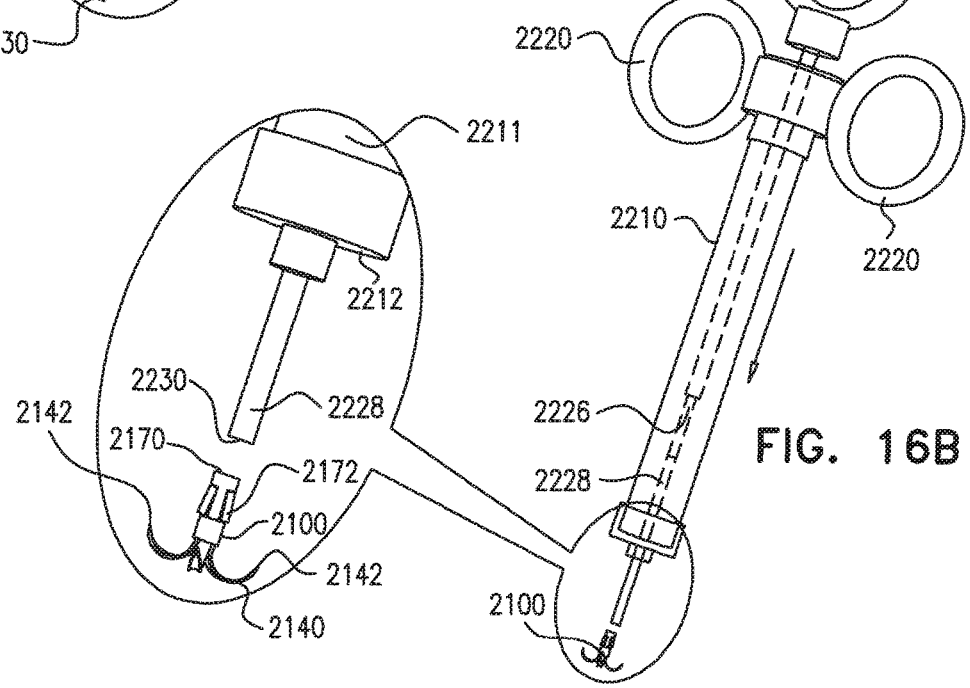
FIG. 16A
FIG. 16B

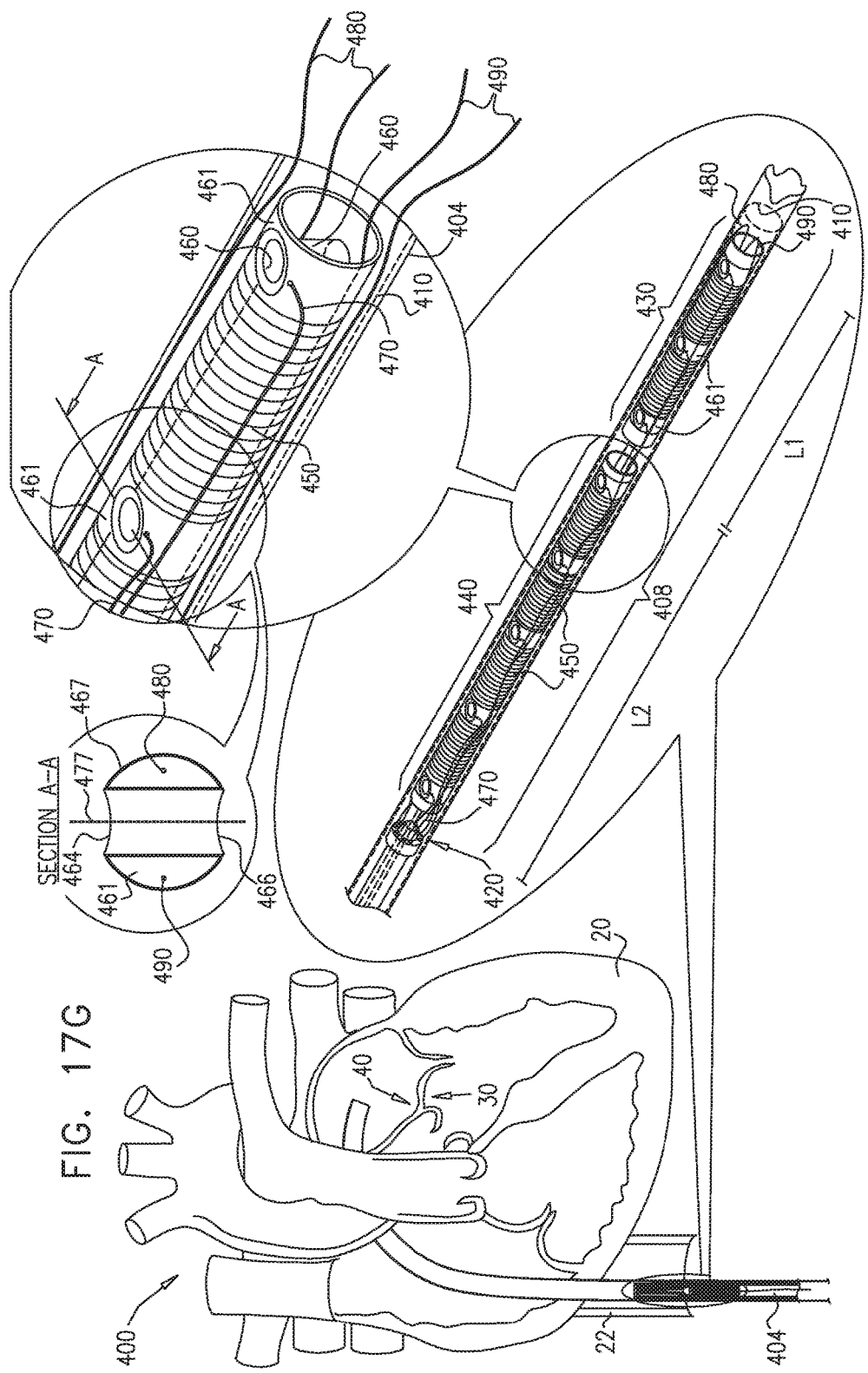

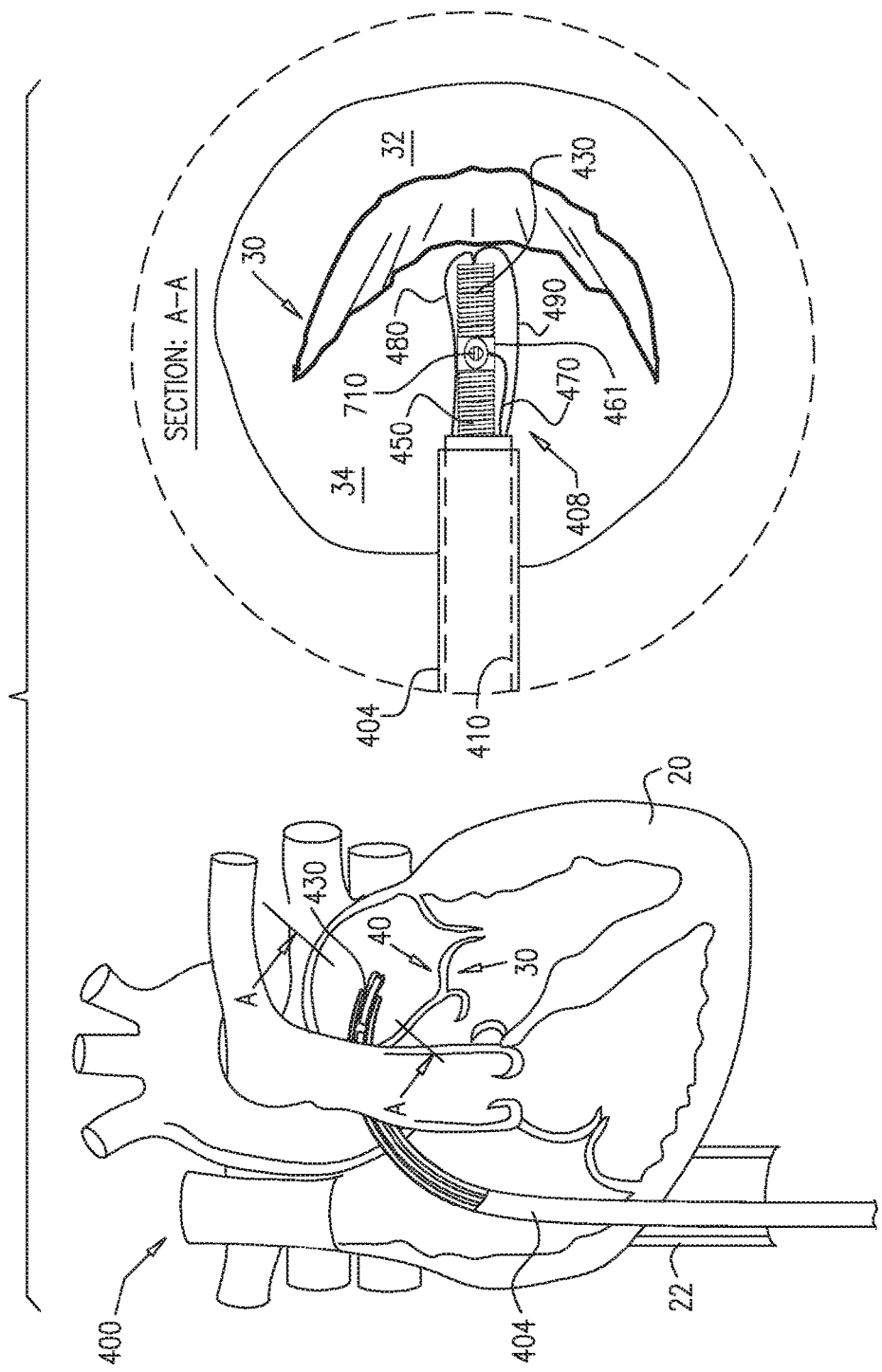

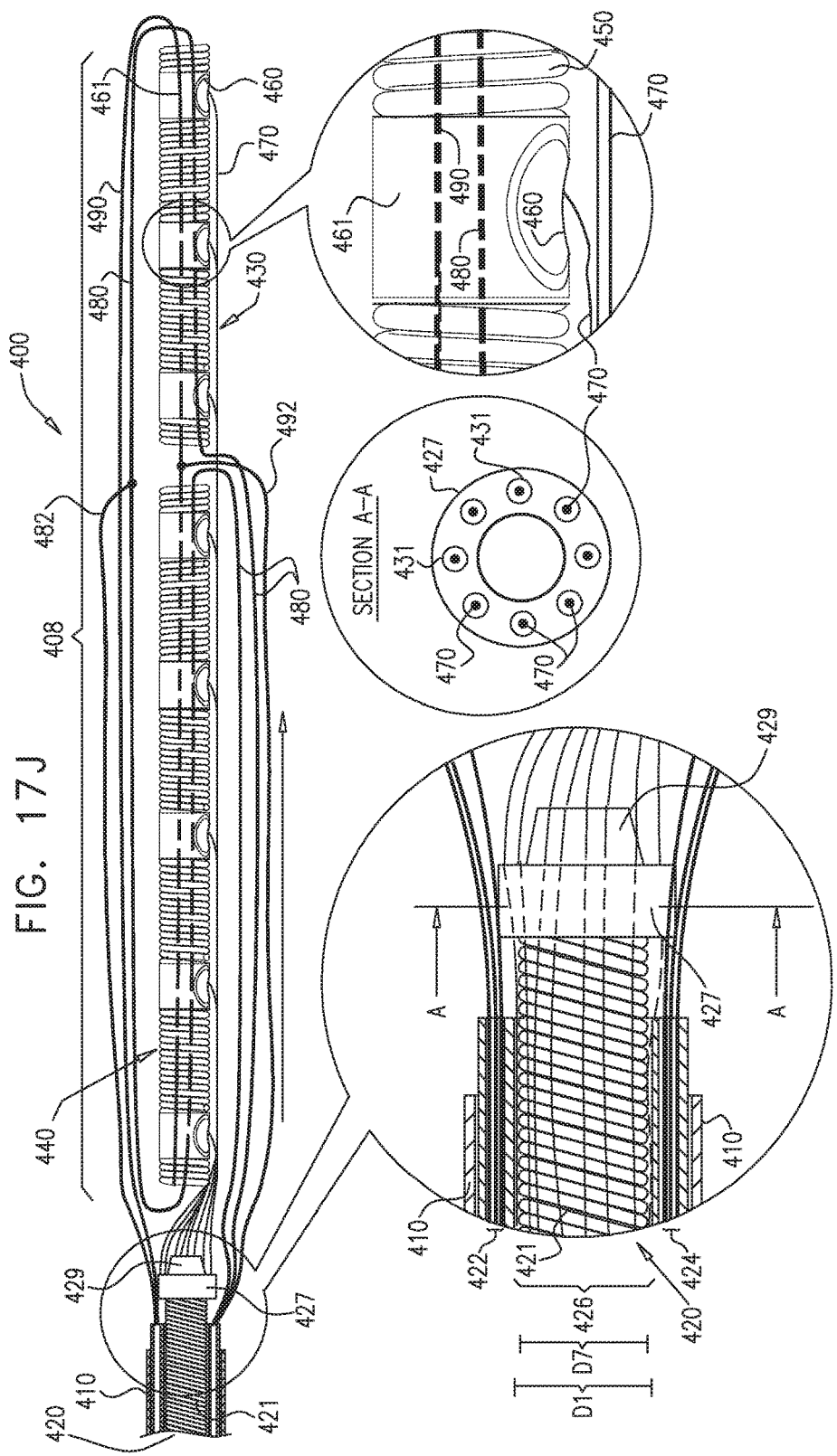

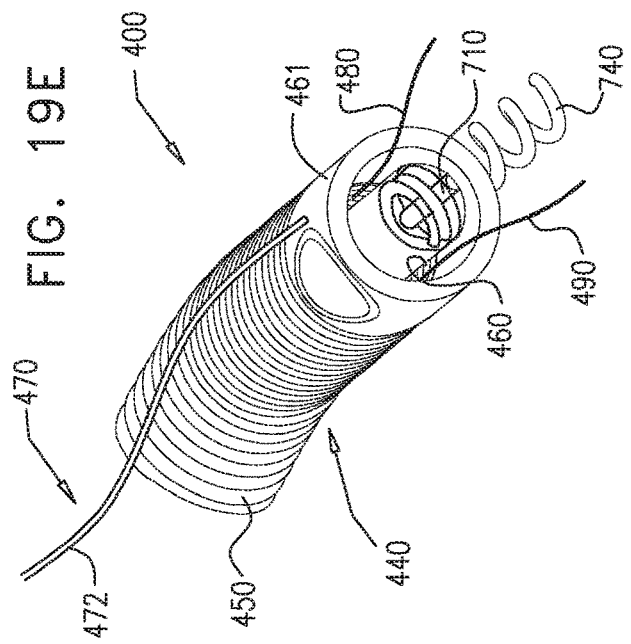
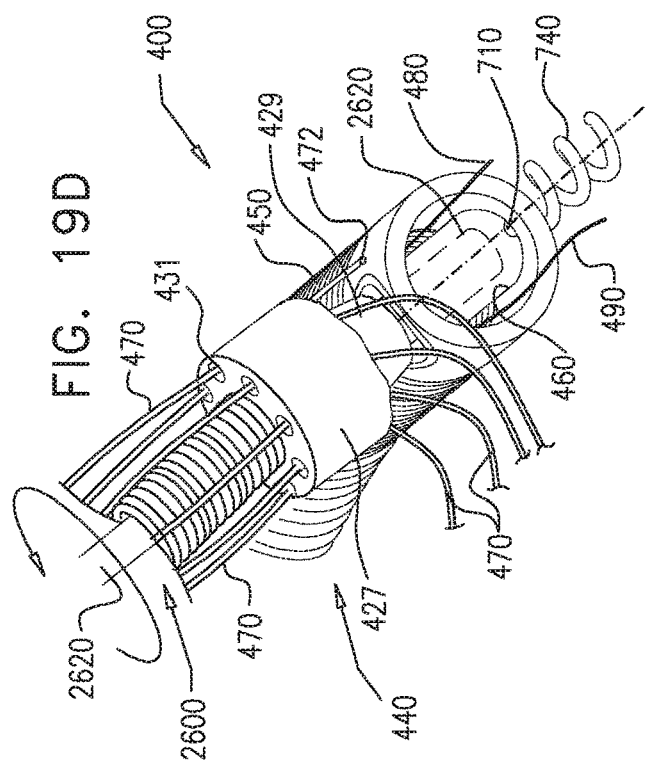

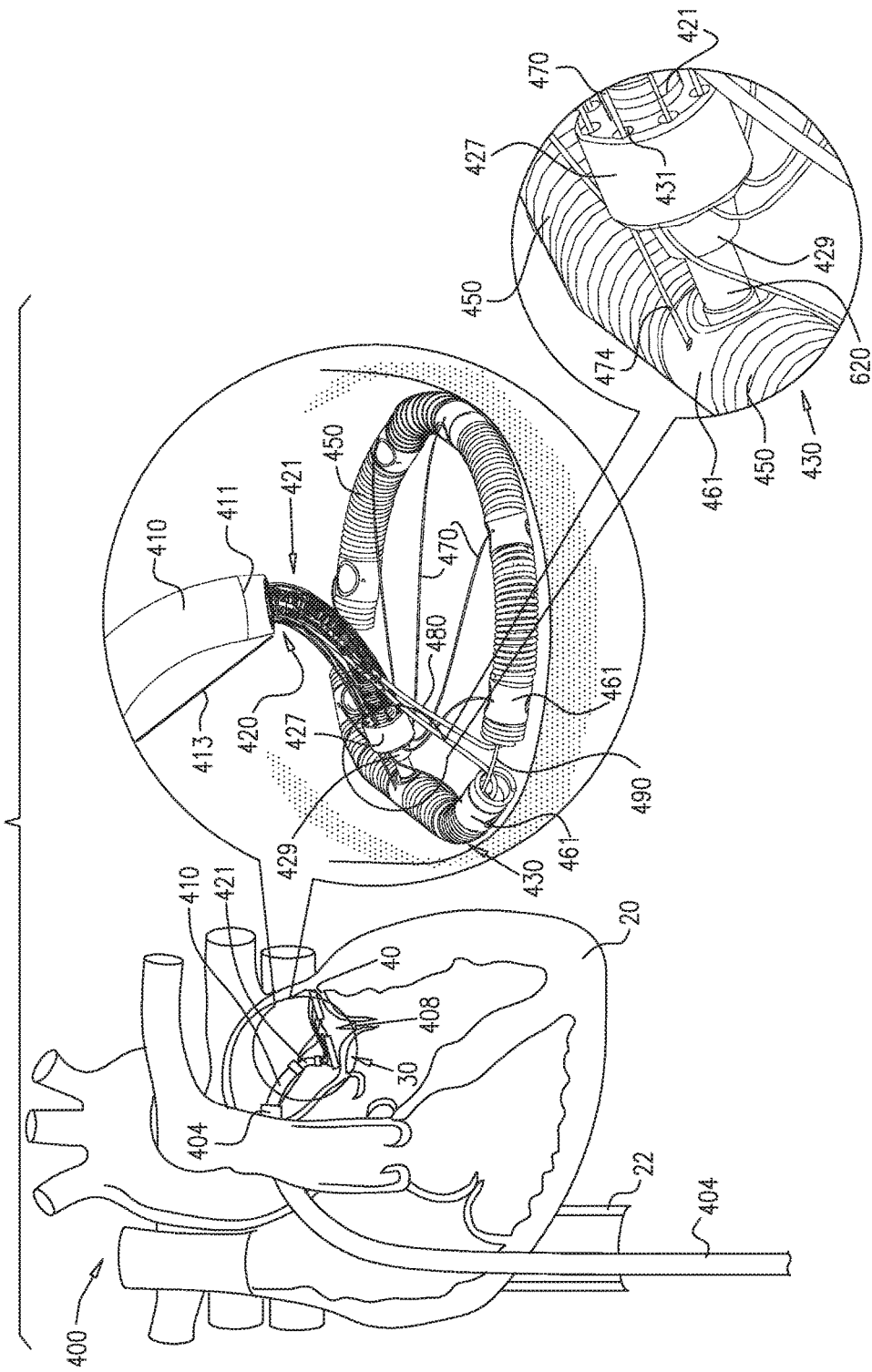

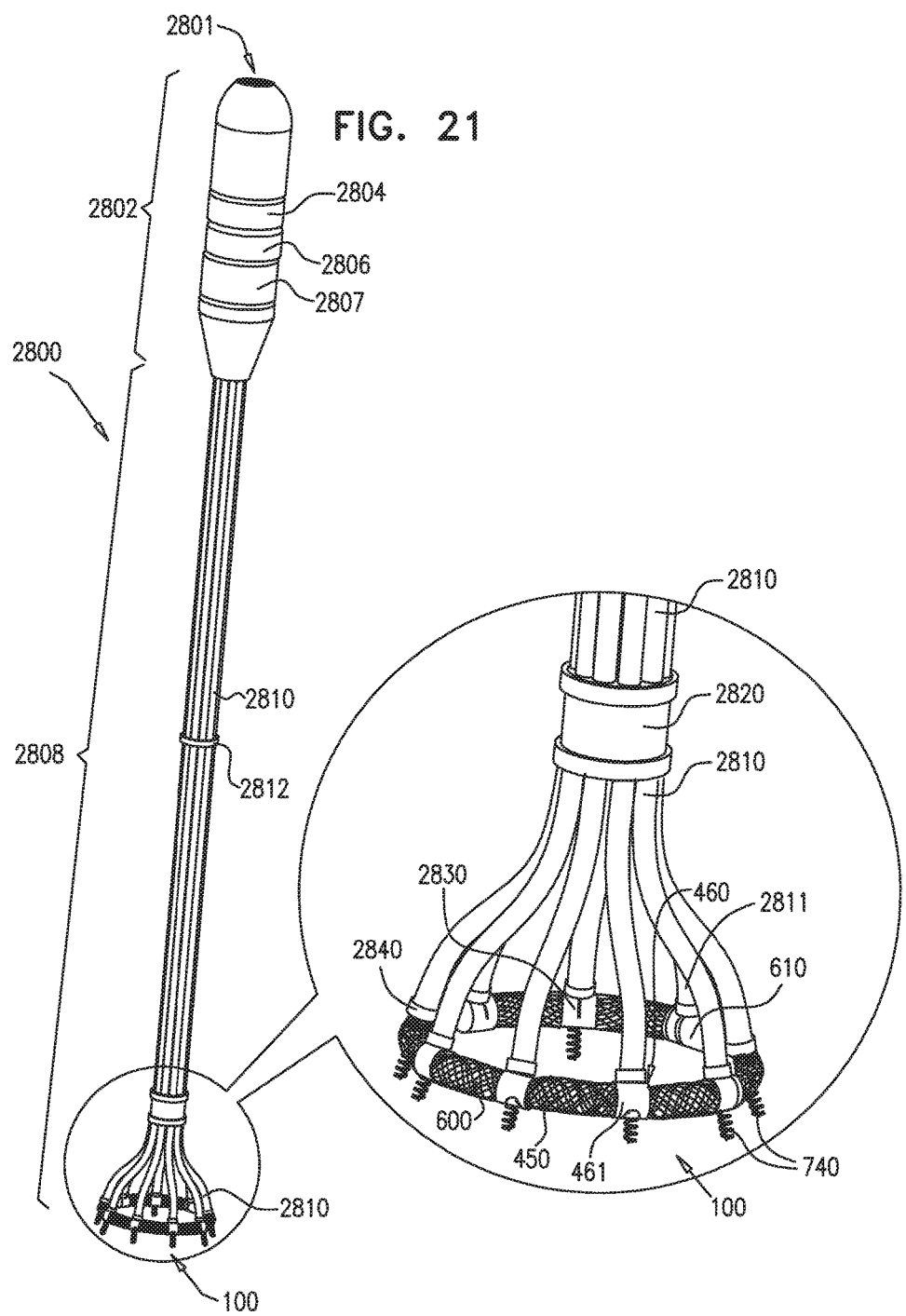

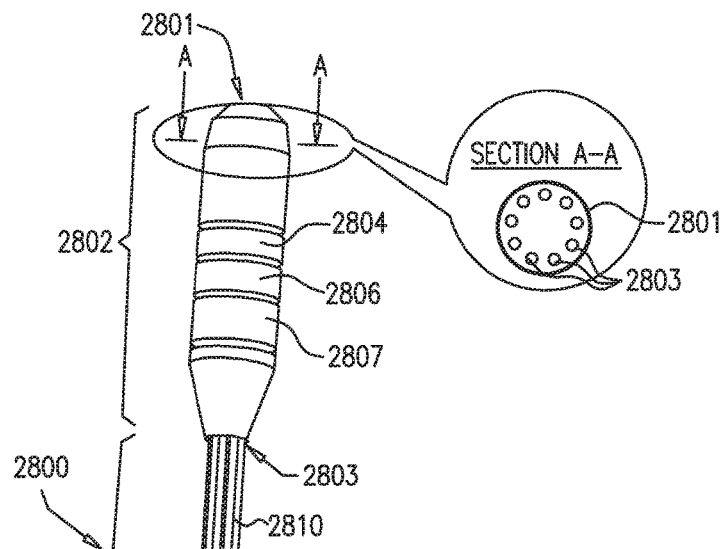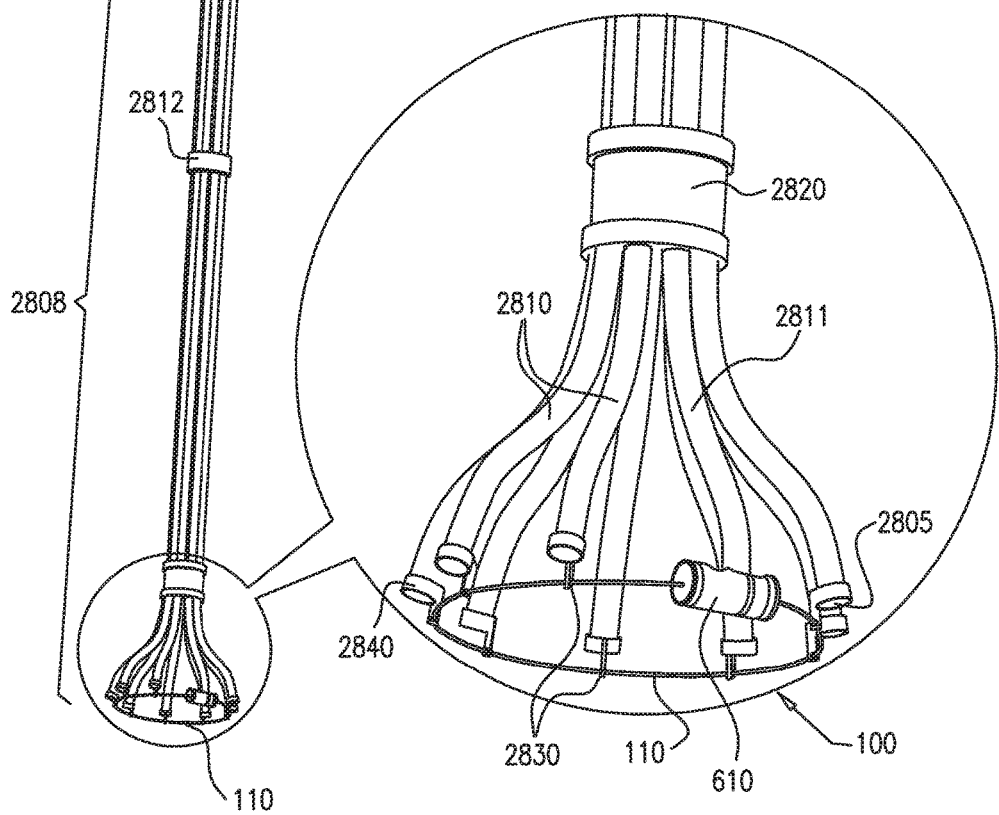
FIG. 22

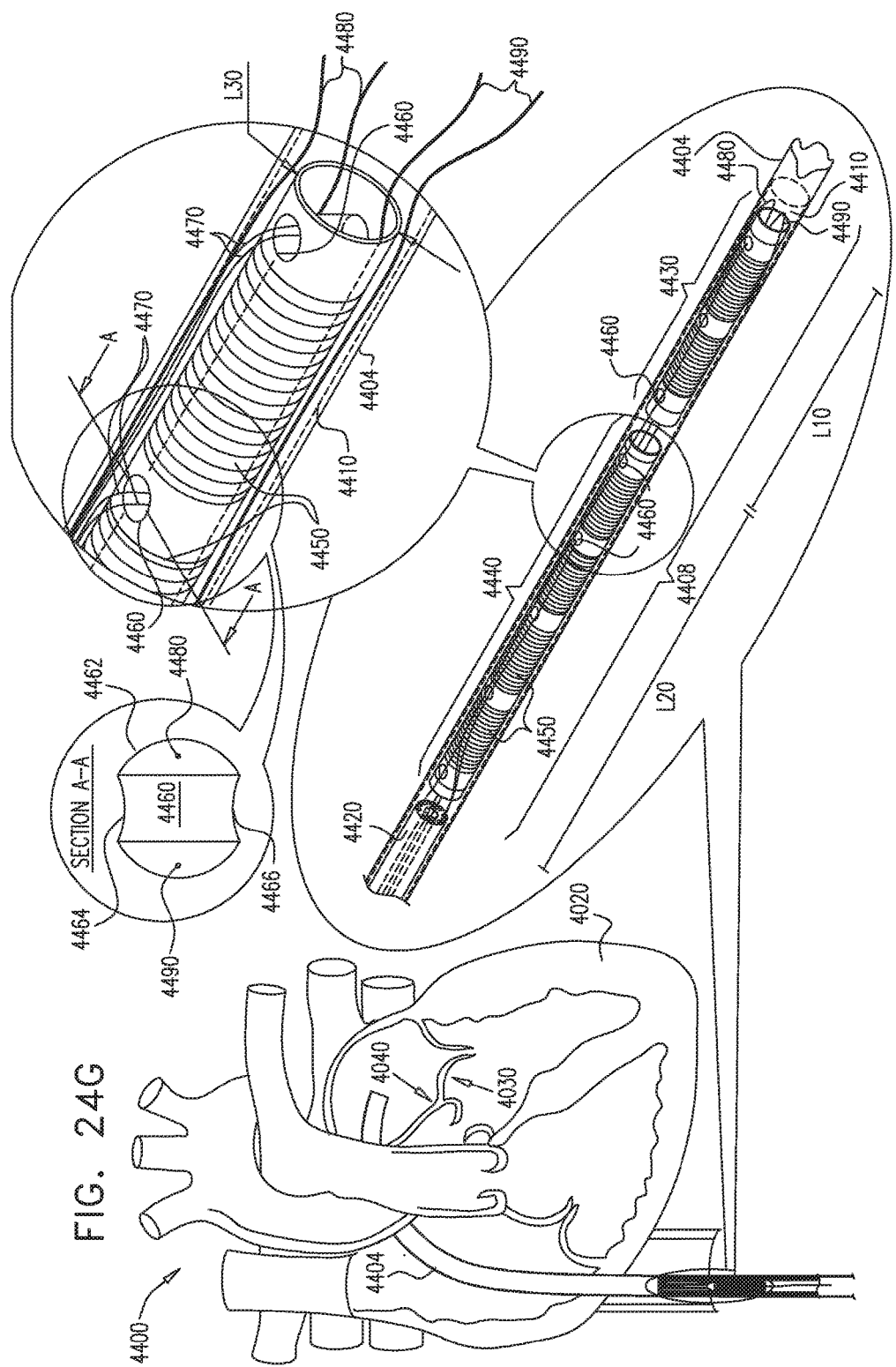

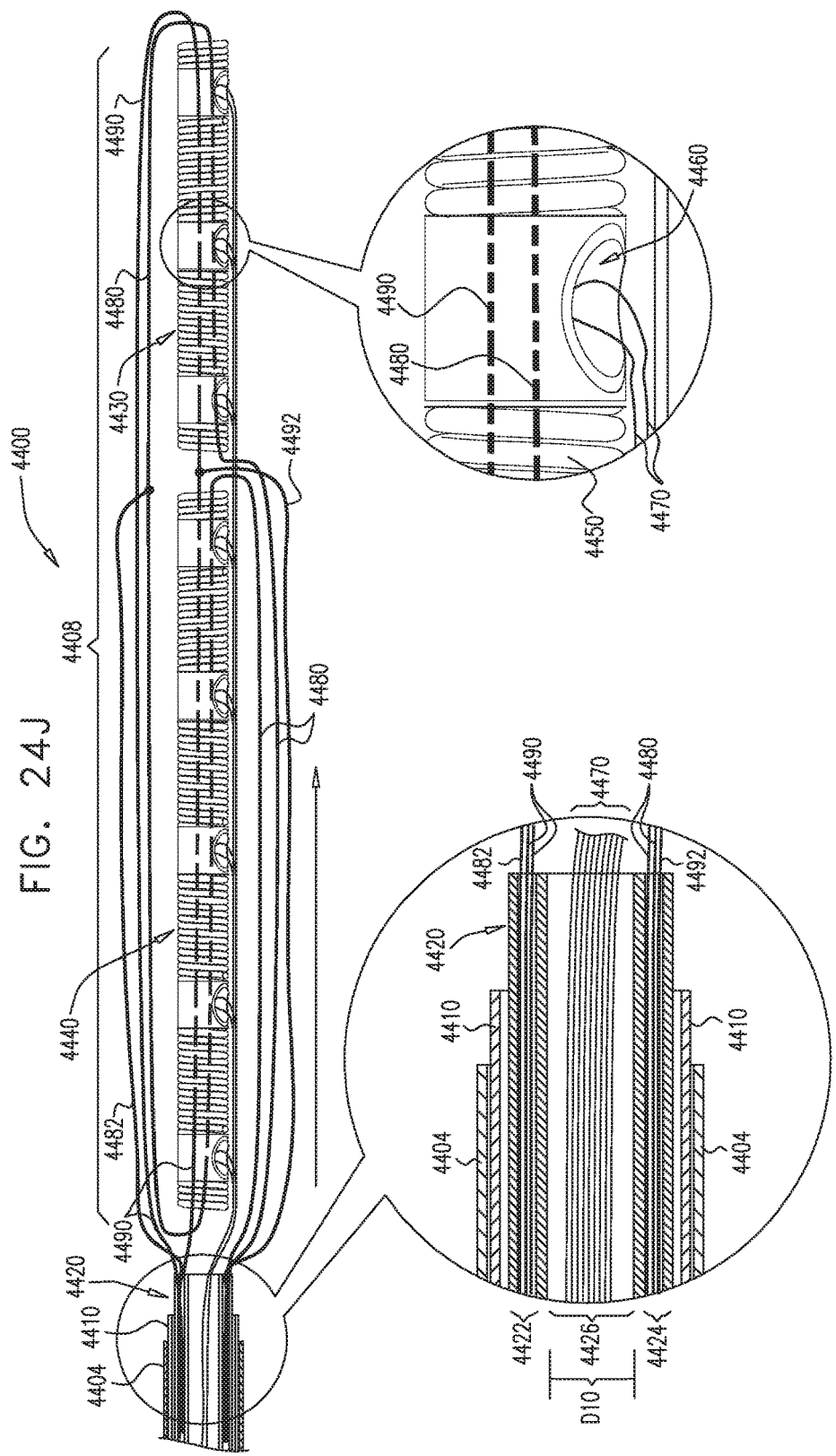

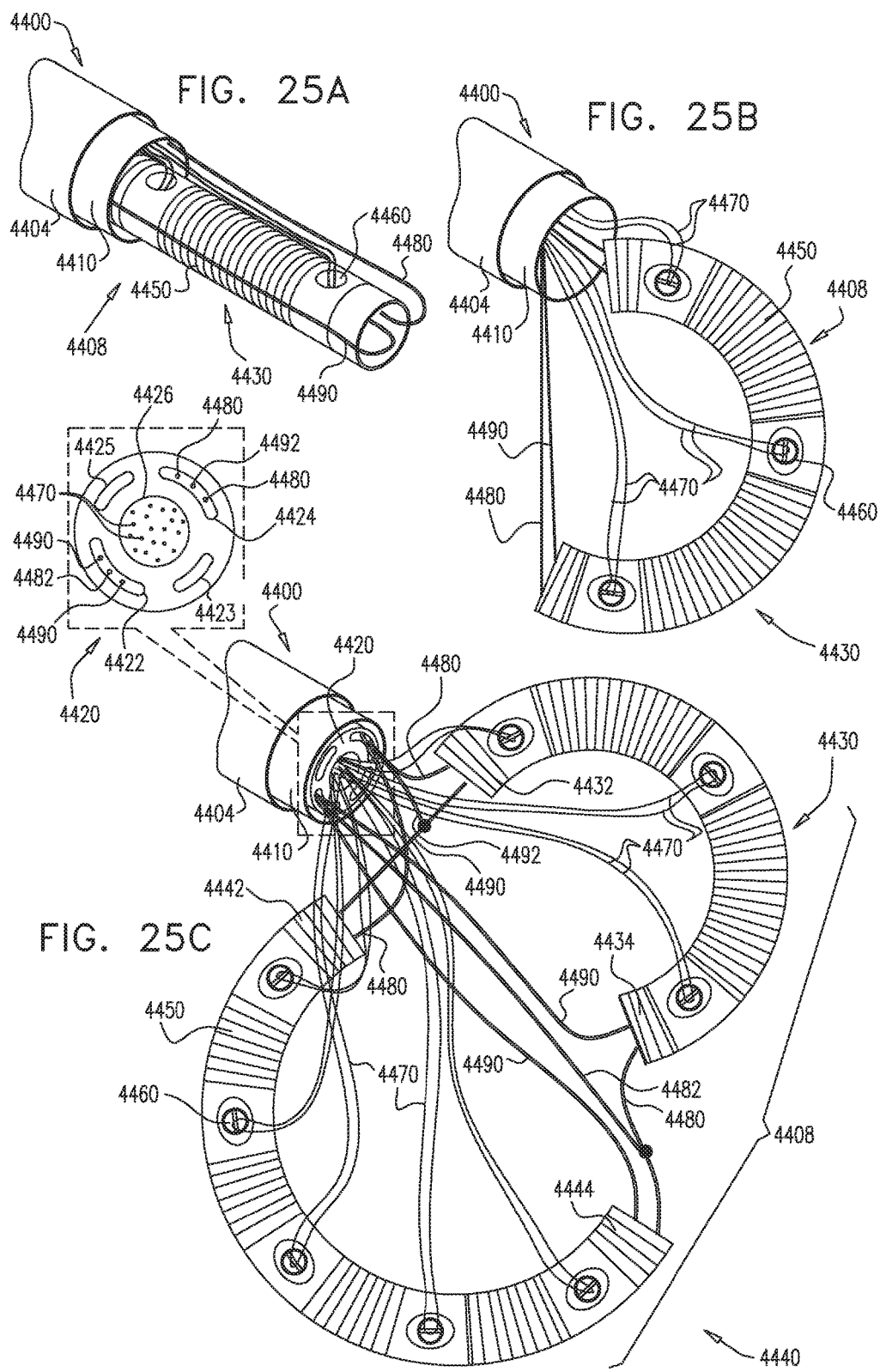

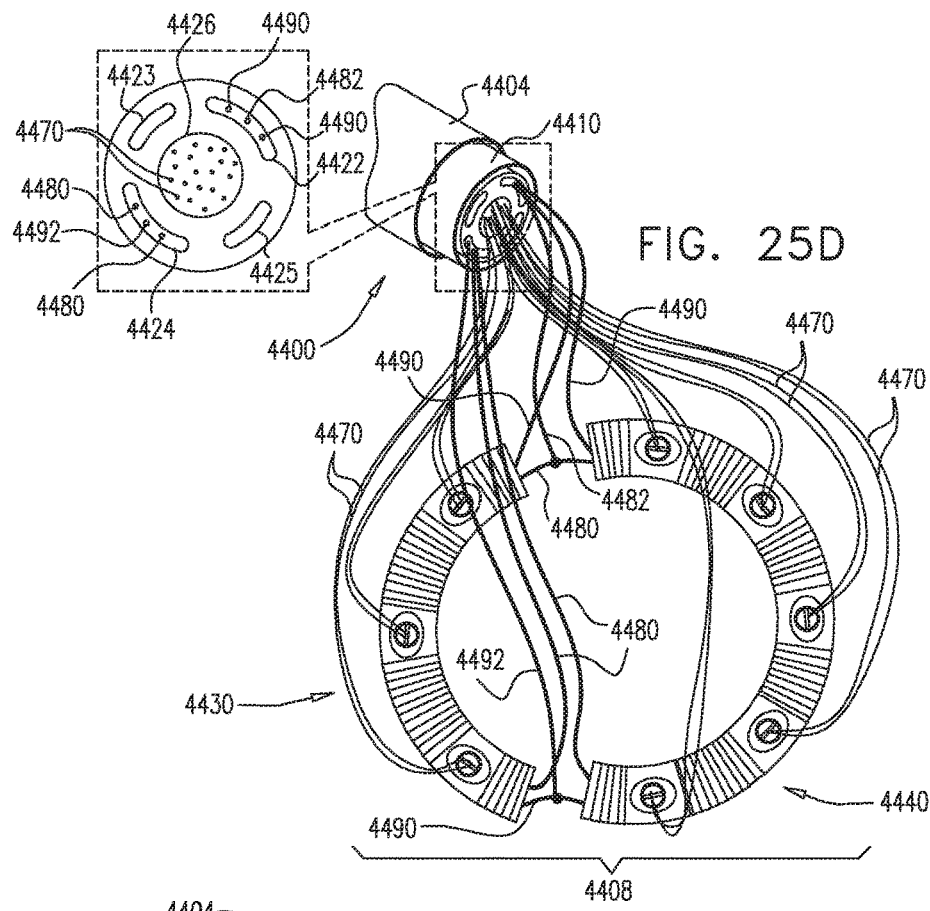
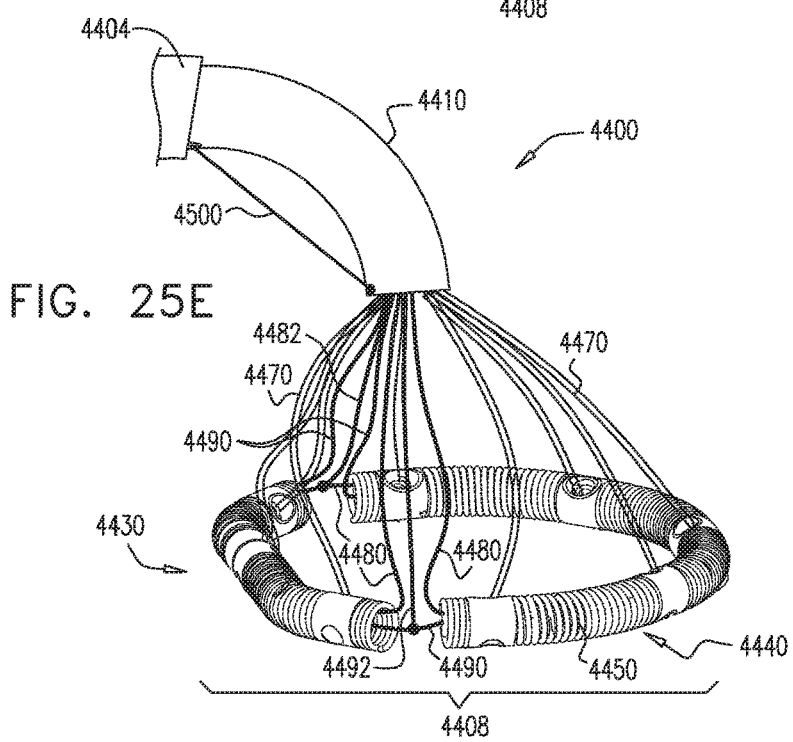

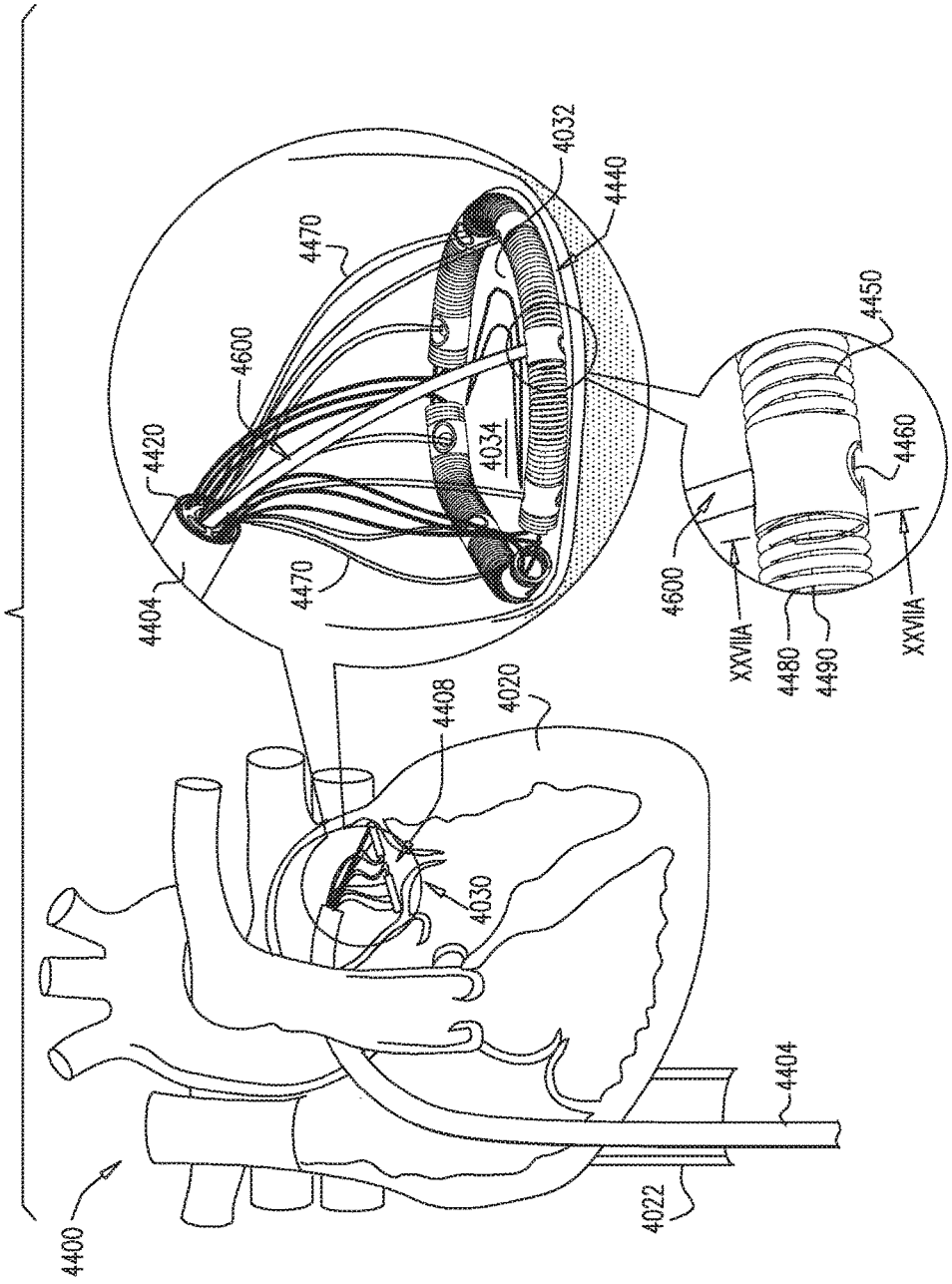

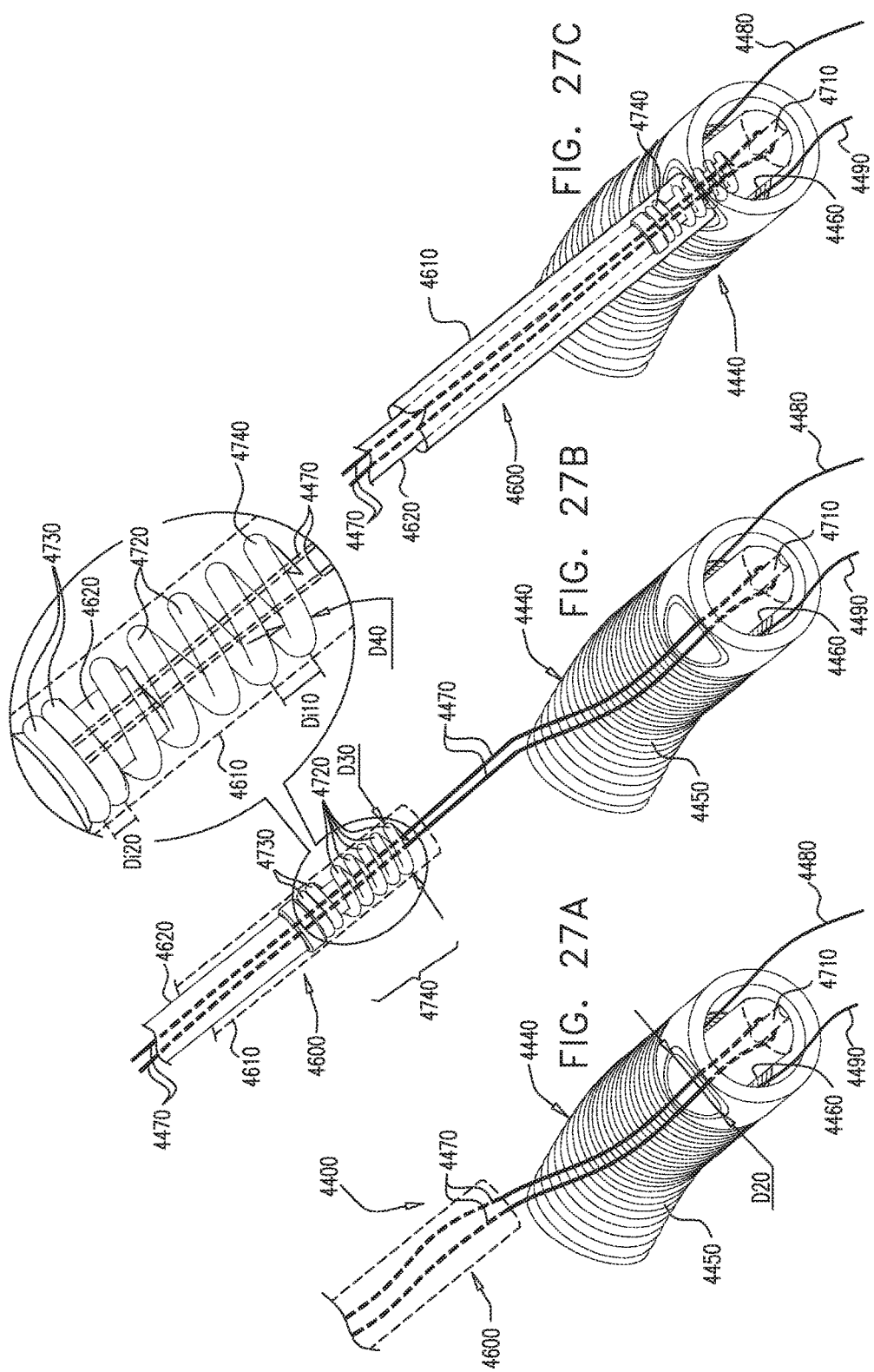

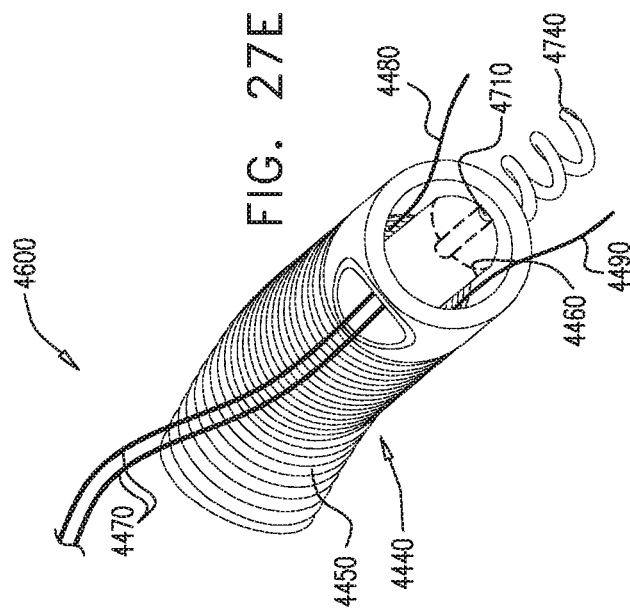
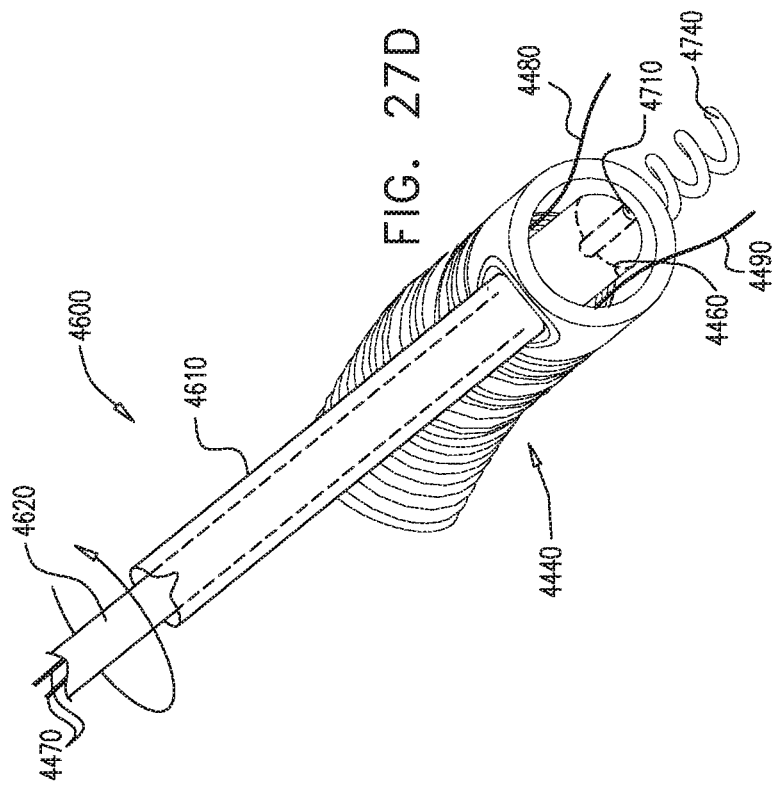

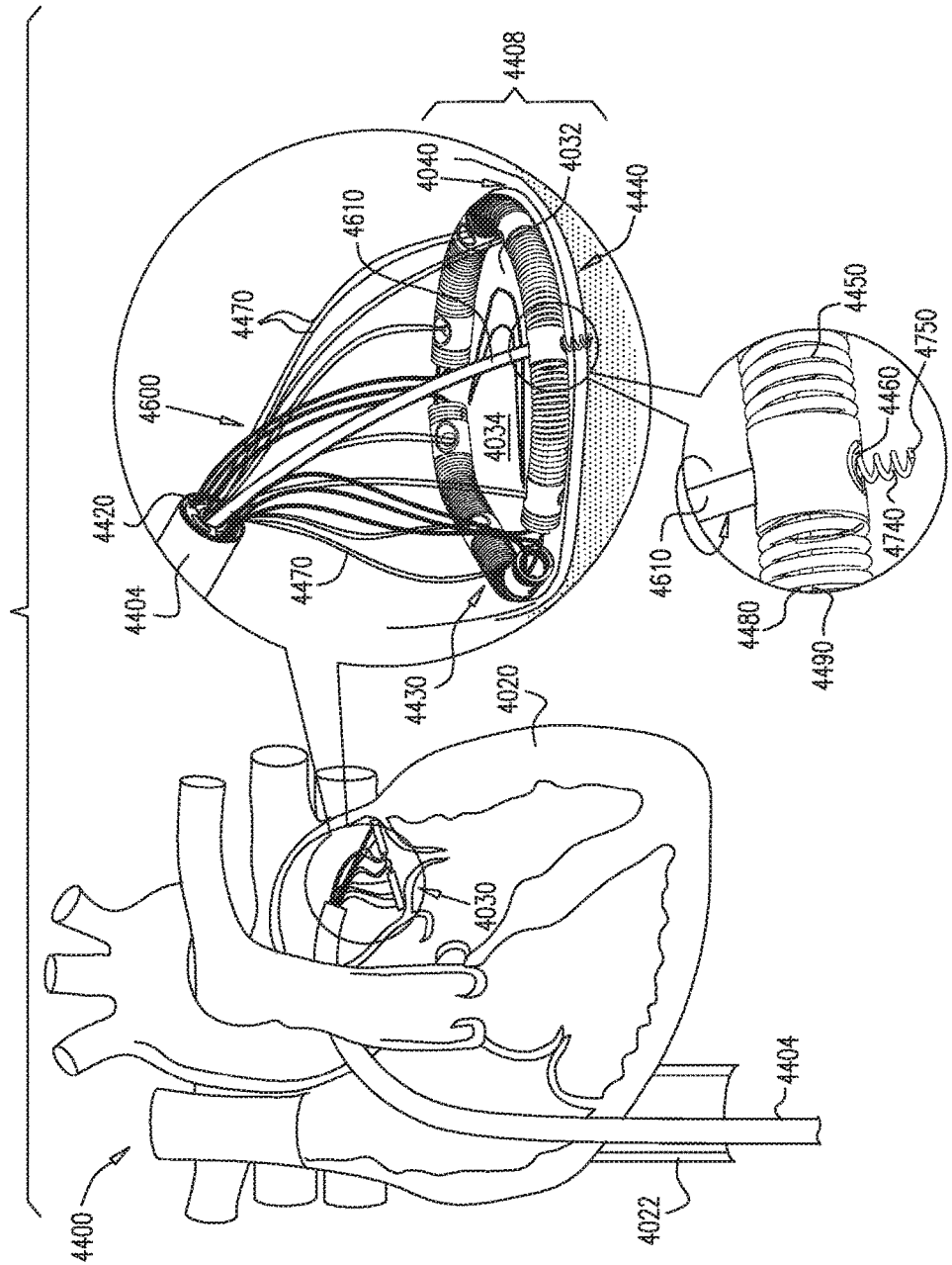

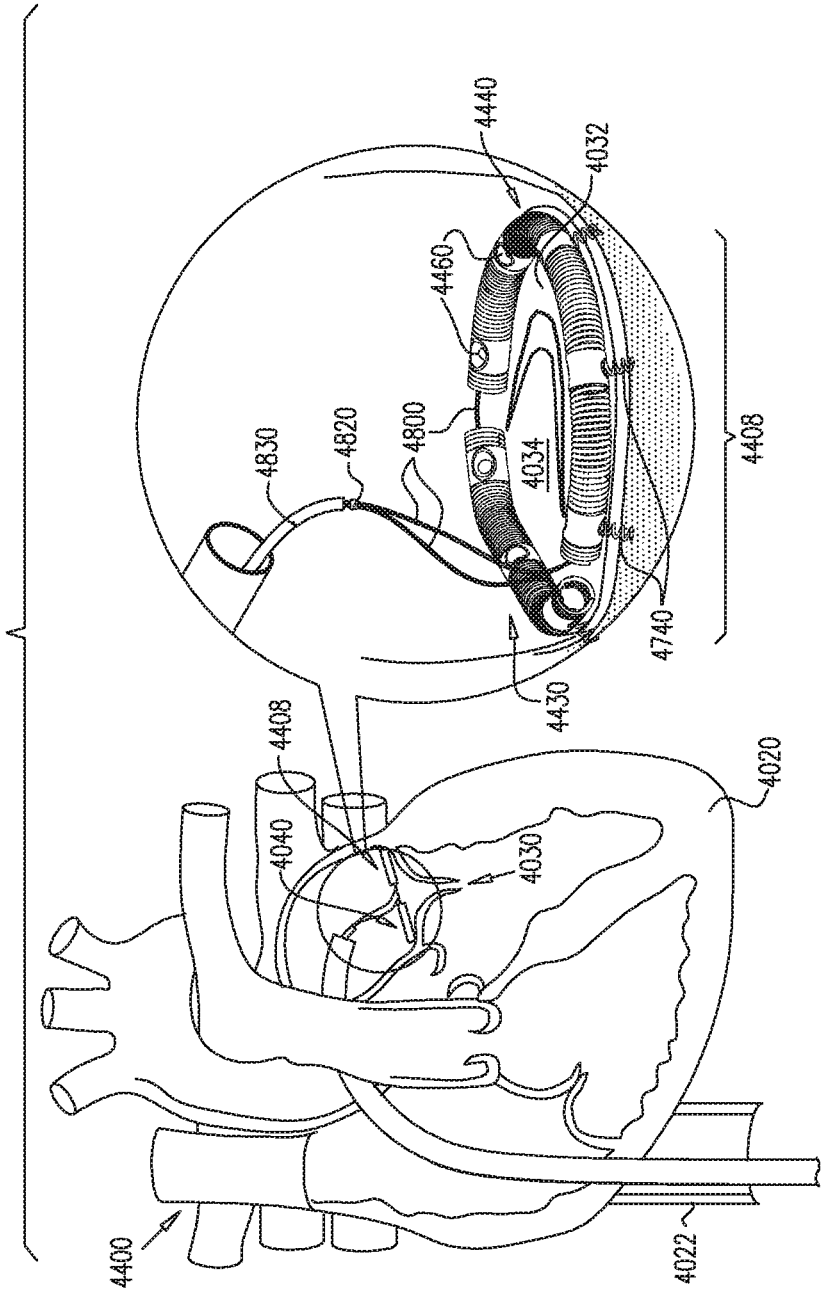

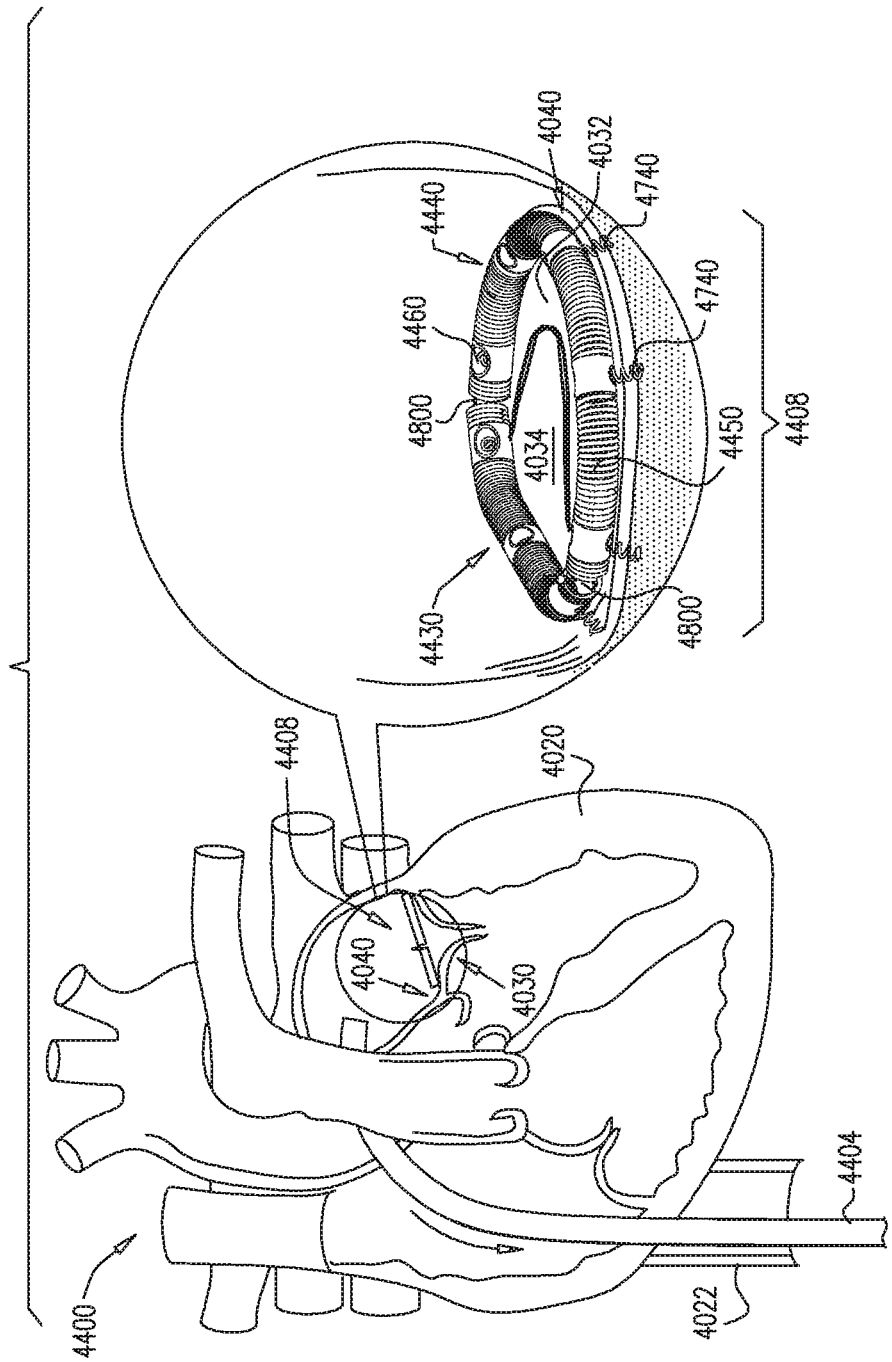

IMPLANTATION OF REPAIR DEVICES IN THE HEART

CROSS-REFERENCES TO RELATED APPLICATIONS

The present application is a continuation of U.S. Ser. No. 15/249,957 to Gross et al., entitled, "Implantation of Repair Devices in the Heart," filed Aug. 29, 2016 (U.S. Pat. No. 9,974,653), which is a continuation of U.S. Ser. No. 15/144,127 to Gross et al., entitled, "Implant and anchor placement," filed May 2, 2016 (U.S. Pat. No. 9,872,769), which is a continuation of U.S. patent application Ser. No. 14/551,951 to Gross et al., entitled, "Implant and anchor placement," filed Nov. 24, 2014 (U.S. Pat. No. 9,351,830), and which:

(a) is a continuation of U.S. patent application Ser. No. 12/996,954 to Gross et al., entitled, "Annuloplasty devices and methods of delivery therefor," filed Mar. 24, 2011, which published as US 2011/0166649, which issued as U.S. Pat. No. 9,192,472 and which is a US national phase application of PCT Patent Application PCT/IL2009/000593 to Gross et al., entitled, "Annuloplasty devices and methods of delivery therefor," filed Jun. 15, 2009, which published as WO 10/004546, which claims priority from U.S. Provisional Patent Application 61/132,295 to Gross et al., entitled, "Annuloplasty devices and methods of delivery therefor," filed Jun. 16, 2008; and (b) is a continuation-in-part of U.S. patent application Ser. No. 11/950,930 to Gross et al., entitled, "Segmented ring placement," filed Dec. 5, 2007, which published as US 2008/0262609, which issued as U.S. Pat. No. 8,926,695, and which claims priority from:

(i) U.S. Provisional Patent Application 60/873,075 to Gross et al., entitled, "Mitral valve closure techniques," filed Dec. 5, 2006;
(ii) U.S. Provisional Patent Application 60/902,146 to Gross et al., entitled, "Mitral valve closure techniques," filed on Feb. 16, 2007; and
(iii) U.S. Provisional Patent Application 61/001,013 to Gross et al., entitled, "Segmented ring placement," filed Oct. 29, 2007.

All of these applications are incorporated herein by reference.

FIELD OF THE INVENTION

The present invention relates in general to valve repair. More specifically, the present invention relates to percutaneous repair of a mitral valve of a patient.

BACKGROUND OF THE INVENTION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

US 2007/0299424 to Cumming et al. describes a catheter assembly includes an inner liner made of flexible material and an outer layer having a steering mechanism. The steering mechanism includes at least one flat wire and a corresponding lumen through which the flat wire may travel. The steering mechanism may also include at least one pull ring to which the flat wires are attached. A layer of heat shrink material may encompass the outer layer. A braided wire assembly, which may have a braid density that varies along the length of the catheter, may also be provided in the outer layer. The overall cross-section of the catheter assembly is preferably substantially circular. A catheter shaft may include a plurality of segments of differing hardness characteristics. The outer layer typically comprises a melt processing polymer such that the catheter assembly may be laminated using heat.

PCT Publication WO 96/40344 to Stevens-Wright et al. describes a bidirectional steering catheter comprising a distal electrode assembly, a flexible tip assembly, an elongated shaft having a central lumen running the length of the shaft, and a handle/actuator. A plurality of ring electrodes are attached to the surface of the flexible tip assembly. Signal wires running the length of the catheter are electrically connected to each ring electrode. At least two pull cables having first and second ends extend distally through the central lumen. The first end of each pull cable is attached to the handle/actuator. The second end of each pull cable is attached to the distal electrode assembly, such that the distal electrode assembly may be moved between a first and second position within a single plane by manipulating the handle/actuator. At least two reinforcement members are located inside the flexible tip assembly. Each reinforcement member has a proximal section, a middle section and a distal section. Each proximal section has a larger diameter than each middle section, thus being stiffer than the middle section. This variable stiffness along the length of each reinforcement member distributes stresses evenly along the length of the tip assembly.

US 2005/0004668 to Aklog et al. describes implantable devices and methods for the repair of a defective cardiac valve. The implantable devices include an annuloplasty ring and a restraining and/or a remodeling structure or mechanism. The annuloplasty ring functions to reestablish the normal size and shape of the annulus bringing the leaflets in proximity to each other. A device having a remodeling structure further facilitates remodeling of the valve but allows the use of a flexible ring. The restraining structure functions to restrain the abnormal motion of at least a portion of the valve being repaired. The restraining and remodeling structures may include at least one strut across the interior of the circumference of the ring.

US 2005/0171601 to Cosgrove describes an annuloplasty repair segment and template for heart valve annulus repair. The elongate flexible template may form a distal part of a holder that also has a proximal handle. Alternatively, the template may be releasably attached to a mandrel that slides within a delivery sheath, the template being released from the end of the sheath to enable manipulation by a surgeon. A tether connecting the template and mandrel may also be provided. The template may be elastic, temperature responsive, or multiple linked segments. The template may be aligned with the handle and form a two- or three-dimensional curve out of alignment with the handle such that the annuloplasty repair segment attached thereto conforms to the curve. The template may be actively or passively converted between its straight and curved positions. The combined holder and ring are suited for minimally-invasive surgeries in which the combination is delivered to an implantation site through a small access incision with or without a cannula, or through a catheter passed through the patient's vasculature.

U.S. Pat. No. 6,102,945 to Campbell describes a support ring for a natural human heart valve, including a first ring portion having opposite terminal ends and a second ring portion having opposite terminal ends. An interconnector extends through and interconnects the first and second ring portions, to maintain the opposite terminal ends of the first ring portion adjacent the opposite terminal ends of the second ring portion, to form a segmented ring having a first and a second interface between the first and second ring portions. The first ring portion is of a greater length than the second ring portion. The ring portions are separable by severing the interconnector at the first and second interfaces, thus producing two variable size ring segments.

U.S. Pat. No. 5,593,424 to Northrup III describes an apparatus and method for reducing the circumference of a vascular structure comprising the steps of providing a plurality of sutures and a plurality of discrete suture support segments of a biocompatible, inert material. Each suture support segment has at least two suture holes spaced a predetermined distance apart. The method includes individually suturing each discrete suture support segment to the vascular structure with one of the plurality of sutures by effecting a horizontal mattress (U-shaped) suture along the vascular structure through a length of tissue of the vascular structure such that the length (D') of tissue sutured is greater than distance (D); and tightening and tying off the suture, whereby each sutured suture support segment creates an imbrication in the vascular structure, thereby reducing the circumference thereof. A biocompatible, inert stabilizing material is described as being optionally affixed over the suture support segments and the vascular structure prior to tying off the suture to stabilize the interval between the suture support segments and eliminate direct exposure of the segmented apparatus to blood.

The following patents and patent applications may be of interest:

EP Patent EP 06/14342 to Pavcnik et al.
EP Patent EP 10/06905 to Organ
PCT Publication WO 00/22981 to Cookston et al.
PCT Publication WO 01/26586 to Seguin
PCT Publication WO 01/56457 to Pruitt
PCT Publication WO 03/047467 to Cosgrove et al.
PCT Publication WO 04/103434 to Martin et al.
PCT Publication WO 05/046488 to Douk et al.
PCT Publication WO 06/012013 to Rhee et al.
PCT Publication WO 06/012038 to Shaoulian et al.
PCT Publication WO 06/086434 to Powell et al.
PCT Publication WO 06/097931 to Gross et al.
PCT Publication WO 06/105084 to Cartledge et al.
PCT Publication WO 07/011799 to Navia et al.
PCT Publication WO 07/121314 to Rafiee et al.
PCT Publication WO 07/136981 to Cumming et al.
PCT Publication WO 96/39963 to Abela et al.
PCT Publication WO 97/01369 to Taylor et al.
PCT Publication WO 98/46149 to Organ
U.S. Pat. No. 3,656,185 to Carpentier
U.S. Pat. No. 4,961,738 to Mackin
U.S. Pat. No. 5,306,296 to Wright et al.
U.S. Pat. No. 5,325,845 to Adair
U.S. Pat. No. 5,716,370 to Williamson, IV et al.
U.S. Pat. No. 5,855,614 to Stevens et al.
U.S. Pat. No. 6,074,401 to Gardiner et al.
U.S. Pat. No. 6,524,338 to Gundry
U.S. Pat. No. 6,533,772 to Sherts et al.
U.S. Pat. No. 6,569,198 to Wilson et al.
U.S. Pat. No. 6,619,291 to Hlavka et al.
U.S. Pat. No. 6,626,899 to Houser et al.
U.S. Pat. No. 6,629,534, PCT Publication WO 06/116558 and US 2004/0039442 to St. Goar et al.
U.S. Pat. No. 6,752,813 to Golfarb et al.
U.S. Pat. No. 6,764,510 to Vidlund et al.
U.S. Pat. No. 6,893,459 to Macoviak
U.S. Pat. No. 6,918,917 to Nguyen et al.
U.S. Pat. No. 6,926,730 to Nguyen et al.
U.S. Pat. No. 6,986,775 to Morales et al.
U.S. Pat. No. 7,004,176 to Lau
U.S. Pat. No. 7,101,395 to Tremulis et al.
U.S. Pat. No. 7,150,737 to Purdy et al.
U.S. Pat. No. 7,172,625 to Shu et al.
U.S. Pat. No. 7,175,660 to Cartledge et al.
U.S. Pat. No. 7,220,277 to Arm et al.
U.S. Pat. No. 7,226,467 to Lucatero et al.
US 2001/0021874 to Capentier
US 2002/0198586 to Inoue
US 2003/0050693 to Quijano et al.
US 2003/0078465 to Pai et al.
US 2003/0114901 to Loeb et al.
US 2003/0191528 and U.S. Pat. No. 6,805,711 to Quijano et al.
US 2003/0199974 to Lee et al.
US 2004/0127983 to Mortier et al.
US 2004/0138744 to Lashinski et al.
US 2004/0148021 to Cartledge et al.
US 2004/0193191 to Starksen et al.
US 2004/0236419 to Milo
US 2004/0243227 to Starksen et al.
US 2004/0260394 to Douk et al.
US 2005/0055038 to Kelleher et al.
US 2005/0096740 to Langberg et al.
US 2005/0222678 to Lashinski et al.
US 2005/0288778 to Shaoulian et al.
US 2005/0288781 to Moaddeb et al.
US 2006/0095009 to Lampropoulos et al.
US 2006/0195134 to Crittenden
US 2006/0282161 to Huynh et al.
US 2006/0247763 to Slater
US 2007/0080188 to Spence et al.
US 2007/0244556 to Rafiee et al.
US 2007/0299424 to Cumming et al.
US 2008/0027483 to Cartledge et al.
US 2004/0148019 and US 2004/0148020 to Vidlund et al.
US 2004/0260393 to Randert et al. and US 2004/0127982 to Machold et al.
US 2005/0010287 and 2004/0138745 to Macoviak et al.

The following articles may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

SUMMARY OF THE INVENTION

In some embodiments of the present invention, systems and surgical methods are provided for repair of a dilated mitral valve of a patient. Typically, an annuloplasty structure, e.g., at least one elongate segment of an annuloplasty ring, is transcatheterally advanced toward an atrial surface of an annulus of the mitral valve, using a percutaneous transcatheter approach. In some embodiments, the annuloplasty structure is positioned at the annulus using a minimally-invasive approach, e.g., intercostal access. In some embodiments of the present invention, systems and methods are provided for repairing the valve of the patient using an open-heart procedure. For embodiments in which the annuloplasty structure is transcatheterally advanced toward the annulus, the annuloplasty structure assumes (1) a linear configuration having first and second ends as it is advanced transcatheterally toward the left atrium of the patient, and (2) a closed configuration, e.g., a substantially ring-shaped or "D"-shaped configuration, once deployed within the left atrium of the patient.

In some embodiments, the annuloplasty structure has a longitudinal axis when disposed in a linear state thereof and comprises one or more, e.g., a plurality, of subunits that are compressible along the longitudinal axis of the annuloplasty structure. Typically, the annuloplasty structure comprises one or more, e.g., a plurality, of anchor mounts which are each configured to facilitate anchoring of the annuloplasty structure to the annulus of the patient.

Typically, the annuloplasty structure is shaped to define a substantially tubular structure which defines at least one hollow lumen configured for passage therethrough of a ratchet mechanism and/or at least one contracting element, e.g., wire or cable. In some embodiments, the annuloplasty structure is shaped to define a first lumen for passage therethrough of the ratchet mechanism and a second lumen for passage therethrough of the at least one contracting wire.

Typically, the ratchet of the ratchet mechanism is shaped to define an elongate structure shaped to define a plurality of engaging structures, e.g., holes, slots, grooves, etc., therealong. The engaging structures maintain various locked configurations of the annuloplasty structure. As the annuloplasty structure is advanced toward a heart of the patient, the annuloplasty structure is shaped to define a substantially linear configuration having first and second ends. Once the annuloplasty structure has been positioned within the atrium of the patient, the contracting wire is pulled, thereby drawing together the respective ends of the ratchet such that the annuloplasty structure, in turn, assumes a generally circular configuration. Ultimately, the ratchet mechanism locks in place the respective ends of the ratchet, thereby maintaining an adjusted perimeter of the annuloplasty structure.

In some embodiments of the present invention, a delivery system is provided for positioning and anchoring of the annuloplasty structures described herein to the annulus of the patient. The delivery system comprises an advancement catheter housing (a) the annuloplasty structure in a distal portion thereof, and (b) a steerable catheter disposed proximally with respect to the annuloplasty structure. A plurality of guide members are reversibly coupled to the annuloplasty structure and to the steerable catheter. These guide members facilitate steering of the steerable catheter toward specific locations along the annuloplasty structure. Typically, by pulling on the proximal end of a given guide member, the distal end of the catheter is steered toward a given location of annuloplasty structure.

Once the distal end of the catheter is disposed in proper orientation with respect to the given location along the annuloplasty structure, an anchoring device, e.g., an anchor or a suture, is delivered through the steerable catheter and toward the given location. The annuloplasty structure is then anchored to the annulus via the anchoring device. Thus, the steerable catheter and guide members facilitate target-specific anchoring of the annuloplasty structure to the annulus.

In some embodiments, the anchoring device comprises a helical anchor configured to be corkscrewed into the annulus of the patient. In some embodiments, the anchoring device comprises an anchor configured to assume a predetermined shape once it emerges from within the distal end of the catheter.

In some embodiments, the annuloplasty structure is shaped to define a single tubular element having first and second ends which meet and form a ring structure once inside the left atrium and manipulated by the operating physician. In some embodiments, the annuloplasty structure comprises at least two discrete hollow ring segments which are each anchored at respective positions along the annulus circumference of the mitral valve. In either embodiment, the contracting wire functions as a drawstring to pull the segment(s) into proper orientation once the segment(s) has been anchored to the annulus.

Using real-time monitoring, tactile feedback and optionally in combination with fluoroscopic imaging, the contracting wire is then pulled. Consequently, the leaflets are drawn toward one another in accordance with the level of dilation of the preoperative mitral valve. Thus, generally, the normal structural configuration is returned to the leaflets, effecting a reduction in mitral valve perimeter/size and in valve regurgitation.

In some embodiments of the present invention, a delivery tool is provided for use during an open-heart procedure in order to anchor to the annulus the annuloplasty structures described herein. The handle of the tool is coupled to a plurality of hollow-lumen tubes. The respective proximal ends of tubes are accessible from a proximal portion of the handle, and the respective distal portions of the tubes are attached to the annuloplasty structure at respective locations thereof. The annuloplasty structure is advanced by the tool and toward the annulus while assuming its closed configuration. Once positioned along the annulus, a respective anchoring device is advanced through each of the tubes, through the annuloplasty structure, and subsequently into the tissue of the annulus.

Particular embodiments are described herein for implementing these techniques.

There is therefore provided, in accordance with respective embodiments of the present invention, the following inventive concepts:

1. Apparatus, including:
    a tube shaped to define a tube lumen;
    at least one implant reversibly coupled to the tube, and configured for implantation within a body of a patient; and
    two or more longitudinal guide members disposed at least in part along a distal portion of the tube, the longitudinal guide members having distal portions thereof configured to be reversibly coupled to the implant, and arranged such that application of a force to a first one of the longitudinal guide members steers the distal portion of the tube toward a first location along the implant, and application of a force to a second one of the longitudinal guide members steers the distal portion of the tube toward a second location along the implant.
2. The apparatus according to inventive concept 1, wherein the implant includes an annuloplasty structure.
3. The apparatus according to inventive concept 1, wherein the implant includes a braided mesh.

4. The apparatus according to inventive concept 1, wherein the implant includes at least one subunit that is compressible along a longitudinal axis of the implant.
5. The apparatus according to inventive concept 1, wherein the implant is configured for transcatheter advancement into a body cavity of the patient.
6. The apparatus according to inventive concept 1, wherein the implant is configured for transcatheter advancement into an atrium of a heart of the patient.
7. The apparatus according to inventive concept 1, wherein the apparatus further includes a housing configured to surround at least a portion of the tube, the housing being shaped to define one or more channels configured for passage therethrough of the two or more longitudinal guide members, and wherein the housing is configured to move rotationally with respect to a longitudinal axis of the tube.
8. The apparatus according to inventive concept 7, wherein the housing is shaped to define two or more channels, wherein each channel is configured for passage therethrough of a respective one of the two or more longitudinal guide members.
9. The apparatus according to inventive concept 1, wherein the implant includes at least one elongate segment.
10. The apparatus according to inventive concept 9, wherein the elongate segment includes a shape-memory alloy, the alloy being configured to assume a curved configuration once the segment has been advanced into an atrium of a heart of the patient.
11. The apparatus according to inventive concept 9, wherein the elongate segment includes a ratchet mechanism including a body portion, a first end shaped to define at least one first engaging structure, and a second end shaped to define at least one second engaging structure configured to engage the first engaging structure.
12. The apparatus according to inventive concept 11, wherein:
the body portion is shaped to define at least one tubular body portion having at least one lumen therein,
the apparatus further includes a wire disposed at least in part within the lumen of the body portion, and
the tubular body portion is configured to be advanced toward a left atrium of the patient in a generally straight configuration and subsequently to assume a curved configuration in response to a contracting force applied thereto by contraction of the wire.
13. The apparatus according to inventive concept 11, wherein:
the body portion is shaped to define a flat body portion,
the apparatus further includes a wire disposed at least alongside the body portion, and
the elongate segment is configured to be advanced toward a left atrium of the patient in a generally straight configuration and subsequently to assume a curved configuration in response to a contracting force applied thereto by contraction of the wire.
14. The apparatus according to inventive concept 9, wherein:
the elongate segment is shaped to define an elongate tube having a lumen therein, and
the apparatus further includes a ratchet mechanism configured to be disposed within the lumen of the elongate segment, the ratchet mechanism including a body portion, a first end shaped to define at least one first engaging structure, and a second end shaped to define at least one second engaging structure configured to engage the first engaging structure.
15. The apparatus according to inventive concept 14, the apparatus further includes a wire disposed at least in part within the lumen of the elongate segment, wherein the elongate segment is configured to be advanced toward a left atrium of the patient in a generally straight configuration and subsequently to assume a curved configuration in response to a contracting force applied thereto by contraction of the wire.
16. The apparatus according to inventive concept 15, wherein the ratchet mechanism is configured to be advanced toward the left atrium of the patient in a generally straight configuration and subsequently to assume a curved configuration in response to the contracting force.
17. The apparatus according to inventive concept 15, wherein, in response to the contracting force, the wire is configured to draw together opposing ends of the ratchet mechanism and opposing ends of the elongate segment, and wherein the ratchet mechanism is configured to maintain respective first ratcheted perimeters of the elongate segment and the ratchet mechanism.
18. The apparatus according to inventive concept 17, wherein, in response to an additional contracting force by additional contraction of the wire, the wire is configured to contract the ratchet mechanism and the elongate segment to respective second ratcheted perimeters thereof, each second ratcheted perimeter being smaller than the respective first ratcheted perimeters, and wherein the ratchet mechanism is configured to maintain the respective second ratcheted perimeters of the ratchet mechanism and the elongate segment.
19. The apparatus according to inventive concept 9, wherein the elongate segment includes first and second segments configured for simultaneous advancement toward an atrium of a heart of the patient.
20. The apparatus according to inventive concept 19, wherein the first and second segments are configured to be advanced toward the atrium of the patient in a generally straight configuration and subsequently to assume a curved configuration.
21. The apparatus according to inventive concept 19, wherein the first and second segments include a shape-memory alloy, the alloy being configured to assume a curved configuration once the segments have been advanced into the atrium of the patient.
22. The apparatus according to inventive concept 9, wherein the elongate segment includes two or more anchor mounts each having longitudinal axes thereof that are transverse to a longitudinal axis of the elongate segment, each mount shaped to provide a channel aligned along the longitudinal axis of the respective anchor mount that is transverse to the longitudinal axis of the anchor mount.
23. The apparatus according to inventive concept 22, wherein application of the force to the first one of the longitudinal guide members steers the distal portion of the tube toward a first one of the two or more anchor mounts, and wherein application of the force to the second one of the longitudinal guide members steers the distal portion of the tube toward a second one of the two or more anchor mounts.
24. The apparatus according to inventive concept 22, wherein the elongate segment includes at least one subunit disposed between the two or more anchor mounts, the subunit being compressible along the longitudinal axis of the elongate segment.

25. The apparatus according to inventive concept 22, wherein a respective one of the two or more longitudinal guide members is reversibly coupled to each of the two or more anchor mounts.

26. The apparatus according to inventive concept 25, wherein a distal end of each of the two or more longitudinal guide members is reversibly coupled to a lateral wall of a respective one of the two or more anchor mounts.

27. The apparatus according to inventive concept 25, wherein:
the elongate segment is shaped to define an elongate tube having a lumen thereof,
the two or more anchor mounts are each shaped to define at least one lumen having a longitudinal axis thereof aligned in parallel with a longitudinal axis of the lumen of the elongate tube, and
the apparatus further includes a ratchet mechanism configured to be disposed within the lumen of the elongate segment and within respective lumens of the two or more anchor mounts, the ratchet mechanism including a body portion, a first end shaped to define at least one first engaging structure, and a second end shaped to define at least one second engaging structure configured to engage the first engaging structure.

28. The apparatus according to inventive concept 27, further comprising a wire disposed at least in part within the lumen of the elongate segment and within respective lumens of the two or more anchor mounts, wherein the elongate segment is configured to be advanced toward an atrium of a heart of the patient in a generally straight configuration and subsequently to assume a curved configuration in response to a contracting force applied thereto by contraction of the wire.

29. The apparatus according to inventive concept 28, wherein the ratchet mechanism is configured to be advanced toward the atrium of the patient in a generally straight configuration and subsequently to assume a curved configuration in response to the contracting force.

30. The apparatus according to inventive concept 28, wherein, in response to the contracting force, the wire is configured to draw together opposing ends of the ratchet mechanism and opposing ends of the elongate segment, and wherein the ratchet mechanism is configured to maintain respective first ratcheted perimeters of the ratchet mechanism and the elongate segment.

31. The apparatus according to inventive concept 30, wherein, in response to an additional contracting force by additional contraction of the wire, the wire is configured to contract the ratchet mechanism and the elongate segment to respective second ratcheted perimeters thereof, each second ratcheted perimeters being smaller than the respective first ratcheted perimeters, and wherein the ratchet mechanism is configured to maintain the respective second ratcheted perimeters of the ratchet mechanism and the elongate segment.

32. The apparatus according to inventive concept 25 a bar configured to be disposed within the channel.

33. The apparatus according to inventive concept 32, wherein the bar is disposed within the channel angularly with respect to the longitudinal axis of the channel.

34. The apparatus according to inventive concept 33, wherein the bar is disposed within the channel substantially parallel to the longitudinal axis of the elongate segment.

35. The apparatus according to inventive concept 25, further including at least one anchor configured to be advanced through the lumen of the tube, wherein the anchor is configured to be advanced through the channel of a first one of the two or more anchor mounts in response to steering the distal portion of the tube toward the anchor mount by applying the force to the first one of the longitudinal guide members.

36. The apparatus according to inventive concept 35, wherein the anchor includes a pointed distal tip.

37. The apparatus according to inventive concept 35, wherein the longitudinal guide member is configured to be decoupled from the anchor mount subsequent to the anchoring of the anchor to an annulus.

38. The apparatus according to inventive concept 35, wherein the anchor is configured to assume a first configuration as it is advanced through the channel and to assume a second configuration as it is implanted within tissue of the patient.

39. The apparatus according to inventive concept 38, wherein the anchor is configured to assume a straight configuration as it is advanced distally through the channel and to assume a curved configuration as it is implanted within tissue of the patient.

40. The apparatus according to inventive concept 39, wherein the anchor is configured to assume a straight configuration as it is advanced distally through the channel and wherein a portion thereof is configured to curve proximally as it is implanted within tissue of the patient.

41. The apparatus according to inventive concept 35, wherein the anchor includes a helical element at a distal portion thereof, the helical element shaped to define a proximal end of the helical element and a distal end of the helical element.

42. The apparatus according to inventive concept 41, further including an advancement structure having a distal tip thereof, wherein at least a portion of the proximal end of the helical element is configured to be coupled to the distal tip of the advancement structure.

43. The apparatus according to inventive concept 42, wherein the helical element is shaped to define a first number of proximal rotational subunits and a second number of distal rotational subunits, and wherein the proximal rotational subunits are wrapped around the distal tip of the advancement structure.

44. The apparatus according to inventive concept 43, wherein the proximal rotational subunits are coupled to the distal tip of the advancement structure by a first frictional force.

45. The apparatus according to inventive concept 44, wherein the second number is greater than the first number.

46. The apparatus according to inventive concept 45, wherein the advancement structure is configured to be rotated and, in response to the rotation, the distal rotational subunits are configured to be implanted within an annulus of the patient.

47. The apparatus according to inventive concept 46, wherein at least a portion of the distal tip is shaped to define a protrusion disposed adjacent to the proximal end of the helical element, the protrusion being configured to apply a circumferentially-directed force to the proximal end of the helical element as the advancement structure is rotated.

48. The apparatus according to inventive concept 46, wherein during the rotation of the advancement structure: the proximal rotational subunits are configured to slide distally along the distal tip of the advancement structure, and in response to the sliding, a portion of the first number of proximal rotational subunits remains wrapped around the distal tip of the advancement structure.
49. The apparatus according to inventive concept 48, wherein a number of proximal rotational subunits in the portion is less than the first number of proximal rotational subunits.
50. The apparatus according to inventive concept 41, wherein:
the helical element is shaped to define at least two adjacent distal rotational subunits and at least two adjacent proximal rotational subunits, and
a distance between the two adjacent distal rotational subunits is greater than a distance between the two adjacent proximal rotational subunits.
51. The apparatus according to inventive concept 50, further including a bar configured to be disposed within the channel.
52. The apparatus according to inventive concept 50, wherein the bar is disposed within the channel angularly with respect to the longitudinal axis of the channel.
53. The apparatus according to inventive concept 52, wherein the bar is disposed within the channel substantially parallel to the longitudinal axis of the elongate segment.
54. The apparatus according to inventive concept 52, wherein the distance between the distal rotational subunits enables the distal rotational subunits to be corkscrewed around the bar and subsequently into an annulus of the patient.
55. The apparatus according to inventive concept 52, wherein a diameter of the bar is greater than the distance between the two adjacent proximal rotational subunits and less than the distance between the two adjacent distal rotational subunits.
56. The apparatus according to inventive concept 52, wherein the distance between the proximal rotational subunits restricts the proximal rotational subunits from being corkscrewed around the bar and into an annulus of the patient.
57. Apparatus, including:
a tube shaped to define a tube lumen;
at least one implant reversibly coupled to the tube and configured for implantation within a body of a patient; and
one or more longitudinal guide members disposed at least in part along a distal portion of the tube, the one or more longitudinal guide members having a distal portions thereof configured to be reversibly coupled to the implant, and arranged such that application of a force to the one or more longitudinal guide members steers the distal portion of the tube toward a first location along the implant.
58. A method for repairing a valve of a body of a patient, the valve including an annulus and at least first and second leaflets, including:
advancing a tube shaped to define a tube lumen toward the valve of the patient;
advancing toward the valve at least one annuloplasty structure reversibly coupled to the tube and at respective locations thereof to two or more longitudinal guide members at respective distal portions thereof, the longitudinal guide members being disposed at least in part along a distal portion of the tube;
positioning the annuloplasty structure against the annulus of the patient;
steering the distal portion of the tube toward a first location along the annuloplasty structure by pulling a first one of the two or more longitudinal guide members; and
steering the distal portion of the tube toward a second location along the annuloplasty structure by pulling a second one of the two or more longitudinal guide members.
59. The method according to inventive concept 58, wherein advancing the tube and the annuloplasty structure includes transcatheterally advancing the tube and the annuloplasty structure during a single transcatheter advancement thereof.
60. The method according to inventive concept 58, further including:
advancing a first anchor through the lumen of the tube subsequently to steering the tube toward the first location,
anchoring the annuloplasty structure at the first location thereof to the annulus by advancing the first anchor through the annuloplasty structure and into tissue of the annulus,
advancing a second anchor through the lumen of the tube subsequently to steering the tube toward the second location, and
anchoring the annuloplasty structure to the annulus at the second location thereof by advancing the second anchor through the annuloplasty structure and into tissue of the annulus.
61. The method according to inventive concept 58, wherein the annuloplasty structure includes at least one elongate structure, and wherein advancing toward the valve the at least one annuloplasty structure includes advancing toward the valve the at least one elongate structure.
62. The method according to inventive concept 61, wherein advancing toward the valve the at least one elongate structure includes advancing toward the valve the at least one elongate structure in a substantially linear configuration thereof.
63. The method according to inventive concept 62, further including pulling the elongate structure into a curved configuration following the advancing of the elongate structure toward the valve.
64. The method according to inventive concept 62, further including allowing the elongate structure to assume a curved configuration following the advancing of the elongate structure toward the valve.
65. A method for repairing a valve of a body of a patient, the valve including an annulus and at least first and second leaflets, including:
advancing a tube shaped to define a tube lumen toward the valve of the patient;
advancing toward the valve at least one annuloplasty structure reversibly coupled to the tube and at respective locations thereof to one or more longitudinal guide members at respective distal portions thereof, the one or more longitudinal guide members being disposed at least in part along a distal portion of the tube;
positioning the annuloplasty structure against the annulus of the patient; and
steering the distal portion of the tube toward a first location along the annuloplasty structure by pulling the one or more longitudinal guide members.
66. Apparatus, including:
a tubular structure having a lumen therein having a longitudinal axis;
a wire disposed at least in part within the lumen of the tubular structure;
at least one elongate tube configured to be reversibly coupled at a distal portion thereof to the tubular structure; and
an extension coupled at a proximal portion thereof to the distal portion of the elongate tube, a distal portion of the extension being configured to be disposed within the lumen of the tubular structure and to surround at least a portion of the wire that is disposed at least in part within the lumen of the tubular structure.

67. The apparatus according to inventive concept 66, wherein the tubular structure includes an annuloplasty structure.
68. The apparatus according to inventive concept 66, wherein the tubular structure includes at least one subunit that is compressible along a longitudinal axis of the tubular structure.
69. The apparatus according to inventive concept 66, wherein the tubular structure includes a braided mesh.
70. The apparatus according to inventive concept 66, wherein the tubular structure includes at least one anchor mount having a longitudinal axis thereof that is transverse to the longitudinal axis of the tubular structure, and wherein the anchor mount is shaped to provide at least one first channel aligned along the longitudinal axis of the anchor mount.
71. The apparatus according to inventive concept 70, wherein the at least a first channel includes first and second channels, wherein the anchor mount is shaped to provide the first channel in a vicinity adjacent to the second channel.
72. The apparatus according to inventive concept 71, wherein the distal portion of the channel is configured to be disposed within the second channel.
73. The apparatus according to inventive concept 71, wherein the distal portion of the elongate tube is configured to be disposed proximally to the first channel of the anchor mount.
74. The apparatus according to inventive concept 73, further including at least one anchor configured to anchor the tubular structure to tissue of a patient, wherein the anchor is configured to be:
    advanced toward the tubular structure via the elongate tube,
    advanced through the first channel of the anchor mount, and
    implanted within the tissue.
75. The apparatus according to inventive concept 66, further including a ratchet mechanism configured to be disposed within the lumen of the tubular structure, the ratchet mechanism including a body portion, a first end shaped to define at least one first engaging structure, and a second end shaped to define at least one second engaging structure configured to engage the first engaging structure, wherein the ratchet mechanism is configured to maintain a ratcheted perimeter of the tubular structure.
76. The apparatus according to inventive concept 75, wherein:
    the body portion is shaped to define at least one tubular body portion having at least one lumen therein,
    the apparatus further includes a wire disposed at least in part within the lumen of the body portion, and
    the tubular structure is configured to be advanced toward a left atrium of a patient in a generally straight configuration and subsequently to assume a curved configuration in response to a contracting force applied thereto by contraction of the wire.
77. The apparatus according to inventive concept 75, wherein:
    the body portion is shaped to define a flat body portion,
    the apparatus further includes a wire disposed at least alongside the body portion, and
    the tubular structure is configured to be advanced toward a left atrium of a patient in a generally straight configuration and subsequently to assume a curved configuration in response to a contracting force applied thereto by contraction of the wire.
78. Apparatus, including:
    a tubular structure having a lumen thereof having a longitudinal axis;
    at least one anchor mount coupled to the tubular structure, the anchor mount being shaped to provide at least one channel having a longitudinal axis that is at a non-zero angle with respect to the longitudinal axis of the tubular structure; and
    a ratchet mechanism configured to be disposed within the lumen of the tubular structure, the ratchet mechanism including a body portion, a first end shaped to define at least one first engaging structure, and a second end shaped to define at least one second engaging structure configured to engage the first engaging structure, the ratchet mechanism configured to maintain a ratcheted perimeter of the tubular structure.
79. The apparatus according to inventive concept 78, wherein the tubular structure includes a braided mesh.
80. The apparatus according to inventive concept 78, wherein the tubular structure includes an annuloplasty structure.
81. The apparatus according to inventive concept 78, wherein the tubular structure includes at least one subunit that is compressible along the longitudinal axis of the tubular lumen.
82. The apparatus according to inventive concept 78, wherein the tubular structure is configured for transcatheter advancement into an atrium of a heart of a patient.
83. The apparatus according to inventive concept 78, wherein the tubular structure includes a shape-memory alloy, the alloy being configured to assume a curved configuration once the structure has been advanced into a left atrium of a patient.
84. The apparatus according to inventive concept 78, wherein the at least one anchor mount includes two or more anchor mounts, and wherein the tubular structure includes at least one subunit disposed between the two or more anchor mounts, the subunit being compressible along the longitudinal axis of the tubular lumen.
85. The apparatus according to inventive concept 78, wherein the anchor mount is shaped to define an anchor mount lumen having a longitudinal axis that is parallel with respect to the longitudinal axis of the tubular structure, and wherein the channel is disposed at the non-zero angle with respect to the longitudinal axis of the anchor mount lumen.
86. The apparatus according to inventive concept 85, wherein the ratchet mechanism is configured to be disposed within the lumen of the tubular structure and within the anchor mount lumen.
87. The apparatus according to inventive concept 86, further including a wire disposed at least in part within the lumen of the tubular structure and within the anchor mount lumen.
88. The apparatus according to inventive concept 86, wherein:
    the body portion of the ratchet mechanism is shaped to define at least one tubular body portion having at least one lumen therein,
    the apparatus further includes a wire is disposed at least in part within the lumen of the body portion, and
    the tubular structure is configured to be advanced toward an atrium of a heart of a patient in a generally straight configuration and subsequently to assume a curved configuration in response to a contracting force applied thereto by contraction of the wire.

89. The apparatus according to inventive concept 86, wherein the tubular structure includes at least one subunit that is compressible along a longitudinal axis of the tubular structure.

90. The apparatus according to inventive concept 86, wherein:
the body portion is shaped to define a flat body portion,
the wire is disposed at least alongside the body portion, and
the tubular structure is configured to be advanced toward an atrium of a heart of a patient in a generally straight configuration and subsequently to assume a curved configuration in response to a contracting force applied thereto by contraction of the wire.

91. The apparatus according to inventive concept 86, wherein the anchor mount lumen has a major axis that is (a) transverse with respect to the longitudinal axis of the anchor mount lumen and (b) at a non-zero angle with respect to the longitudinal axis of the first channel.

92. The apparatus according to inventive concept 91, wherein:
the apparatus includes a plurality of anchor mounts,
each anchor mount of a first portion of the plurality of anchor mounts has a respective anchor mount lumen having a major axis that is disposed at a first angle with respect to the longitudinal axis of the channel, and
each anchor mount of a second portion of the plurality of anchor mounts has a respective anchor mount lumen having a major axis that is disposed at a second angle with respect to the longitudinal axis of the channel.

93. The apparatus according to inventive concept 78, further including a wire disposed at least in part within the lumen of the tubular structure, wherein the tubular structure is configured to be advanced toward an atrium of a heart of a patient in a generally straight configuration and subsequently to assume a curved configuration in response to a contracting force applied thereto by contraction of the wire.

94. The apparatus according to inventive concept 93, wherein the ratchet mechanism is configured to be advanced toward the atrium of the patient in a generally straight configuration and subsequently to assume a curved configuration in response to the contracting force.

95. The apparatus according to inventive concept 93, wherein, in response to the contracting force, the wire is configured to draw together opposite ends of the ratchet mechanism and opposing ends of the tubular structure, and wherein the ratchet mechanism is configured to maintain respective first ratcheted perimeters of the tubular structure and the ratchet mechanism.

96. The apparatus according to inventive concept 95, wherein, in response to an additional contracting force by additional contraction of the wire, the wire is configured to contract the ratchet mechanism and the tubular structure to respective second ratcheted perimeters thereof, each second ratcheted perimeter being smaller than the respective first ratcheted perimeters, and wherein the ratchet mechanism is configured to maintain the respective second ratcheted perimeters of the ratchet mechanism and the tubular structure.

97. The apparatus according to inventive concept 78, further including a plurality of longitudinal guide members, wherein each guide member is removably coupled to the tubular element and is configured to facilitate anchoring of the tubular structure to the annulus of the patient.

98. The apparatus according to inventive concept 97, wherein a distal end of the longitudinal guide member is coupled to the tubular element in a vicinity of the anchor mount.

99. The apparatus according to inventive concept 97, further including a bar configured to be disposed within the channel.

100. The apparatus according to inventive concept 99, further including at least one anchor configured to be guided toward the anchor mount via the longitudinal guide member and advanced through the channel of the anchor mount, around the bar, and into tissue of an annulus of the patient.

101. The apparatus according to inventive concept 100, wherein the longitudinal guide member is configured to be looped around the bar and to be decoupled from the bar following the advancement of the anchor into the annulus.

102. The apparatus according to inventive concept 99, wherein the bar is disposed within the channel angularly with respect to an axis of the channel.

103. The apparatus according to inventive concept 102, wherein the bar is disposed within the channel substantially parallel to the longitudinal axis of the tubular lumen.

104. The apparatus according to inventive concept 97, wherein the at least one anchor mount includes two or more anchor mounts, and wherein the at least one longitudinal guide member includes two or more longitudinal guide members having respective distal ends thereof configured to be reversibly coupled to the tubular structure.

105. The apparatus according to inventive concept 104, wherein each one the two or more anchor mounts has a longitudinal axis thereof that is transverse to the longitudinal axis of the tubular structure, and wherein each mount shaped to provide a channel aligned along the longitudinal axis of the respective anchor mount.

106. The apparatus according to inventive concept 105, wherein:
the apparatus further includes an elongate tube shaped to define an elongate tube lumen, the elongate tube being configured to be coupled to the tubular structure, and
the two or more longitudinal guide members are aligned in parallel with the elongate tube and coupled to a distal portion of the tube, the longitudinal guide members having distal ends thereof configured to be reversibly coupled to the tubular structure, and arranged in a manner in which:
application of a force to a first one of the longitudinal guide members steers the distal portion of the elongate tube toward a first location along the tubular structure, and
application of a force to a second one of the longitudinal guide members steers the distal portion of the elongate tube toward a second location along the tubular structure.

107. The apparatus according to inventive concept 106, wherein:
the first location includes a second one of the two or more anchor mounts,
the second location includes a second one of the two or more anchor mounts,
a respective one of the two or more longitudinal guide members is reversibly coupled to each of the two or more anchor mounts, and
application of the force to the first one of the longitudinal guide members steers the distal portion of the elongate tube toward the first anchor mount, and application of the force to the second one of the longitudinal guide members steers the distal portion of the elongate tube toward the second anchor mount.

108. The apparatus according to inventive concept 107, further including at least one anchor configured to be advanced through the lumen of the elongate tube, wherein the anchor is configured to be advanced through the channel of a first one of the two or more anchor mounts in response to steering the distal portion of the elongate tube toward the anchor mount by applying the force to the first one of the longitudinal guide members.

109. Apparatus, including:
a tubular structure having a lumen therein having a longitudinal axis;
a wire disposed in part within the lumen of the tubular structure, the wire having first and second portions thereof, the first and second portions of the wire being disposed externally to the lumen of the tubular structure; and
a handle assembly including at least one rotating element configured to be coupled to the first and second ends of the wire, in a manner in which rotation of the rotating element applies a force to the wire disposed within the tubular structure and adjusts a perimeter of the tubular structure.

110. The apparatus according to inventive concept 109, wherein the tubular structure includes an annuloplasty structure.

111. The apparatus according to inventive concept 109, wherein the tubular structure includes at least one subunit that is compressible along a longitudinal axis of the tubular structure.

112. The apparatus according to inventive concept 109, wherein the tubular structure includes at least one anchor mount coupled to the tubular structure, the anchor mount having a longitudinal axis that is transverse to the longitudinal axis of the tubular structure and shaped to provide a channel aligned along the longitudinal axis of the anchor mount.

113. The apparatus according to inventive concept 109, wherein the tubular structure includes a braided mesh.

114. The apparatus according to inventive concept 109, wherein:
in response to a rotation of the rotating element, the wire is configured to contract the tubular structure to a first perimeter thereof, and
in response to an additional rotation of the rotating element, the wire is configured to contract the tubular structure to a second perimeter thereof, the second perimeter being smaller than the first perimeter.

115. The apparatus according to inventive concept 109, further including a ratchet mechanism configured to be disposed within the lumen of the tubular structure, the ratchet mechanism including a body portion, a first end shaped to define at least one first engaging structure, and a second end shaped to define at least one second engaging structure configured to engage the first engaging structure, wherein the ratchet mechanism is configured to maintain a ratcheted perimeter of the tubular structure.

116. The apparatus according to inventive concept 115, wherein:
in response to a first contracting force by contraction of the wire, the wire is configured to contract the ratchet mechanism and the tubular structure to respective first ratcheted perimeters thereof,
in response to a second contracting force by additional contraction of the wire, the wire is configured to contract the ratchet mechanism and the tubular structure to respective second ratcheted perimeters thereof, each second ratcheted perimeter being smaller than the respective first ratcheted perimeters, and
the ratchet mechanism is configured to maintain the respective second ratcheted perimeters of the ratchet mechanism and the tubular structure.

117. The apparatus according to inventive concept 115, wherein:
the body portion is shaped to define at least one tubular body portion having at least one lumen therein,
the wire is disposed at least in part within the lumen of the body portion, and
the tubular structure is configured to be advanced toward a left atrium of a patient in a generally straight configuration and subsequently to assume a curved configuration in response to a contracting force applied thereto by contraction of the wire.

118. The apparatus according to inventive concept 115, wherein:
the body portion is shaped to define a flat body portion,
the wire is disposed at least alongside the body portion, and
the tubular structure is configured to be advanced toward a left atrium of a patient in a generally straight configuration and subsequently to assume a curved configuration in response to a contracting force applied thereto by contraction of the wire.

119. Apparatus for use with tissue of a patient, including:
a housing having a lateral wall having a proximal and a distal portion, the lateral wall being shaped to define a channel extending from a first opening in the proximal portion to a second opening in the distal portion, the channel having a longitudinal axis thereof; and
an anchor structure configured for passage through the channel and into the tissue, including:
a plurality of coils; and
a head portion defining a diameter of the structure that is larger than a diameter of the first opening, the head portion configured to:
restrict distal motion of the plurality of coils beyond a predetermined depth by abutting against the first opening of the proximal portion, and
draw tissue proximally by rotation of the head portion around the longitudinal axis of the channel.

120. Apparatus, including:
a tubular implant shaped to define an implant lumen;
a flexible longitudinal member disposed within the implant lumen, the flexible longitudinal member having a first end that is slidable with respect to a second end thereof to form the longitudinal member into a closed loop having a perimeter thereof which (a) shortens when the first end is advanced in a first direction with respect to the second end in a first direction, and (b) expands when the first end is advanced with respect to the second end in a second direction opposite to the first direction; and
a flexible contracting member being disposed alongside the longitudinal member and within and slidably advanceable through the implant lumen to facilitate reduction of the perimeter of the longitudinal member by application of a compression force to the longitudinal member.

121. The apparatus according to inventive concept 120, wherein the contracting wire facilitates sliding of the first end of the flexible member with respect to the second end in the second direction, even in the absence of a force applied to the contracting wire.

122. The apparatus according to inventive concept 120, wherein, in response to a pulling force applied to the contracting member, the flexible member is configured to facilitate compression of the implant, and responsively to the compression of the implant, to facilitate sliding of the first end of the longitudinal member with respect to the second end in the first direction.

123. The apparatus according to inventive concept 120, wherein:

when formed into the closed loop, the longitudinal member is shaped to provide an inner surface and an outer surface with respect to a center of the closed loop, the flexible contracting member is disposed alongside the longitudinal member externally to the outer surface thereof, and in response to the pulling force applied to the contracting wire, the contracting wire is configured to facilitate sliding of the first end of the longitudinal member with respect to the second end in the first direction.

124. A method, including:

providing:

a tubular implant having an implant lumen, a flexible longitudinal member disposed within the implant lumen, the flexible longitudinal member having a first end that is slidable with respect to a second end thereof, and a flexible contracting member being disposed alongside the longitudinal member and within and slidably advanceable through the implant lumen, the flexible longitudinal member having a first end that is slidable with respect to a second end thereof to form the longitudinal member into a closed loop having a perimeter thereof which (a) shortens when the first end is advanced in a first direction with respect to the second end in a first direction, and (b) expands when the first end is advanced with respect to the second end in a second direction opposite to the first direction; and reducing the perimeter of the longitudinal member by applying a compression force to the longitudinal member.

125. The method according to inventive concept 124, further comprising facilitates sliding of the first end of the flexible member with respect to the second end in the second direction, even in the absence of a force applied to the contracting wire.

126. The method according to inventive concept 124, further comprising applying a pulling force to the contracting member, and wherein applying the compression force to the longitudinal member comprises:

responsively to the applying the pulling force to the contracting member, compressing the implant, and responsively to the compressing the implant:

applying the compression force to the longitudinal member, facilitating sliding of the first end of the longitudinal member with respect to the second end in the first direction, and compressing the longitudinal member.

127. The method according to inventive concept 124, wherein:

the method further comprises forming the longitudinal member into the closed loop wherein the flexible member has an inner surface and an outer surface with respect to a center of the closed loop, and the flexible contracting member is disposed alongside the longitudinal member externally to the outer surface thereof, and reducing the perimeter of the longitudinal member comprises:

applying a pulling force to the contracting wire, and responsively to the applying the pulling force, facilitating sliding of the first end of the longitudinal member with respect to the second end in the first direction.

There is therefore provided, in accordance with an embodiment of the present invention, apparatus for repairing a valve of a body of a patient, the valve including an annulus and at least first and second leaflets, including:

at least a first discrete segment and a second discrete segment of an annuloplasty structure, each segment being shaped to provide a respective lateral wall, each lateral wall being shaped to define at least one lumen of the respective segment; and at least a first and a second control wire, each control wire configured for sliding advancement through both the first and second segments:

the first control wire is configured to control a relative disposition of a first end of the first segment and a first end of the second segment, and the second control wire is configured to control a relative disposition of a second end of the first segment and a second end of the second segment.

In an embodiment, the first and second segments are configured for transcatheter advancement into a left atrium of a patient.

In an embodiment, the first and second segments are configured for simultaneous advancement toward a left atrium of a patient.

In an embodiment, for each lateral wall of each segment, the lateral wall has a first and a second portion, and the segment is shaped to provide a channel extending from the first portion to the second portion.

In an embodiment, the apparatus includes a bar configured to be disposed within the channel.

In an embodiment, the bar is disposed within the channel substantially perpendicular to an axis of the channel.

In an embodiment, the apparatus includes a flexible longitudinal guide member configured to be removably coupled to the bar.

In an embodiment, the apparatus includes an anchoring structure, and while the guide member is disposed within the body of the patient, the anchoring structure is configured to be advanced via the guide member, through the channel, and subsequently anchored to the annulus of the patient.

In an embodiment, the anchoring structure includes a pointed distal tip.

In an embodiment, while the guide member is disposed within the body of the patient, the anchoring structure is configured to be advanced along the guide member from a site outside the body of the patient.

In an embodiment, while the guide member is disposed within the body of the patient, the guide member is configured to be decoupled from the bar subsequent to the anchoring of the anchoring structure to the annulus.

In an embodiment, the anchoring structure includes a helical element at a distal end thereof, the helical element shaped to provide a proximal end of the helical element and a distal end of the helical element.

In an embodiment, the apparatus includes an advancement tube having a distal tip thereof, at least a portion of the proximal end of the helical element is configured to be coupled to the distal tip of the advancement tube.

In an embodiment, the helical element is shaped to define a first number of proximal rotational subunits and a second number of distal rotational subunits, and the proximal rotational subunits are wrapped around the distal tip of the advancement tube.

In an embodiment, the proximal rotational subunits are coupled to the distal tip of the advancement tube by a first frictional force.

In an embodiment, the second number is greater than the first number.

In an embodiment, the advancement tube is configured to be rotated and, in response to the rotation, the distal rotational subunits are configured to be implanted within the annulus of the patient.

In an embodiment, at least a portion of the distal tip is shaped to define a protrusion disposed adjacent to the proximal end of the helical element, the protrusion being configured to apply a circumferentially-directed force to the proximal end of the helical element as the advancement tube is rotated.

In an embodiment, during the rotation of the advancement tube:

the proximal rotational subunits are configured to slide distally along the distal tip of the advancement tube, and in response to the sliding, a portion of the first number of proximal rotational subunits remains wrapped around the distal tip of the advancement tube.

In an embodiment, a number of proximal rotational subunits in the portion is less than the first number of proximal rotational subunits.

In an embodiment, the portion of the proximal rotational subunits is coupled to the distal tip of the advancement tube by a second frictional force, the second frictional force being weaker than the first frictional force.

In an embodiment, the second frictional force being weaker than the first frictional force facilitates decoupling of the distal tip of the advancement tube from the helical element.

In an embodiment:

the helical element is shaped to define at least two adjacent distal rotational subunits and at least two adjacent proximal rotational subunits, and a distance between the two adjacent distal rotational subunits is greater than a distance between the two adjacent proximal rotational subunits.

In an embodiment, the distance between the distal rotational subunits enables the distal rotational subunits to be corkscrewed around the bar and subsequently into the annulus of the patient.

In an embodiment, the distance between the proximal rotational subunits restricts the proximal rotational subunits from being corkscrewed around the bar and into the annulus of the patient.

In an embodiment, the first and second segments are configured to be advanced toward a left atrium of the patient in a generally straight configuration and subsequently are made to assume a curved configuration.

In an embodiment, the first and second control wires are configured to pull the first and second segments into curved configurations.

In an embodiment, the first and second segments include a shape-memory alloy, the alloy being configured to assume a curved configuration once the segments have been advanced into the left atrium of the patient.

In an embodiment, the apparatus includes at least first and second flexible longitudinal guide members, the first and second guide members configured to be removably coupled to the first and second segments, respectively, each guide member being configured to facilitate anchoring of the respective segment to the annulus of the patient.

In an embodiment, the apparatus includes respective at least first and second anchoring structures, the first and second anchoring structures configured to be disposed at respective distal ends of the first and second guide members, respectively, the anchoring structures being configured to be screwed into the annulus of the patient in response to a rotational force applied to a respective proximal end of the respective guide members.

In an embodiment, each of the anchoring structures includes a pointed distal tip.

In an embodiment, the first and second control wires are configured to control a relative disposition of the first and second segments.

In an embodiment, the first and second control wires are configured to separate the first and second segments.

In an embodiment, the first and second control wires are configured to facilitate positioning of the first and second segments along the annulus.

In an embodiment, the first and second segments are configured to be advanced toward a left atrium of the patient in a generally straight configuration thereof, and the first and second control wires are configured to pull the first and second segments into a curved configuration.

In an embodiment, the first and second segments are configured to be advanced toward an atrium of a heart of the patient in a generally straight configuration, the straight configuration defining a longitudinal axis of the respective first and second segments, at least a portion of the first and second segments is shaped to define one or more compressible units, and the compressible units are configured to be compressed in parallel with the longitudinal axis of the respective segments.

In an embodiment, the compressible units are configured to be compressed in response to an application of a pulling force to the first and second control wires.

In an embodiment, the first control wire is configured to compress the first segment at least in part in response to an application of a pulling force to at least a portion of the first control wire, and the second control wire is configured to compress the second segment at least in part in response to an application of a pulling force to at least a portion of the second control wire.

In an embodiment, the apparatus includes first and second adjustment wires, coupled to the first and second control wires, respectively, the first adjustment wire is coupled to the first control wire at a first junction between the first and second segments, and the second adjustment wire is coupled to the second control wire at a second junction between the first and second segments.

In an embodiment, the adjustment wires are configured to facilitate aligning of the first and second segments with the annulus by separating the segments.

In an embodiment, the adjustment wires are configured to facilitate aligning of the first and second segments with the annulus by elevating portions of the first and second segments.

There is further provided, in accordance with an embodiment of the present invention apparatus for repairing a valve of a body of a patient, the valve including an annulus and at least first and second leaflets, including:

an annuloplasty structure, shaped to provide one or more channels, each channel extending from a respective first portion of a lateral wall of the annuloplasty structure to a respective second portion of the lateral wall of the annuloplasty structure, and including one or more bars, each bar configured to be disposed within a respective one of the channels; and one or more flexible longitudinal guide members, each guide member configured to be removably coupled to a respective one of the bars.

In an embodiment, each guide member is removably coupled to the respective bar by being looped around the respective bar.

In an embodiment, the annuloplasty structure includes an annuloplasty ring.

In an embodiment, the annuloplasty structure includes a partial annuloplasty ring.

In an embodiment, the structure and the one or more guide members are configured to be transcatheterally advanced into a left atrium of the patient.

In an embodiment, the structure and the one or more guide members are configured to be simultaneously advanced toward a left atrium of the patient.

In an embodiment, the annuloplasty structure includes two or more segments of an annuloplasty ring.

In an embodiment, each bar is disposed within a respective one of the channels substantially perpendicular to an axis of the channel.

In an embodiment, the structure includes a shape-memory alloy.

In an embodiment, the structure is configured to be advanced toward a left atrium of the patient in a generally straight configuration and subsequently to be made to assume a curved configuration.

In an embodiment, the apparatus includes at least one control wire, and the control wire is configured to pull the structure into the curved configuration.

In an embodiment, the structure includes a shape-memory alloy, the alloy being configured to assume a curved configuration once the structure has been advanced into the left atrium of the patient.

In an embodiment, the apparatus includes at least one control wire in communication with the structure configured to adjust a disposition of the structure.

In an embodiment, the lateral wall of the annuloplasty structure is shaped to define at least one lumen of the structure.

In an embodiment, the at least one control wire is configured for sliding advancement through the at least one lumen, and to control from within the lumen a conformation of the structure.

In an embodiment,
the structure is configured to be advanced toward a left atrium of the patient in a generally straight configuration, the straight configuration defining a longitudinal axis thereof,
at least a portion of the structure is shaped to define one or more compressible units, and
the compressible units are configured to be compressed in parallel with the longitudinal axis.

In an embodiment, the compressible units are configured to be compressed in response to an application of a pulling force to the at least one control wire.

In an embodiment, the structure includes a first and a second segment, the first and second segments each shaped to provide a respective lateral wall, each lateral wall being shaped to define at least one respective lumen of the respective segment.

In an embodiment, the apparatus includes at least one adjustment wire coupled to the at least one control wire, and the at least one adjustment wire is configured to be coupled to the at least one control wire at a junction between the first and second segments.

In an embodiment, the at least one adjustment wire is configured to facilitate aligning of the first and second segments with the annulus by separating the segments.

In an embodiment, the at least one adjustment wire is configured to facilitate aligning of the first and second segments with the annulus by elevating portions of at least one of the segments.

In an embodiment, the control wire is configured for sliding advancement through the at least one lumen of each of the first and second segments.

In an embodiment, the at least one control wire includes a first and a second control wire.

In an embodiment:
the first and second segments are each shaped to provide respective first and second lumens, and
the first control wire is configured for sliding advancement through each of the first lumens, and the second control wire is configured for sliding advancement through each of the second lumens.

In an embodiment, the first and second control wires are configured to control a relative disposition of the first and second segments.

In an embodiment, the first and second control wires are configured to separate portions of the first and second segments.

In an embodiment, the first and second control wires are configured to facilitate positioning of the first and second segments along the annulus.

In an embodiment, the first and second segments are configured to be advanced toward a left atrium of the patient in a generally straight configuration thereof, and the first and second control wires are configured to pull the first and second segments into a curved configuration.

In an embodiment,
the first and second segments are configured to be advanced toward a left atrium of the patient in a generally straight configuration, the straight configuration defining a longitudinal axis of the respective first and second segments,
at least a portion of each of the first and second segments is shaped to define one or more compressible units, and
the compressible units are configured to be compressed in parallel with the longitudinal axis of the respective segments.

In an embodiment, the compressible units are configured to be compressed in response to an application of a pulling force to the first and second control wires.

In an embodiment:
the first control wire is configured to compress the first segment at least in part in response to an application of a pulling force to at least a portion of the first control wire, and
the second control wire is configured to compress the second segment at least in part in response to an application of a pulling force to at least a portion of the second control wire.

In an embodiment, the apparatus includes one or more anchoring structures, each anchoring structure configured to be advanced through a respective one of the channels and subsequently anchored to the annulus of the patient.

In an embodiment, the anchoring structure is shaped to define a pointed distal tip.

In an embodiment, while the guide member is disposed within the body of the patient, each anchoring structure is configured to be advanced along a respective one of the guide members from a site outside the body of the patient.

In an embodiment, the guide member is configured to be decoupled from the bar subsequent to the anchoring of the anchoring structure to the annulus.

In an embodiment, each of the anchoring structures includes a helical element at a distal end thereof.

In an embodiment:

the helical element is shaped to define at least two adjacent distal rotational subunits and at least two adjacent proximal rotational subunits, and a distance between the two adjacent distal rotational subunits is greater than a distance between the two adjacent proximal rotational subunits.

In an embodiment, the distance between the distal rotational subunits enables the distal rotational subunits to be corkscrewed around the bar and subsequently into the annulus of the patient.

In an embodiment, the distance between the proximal rotational subunits restricts the proximal rotational subunits from being corkscrewed fully around the bar and into the annulus of the patient.

There is yet further provided, in accordance with an embodiment of the present invention apparatus for repairing a valve of a body of a patient, the valve including an annulus and at least first and second leaflets, including:

an annuloplasty structure including a bar; and an anchoring structure including a helical element, the helical element shaped to define at least two adjacent distal rotational subunits and at least two adjacent proximal rotational subunits, a distance between the two adjacent distal rotational subunits is greater than a distance between the two adjacent proximal rotational subunits, and:

the distance between the distal rotational subunits enables the distal rotational subunits to be corkscrewed around the bar and subsequently into tissue of a patient, and the distance between the proximal rotational subunits restricts the proximal rotational subunits from being corkscrewed into tissue of the patient.

In an embodiment, the annuloplasty structure includes an annuloplasty ring.

In an embodiment, the annuloplasty structure includes a partial annuloplasty ring.

In an embodiment, the annuloplasty structure includes two or more segments of an annuloplasty ring.

In an embodiment, the apparatus includes a flexible longitudinal guide member reversibly coupled to the structure, and configured to facilitate anchoring of the annuloplasty structure to the annulus of the patient.

In an embodiment, the annuloplasty structure is shaped to provide a lateral wall having at least first and second portions, and shaped to provide at least one channel, the at least one channel extends from the first portion of the lateral wall of the structure to the second portion of the lateral wall of the structure, the bar is disposed within the at least one channel substantially perpendicular to an axis of the channel, and the guide member is reversibly coupled to the bar.

In an embodiment, the anchoring structure is disposed at a distal end of the guide member.

In an embodiment, the anchoring structure is configured to be screwed into the annulus in response to a rotational force applied to a proximal end of the guide member.

In an embodiment, the apparatus includes a hollow tube configured to be reversibly coupled to the helical element, and to push the anchoring structure toward the annuloplasty structure.

In an embodiment, the hollow tube is configured to be advanced around the guide member while the guide member is disposed within the body of the patient.

In an embodiment, the helical element is disposed around the hollow tube, the hollow tube is configured to be rotated at a proximal portion thereof, and the anchoring structure is corkscrewed into the annulus of the patient in response to the rotation of the tube.

In an embodiment, a diameter of the bar is greater than the distance between the proximal rotational subunits, and during an attempt to corkscrew the proximal rotational subunits therearound:

the bar restricts the proximal rotational subunits from being corkscrewed into tissue of the patient by applying a counterforce to a torque applied by the rotation of the tube, and the proximal rotational subunits are configured to expand radially in response to the counterforce applied by the bar.

In an embodiment, the helical element is configured to be detached from the hollow tube in response to the radial expansion of the proximal rotational subunits.

There is additionally provided, in accordance with an embodiment of the present invention, a method for performing an annuloplasty on a valve of a body of a patient the valve including an annulus and at least first and second leaflets, including:

deploying an annuloplasty structure in an atrium of a heart of the patient, the structure including one or more bars and one or more respective flexible longitudinal guide members, each guide member reversibly coupled to a respective one of the bars;

positioning the annuloplasty structure along the annulus of the valve of the patient;

advancing one or more respective anchoring structures, each anchoring structure each anchoring structure being passed along a respective one of the flexible longitudinal guide members while the one or more guide members are disposed within the body of the patient;

advancing at least a portion of each anchoring structure beyond the respective bar and into tissue of the patient; and decoupling each guide member from the respective bar.

In an embodiment, deploying the annuloplasty structure includes placing the annuloplasty structure in the atrium during an open heart procedure.

In an embodiment, deploying the annuloplasty structure includes deploying at least one segment of an annuloplasty ring.

In an embodiment, deploying the annuloplasty structure includes deploying an annuloplasty ring.

In an embodiment, deploying the annuloplasty structure includes deploying a partial annuloplasty ring.

In an embodiment, the method includes advancing the annuloplasty structure to the atrium transcatheterally.

In an embodiment, the method includes performing, during a single transcatheter advancement, the steps of: (a) deploying the annuloplasty structure, (b) positioning the annuloplasty structure, (c) advancing the one or more respective anchoring structures, (d) advancing the at least a portion of each anchoring structure, and (e) decoupling each guide member.

In an embodiment, positioning the annuloplasty structure includes adjusting a configuration of the annuloplasty structure with respect to a configuration of the annulus of the patient.

In an embodiment, the annuloplasty structure is generally ring-shaped following the deployment, thereby defining a radius characteristic thereof, and adjusting the configuration of the structure includes reducing the radius by compressing at least a portion of the structure.

In an embodiment, compressing includes applying a pulling force to a control wire disposed within a lumen of the structure.

In an embodiment, deploying the structure includes deploying two segments of the annuloplasty ring.

In an embodiment, the method includes drawing together the first and second segments.

In an embodiment, positioning the structure along the annulus of the patient includes positioning the first and second segments along the annulus.

In an embodiment, positioning the first and second segments includes positioning the first segment on the annulus along a junction between a base of a first leaflet and the annulus, and positioning the second segment on the annulus along a junction between a base of a second leaflet and the annulus.

In an embodiment, positioning the first and second segments includes adjusting a relative disposition of the first and second segments with respect to a configuration of the annulus of the patient.

In an embodiment, adjusting the disposition of the first and second segments includes elevating at least a portion of the first segment and at least a portion of the second segment.

In an embodiment, adjusting the first and second segments includes adjusting the first segment independently of the adjusting of the second segment.

In an embodiment, the annuloplasty structure is configured to assume a generally straight configuration following the deployment, the straight configuration defining a longitudinal axis of the structure, and adjusting the disposition of the first and second segments includes adjusting a disposition of the first and second segments by compressing in parallel with the longitudinal axis of the structure at least a portion of the first segment and at least a portion of the second segment.

In an embodiment, compressing includes applying a pulling force to at least one control wire disposed within a lumen of each of the first and second segments.

There is also provided, in accordance with an embodiment of the present invention, apparatus for repairing a valve of a body of a patient, the valve including an annulus and at least first and second leaflets, including:
  an annuloplasty structure; and
  a flexible longitudinal guide member removably coupled to the structure:
    the guide member is configured to facilitate anchoring of the annuloplasty structure to the annulus of the patient, and
    the guide member is configured to be advanced toward the annulus simultaneously with the annuloplasty structure.

In an embodiment, the annuloplasty structure includes an annuloplasty ring.

In an embodiment, the annuloplasty structure includes a partial annuloplasty ring.

In an embodiment, the annuloplasty structure includes at least first and second segments of an annuloplasty ring.

In an embodiment, the apparatus includes an anchoring structure configured to anchor the structure to the annulus via the guide member.

In an embodiment, the anchoring structure includes a pointed distal tip.

In an embodiment, of the anchoring structure is disposed at a distal end of the guide member, and is configured to be screwed into the annulus in response to a rotational force applied to a proximal end of the guide member.

In an embodiment, the annuloplasty structure is shaped to define a lateral wall having first and second portions, and to provide a channel extending from the first portion of the lateral wall to the second portion of the lateral wall of the structure.

In an embodiment, the anchoring structure is configured to be advanced through the channel and subsequently anchored to the annulus of the patient while the one or more guide members are disposed within the body of the patient.

In an embodiment, the apparatus includes a bar configured to be disposed within the channel.

In an embodiment, the bar is disposed within the channel substantially perpendicular to an axis of the channel.

In an embodiment, the guide member is configured to be removably coupled to the bar.

In an embodiment, the anchoring structure is configured to be advanced along the guide member from a site outside the body of the patient while the guide member is disposed within the body of the patient.

In an embodiment, the guide member is configured to be decoupled from the bar subsequent to the anchoring of the anchoring structure to the annulus.

In an embodiment, the anchoring structure includes a helical element at a distal end thereof, the helical element being configured to be corkscrewed at least in part into the annulus of the patient.

In an embodiment, the helical element is shaped to define at least two adjacent distal rotational subunits and at least two adjacent proximal rotational subunits, and a distance between the two adjacent distal rotational subunits is greater than a distance between the two adjacent proximal rotational subunits.

In an embodiment, the distance between the distal rotational subunits enables the distal rotational subunits to be corkscrewed around the bar and subsequently into the annulus of the patient.

In an embodiment, the distance between the proximal rotational subunits restricts the proximal rotational subunits from being corkscrewed around the bar and into the annulus of the patient.

The present invention will be more fully understood from the following detailed description of embodiments thereof, taken together with the drawings, in which:

BRIEF DESCRIPTION OF THE DRAWINGS

FIG. 3 is a schematic illustration of the ratchet mechanism of FIG. 2A coupled to an anchor mount, in accordance with an embodiment of the present invention;

FIG. 4 is a schematic illustration of an anchor coupled to the anchor mount of FIG. 3, in accordance with an embodiment of the present invention;

FIGS. 16A-B are schematic illustrations of an anchor advancement structure, in accordance with an embodiment of the present invention;

FIGS. 17A-J are schematic illustrations of transcatheter advancement and deploying of a system for repairing an annulus of the patient, in accordance with an embodiment of the present invention;

FIGS. 19A-E are schematic illustrations of an anchoring apparatus comprising a steerable catheter configured to facilitate anchoring of the two annuloplasty ring segments to the annulus of the patient, in accordance with an embodiment of the present invention;

FIGS. 20A-B are schematic illustrations of the anchoring apparatus configured to anchor the two annuloplasty ring segments to the annulus of the patient, in accordance with an embodiment of the present invention;

FIGS. 21-22 are schematic illustrations of a handle for anchoring an annuloplasty structure to the annulus of the patient, in accordance with an embodiment of the present invention;

FIGS. 24A-J are schematic illustrations of transcatheter advancement and deploying of a system for repairing an annulus of the patient, in accordance with an embodiment of the present invention;

FIGS. 25A-F are schematic illustrations of the deployment of two annuloplasty ring segments of the system toward the annulus of the patient, in accordance with an embodiment of the present invention;

FIGS. 26A-B, 27A-E, and 28A-B are schematic illustrations of anchoring apparatus configured to anchor the two annuloplasty ring segments to the annulus of the patient, in accordance with an embodiment of the present invention; and FIGS. 28C-D are schematic illustrations of the drawing together and locking of the two segments of the annuloplasty ring to the annulus of the patient, in accordance with an embodiment of the present invention.

DETAILED DESCRIPTION OF THE EMBODIMENTS

Figure 1:
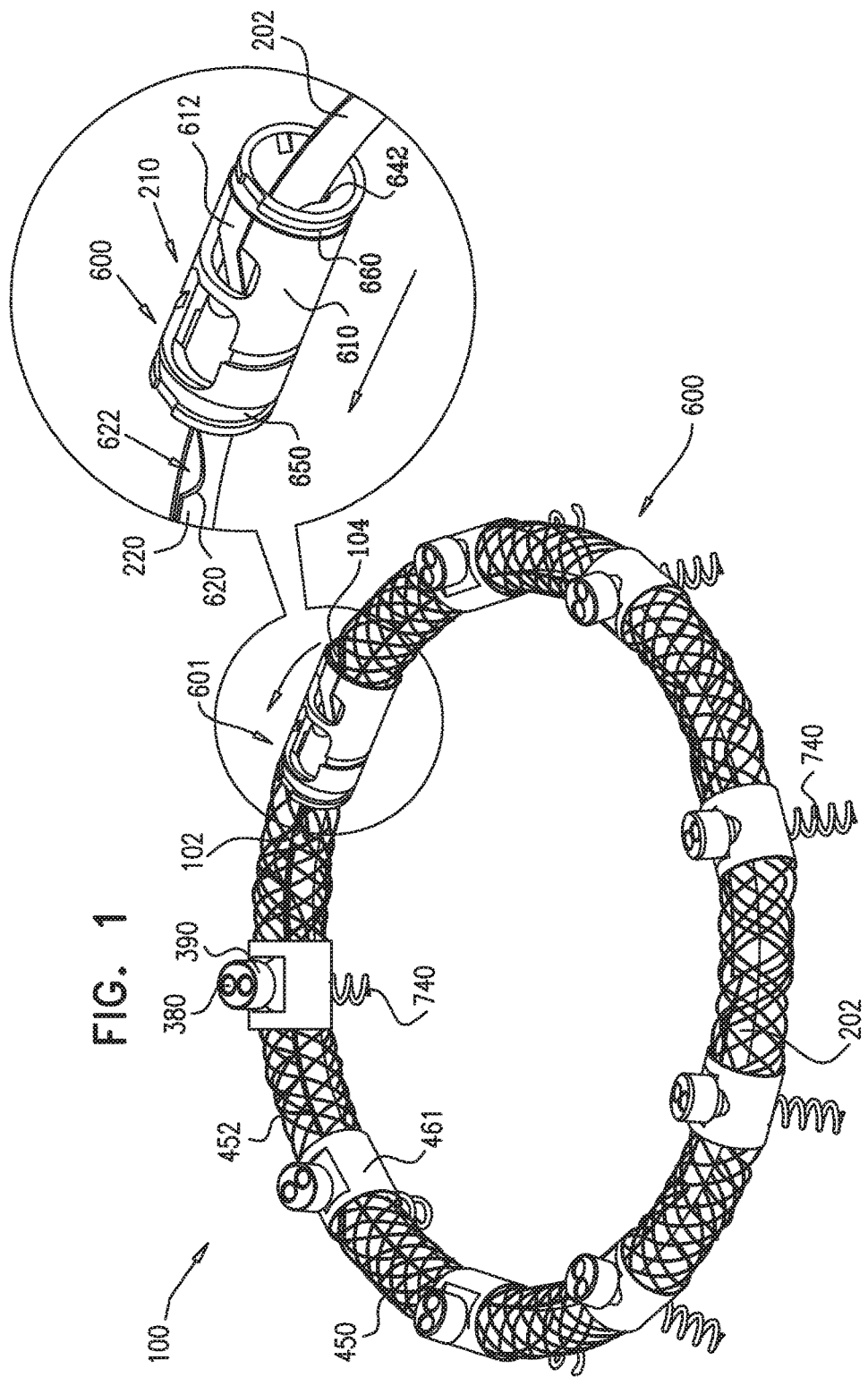
FIG. 1 is a schematic illustration of an annuloplasty structure comprising a ratchet mechanism, in accordance with an embodiment of the present invention.

Reference is now made to FIG. 1, which is a schematic illustration of an annuloplasty structure 100, e.g., at least one elongate segment or tubular element, comprising a plurality of compressible subunits 450 and a plurality of anchor mounts 461, in accordance with an embodiment of the present invention. Structure 100 comprises a modular annuloplasty structure in which the plurality of compressible subunits 450 are alternately disposed with respect to the plurality of anchor mounts 461. Typically, structure 100 comprises an implant shaped to define a tubular structure having a cross-section of any suitable shape, e.g., circular or elliptical. Compressible subunits 450 are shaped to define a hollow lumen and comprise a braided mesh 452 (e.g., wire or polyester), by way of illustration and not limitation. For example, compressible subunits 450 may comprise a plurality of coils, braided structures, stent-shaped struts, or accordion- or bellows-shaped structures. A ratchet mechanism 600 (described hereinbelow with reference to FIGS. 6A-B) is disposed within the hollow lumen of structure 100. Ratchet mechanism 600 comprises a ratchet body 202 having a fixed end 210 and a dynamic end 220. Although ratchet mechanism 600 is shown as being used in combination with structure 100, it is to be noted that any of the ratchet mechanisms described herein may be used in combination with structure 100.

Typically compressible subunits 450 and anchor mounts 461 comprise a biocompatible material, e.g., nitinol, ePTFE, PTFE, stainless steel, platinum iridium, titanium, or cobalt chrome. In some embodiments, compressible subunits 450 and anchor mounts 461 are coated with PTFE (Polytetrafluoroethylene). In some embodiments, compressible subunits 450 function as accordion- or bellows-shaped compressible structures which facilitate proper cinching of the annulus when structure 100 is contracted. The configuration of the annulus of the mitral valve differs from patient to patient. Compressible subunits 450, when compressed, e.g., typically along a longitudinal axis of structure 100, enable respective portions of annuloplasty structure 100 to independently conform to the configuration of each portion of the annulus that is in alignment with a given portion of the annuloplasty structure.

It is to be noted that for some applications, annuloplasty structure 100 is shaped to define a single tubular structure independently of the plurality of anchor mounts 461. In such an embodiment, the single tubular structure comprises an elongate sheath of compressible material, as described hereinabove with respect to compressible subunits 450.

A contracting wire (not shown) is disposed within the lumen of structure 100 generally alongside ratchet body 202. Typically, pulling on the contracting wire controls the structural configuration of ratchet body 202 which in turn controls the structural configuration of structure 100, as will be described hereinbelow. In response to the pulling of the wire, an inward radial force is applied to structure 100, and a perimeter of structure 100 is modulated, i.e., reduced.

The contracting wire comprises a flexible and/or superelastic material, e.g., nitinol, polyester, PTFE, ePTFE, stainless steel, or cobalt chrome, and is configured to reside chronically within structure 100. In some embodiments, the contracting wire comprises a braided polyester suture (e.g., Ticron). In some embodiments, the contracting wire is coated with polytetrafluoroethylene (PTFE). In some embodiments, the contracting wire comprises a plurality of wires that are intertwined to form a rope structure.

Typically, structure 100 is shaped to provide at least one longitudinal lumen for passage therethrough of ratchet body 202 and the contracting wire. In some embodiments, structure 100 is shaped to provide a first longitudinal lumen passage therethrough of the contracting wire and a second longitudinal lumen for passage therethrough of ratchet body 202.

Fixed end 210 is fixed within a substantially tubular ratchet-coupling housing 610, while dynamic end 220 slides through housing 610 along a track 642 in the direction as indicated by the arrow. Ratchet body 202 is shaped to define a plurality of first engaging structures, e.g., first grooves 620, which are engageable by a tooth 612 of housing 610. As dynamic end 220 is slid away from fixed end 210 (i.e., in the direction as indicated by the arrow), grooves 620 are engaged by a second engaging structure, e.g., tooth 612, thereby allowing ratchet body 202 to slide in only one direction, i.e., the direction in which dynamic end 220 is first fed through housing 610 and as indicated by the arrow. As dynamic end 220 advances beyond fixed end 210, dynamic end 220 slides alongside the portion of body 202 that is adjacent to fixed end 210.

Each anchor mount 461 is shaped to provide at least one longitudinal anchor mount lumen having an axis that is parallel with the longitudinal axis of the annuloplasty structure. The anchor mount lumen facilitates passage therethrough of ratchet body 202 and the contracting wire. In some embodiments, each anchor mount 461 is shaped to provide a first longitudinal lumen passage therethrough of the contracting wire and a second longitudinal lumen for passage therethrough of ratchet body 202.

Each anchor mount 461 is shaped to provide an anchor channel for passage therethrough of a helical anchor 740. As will be described hereinbelow, the channel is shaped to define a lumen having a channel axis that is disposed at a non-zero angle, e.g., transverse, with respect to a longitudinal axis of the longitudinal lumen of the anchor mount through which ratchet body 202 and the contracting wire pass. As such, in response to pulling of the contracting wire, the resultant sliding of portions of the contracting wire and of ratchet body 202 through the longitudinal lumen mount 461, does not interfere with the anchor channel and anchor 740 disposed therein. The angle of the anchor channel with respect to the longitudinal lumen of anchor mount 461 facilitates corkscrewing of the anchor into the annulus of the valve of the patient at an angle as defined by the intersecting axes of the anchor channel and the longitudinal lumen of mount 461, as described hereinbelow with reference to FIG. 8.

Typically, for embodiments in which annuloplasty structure 100 comprises a plurality of anchor mounts 461, the respective angles defined by the intersecting axes of each anchor channel with the respective axis of the longitudinal lumen of each mount 461 is identical for all mounts 461. Alternatively, a first portion of the plurality of anchor mounts 461 has an angle that differs from the angle of a second portion of the plurality of anchor mounts. For example, a portion of anchor mounts 461 designated to be anchored to the anterior portion of the annulus has an angle that is different from a portion of anchor mounts 461 designated to be anchored to the posterior portion of the annulus. Thus, the anchors may be anchored to different portions of the annulus at different angles in response to a need therefor.

It is to be noted that although helical anchors 740 are used in combination with structure 100, any anchor described herein may be used in combination with structure 100.

For embodiments in which structure 100 is implanted during an open-heart or minimally-invasive procedure, structure 100 is advanced toward the valve in a closed configuration (e.g., substantially ring-shaped or "D"-shaped), as shown. It is to be noted that structure 100 may be advanced toward the valve of the patient in a linear configuration during an open-heart or minimally-invasive valve repair procedure. In such an embodiment, once structure 100 is properly positioned within the left atrium of the heart, the contracting wire (not shown) is pulled and first and second ends 102 and 104 of annuloplasty structure 100 are drawn toward each other such that structure 100 assumes its closed configuration.

For embodiments in which structure 100 is advanced during a percutaneous valve repair procedure, structure 100 is manufactured having a first end 102 that is typically coupled to, e.g., welded to, housing 610 and a second end 104 that is not coupled to housing 610 during the advancing. Thus, structure 100, in such an embodiment, is advanced toward the left atrium of the patient in a generally linear configuration thereof.

For embodiments in which structure 100 is advanced toward the valve in a linear configuration, second end 104 is coupled to an engaging structure configured to engage housing 610 as structure 100 is made to assume its closed configuration. In some embodiments, the engaging structure coupled to second end 104 comprises a tube having a diameter that is smaller than an inner diameter of housing 610 and is configured to slide within housing 610 as structure 100 is drawn into its closed configuration.

Housing 610 comprises first and second coupling sites 650 and 660, for coupling of first end 102 and second end 104 of structure 100, respectively, to housing 610.

It is to be noted that annuloplasty structure 100 may be used independently of ratchet mechanism 600. For example, annuloplasty structure 100 may comprise only the contracting wire passing through the lumen of structure 100. In such an embodiment, once annuloplasty structure 100 is deployed from its linear state, the respective ends of the contracting wire are: (1) pulled such that the annuloplasty structure assumes its closed configuration, and (2) locked together in order to maintain the closed configuration.

As described herein, structure 100 typically comprises a braided mesh in embodiments in which sutures pass through structure 100 and facilitate anchoring or suturing of structure 100 to the annulus. For embodiments in which annuloplasty structure 100 is positioned using an open-heart procedure, the mesh facilitates suturing of structure 100 to the annulus of the patient. In such an embodiment, the physician passes the suture through the mesh at a first location thereof, through tissue of the annulus, and subsequently, through a second location of the mesh, thereby suturing structure 100 to the annulus. In some embodiments, the suturing is performed following placement of the annuloplasty structure along the annulus. In some embodiments, a plurality of sutures are sutured to the annulus of the patient and the annuloplasty structure is slid along the sutures and toward the annulus. In such an embodiment, respective ends of each of the plurality of sutures are threaded through the mesh prior to the sliding, and are knotted together and clipped following the sliding. The knotting of the sutures maintains the positioning of the annuloplasty structure along the annulus.

For some embodiments, the mesh facilitates anchoring of the annuloplasty structure to the annulus of the patient. In such an embodiment, the physician passes the anchor through the mesh at a first location thereof and then through tissue of the annulus.

It is to be understood that the braided mesh may be used independently of or in combination with the compressible subunits and/or with the anchor mounts. For example, the mesh may surround at least compressible subunits 450 of structure 100. Alternatively, the braided mesh may be used independently of compressible subunits 450 and/or anchor mounts 461. In such an embodiment, structure 100 may comprise only ratchet mechanism 600 and/or the contracting wire surrounded by a sheath of braided mesh.

Figure 2A:
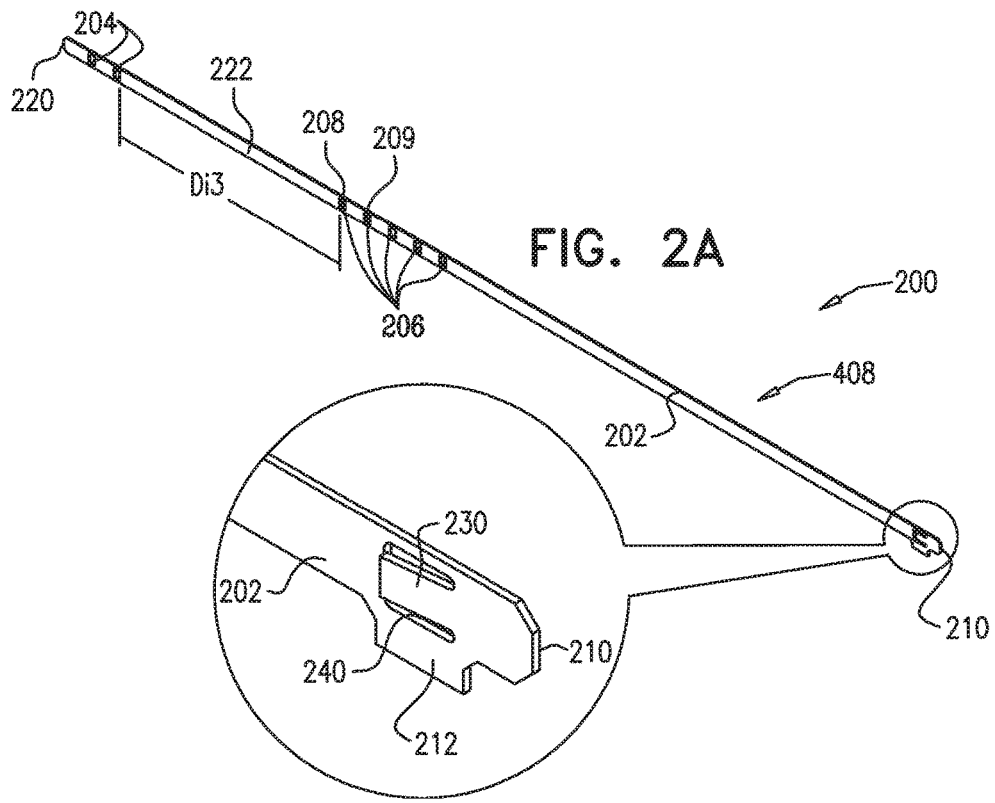
FIGS. 2A-B are schematic illustrations of a ratchet mechanisms for use with an annuloplasty structure, in accordance with respective embodiments of the present invention.

Reference is now made to FIG. 2A, which is a schematic illustration of a flat-ribbon ratchet mechanism 200, in accordance with an embodiment of the present invention. Typically, ratchet mechanism 200 is used in combination with annuloplasty structure 100 as described hereinabove with reference to FIG. 1, in accordance with an embodiment of the present invention. It is to be noted that ratchet mechanism 200 may be used in combination with any of the annuloplasty structures described herein. Ratchet mechanism 200 comprises a ratchet body 202 defining a flat ribbon having a proximal fixed end 210 and a distal dynamic end 220. Although FIG. 1 shows ratchet mechanism 600 disposed within annuloplasty structure 100, it is to be noted that ratchet mechanism 200 may be disposed within annuloplasty structure 100. Ratchet mechanism 200 is disposed within the lumen of structure 100 such that fixed end 210 is disposed within the lumen of structure 100 in the vicinity of first end 102 thereof, and dynamic end 220 is disposed within the lumen of structure 100 in the vicinity of second end 104 thereof.

As described hereinabove, in some embodiments, structure 100 is advanced toward the left atrium of the patient in a generally linear configuration. Although ratchet body 202 is shown in a linear configuration, it is to be noted that ratchet body 202 is later drawn into a closed configuration (e.g., substantially ring-shaped or "D"-shaped configuration) simultaneously with structure 100 assuming its closed configuration (e.g., substantially ring-shaped or "D"-shaped configuration). As the contracting wire is pulled and first and second ends 102 and 104 of annuloplasty structure 100 are drawn toward each other such that structure 100 assumes its closed configuration, dynamic end 220 is advanced past fixed end 210 such that ratchet body 202 assumes its closed configuration as well. As dynamic end 220 advances beyond fixed end 210, dynamic end 220 and the distal portion of body 202 are slid alongside fixed end 210 and the proximal portion of body 202. Dynamic end 220 and fixed end 210 are able to meet each other due to the sliding of ratchet body 202 along a track within the a respective lumen of each anchor mount 461 of structure 100, as will be described hereinbelow.

Ratchet body 202 is shaped to define a plurality, e.g., at least two as shown, of first engaging structures, e.g., first windows 204, in the vicinity of dynamic end 220 and a plurality of second windows 206 in the general vicinity of the middle of ratchet body 202. It is to be noted that the number of second windows 206 is shown by way of illustration and not limitation. Fixed end 210 is shaped to define a second engaging structure, e.g., a tooth 230, which projects angularly away from a longitudinal axis of ratchet body 202 and is configured to engage the first engaging structures, e.g., windows 204 and 206. Fixed end 210 is shaped to define a slit 240 surrounding tooth 230. As ratchet mechanism 200 is initially drawn into its closed configuration, dynamic end 220 slides alongside tooth 230 and slit 240 of fixed end 210.

Ratchet body 202 provides a portion 222 disposed between first windows 204 and second windows 206. Typically, portion 222 provides a smooth surface for unobstructed back and forth sliding of dynamic end 220 past fixed end 210 and enables the physician to adjust the size/perimeter of the annuloplasty structure before it is positioned along the annulus. Additionally, portion 222 enables the physician to adjust the size/perimeter of the ratchet mechanism 200 prior to being locked in place in response to the engaging of second windows 206 by tooth 230. Typically, portion 222 has a distance Di3 that is between 30 mm and 70 mm, e.g., 50 mm.

For embodiments in which ratchet mechanism 200 is disposed within structure 100, ratchet mechanism 200 is typically disposed alongside the portion of contracting wire 110 which is disposed within the lumen of structure 100. As structure 100 is pulled into its closed configuration in response to the pulling of contracting wire 110, dynamic end 220 is pulled toward fixed end 210. Dynamic end 220 is passively advanced alongside fixed end 210 due to the compression force applied by structure 100 in response to the pulling of contracting wire 110. That is, dynamic end 220 is not pulled by contracting wire 110, rather it is passively pushed in response to the pulling of wire 110. Additionally, wire 110 is aligned alongside an external surface of ratchet body 202 and at an external perimeter thereof. In response to pulling of contracting wire 110, contracting wire 110 pushes against the external surface of ratchet body 202 and applies a compression force thereto. Responsively to the compression force of wire 110 on the external surface of ratchet body 202, ratchet body 202 passively compresses. Further additional pulling of wire 110 reduces the perimeter of ratchet mechanism 200, and thereby of structure 100.

In response to continued pulling of contracting wire 110, structure 100 radially contracts and, in turn, applies an additional compression force to ratchet mechanism 200. In response to the compression force to the ratchet mechanism by structure 100, ratchet body 202 radially contracts as dynamic end 220 is passively slid further distally away from fixed end 210 thereby drawing second windows 206 closer toward tooth 230 of fixed end 210. Dynamic end 220 is slid distally away from fixed end 210 until tooth 230 engages a first window 208 of second windows 206. Tooth 230 remains locked in position with respect to first window 208 until an additional compression force is applied to ratchet body 202 in response to additional pulling of contracting wire 110. This additional force slides dynamic end 220 even further away from fixed end 210 until tooth 230 engages a second window 209 of second windows 206. Tooth 230 prevents ratchet body 202 from sliding in an opposite direction with respect to the direction by which dynamic end 220 is fed beyond fixed end 210. Thus, second windows 206 maintain respective ratcheted perimeters of the now substantially ring-shaped or "D"-shaped ratchet body 202, and thereby maintain respective ratcheted perimeters of structure 100.

Alternatively, for some embodiments, dynamic end 220 is shaped to define one or more holes configured for looping of contracting wire 110 therethrough. In such an embodiment, dynamic end 220 is pulled in response to tensile force applied to contracting wire 110 as it is pulled. Additional force applied to wire 110 pulls ratchet mechanism 200 into a closed configuration, e.g., a substantially ring-shaped configuration.

For embodiments in which structure is advanced toward the left atrium in its closed configuration, prior to the advancing, the physician forms structure 100 into a closed configuration by advancing dynamic end 220 beyond fixed end 210 until first windows 204 are in alignment with tooth 230 and ratchet body 202 locks in place. At this stage, structure 100 defines a generally ring-shaped structure having a relatively large perimeter. As described hereinabove, once positioned along the annulus of the patient, the physician pulls wire 110 and dynamic end 220 slides and is pushed further away from fixed end 210 until second windows 206 lock and maintain a reduced perimeter of ratchet body 202, and thereby, structure 100.

It is to be noted that the plurality of second windows 206 are provided such that ratchet body 202, and thereby structure 100, can lock in place and maintain respective ratcheted perimeters thereof. Thus, the length of ratchet mechanism 200 in its linear configuration, the locking mechanism of ratchet mechanism 200, and compressible subunits 450 described hereinabove are provided so as to enable annuloplasty structure 100 to accommodate various sizes of dilated annuli of given patients. Additionally, ratchet mechanism 200 facilitates: (1) positioning and anchoring structure 100 along the dilated annulus while body 202 (and thereby structure 100) has a first perimeter thereof, (2) contracting the dilated annulus in response to the contracting of body 202 (and thereby structure 100), and (3) maintaining the contracted state of the annulus while body 202 (and thereby structure 100) has a second perimeter thereof that is typically smaller than the first perimeter.

It is to be further noted that ratchet mechanism 200 is described herein as being used in combination with structure 100 by way of illustration and not limitation. For example, ratchet mechanism 200 may be surrounded by a tubular sheath comprising a braided mesh, e.g., metal or fabric such as polyester. The braided mesh facilitates passage of sutures or longitudinal guide members through the sheath in order to anchor or suture the sheath to the annulus. In some embodiments, during expansion of the sheath, by pulling on opposite ends thereof, the braided mesh is longitudinally pulled such that the mesh decreases in diameter, i.e., the transverse cross-sectional diameter that is perpendicular with respect to the longitudinal axis of structure 100. During contraction of the sheath from its relaxed state, the mesh is compressed such that the diameter of the mesh closely resembles the diameter of the mesh in its relaxed state.

Figure 2B:
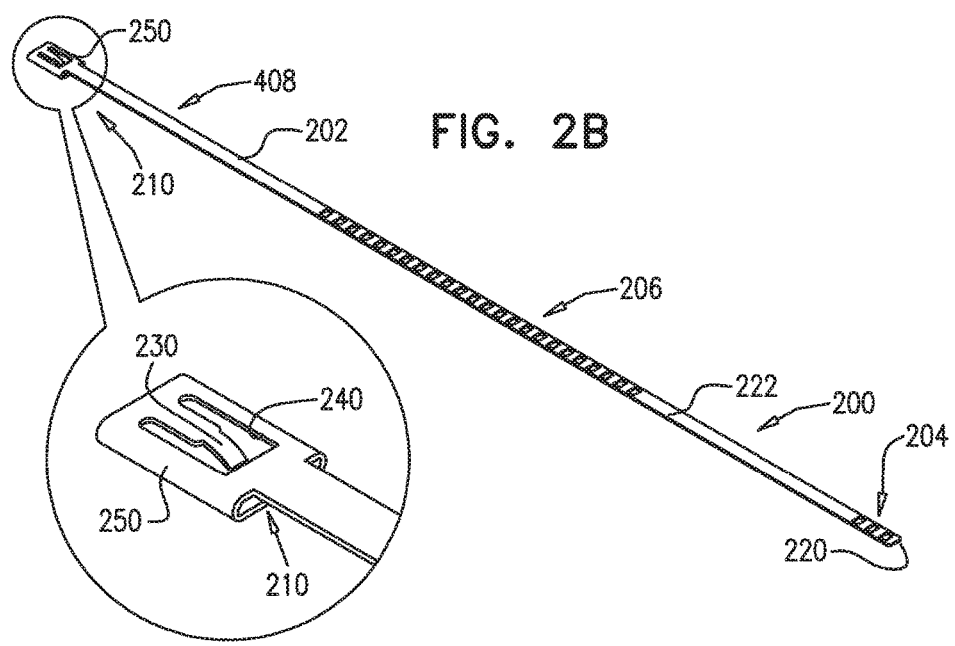

FIG. 2B shows ratchet mechanism 200 as described hereinabove with respect to FIG. 2A, with the exception that fixed end 210 is shaped to define a housing 250, in accordance with an embodiment of the present invention. Typically, housing 250 of fixed end 210 is shaped to define tooth 230 and slit 240 and is configured to receive dynamic end 220 in a manner as described hereinabove with respect to FIG. 2A. Typically, housing 250 is configured to provide stability to mechanism 200 during the aligning of windows 204 and 206 with tooth 230 of fixed end 210.

During the initial contraction of structure 100, dynamic end 220 is fed into housing 250. As described hereinabove, ratchet body 202 assumes a closed configuration as dynamic end 220 is initially locked in place when tooth 230 of housing 250 engages first windows 204. A compression force is further applied to ratchet body 202 (e.g., a radial force or a tensile force applied in response to pulling the contracting wire, as described hereinabove) which further advances dynamic end 220 away from housing 250.

FIG. 3 shows a system 300 comprising ratchet body 202 passing through a first one of anchor mounts 461 of annuloplasty structure 100, in accordance with an embodiment of the present invention. Anchor mount 461 comprises a lateral-aperture anchor mount 341 which comprises a substantially hollow, tubular element 463 configured for passage therethrough of ratchet body 202 and contracting wire 110. The anchor mount shown is configured to fix in place fixed end 210 of ratchet body 202. It is to be noted that anchor mount 341 may fix in place any of the ratchet bodies described herein. Additionally, anchor mount 341 is shaped to define an aperture 340 configured for passage therethrough of an anchor, as will be described hereinbelow. In some embodiment, a tubular channel (configuration shown hereinbelow with reference to FIG. 4) for passage of an anchor is coupled to, e.g., welded to, mount 341 along portions of mount 341 which define aperture 340. As shown, aperture 340 is provided at a location along mount 461 such that passage of a tissue anchor therethrough (e.g., directly or indirectly through a channel coupled to portions of mount 341 defining aperture 340), does not interfere with contracting wire 110 and/or ratchet body 202 disposed within the annuloplasty structure.

It is to be noted that only one anchor mount 341 is shown for clarity of illustration.

For example, ratchet mechanism 200 may be coupled to a plurality of anchor mounts 341 which are disposed at various sites with respect to ratchet body 202. It is to be further noted that a respective compressible subunit 450 may be coupled to either end of anchor mount 341. As shown, anchor mount 461 is shaped to define a first coupling site 302 and a second coupling site 304. For embodiments in which ratchet mechanism 200 is used in combination with compressible subunits 450, as described hereinabove with reference to FIG. 1, a respective compressible subunit 450 is coupled to coupling sites 302 and 304.

Reference is now made to FIG. 4, which is a schematic illustration of system 300 comprising a tissue anchor 360 coupled to anchor mount 341, in accordance with an embodiment of the present invention. Anchor mount 341 fixes in place fixed end 210 of ratchet body 202 as described herein. Ratchet body 202 of FIG. 3 is shown in an open, linear configuration thereof, i.e., dynamic end 220 is not aligned alongside fixed end 210. An anchor 360 is shown coupled to mount 461. In some embodiments, a tube-channel 1200 (as described in more detail hereinbelow with reference to FIG. 11) is coupled to mount 461 portions of mount 341 defining aperture 340. In some embodiments, channel 1200 is welded to mount 461 during the manufacturing of mount 341.

In some embodiments, tube-channel 1200 is not welded to mount 341 but rather is advanced toward mount 341 together with, e.g., surrounding, anchor 360. In such an embodiment, channel 1200 is free to rotate with respect to aperture 340 along the longitudinal axis of mount 341.

As shown, anchor 360 is shaped to define a helix having a pointed distal end 370 which punctures through tissue of the annulus of the heart. It is to be noted that a helical anchor is shown by way of illustration and not limitation, and that any suitable anchor may be used to anchor the annuloplasty structure to the annulus. For embodiments in which a helical anchor is used, tube-channel 1200 may comprise a bar, as described in U.S. Provisional Patent Application 61/001,013, PCT Patent Application PCT/IL07/001503, which published as WO 08/068756, and U.S. patent application Ser. No. 11/950,930 to Gross et al., entitled, "Segmented ring placement" which published as US 2008/0262609 and which issued as U.S. Pat. No. 8,926,695. This bar is configured to restrict continued corkscrewing of helical anchor 360 into the tissue of the annulus beyond a predetermined distance, e.g., between 3 mm and 10 mm. Additionally, the bar functions as a nut providing a thread for the helical anchor to be advanced distally and corkscrewed around the bar and into the tissue of the annulus.

As shown, helical anchor 360 is coupled at a proximal end thereof (i.e., the portion of anchor 360 that is not configured to be advanced into the annulus tissue) to a head portion 380. Typically, a distal end of head portion 380 has a diameter that is larger than a diameter of tube-channel 1200. Once anchor 360 is advanced distally through tube-channel 1200, the distal portion of head portion 380 abuts a proximal portion of tube-channel 1200 and prevents continued distal motion of anchor 360. Even when head portion 380 abuts tube-channel 1200, anchor 360 is allowed to continue rotational motion. This continued rotational motion draws tissue of the annulus toward the annuloplasty structure. In the event that a gap between the annulus tissue and the annuloplasty structure is created during the initial anchoring of the structure to the annulus of the valve, the continued rotation of anchor 360 minimizes and substantially eliminates the gap. As shown, head portion 380 is shaped to define one or more, e.g., two as shown, engaging elements, e.g., holes, 390. In some embodiments, engaging elements 390 are configured for coupling and/or passage therethrough of an actuation means by way of illustration and not limitation, and the anchoring means is configured to corkscrew the anchor into the tissue of the annulus.

It is to be noted that engaging elements 390 are shown as being circular by way of illustration and not limitation, and that elements 390 may be shaped to define any suitable shape, e.g., rectangles, ovals, etc.

Typically, head portion 380 prevents continued distal motion of anchor 360 into the annulus with respect to the distal surface of the anchor mount, i.e., the portion of the mount designated to align with and contact the annulus. For embodiments in which tube-channel 1200 is advanced together with anchor 360, the tube-channel 1200 rotates within aperture 340 along the longitudinal axis of mount 461 together with the rotating of anchor 360.

Figure 5A:
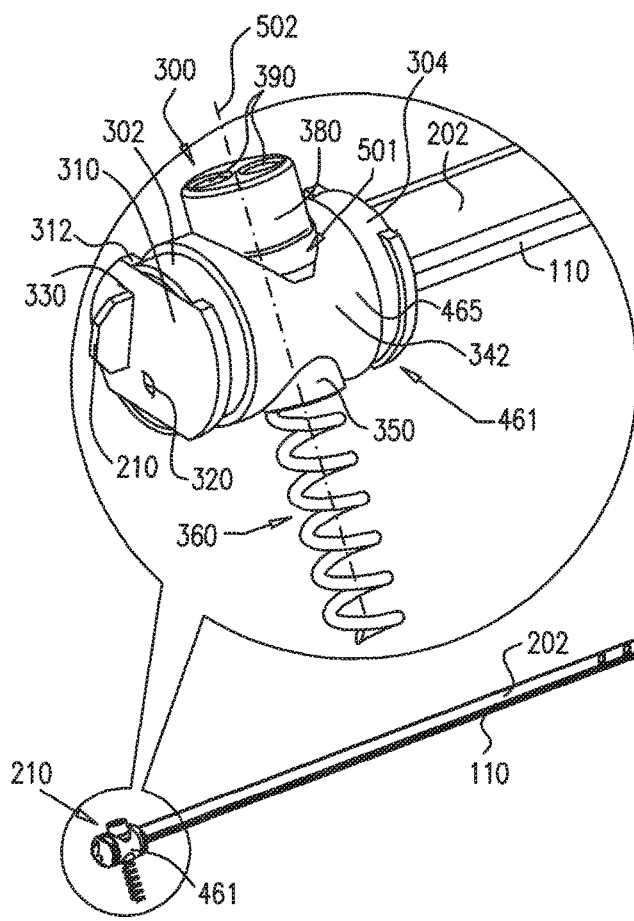
FIGS. 5A-C are schematic illustrations of the ratchet mechanism of FIG. 2A coupled to an anchor mount, in accordance with another embodiment of the present invention.
Figure 5B:
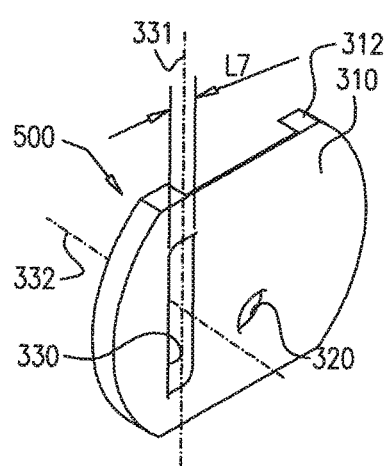
Figure 5C:
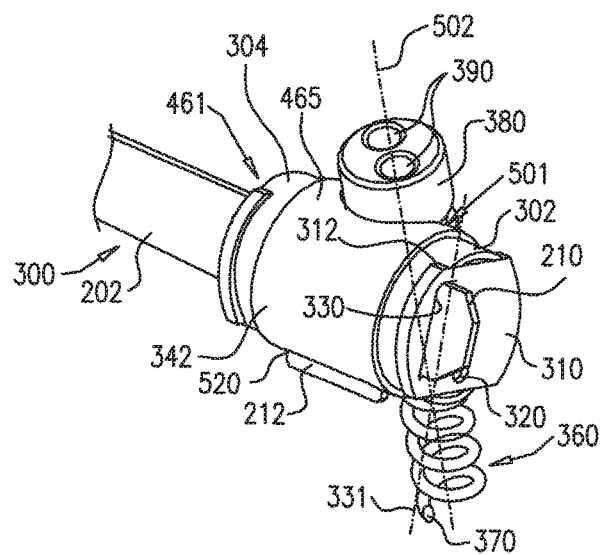

Reference is now made to FIGS. 5A-C, which are schematic illustrations of system 300 as described hereinabove with reference to FIG. 4, with the exception that anchor mount 461 comprises a transverse-lumen anchor mount 342 comprising a tubular element 465 shaped to define an anchor lumen 501 having an longitudinal axis 502 thereof, in accordance with an embodiment of the present invention. Tubular element 465 fixes in place fixed end 210 of ratchet body 202 as described hereinabove with reference to FIG. 2A. Typically, anchor mount 461 provides at least one longitudinal anchor mount lumen having an axis that is parallel with the longitudinal axis of the annuloplasty structure. Anchor mount lumen facilitates passage therethrough of ratchet mechanism 200 and contracting wire 110. Longitudinal axis 502 of anchor lumen 501 is at a non-zero angle, e.g., transverse, with respect to the longitudinal axis of the anchor mount lumen of anchor mount 461. Transverse lumen 501 is shaped to facilitate passage therethrough of tube-channel 1200, as described hereinabove with reference to FIG. 4. As shown, transverse lumen 501 does not interfere with ratchet body 202 and contracting wire 110.

Reference is now made to FIGS. 5A-B. Anchor mount 461 is coupled at either end thereof to a respective stabilizing structure 310. Typically, since anchor mount 461 comprises hollow tubular element 465, anchor mount 461 has a tendency to pivot laterally with respect to ratchet body 202. Stabilizing structure 310 is shaped to define mounts 312 which are configured to surround and lock in place a portion of anchor mount 461 and to prevent swiveling thereof. Ratchet body 202 passes through aperture 330 of stabilizing structure 310 and through the longitudinal anchor mount lumen. Passing of ratchet body 202 through structure 310 and then through mount 461 locks in place stabilizing structure 310 which, in turn, locks in place anchor mount 461 and prevents it from pivoting laterally. Additionally, aperture 330 of stabilizing structure 310 provides a suitable track for advancement of ratchet body 202 along a defined path. For example, this track enables the proper positioning of dynamic end 220 with respect to fixed end 210.

Typically, aperture 330 has a major axis 331 and has a longitudinal axis 332 that is transverse with respect to major axis 331. Major axis 331 of aperture 330 is typically disposed at a non-zero angle with respect to axis 502 of anchor lumen 501. A portion of ratchet body 202 passes through aperture 330 along longitudinal axis 332 thereof. Typically, ratchet body 202 passes through aperture 330 of a first stabilizing structure 310, through the lumen of anchor mount 461, and subsequently through aperture 330 of a second stabilizing structure 310. Prior to the coupling of mount 461 to a pair of structures 310, mount 461, and thereby lumen 501, is allowed to pivot laterally. Following the coupling of structures 310 to mount 461, structures 310 restrict the lateral pivoting of mount 461.

During the manufacture of structure 310, aperture 330 is created such that major axis 331 is disposed at a desired angle with respect to axis 502 of anchor lumen 501 when coupled to mount 461. A portion of ratchet body 202 is then passed through mount 461 and subsequently through aperture 330, thereby fixing the angle of the major axis of aperture 330 with respect to axis 502 of anchor lumen 501. Typically, (a) longitudinal axis 332 of aperture 330 is substantially parallel with respect to a plane of the annulus and parallel with the longitudinal axis of the annuloplasty structure, and (b) axis 502 of anchor lumen 501 is at a non-zero angle with respect to major axis 331 of the aperture 330. Thus, the angle of anchor lumen 501 with respect to longitudinal axis 332 facilitates corkscrewing of the tissue anchor into the annulus at an angle as defined by the intersecting axes 502 of lumen 501 and major axis 331 of aperture 330 (shown in FIG. 5C).

For embodiments in which system 300 comprises a plurality of anchor mounts 461, the respective pairs of structures 310 coupled on either end of each mount 461 may be manufactured differently. For example, (1) a first pair of structures 310 may be shaped to define apertures 330 having a major axis at a first desired angle with respect to axis 502 of anchor lumen 501 of a first anchor mount 461, and (2) a second pair of structures 310 may be shaped to define apertures 330 having a major axis at a second desired angle with respect to the longitudinal axis of anchor lumen 501 of a second anchor mount 461. Thus, the respective anchors configured to be passed through each of the first and second anchor mounts are anchored to the tissue at the desired first and second angles, respectively. In some embodiments, the anchors which pass through the anchor mounts positioned along the annulus in alignment with the base of the posterolateral leaflet may be anchored at an angle that is different from an angle at which the anchors which pass through the anchor mounts positioned along the annulus in alignment with the base of the anteromedial leaflet are anchored.

FIG. 5C shows a perspective view of system 300 from an opposite view than that shown in FIG. 5A. Ratchet body 202 passes unobstructed alongside anchor lumen 501 of anchor mount 461. As described hereinabove, anchor mount 461 may also function as a housing for fixed end 210 of ratchet body 202. Anchor mount 461 is shaped to define a slit 520 which engages and fixes in place a portion 212 of fixed end 210. Typically, portion 212 projects away perpendicularly from a longitudinal axis of ratchet body 202.

Reference is now made to FIGS. 3 and 5B-C. Anchor mount 461 is flanked by stabilizing structures 310. FIG. 5B shows a stabilizing unit 500 having a stabilizing structure 310 is shaped to define: (1) a hole 320 configured for passage therethrough of contracting wire 110, and (2) a longitudinal aperture 330 configured for passage therethrough of ratchet body 202, in accordance with an embodiment of the present invention. Typically, aperture 330 has a width L7 of between 0.3 mm and 0.8 mm. Such a width facilitates passage therethrough of at least a portion of ratchet body 202. For embodiments in which a first portion of body 202 is slid alongside a second portion of body 202 (e.g., dynamic end 220 slides alongside fixed end 210), width L7 accommodates for the widths of both the first and second portions of ratchet body 202 and facilitates passage therethrough of both portions.

FIG. 3 shows ratchet body 202 in a closed configuration thereof. It is to be noted that ratchet body 202 assumes a substantially circular configuration thereof and that only a portion of ratchet body 202 is shown. Typically, dynamic end 220 is passively fed through aperture 330 alongside fixed end 210. As such, a portion of body 202 distal to fixed end 210 aligns alongside a portion proximal to dynamic end 220, as shown in FIG. 3. Thus, width L7 of aperture 330 accommodates for the widths of: (1) the portion of body 202 distal to fixed end 210, and (2) the portion of body 202 proximal to dynamic end 220.

Figure 6A:
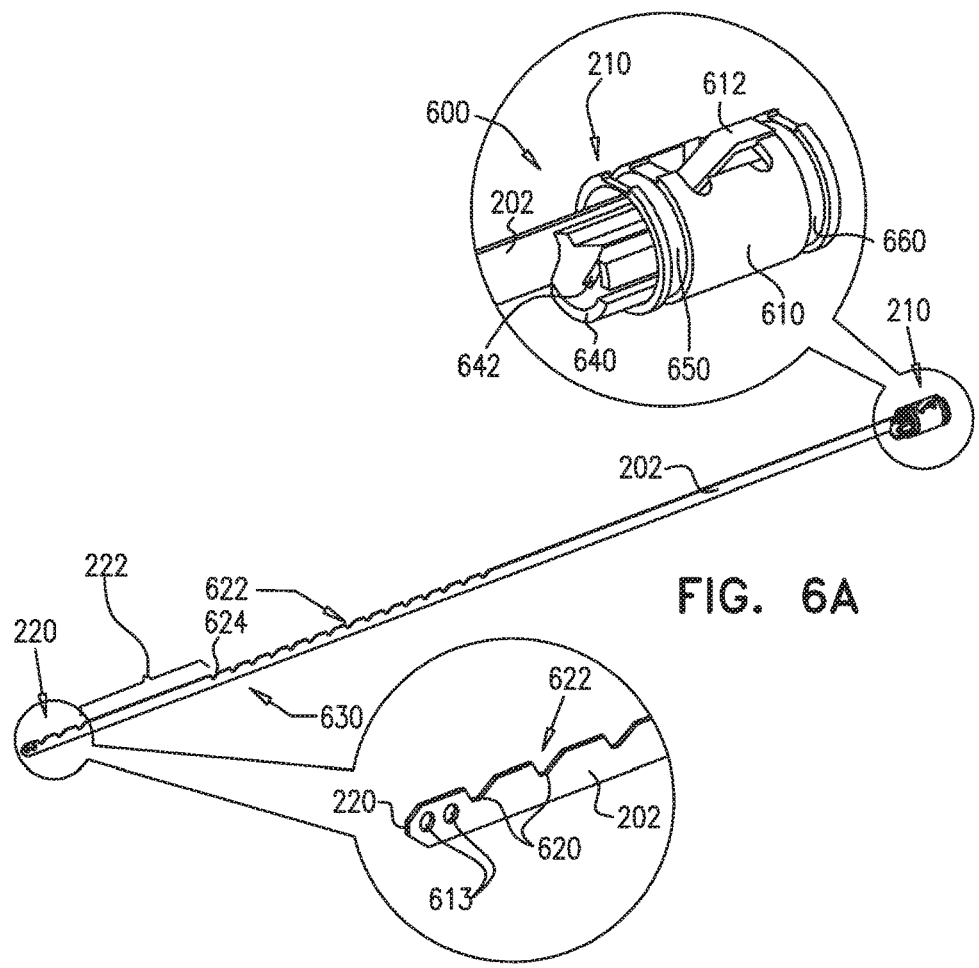
FIGS. 6A-B and 7 are schematic illustrations of a ratchet mechanism for use with an annuloplasty structure, in accordance with respective embodiments of the present invention.
Figure 6B:
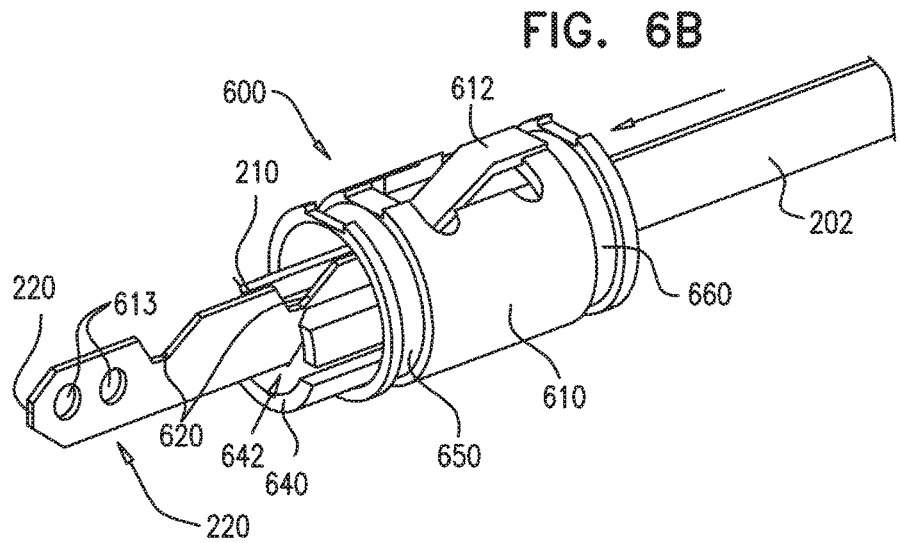

Reference is now made to FIGS. 6A-B which are schematic illustrations of a ratchet mechanism 600, in accordance with an embodiment of the present invention. Ratchet body 202 is shaped to define dynamic distal end 220 and fixed proximal end 210. As shown, ratchet body 202 is shaped to define a plurality of first engaging structures, e.g., grooves 622, configured to be engaged by a second engaging structure, a tooth 612, at fixed end 210. Fixed end 210 is coupled to a substantially tubular ratchet-coupling housing 610 which is shaped to define a first coupling site 650 and a second coupling site 660. For embodiments in which ratchet mechanism 600 is used in combination with compressible subunits 450 as described hereinabove with reference to FIG. 1, a respective compressible subunit 450 is coupled to coupling sites 650 and 660.

As described hereinabove with reference to FIG. 1, ratchet mechanism 600 is disposed within the lumen of structure 100 such that fixed end 210 is disposed within the lumen of structure 100 in the vicinity of first end 102 thereof and dynamic end 220 is disposed within the lumen of structure 100 in the vicinity of second end 104 thereof. Although ratchet body 202 is shown in a linear configuration, it is to be noted that ratchet body 202 is drawn into its closed configuration simultaneously with structure 100 assuming its closed configuration. As contracting wire 110 is pulled and first and second ends 102 and 104 of annuloplasty structure 100 are drawn toward each other such that structure 100 assumes its closed configuration, dynamic end 220 is fed into housing 610 and is advanced past fixed end 210 such that ratchet body 202 assumes its closed configuration as well. As dynamic end 220 advances beyond fixed end 210, dynamic end 220 and the portion of body 202 that is proximal to end 220 are slid alongside fixed end 210 and the portion of body 202 that is distal to fixed end 210. As shown, housing 610 is coupled to an insert 640 that is shaped to define a longitudinal track 642. As dynamic end 220 is fed into housing 610 of fixed end 210, dynamic end slides along track 642. Thus, dynamic end 220 and fixed end 210 are able to meet each other due to the sliding dynamic end 220 along track 642 within the lumen housing 610.

Ratchet body 202 is shaped to define a plurality, e.g., at least two as shown, of first grooves 620 in the vicinity of dynamic end 220 and a plurality of second grooves 630 in the general vicinity of the middle of ratchet body 202. It is to be noted that the respective numbers of first grooves 620 and second grooves 630 are shown by way of illustration and not limitation. As ratchet mechanism 600 is initially drawn into its closed configuration, dynamic end 220 slides alongside track 642 and tooth 612 engages respective grooves 622 of ratchet body 202.

Ratchet body 202 provides a portion 222 disposed between first grooves 620 and second grooves 630. Typically, portion 222 provides a smooth surface for unobstructed back and forth sliding through fixed end 210 and enables the physician to adjust the size/perimeter of the annuloplasty structure before it is positioned along the annulus. Additionally, portion 222 enables the physician to adjust the size/perimeter of ratchet mechanism 600 prior to the locking of second grooves 630 by tooth 612. Typically, portion 222 has a distance that is between 30 mm and 70 mm, e.g., 50 mm.

It is to be noted that ratchet mechanism 600 may be anchored to the annulus independently of annuloplasty structure 100 described hereinabove with reference to FIG. 1 and with reference to ratchet mechanism 200 described hereinabove with reference to FIGS. 2A-B. Alternatively, for embodiments in which ratchet mechanism 600 is disposed within structure 100, ratchet mechanism 600 is typically disposed alongside the portion of contracting wire 110 which is disposed within the lumen of structure 100. As structure 100 is pulled into its closed configuration in response to the pulling of contracting wire 110, dynamic end 220 is pulled toward fixed end 210. Dynamic end 220 is passively advanced within housing 610, typically alongside fixed end 210, due to the compression force applied by structure 100 in response to the pulling of contracting wire 110.

In response to continued pulling of contracting wire 110, structure 100 radially contracts and, in turn, applies an additional compression force to ratchet mechanism 600. As described hereinabove, in response to the compression force, ratchet body 202 radially contracts as dynamic end 220 is passively slid further distally away from fixed end 210 thereby drawing second grooves 630 closer toward tooth 612 of housing 610. Dynamic end 220 is slid distally away from fixed end 210 until tooth 612 engages a first groove 624 of second grooves 630. Tooth 612 remains locked in position with respect to first groove 624 until an additional compression force of structure 100 is applied to ratchet body 202 (i.e., in response to the pulling of contracting wire 110). This additional force slides dynamic end 220 even further away from fixed end 210 until tooth 612 engages a second groove 626 of second grooves 630. Tooth 612 prevents body 202 of mechanism 600 from sliding in an opposite direction with respect to the direction by which dynamic end 220 is fed beyond fixed end 210. Thus, second grooves 630 maintain respective ratcheted perimeters of the now closed ratchet body 202, and thereby maintain respective ratcheted perimeters of structure 100.

For embodiments in which structure is advanced toward the left atrium in its closed configuration (e.g., during an open-heart procedure or during a minimally-invasive procedure), dynamic end 220 is advanced past fixed end 210 until first grooves 620 are in alignment with tooth 612 and ratchet body 202 is locked in an expanded configuration thereof and has a relatively large perimeter. As described hereinabove, once positioned along the annulus of the patient, the dynamic end 220 is pushed further distally away (i.e., in the direction as indicated by the arrow in FIG. 6B) from fixed end 210 until locking grooves 630 lock and fix a perimeter of body 202, and thereby, fix a perimeter of structure 100.

It is to be noted that the plurality of second grooves 630 is provided such that ratchet body 202, and thereby structure 100, can lock in place and maintain respective ratcheted perimeters thereof. Thus, the length of ratchet mechanism 600 in its linear configuration, the locking mechanism of ratchet mechanism 600, and compressible subunits 450 described hereinabove are provided so as to enable annuloplasty structure 100 to accommodate various sizes of dilated annuli of given patients. Additionally, ratchet mechanism 600 facilitates: (1) positioning and anchoring structure 100 along the dilated annulus while body 202 (and thereby structure 100) has a first perimeter thereof, (2) contracting the dilated annulus in response to the contracting of body 202 (and thereby structure 100), and (3) maintaining the contracted state of the annulus while body 202 (and thereby structure 100) has a second perimeter thereof that is typically smaller than the first perimeter.

It is to be further noted that ratchet mechanism 600 is described as being used in combination with structure 100 by way of illustration and not limitation. For example, ratchet mechanism 600 may be surrounded by a tubular sheath comprising a braided mesh, e.g., metal or fabric such as polyester.

FIG. 6B shows dynamic end 220 having already passed through housing 610 of fixed end 210. As such, ratchet body 202 assumes a closed configuration (partially shown for clarity of illustration). As shown, dynamic end 220 is shaped to define one or more holes 613 configured for looping of the contracting wire therethrough. In such an embodiment, dynamic end 220 is pushed in response to tensile force applied to the contracting wire as it is pulled. As described hereinabove, additional force applied to the contracting wire pushes ratchet mechanism 200 into a closed configuration, e.g., a substantially ring-shaped configuration. Further additional pulling of the contracting wire reduces the perimeter of ratchet mechanism 600, and thereby of the annuloplasty structure.

Figure 7:
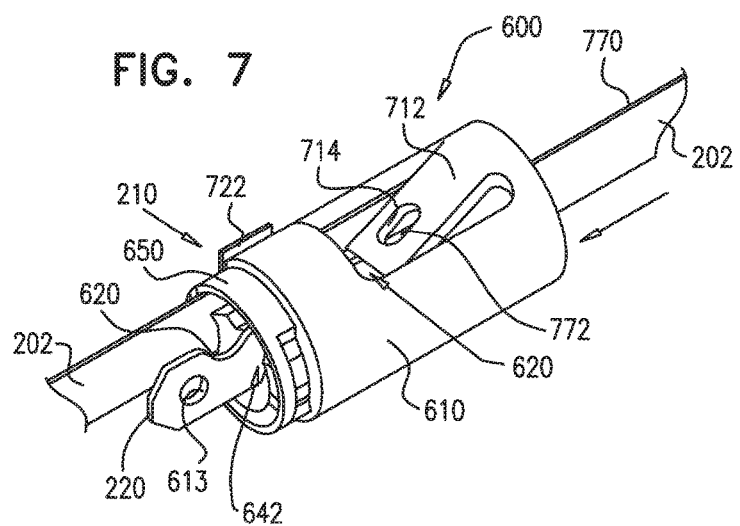

FIG. 7 shows ratchet mechanism 600 as described hereinabove with reference to FIGS. 6A-B, with the exception that housing 610 provides a tooth 712 is shaped to define a window 714, in accordance with an embodiment of the present invention. Tooth 712 is coupled to housing 610 along a junction and bends along the junction. As tooth 712 engages groove 620 of ratchet body 202, window 714 surrounds a portion 772 of an upper surface 770 of ratchet body 202 which defines groove 620. Window 714 thus enables tooth 712 to advance distally and bend as far as possible within groove 620 without being obstructed by portion 772 of upper surface 770 which defines groove 620. Tooth 712 engages groove 620 and locks ratchet body 202 in place until an additional inward, radial pushing force is applied thereto, e.g., typically, in response to the pulling of contracting wire 110 described herein. In response to the additional inward, radial force applied to ratchet body 202, (a) dynamic end 220 is slid further away from housing 610 in the same direction in which dynamic end 220 was initially fed into housing 610 (i.e., the direction as indicated by the arrow), and (b) tooth 712 slides along upper surface 770 of ratchet body 202 until tooth 712 engages another groove 620 of ratchet body 202.

Dynamic end 220 is shaped to define one or more holes 613 configured for looping of the contracting wire therethrough. In such an embodiment, dynamic end 220 is pulled in response to tensile force applied to the contracting wire as it is pulled. Additional force applied to the contracting wire pulls ratchet mechanism 600 into the closed configuration. Further additional pulling of the contracting wire reduces the perimeter of ratchet mechanism 600, and thereby of the annuloplasty structure.

It is to be noted that ratchet body 202 may be pulled by contracting wire 110 in some embodiments. Ratchet body 202 is typically pushed in response to the radial, compressing force applied to body 202 by the annuloplasty structure in response to the pulling of contracting wire 110.

Reference is now made to FIGS. 6A-B and 7. Fixed end 210 of ratchet body 202 is shaped to define a protrusion 722 (not shown in FIGS. 6A-B). Housing 610 is shaped to define a slit (not shown for clarity of illustration) for passage therethrough of protrusion 722 in order to fix fixed end 210 in place with respect to housing 610.

Figure 8:
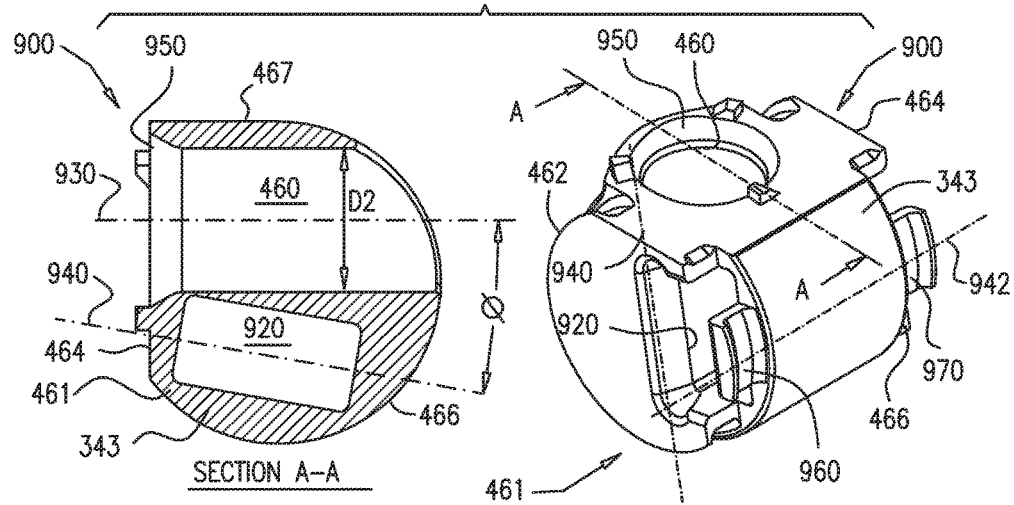
FIGS. 8-10 are schematic illustrations of a mount for use in anchoring an annuloplasty structure to the annulus of the patient, in accordance with respective embodiments of the present invention.

FIG. 8 shows an anchor mount system 900 comprising an anchor mount 461 comprising a double-lumen anchor mount 343 that is shaped to define a channel 460 and a lumen 920, or channel, in accordance with an embodiment of the present invention. Anchor mount 461 is shaped to define a lateral wall 467 having a first portion 464 and a second portion 466 generally at opposite sites of mount 461 when viewed in cross-section (e.g., at 12 o'clock and 6 o'clock). Typically, first portion 464 is shaped to define an opening thereof, and second portion 466 is shaped to define an opening thereof. Channel 460 extends from the opening of first portion 464, through the anchor mount, to the opening in second portion 466. As described hereinabove with reference to FIG. 1, anchor mount 461 is configured for facilitating passage therethrough any anchor described herein in order to facilitate anchoring of an annuloplasty structure (e.g., any annuloplasty structure comprising mount system 900) to the annulus of the patient. Channel 460 has a diameter between about 0.8 mm and 2.5 mm, e.g., 1.8 mm, that is sized to facilitate passage therethrough of any one of the anchors, anchoring structures, or anchoring systems described herein. Typically, the anchors described herein are configured for passage through channel 460 have a diameter of between about 0.5 mm and 2.4 mm, e.g., 1.6 mm.

First portion 464 of lateral wall 467 of mount 461 is shaped to define a tapered opening 950 above channel 460. Opening 950 has a diameter that is typically larger than a diameter D2 of channel 460. Typically, during the anchoring of the annuloplasty structure to the annulus, an anchor is coupled to an advancement structure, e.g., a tube or a rod, at a distal end thereof and is advanced via the advancement structure toward channel 460. In some embodiments, a portion of the distal end of the advancement structure has a diameter that is slightly larger than the proximal end of channel 460, i.e., opening 950 of anchor mount 461. Thus, the advancement of the advancement structure is restricted from passage through channel 460 beyond the portion of the distal end of the tube that has a diameter larger than the diameter of channel 460. This restriction helps ensure that the anchor is not advanced too deeply within tissue of the annulus.

In some embodiments, a proximal portion (e.g., the portion of the anchor that is coupled to the distal end of the advancement structure) of the anchor is configured to expand. In such an embodiment, the proximal portion of the anchor is compressed within an overtube during the advancement of the anchor toward the annulus of the valve. Once the anchor is positioned properly within channel 460 and is initially anchored to the annulus of the valve, the overtube is slid proximally from the proximal end of the anchor and the proximal portion is allowed to expand. In such an embodiment, the expanded portion of the anchor has a diameter that is (a) larger than diameter D2 of channel 460 and (b) smaller than the diameter at the distal end of opening 950. Thus, the expanded, proximal portion of the anchor rests within the proximal end of opening 950 and functions as a cap which restricts further distal advancement of the anchor into the tissue of the annulus.

Anchor mount 461 is shaped to provide an anchor mount and ratchet body lumen 920 for passage of ratchet body 202 of any of the ratchet mechanisms described herein. Ratchet body lumen 920 has (a) a longitudinal axis 942 that is substantially parallel with respect to the plane of the annulus and parallel with the longitudinal axis of the annuloplasty structure, and (b) an axis 940 that is typically at a non-zero angle, e.g., transverse, with respect to longitudinal axis 942. Channel 460 has a first axis 930 is typically at a non-zero angle, e.g., transverse, with respect to longitudinal axis 942. Typically, lumen 920 is disposed with respect to channel 460 such that axis 940 of lumen 920 is disposed at an angle theta, with respect to axis 930 of channel 460. Typically, the anchor is anchored at angle theta with respect to axes 940 and 920 and the plane of the annulus of the valve. It is to be noted angle theta may range between 10 degrees and 70 degrees, typically 30 degrees.

Typically, for embodiments in which the annuloplasty structure comprises a plurality of anchor mount systems 900, angle theta is identical for all mounts 461. Alternatively, a first portion of the plurality of anchor mount systems 900 has an angle theta that differs from the angle theta of a second portion of the plurality of anchor mount systems 900. For example, a portion of anchor mount systems 900 designated to be anchored to the anterior portion of the annulus has an angle theta that is different from a portion of anchor mount systems 900 designated to be anchored to the posterior portion of the annulus. Thus, the anchors may be anchored to different portions of the annulus at different angles in response to a need therefor.

In some embodiments, the contracting wire described herein passes through lumen 920 alongside ratchet body 202. In some embodiments, mount 461 of system 900 is shaped to provide an additional distinct lumen configured for passage therethrough of the contracting wire (configuration not shown).

Anchor mount 461 comprises first and second coupling sites 960 and 970 configured for coupling, e.g., wrapping therearound or welding, respective ends of one or more compressible subunits 450 as described hereinabove.

Figure 9:
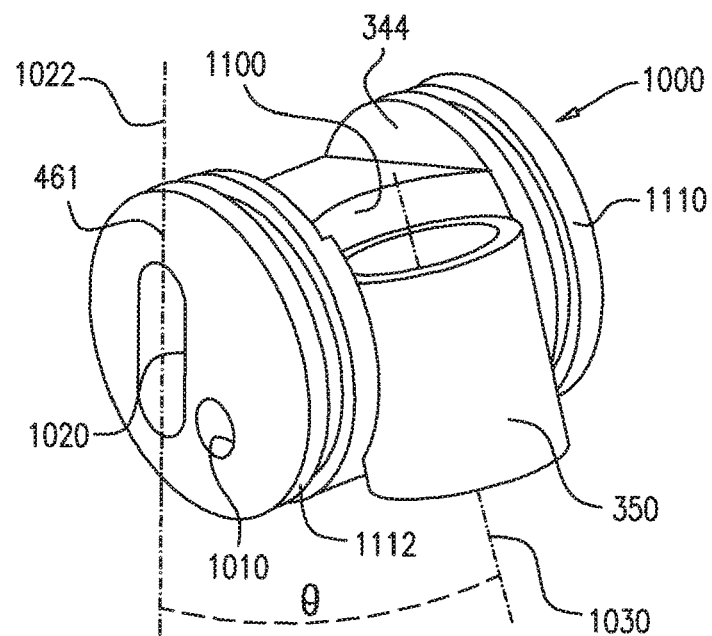

FIG. 9 shows an anchor mount system 1000 comprising an anchor mount 461 having a curved lateral surface 1100 that is coupled to an anchor channel 350 for passage of an anchor therethrough, in accordance with an embodiment of the present invention. Anchor mount 461 is configured for use in combination with any of the annuloplasty structures described herein. Mount 461 and is shaped to define a first lumen 1010 configured for passage therethrough of the contracting wire and a second lumen 1020 for passage therethrough of the ratchet body of any one of the ratchet mechanisms described herein. Lumens 1010 and 1020 facilitate unobstructed passage of the contracting wire and the ratchet body, respectively, with respect to the passage of an anchor through channel 350.

As described hereinabove with respect to FIG. 8, lumen 1020 has a first axis 1022 and channel 350 has a second axis 1030 which is disposed at an angle theta (e.g., between 10 degrees and 70 degrees, typically 30 degrees) with respect to first axis 1022. As such, the anchor passed through channel 350 is anchored to the annulus at angle theta with respect to the ratchet body disposed within lumen 1020.

Anchor mount 461 comprises first and second coupling sites 1110 and 1112 configured for coupling, e.g., wrapping therearound or welding, respective ends of one or more compressible subunits 450 as described hereinabove.

Figure 10:
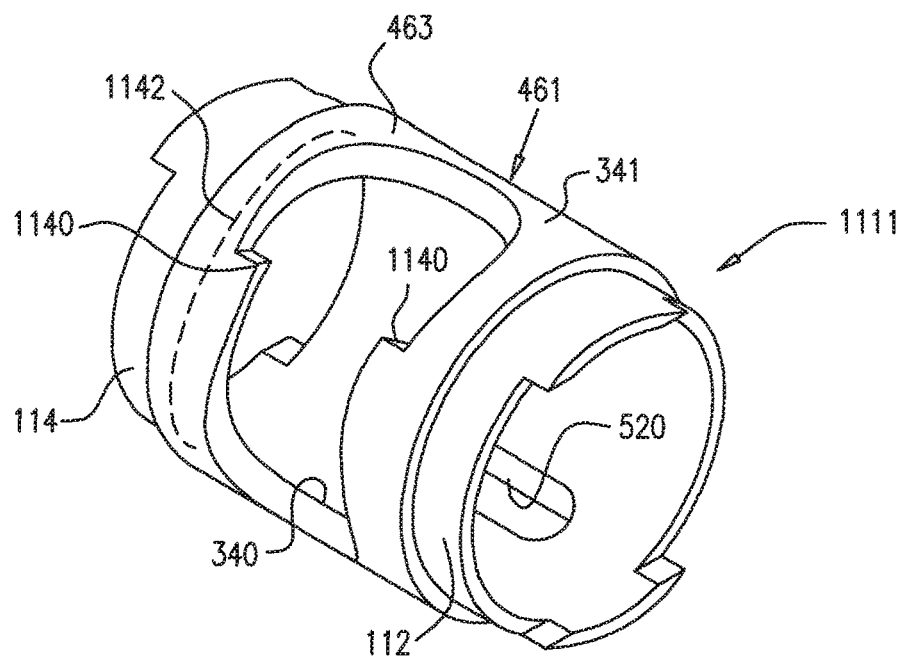

FIG. 10 shows an anchor mount system 1111 comprising an anchor mount 461 comprising lateral-aperture anchor mount 341 which is shaped to define an aperture 340 configured for passage therethrough of an anchor, as described hereinabove with reference to FIG. 3, in accordance with an embodiment of the present invention. In some embodiments, the anchor is slid through aperture 340 and rests against portions 1142 of mount 461 which define aperture 340. Typically, portions 1142 provide horizontal surfaces 1140 which function as shelves impeding continued distal motion of an anchor configured to be advanced through aperture 340. In some embodiment, a channel for passage of the anchor is welded to mount 461 along portions 1142 of mount 461. In some embodiments, the channel is advanced toward mount 461 together with the anchor. In such an embodiment, the channel is free to rotate with respect to aperture 340 along the longitudinal axis of mount 461.

Anchor mount 461 comprises a substantially tubular element 463 which defines a longitudinal anchor mount lumen. Aperture 340 is created at a location of mount 461 such that passage of an anchor via aperture 340, directly or indirectly, does not interfere with the contracting wire and/or ratchet body disposed within the longitudinal lumen of mount 461.

Reference is now made to FIGS. 5C and 10. Anchor mount 461 also functions as a housing for fixed end 210 of ratchet body 202. Anchor mount 461 is shaped to define slit 520 which engages and locks portion 212 of fixed end 210.

Anchor mount 461 comprises first and second coupling sites 112 and 114 configured for coupling, e.g., wrapping therearound or welding, respective ends of one or more compressible subunits 450.

Figure 11:
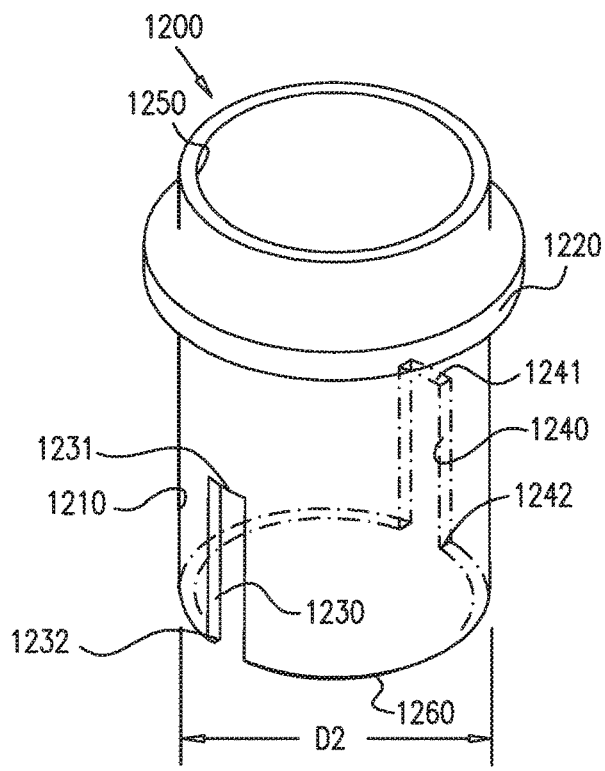
FIG. 11 is a schematic illustration of a channel for use in combination with an annuloplasty structure and for passage therethrough of an anchor in order to anchor the annuloplasty structure to the annulus of the patient, in accordance with an embodiment of the present invention.

Reference is now made to FIG. 11, which is a schematic illustration an anchor tube-channel 1200 configured to be used in combination with any one of anchor mounts 461 described herein, in accordance with an embodiment of the present invention. In some embodiments, anchor channel 1200 is configured to be advanced through lumen 501 of anchor mount 461 shown in FIGS. 5A and 5C. In some embodiments, channel 1200 is welded to anchor mount 461, shown in FIGS. 3, 4, and 10, via aperture 340. In some embodiments, during the manufacture of mount 461, channel 1200 is welded via surface 1100 to anchor mount 461, shown in FIG. 9, in place of channel 350.

Channel 1200 has (a) a proximal end 1250 which provides a passageway for passage of an anchor through a channel 1210 of channel 1200, and (b) a distal end 1260 which typically rests against the annulus of the valve when the annuloplasty structure is positioned along the annulus. Proximal end 1250 of channel 1200 is shaped to define an external ring 1220 having a diameter larger than the diameter of proximal end 1250 of channel 1200. For embodiments in which channel 1200 is configured to be advanced distally through lumen 501 of anchor mount 461 shown in FIGS. 5A and 5C, ring 1220 functions to impede continued distal motion of channel 1200 beyond a predetermined depth, as limited by ring 1220 abutting a proximal opening of channel 1200 of anchor mount 461. In such an embodiment, channel 1200 is free to rotate with respect to aperture 340 along the longitudinal axis of mount 461.

Channel 1200 is shaped to define one or more (e.g., two, as shown) lateral slits 1230 and 1240. In some embodiments, a longitudinal bar (not shown) is configured to be welded between slits 1230 and 1240. Slits 1230 and 1240 enable the bar to be welded to channel 1200 in any given configuration, e.g., substantially perpendicularly to or diagonally with respect to slits 1230 and 1240, and at any angle with respect to slits 1230 and 1240. For embodiments in which the bar is welded diagonally with respect to slits 1230 and 1240, a first end of the bar may be coupled to a portion of channel 1200 defining proximal end 1231 of slit 1230 while a second end of the bar is coupled to a portion of channel 1200 defining distal end 1242 of slit 1240, by way of illustration and not limitation. For example, in some embodiments, the first end of the bar may be coupled to proximal end 1231 of slit 1230 while the second end of the bar is coupled to a portion defining slit 1240 that is between proximal end 1241 and distal end 1242 thereof. For embodiments in which the bar is welded substantially perpendicularly with respect to slits 1230 and 1240, the first and second ends of the bar may be coupled to: (1) proximal end 1231 of slit 1230 and proximal end 1241 of slit 1240, respectively, (2) distal end 1232 of slit 1230 and distal end 1242 of slit 1240, respectively, or (3) parallel portions of slits 1230 and 1240 that are between the respective distal and proximal ends of slits 1230 and 1240.

Typically, the bar provides a reference force to help corkscrew the anchor into tissue of the annulus during the initial corkscrewing thereof. Even when the bar restricts further distal motion of the anchor beyond a predetermined distance (e.g., a predetermined distance from that lateral surface of mount 461 which rests against tissue of the annulus), the anchor is allowed to resume rotational motion together with rotational motion of channel 1200 for embodiments in which channel 1200 is not welded to anchor mount 461. In the event that a gap is created between the annulus tissue and the annuloplasty structure during the initial anchoring of the structure to the annulus of the valve, this continued rotational motion draws tissue of the annulus toward the annuloplasty structure. Such proximal drawing of the tissue thereby minimizes and substantially eliminates the gap. Techniques for use with a helical anchor and the bar as described herein may be used in combination with techniques described in U.S. Provisional Application 61/001,013 to Gross et al., entitled, "Segmented ring placement," filed Oct. 29, 2007, which is incorporated herein by reference.

Figure 12:
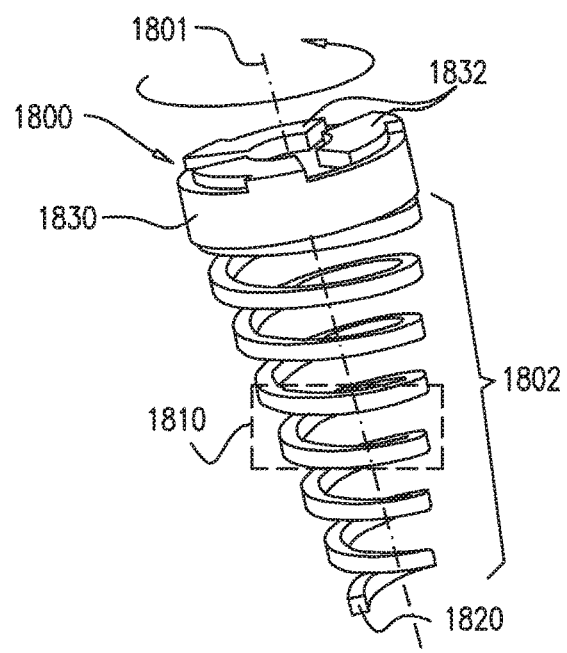
FIGS. 12, 13A-E, 14A-B, and 15 are schematic illustrations of anchors for anchoring an annuloplasty structure to the annulus of the patient, in accordance with respective embodiments of the present invention.

FIG. 12 is a schematic illustration of an anchoring structure 1800 comprising a tapered, conical helical element 1802 comprising a plurality of coils 1810, in accordance with an embodiment of the present invention. Typically, the plurality of coils 1810 comprises a pointed distal end 1820 which punctures tissue of the annulus and allows for coils 1810 to be corkscrewed distally into the tissue of the annulus. A proximal surface of element 1802 is coupled to a head portion 1830 comprising raised surfaces 1832 having a defined conformation. In some embodiments, head portion 1830 functions to prevent distal screwing of structure 1800 into the annulus of the patient beyond a predetermined depth as defined by the combined length of head portion 1830 and coils 1810. Although structure 1800 is not able to be advanced further distally, continued rotation of structure 1800 draws tissue proximally with respect to the annuloplasty structure, thereby substantially minimizing or eliminating a gap that may be created between the annuloplasty structure and the tissue of the annulus.

Typically, an anchor advancement structure, e.g., a tube or a rod, (not shown) is coupled at a distal end thereof to structure 1800 via raised surfaces 1832. In such an embodiment, the distal end of the advancement device is shaped to define recessed portions which are similar in shape to the define conformation of raised surfaces 1832. The advancement device is coupled to structure 1800 when the recessed portions of the device accommodate the conformation of raised surfaces 1832 by surrounding and locking in place surfaces 1832 with respect to the recessed portions of the advancement device. The advancement device is locked together with structure 1800 when a rotational force is applied to the advancement force in a rotational direction as indicated by the arrow. Once the advancement device facilitates the anchoring of structure 1800 to the annulus of the patient, a rotational force is applied to the anchor advancement structure in a direction opposite to the direction indicated by the arrow which detaches the advancement device from structure 1800 by sliding the recessed portions of the advancement device away from raised surfaces 1832.

For embodiments in which structure 1800 is used to percutaneously anchor an annuloplasty structure to the annulus, the anchor advancement structure comprises an advancement structure, e.g., a tube or a rod, which is typically coupled to head portion 1830 prior to being transcatheterally advanced toward the annuloplasty structure. For embodiments in which anchor structure 1800 is used to anchor the annuloplasty structure to the annulus during an open-heart procedure, an external anchoring device (e.g., an advancement tube, an advancement rod, or a screw-driving system) is used in order to facilitate anchoring of structure 1800 to the annulus.

In either embodiment, once the anchor advancement structure advances the anchor toward the annuloplasty structure, the anchor advancement structure is rotated in order to facilitate corkscrewing of anchoring structure 1800 into the annulus of the patient. For embodiments in which the compressible subunits of the annuloplasty structure comprise a braided mesh, as described hereinabove, structure 1800 may be advanced through the mesh and anchor the annuloplasty structure to the annulus via the mesh. For embodiments in which the compressible subunits of the annuloplasty structure comprise a coiled structure, coils 1810 of structure 1800 are coiled around a portion of coils of the coiled compressible subunits of the annuloplasty structure and subsequently through the tissue of the annulus of the patient. During the coiling of coils 1810 of structure 1800 around the portion of coils of the coiled compressible subunits of the annuloplasty structure, a longitudinal axis 1801 of structure 1800 is at a non-zero angle, e.g., perpendicular, with respect to a longitudinal axis of the annuloplasty structure. Such intercoiling of coils 1810 with the coils of the coiled compressible subunits of the annuloplasty structure facilitates the coupling of the annuloplasty structure with anchoring structure 1800 during the corkscrewing of structure 1800 into the tissue of the annulus.

For embodiments in which the annuloplasty structure comprises at least one anchor mount, as described hereinabove, structure 1800 is advanced through the anchor mount and into the annulus of the patient.

Reference is now made to FIGS. 5A, 5C, and 12. Typically, head portion 1830 has a diameter that is larger than the inner diameter of lumen 501 of anchor mount 461. As anchoring structure 1800 is advanced through lumen 501, a distal surface of head portion 1830 abuts a proximal opening of lumen 501 and inhibits continued distal motion of structure 1800 through the tissue of the annulus beyond the predetermined depth.

Reference is now made to FIGS. 8 and 12. Typically, the diameter of head portion 1830 is larger than diameter D2 of channel 460 defined by anchor mount 461. As structure 1800 is advanced through channel 460, the distal surface of head portion 1830 abuts proximal opening 950 and inhibits continued distal motion of structure 1800 through the tissue of the annulus beyond the predetermined depth.

Reference is now made to FIGS. 9 and 12. Typically, the diameter of head portion 1830 is larger than the inner diameter of channel 350 coupled to anchor mount 461. As structure 1800 is advanced through channel 350, the distal surface of head portion 1830 abuts a proximal opening of channel 350 and inhibits continued distal motion of coils 1810 through the tissue of the annulus beyond the predetermined distance.

Reference is now made to FIGS. 10 and 12. As structure 1800 is advanced through channel 350, the distal surface of head portion 1830 abuts horizontal surfaces 1140 defining aperture 340 and inhibits continued distal motion of coils 1810 through the tissue of the annulus beyond the predetermined distance.

Reference is now made to FIGS. 11 and 12. As structure 1800 is advanced through channel 1210 of channel 1200, the distal surface of head portion 1830 abuts proximal end 1250 of channel 1200 and inhibits continued distal motion of coils 1810 through the tissue of the annulus.

Reference is again made to FIG. 12. The proximal coil of helical element 1802 has a diameter that is larger than the diameter of the distal coil of element 1802. The diameters of the coils of helical element 1802 are gradually reduced in each successive coil from the proximal coil to the distal coil. The distal coil is corkscrewed into the tissue of the annulus following the puncturing of the annulus by pointed distal end 1820. As the distal coil is corkscrewed distally through the tissue of the annulus, the distal coil pushes against the surrounding tissue, thereby exerting a radial force against surrounding tissue of the annulus. Each successive proximal coil of helical element 1802 enters an opening defined by the distal coil adjacent thereto. The diameter of the opening is smaller than the diameter of the successive proximal coil. Thus, each successive proximal coil of exerts an outward, radial force on surrounding tissue corresponding to the diameter of successive proximal coil. Thus, the proximal coil exerts a greater force on the surrounding tissue than does the distal coil. It is to be noted that the ratio between the diameter of the proximal coil to the diameter of the distal coil is shown by way of illustration and not limitation. For example, the ratio may be smaller than the ratio that appears in FIG. 12.

In some embodiments, the proximal coil of helical element 1802 has a diameter that is smaller than the diameter of the distal coil of element 1802 (configuration not shown). The diameters of the coils of helical element 1802 are gradually increased in each successive coil from the proximal coil to the distal coil. The distal coil is corkscrewed into the tissue of the annulus following the puncturing of the annulus by pointed distal end 1820. As the distal coil is corkscrewed distally through the tissue of the annulus, the distal coil pushes against the surrounding tissue, thereby exerting a radial force against surrounding tissue of the annulus. Each successive proximal coil of the helical element enters an opening defined by the distal coil adjacent thereto. Thus, the frictional force of the cardiac tissue on the anchor is reduced. The diameter of the opening is larger than the diameter of the successive proximal coil.

Thus, each successive proximal coil of exerts an inward, radial force on tissue disposed within the lumen of the successive proximal coil corresponding to the diameter of the successive coil. Thus, the proximal coil exerts a greater force tissue disposed within the lumen defined by helical element 1802 than does the distal coil. Additionally, each coil of helical element 1802 exerts an inward, radial force on tissue disposed within a lumen of helical element 1802 corresponding to the diameter of each respective coil.

Figure 13A:
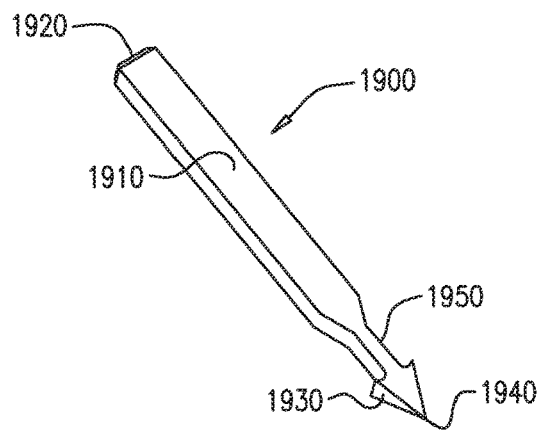
Figure 13B:
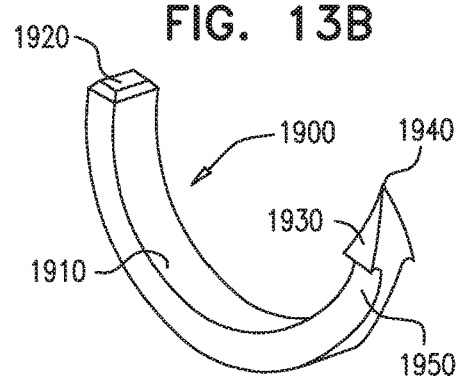

FIGS. 13A-B show an anchor 1900 comprising a distal barb 1930 and body portion 1910 which assume first and second configurations, respectively, in accordance with an embodiment of the present invention. Anchor 1900 has a proximal end 1920 and a distal pointed tip 1940 that punctures tissue of the patient. Body portion 1910 is shaped to define a narrow distal portion 1950 which is proximal to distal barb 1930. Typically, anchor 1900 comprises a shape-memory alloy, e.g., nitinol, which enables structure to transition between the configuration shown in FIG. 13A to the configuration shown in FIG. 13B.

During advancement toward the cardiac tissue, anchor 1900 is typically surrounded by an overtube (not shown) which maintains anchor 1900 in a generally straight configuration (shown in FIG. 13A). A distal end of the overtube contacts tissue of the patient and anchor 1900 is slightly pushed distally so that barb 1930 emerges from within the tube and is able to puncture the tissue. Anchor 1900 is further pushed distally from within the overtube such that anchor 1900 further penetrates the tissue and is allowed to gradually assume its resting configuration (i.e., the configuration anchor 1900 has a tendency to assume, as shown in FIG. 13B) commensurate with the extent of distal pushing of anchor 1900.

For embodiments in which anchor 1900 is used to anchor the annuloplasty structure comprising the braided mesh described hereinabove, anchor 1900 is initially passed through the mesh prior to being advanced through the tissue of the patient. In such an embodiment, prior to anchoring the annuloplasty structure to the annulus of the patient, anchor 1900 anchors itself to the annuloplasty structure by being entwined by the mesh. In some embodiments, prior to being advanced through tissues of the annulus, anchor 1900 is advanced through, and in some embodiments, coupled to, anchor mounts 461 described herein.

In some embodiments, as anchor 1900 assumes its bent configuration (shown in FIG. 13B), the proximal bending of body portion 1910 pushes proximally tissue of the annulus that is disposed between anchor 1900 and the annuloplasty structure positioned at the surface of the annulus. Thus, annulus tissue is pushed proximally toward the annuloplasty structure. For instances in which a gap is created between the annuloplasty structure and the tissue of the annulus, the proximal pushing of the annulus tissue toward the annuloplasty structure in response to the bending of anchor 1900, substantially minimizes or eliminates the gap.

Figure 13C:
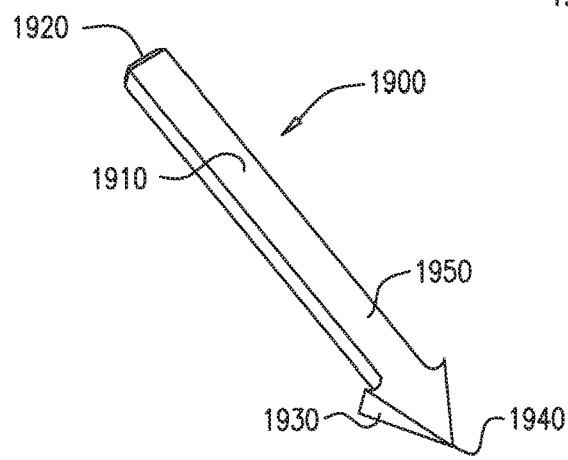
Figure 13D:
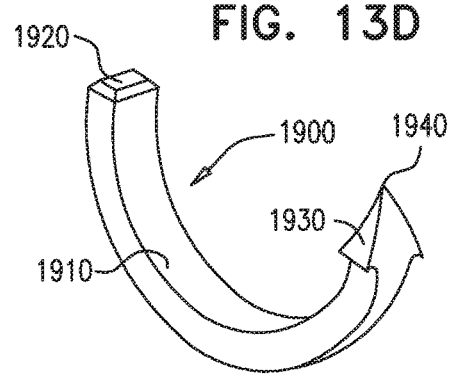

FIGS. 13C-D show anchor 1900 as described hereinabove with reference to FIGS. 13A-B with the exception that body portion 1910 is not shaped to provide narrow distal portion 1950, in accordance with an embodiment of the present invention.

Figure 13E:
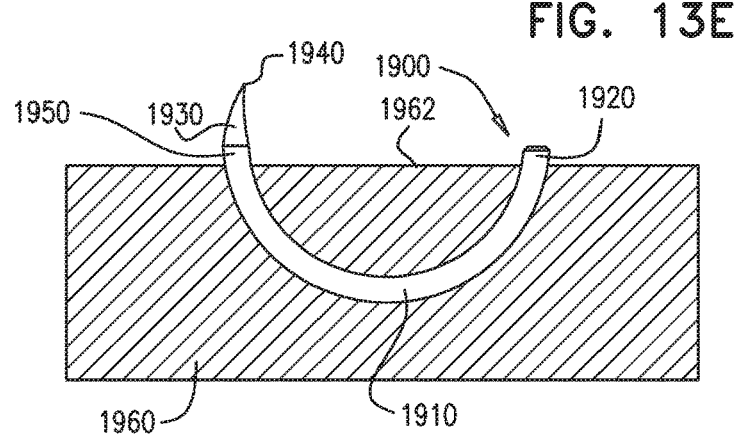

FIG. 13E is a cross-sectional illustration of anchor 1900 anchored within tissue 1960, in accordance with an embodiment of the present invention. For embodiments in which anchor 1900 is used in combination with an annuloplasty structure, the annuloplasty structure is positioned at a surface 1962 of tissue 1960. In such an embodiment, proximal end 1920 is coupled to (e.g., disposed within) the annuloplasty structure at a first location thereof, body portion 1910 of anchor 1900 is disposed within tissue 1960 in a "U"-shaped configuration thereof, and distal barb 1930 is exposed from within tissue 1960 and is coupled to the annuloplasty structure at a second location thereof.

For embodiments in which the annuloplasty structure comprises the braided mesh, barb 1930 is first passed through the braided mesh at the first location of the annuloplasty structure, through tissue 1960, then through the braided mesh at the second location of the annuloplasty structure, thereby anchoring the structure to the annulus while additionally coupling anchor 1900 to the annuloplasty structure.

Figure 14A:
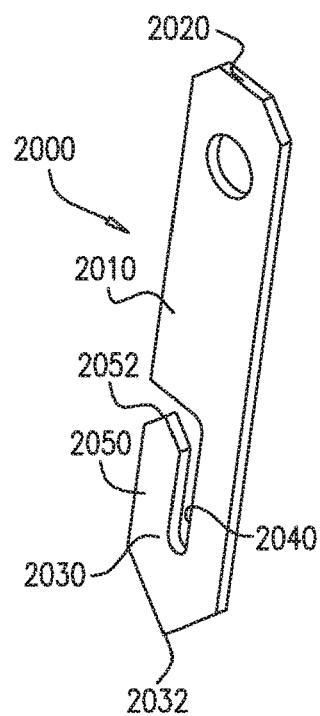
Figure 14B:
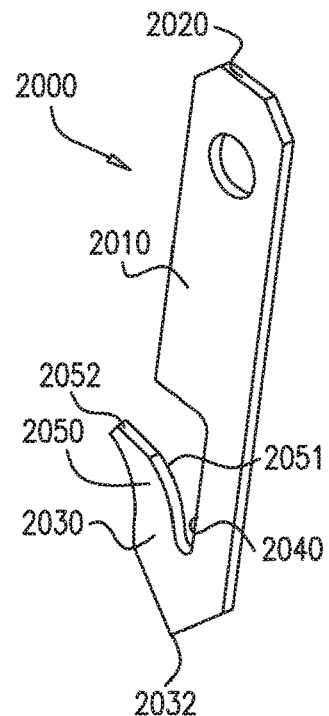

FIGS. 14A-B which are schematic illustrations of an anchor 2000 having a substantially rigid body portion 2010, a distal pointed tip 2032, and a flap 2050 proximal to distal tip 2032 which assume first and second positions, respectively, in accordance with an embodiment of the present invention. Body portion 2010 has a proximal end 2020 and is shaped to define a slit 2040 between a distal portion of body portion 2010 and flap 2050. Slit 2040 enables flap 2050 to transition between the configuration of flap 2050 shown in FIG. 14A to the configuration of flap 2050 shown in FIG. 14B. Typically, anchor 2000 comprises a shape-memory alloy, e.g., nitinol, which enables flap 2050 to transition along a junction 2030 between flap 2050 and body portion 2010 between the configuration shown in FIG. 14A to its resting configuration (i.e., the configuration flap has a tendency to assume, as shown in FIG. 14B).

Anchor 2000 is typically surrounded by a sheath or sleeve (not shown) that is typically rectangular and defines a lumen for surrounding anchor 2000, and enables flap 2050 to maintain a generally straight configuration (shown in FIG. 14A) as it is advanced toward the tissue of the patient. A distal end of the sheath contacts tissue of the patient and anchor 2000 is slightly pushed distally so that distal pointed tip 2032 emerges from within the tube and is able to puncture the tissue. Anchor 2000 is further pushed distally from within the overtube such that anchor 2000 further penetrates the tissue. Structure is then distally advanced to a desired depth and is then pulled proximally enabling flap 2050 to gradually bend along junction 2030 away from a longitudinal axis of body portion 2010. Anchor 2000 assumes its relaxed, or bent, position (shown in FIG. 14B) commensurate with the extent of proximal pulling of anchor 2000. A proximal end of flap 2050 is shaped to define a pointed tip 2052. As flap 2050 assumes its relaxed, or bent, configuration, tip 2052 punctures surrounding tissue in order to further anchor anchor 2000 to tissue of the patient. In its relaxed, or bent, configuration, flap 2050 defines a surface 2051 that is aligned angularly with respect to the longitudinal axis of body portion 2010. Surface 2051 defined by flap 2050 is configured to restrict further proximal motion of anchor 2000.

For embodiments in which anchor 2000 is used to anchor the annuloplasty structure comprising the braided mesh described hereinabove, the sheath or sleeve surrounding anchor 2000 is initially passed through the mesh. In some embodiments, prior to being advanced through tissues of the annulus, anchor 2000 is advanced through, and in some embodiments, coupled to, anchor mounts 461 described herein. For embodiments in which anchor 2000 is advanced through anchor mounts 461, the channel provided by the anchor mount functions to maintain the generally straightened configuration as structure is advanced through the anchor mount toward the tissue of the annulus.

Figure 15:
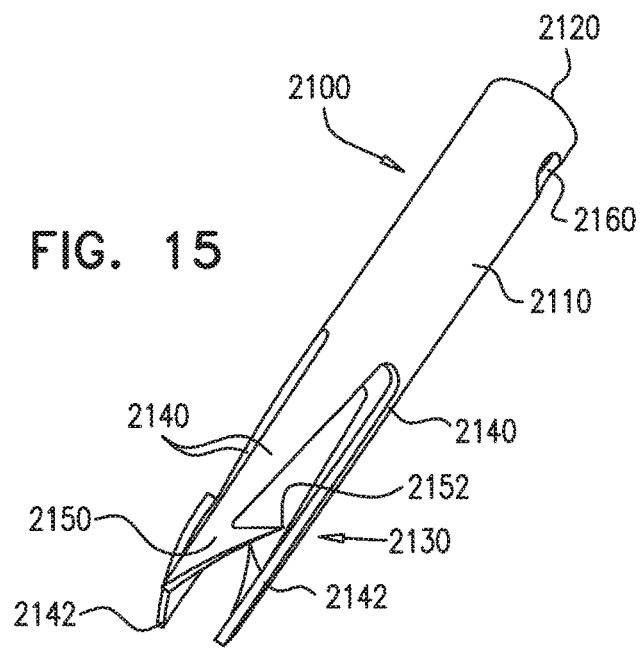

FIG. 15 shows an anchor 2100 having a proximal end 2120, a substantially rigid, cylindrical body portion 2110, and a distal end 2130 shaped to define distal prongs 2140 each having pointed distal end 2142, in accordance with an embodiment of the present invention. Each prong 2140 is shaped to define a tapered body portion and a distal barb 2150 shaped to define distal pointed end 2142 and proximal pointed ends 2152. Typically, anchor 2100 comprises a shape-memory alloy, e.g., nitinol, which enables prongs 2140 to transition from the substantially straight configuration, as shown, to a curved configuration in which pointed distal ends 2142 curve proximally such each prong 2140 assumes a substantially "U"-shaped configuration. It is to be noted that anchor 2100 is shown as comprising three prongs 2140 by way of illustration and not limitation, and that any suitable number or prongs may be used.

During advancement toward the cardiac tissue, anchor 2100 is typically surrounded by an overtube (not shown) which maintains prongs 2140 in a generally straight configuration (as shown). A distal end of the overtube contacts tissue of the patient and anchor 2100 is slightly pushed distally so that distal pointed ends 2142 emerge from within the tube and puncture the tissue. Anchor 2100 is further pushed distally from within the overtube such that anchor 2100 further penetrates the tissue and prongs 2140 are allowed to gradually bend away from a longitudinal axis of body portion 2110 in order to assume their respective bent configurations (shown in FIG. 16B) commensurate with the extent of distal pushing of anchor 2100. As prongs 2140 assume their respective bent configurations, proximal pointed ends 2152 puncture surrounding tissue in order to further anchor anchor 2100 to tissue of the patient. In its expanded, bent configuration, anchor 2100 is configured to restrict proximal motion of anchor 2100 through the tissue.

For embodiments in which anchor 2100 is used to anchor the annuloplasty structure comprising the braided mesh described hereinabove, the overtube is initially passed through the mesh until it contacts cardiac tissue underlying the annuloplasty structure. In such an embodiment, prior to anchoring the annuloplasty structure to the annulus of the patient anchor 2100 is anchored to the annuloplasty structure by being entwined in the braided mesh.

Once the distal end of the overtube contacts tissue of the annulus, anchor 2100 is pushed distally from within the overtube and into tissue of the annulus. In some embodiments, prior to being advanced through tissues of the annulus, anchor 2100 is advanced through, and in some embodiments, coupled to, anchor mounts 461 described herein.

For embodiments in which anchor 2100 is advanced through anchor mounts 461 described herein, the channel provided by the anchor mount functions to maintain the generally straightened configuration as anchor 2100 is advanced through the anchor mount toward the tissue of the annulus.

In some embodiments, as prongs 2140 of anchor 2100 assume their respective bent configurations (shown in FIG. 16B), the proximal bending of prongs 2140 pushes proximally tissue of the annulus that is disposed between anchor 2100 and the annuloplasty structure. Thus, annulus tissue is pushed proximally toward the annuloplasty structure. For instances in which a gap is created between the annuloplasty structure and the tissue of the annulus, the proximal pushing of the annulus tissue toward the annuloplasty structure in response to the bending of prongs 2140 of anchor 2100, substantially minimizes or eliminates the gap.

Anchor 2100 is shaped to define an opening 2160 in a vicinity of proximal end 2120 of anchor 2100. Typically, an anchoring advancement device, an advancement tube, and advancement rod, or a suture, is removably coupled to anchor 2100 by being looped through opening 2160.

It is to be noted that anchor 2100 is shaped to define opening 2160 by way of illustration and not limitation. For example, anchor 2100 may be manufactured without opening 2160. For either embodiment in which anchor 2100 is shaped to define opening 2160 or in which anchor 2100 is not shaped to define opening 2160, an anchor advancement structure, as described herein, may be coupled to anchor 2100 via a lumen defined by cylindrical body portion 2110 of anchor 2100.

FIGS. 16A-B show an anchor delivery system 2200 comprising stationary finger-engaging rings 2220, a displaceable finger-engaging ring 2222, and a tubular housing 2210 configured to advance and facilitate anchoring of anchor 2100, in accordance with an embodiment of the present invention. System 2200 comprises a pushing rod 2224 which is coupled at a distal end thereof to displaceable finer-engaging ring 2222 and is slidably displaced through tubular housing 2210. A distal end of pushing rod 2224 is coupled to a proximal end of a secondary pushing rod 2226 which is configured to slide within a lumen defined by a distal tubular element 2228.

Typically, one or more anchors 2100 are preloaded within distal tubular element 2228. In response to distal displacement of ring 2222, pushing rod 2224 applies a force to secondary pushing rod 2226, which in turn slides in part within element 2228 and applies a force to the at least one anchor 2100 disposed therein. In response to the applied force, anchor 2100 is pushed from within element 2228, and ultimately distally to a distal end 2230 of element 2228. As it is pushed, anchor 2100 is advanced into tissue of the patient, as described hereinabove with reference to FIG. 15.

In some embodiments, distal tubular element 2228 may be attachable to rod 2226 by being slidable around a distal portion of rod 2226. In such an embodiment, one or more anchors are preloaded within tubular element 2228 and subsequently, element 2228 is slid around the distal portion of rod 2226.

As shown in FIG. 16A, anchor 2100 is preloaded within tubular element 2228 of system 2200 in a compressed state thereof. A proximal end of anchor 2100 is coupled to a cap 2170 comprising at least one expandable projection 2172 which is compressed within tubular element 2228. When anchor 2100 is expanded (shown in FIG. 16B), projections 2172 impede continued distal advancement of anchor 2100 within tissue of the patient beyond a predetermined depth that is defined by the combined height of anchor 2100 and a portion of cap 2170 between a distal end thereof and a distal end of projection 2172 in an expanded state thereof.

FIG. 16B shows ring 2222 pushed distally, as indicated by the arrow. A length of an exposed portion of secondary pushing rod 2226 is shorter than the length of the exposed portion of rod 2226, as shown in FIG. 16A, indicating that a distal portion of rod 2226 has been pushed within tubular element 2228, which thereby pushes anchor 2100 distally from within tubular element 2228. Once exposed from within element 2228, anchor 2100 is allowed to assume its relaxed, predetermined configuration, as shown in FIG. 16B, in which prongs 2140 are allowed to curl proximally, as described hereinabove with reference to FIG. 15. Additionally, projections 2172 are allowed to assume their respective relaxed configurations, in which projections 2172 project laterally from cap 2170.

In some embodiments, in response to continued pushing of ring 2222, a distal portion of ring 2222 abuts a proximal portion of tubular housing 2210 and impedes continued distal motion of rod 2226.

Typically, system 2200 is used during an open-heart procedure in order to anchor an annuloplasty device to the annulus of the patient. For embodiments in which the annuloplasty structure comprises a braided mesh as described herein, distal end 2230 of system 2200 is advanced through the braided mesh until it abuts against the lateral surface of the annuloplasty structure, i.e., the surface with is in contact with the annulus. Distal displacement of ring 2222 advances the at least one anchor 2100 distally to distal end 2230 of system 2200, through a portion of the braided mesh, and subsequently into tissue of the patient. Anchor 2100 is coupled to the braided mesh when projections 2172 engage, e.g., are entangled with, at least a portion of the mesh.

For embodiments in which the annuloplasty structure comprises at least one anchor mount, as described herein, distal end 2230 of system 2200 may be advanced at least in part through the anchor mount. Ring 2222 is distally displaced and anchor 2100 is advanced distally to distal end 2230 of system 2200 through the channel of the anchor mount, and subsequently into tissue of the patient. As the anchor is advanced through the channel of the mount, the wall defining the channel maintains the straight configuration of the anchor. As cap 2170 is advanced distally, and projections 2172 emerge from within tubular element 2228, projections 2172 expand. Typically, a diameter defined by expanded projections 2172 is larger than the diameter of the channel of the anchor mount. As such, the distal ends of projections 2172 abut against the proximal opening of the channel and impede continued distal advancement of the anchor through the tissue of the patient.

For embodiments in which a plurality of anchors are housed within tubular element 2228, system 2200 comprises a baffle mechanism or a ratchet mechanism in order to ensure that distal displacement of ring 2222 will advance only one anchor at a time out of tubular element 2228.

It is to be noted that the scope of the present invention includes use of system 2200 for advancement and anchoring of any of the anchors or anchoring structures described herein. For embodiments in which system 2200 is used in order to anchor the helical anchors described herein, system 2200 may be rotated along a longitudinal axis of housing 2210.

Reference is now made to FIGS. 17A-F, which are schematic illustrations of a system 400 for repairing a mitral valve 30, being advanced into a left atrium of a patient, in accordance with an embodiment of the present invention. Typically, a catheter 404 (FIG. 17B) is advanced into the left atrium of the patient using a percutaneous endovascular approach typically combined with monitoring by electromagnetic and/or sound waves, e.g., fluoroscopy, transesophageal echo, transthoracic echo, and/or echocardiography, to maintain real-time orientation of a distal tip of the catheter within the heart of the patient. Typically, catheter 404 is transseptally advanced into the left atrium.

Catheter 404 typically comprises a 13 F catheter, although another size may be appropriate for a given patient. In some embodiments, catheter 404 is advanced through vasculature of the patient and into the right atrium using a suitable point of origin typically determined for a given patient. For example:

(1) Catheter 404 is introduced into the femoral vein of the patient, through the inferior vena cava, into the right atrium of the heart, transseptally, e.g., typically, through the fossa ovalis, and finally into the left atrium;

(2) Catheter 404 is introduced into the basilic vein, through the subclavian vein to the superior vena cava, into the right atrium, transseptally, e.g., typically, through the fossa ovalis, and finally into the left atrium; or (3) Catheter 404 is introduced into the external jugular vein, through the subclavian vein to the superior vena cava, into the right atrium, transseptally, e.g., typically, through the fossa ovalis, and finally into the left atrium.

In some embodiments, catheter 404 is advanced through an inferior vena cava 22 of the patient (as shown) and into the right atrium using a suitable point of origin typically determined for a given patient.

Figure 17A:
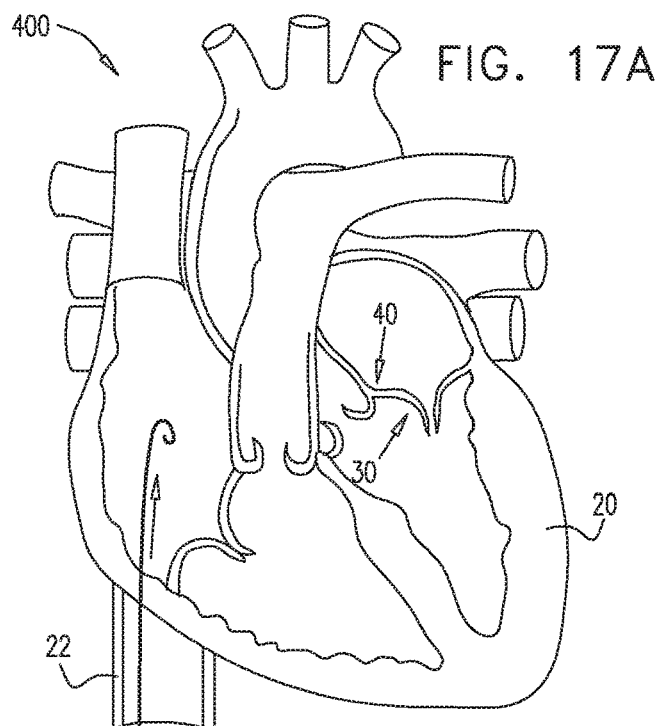
Figure 17B:
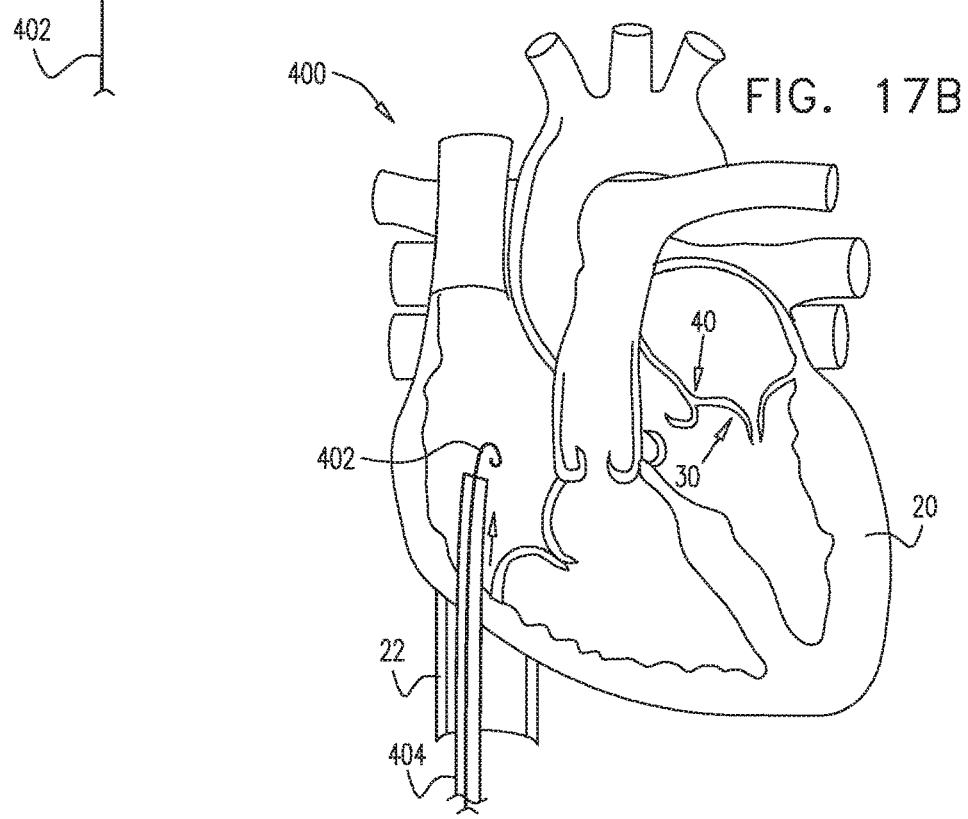
Figure 17C:
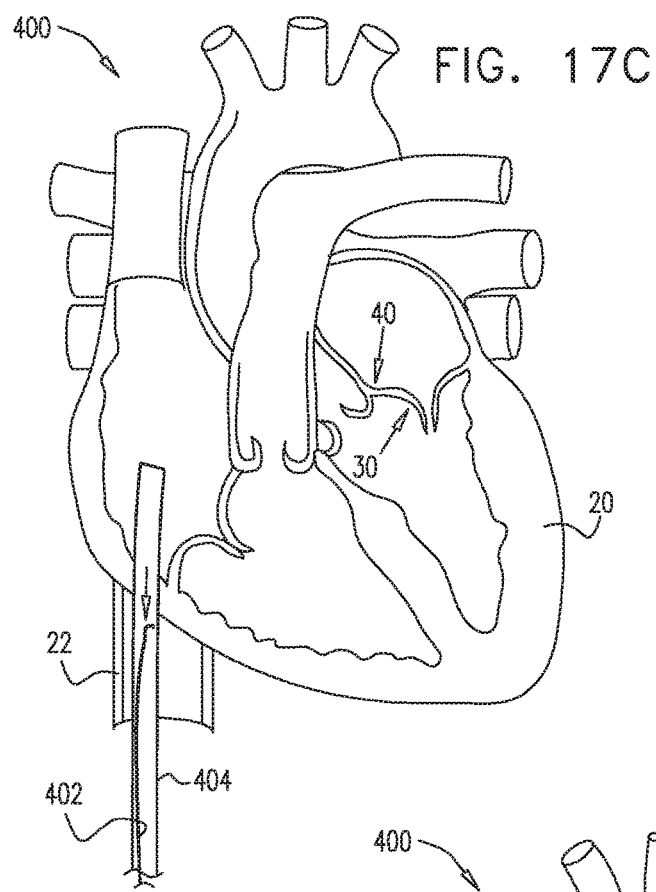
Figure 17D:
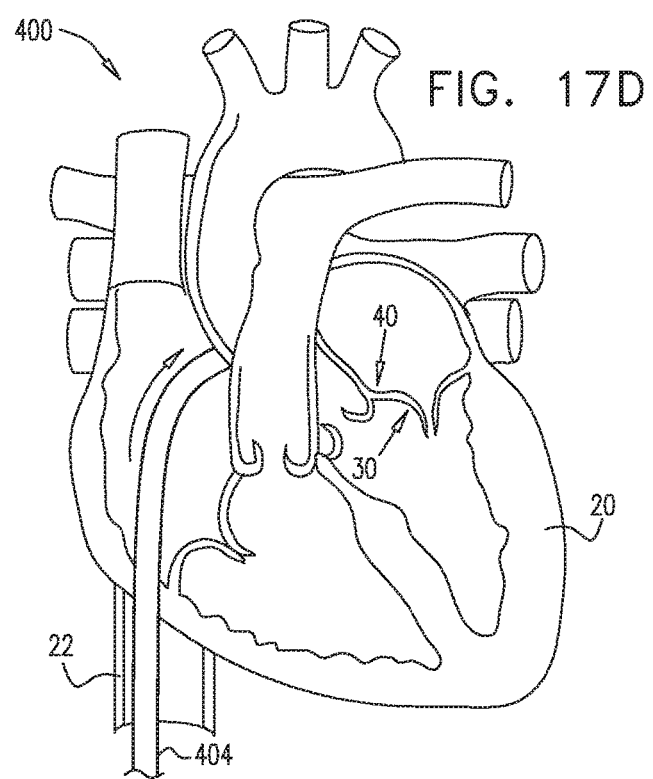

FIG. 17A shows a guide wire 402 being advanced into the right atrium of the patient. Advancement of wire 402 typically precedes advancement of catheter 404 into the right atrium of the patient. Wire 402 comprises a semi-rigid wire which provides a guide for the subsequent advancement of catheter 404 therealong and into the right atrium of the patient, as shown in FIG. 17B. Once catheter 404 has entered the right atrium, guide wire 402 is retracted and extracted from within the body of the patient (FIG. 17C). In FIG. 17D, catheter 404 is pushed distally until it reaches the interatrial septum of heart 20 of the patient.

(In this context, in the specification and in the claims, "proximal" means closer to the orifice through which catheter 404 is originally placed into the vasculature of the patient, and "distal" means further from this orifice.)

Figure 17E:
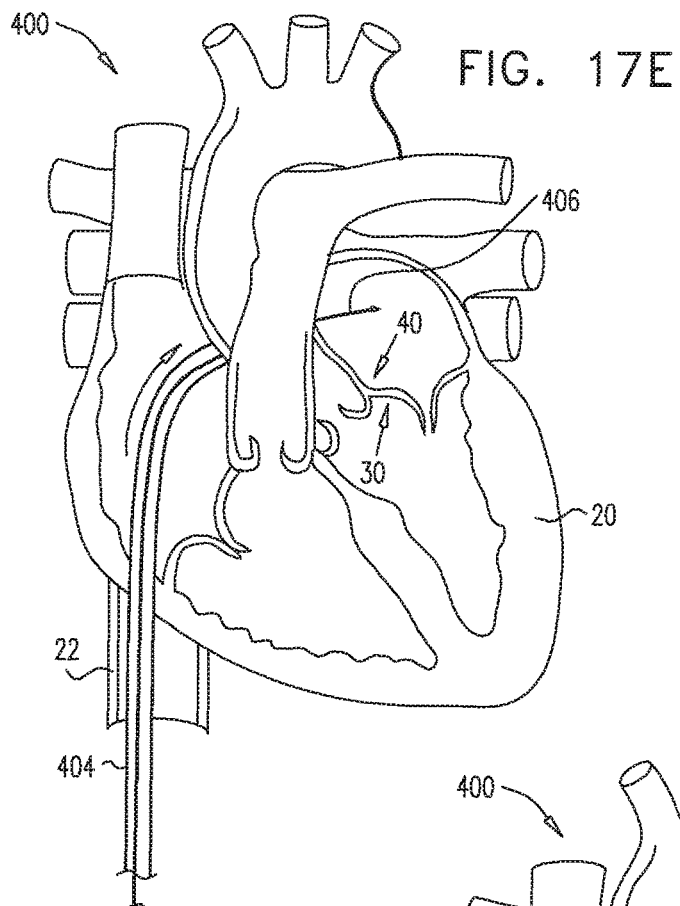
Figure 17F:
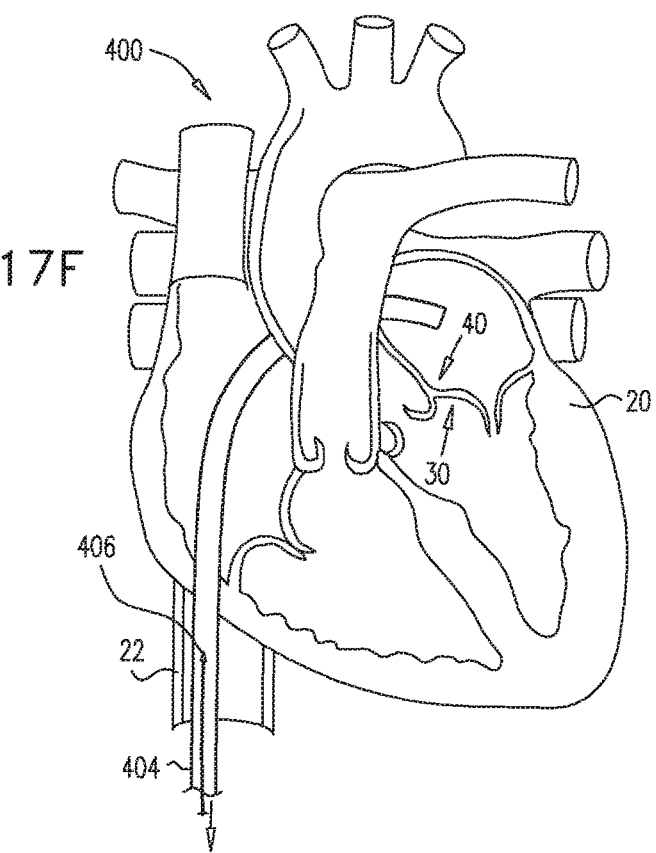

As shown in FIG. 17E, a resilient needle 406 and a dilator (not shown) are advanced through catheter 404 and into heart 20 of the patient. In order to advance catheter 404 transseptally into the left atrium, the dilator is advanced to the septum, and the needle 406 is pushed from within the dilator and is allowed to puncture the septum of heart 20 such that an opening is created which facilitates passage of the dilator and subsequently catheter 404 therethrough and into the left atrium. Subsequently, the dilator is through the hole in the septum of heart 20 created by needle 406. Typically, the dilator is shaped to define a hollow shaft for passage along needle 406, the hollow shaft being shaped to define a tapered distal end. This tapered distal end is first advanced through the hole created by needle 406. The hole is enlarged when the gradually increasing diameter of the distal end of the dilator is pushed through the hole in the septum. The advancement of catheter 404 through the septum and into the left atrium is followed by the extraction of the dilator and needle 406 from within catheter 404 (FIG. 17F).

FIG. 17G is a schematic illustration of a first discrete segment 430 and a second discrete segment 440 of an annuloplasty structure 408, e.g., at least one elongate segment, typically two as shown, being advanced along catheter 404, in accordance with an embodiment of the present invention. Segments 430 and 440 are disposed within catheter 404 in a substantially linear configuration, thereby having a longitudinal axis thereof. Segments 430 and 440 are configured to be chronically implanted within heart 20 along an annulus 40 of mitral valve 30. Typically, segments 430 and 440 comprise a biocompatible material, e.g., ePTFE, PTFE, nitinol, stainless steel, platinum iridium, titanium, or cobalt chrome. In some embodiments, segments 430 and 440 are coated with PTFE (Polytetra-fluoroethylene). Compressible subunits 450 are illustrated as coils, by way of illustration and not limitation, and facilitate bending of the segments into a suitable configuration and compressing of the segments when they are later drawn toward one another. For example, compressible subunits 450 may be shaped as struts of a stent, as a bellows, or as an accordion, or may comprise a braided mesh (as shown in FIG. 1). In some embodiments, a braided mesh comprising an elastic material, e.g., metal or fabric such as polyester, surrounds segments 430 and 440.

In some embodiments of the present invention, segments 430 and 440 comprise coils made of stainless steel, e.g., type 316 LVM. Suitable coil shapes include round wire coils or flat wire coils.

It is to be noted that any one of ratchet mechanisms (e.g., ratchet mechanism 200, ratchet mechanism 600, or tubular ratchet mechanism 3101) described herein may be disposed within the longitudinal lumen of structure 408.

Prior to advancing segments 430 and 440 into the left atrium of the patient, segments 430 and 440 are loaded into an advancement catheter 410 in a substantially linear configuration, as shown in FIG. 17G. The linear configuration defines a longitudinal axis of segments 430 and 440 of structure 408. Segments 430 and 440 are typically advanced into the left atrium of the patient during a single transcatheter advancement.

During advancement of segment 430 within advancement catheter 410, segment 430 has a length L1 between about 20 mm and about 60 mm, e.g., 30 mm. Typically, segment 430 is configured for positioning along a portion of annulus 40 at the junction between annulus 40 and the base of the anteromedial leaflet of valve 30. Similarly, second segment 440 is designated to be anchored to annulus 40 at the base of the posterolateral leaflet, and thus is sized in accordance therewith. For example, segment 440 may have a length L2 of between about 30 mm and about 100 mm, e.g., 50 mm. The respective lengths of segments 430 and 440 enable the segments to dynamically support the mitral valve in accordance with the relative motion of the anteromedial and posterolateral leaflets. Typically, segments 430 and 440 each have a diameter L3 of between about 2.0 mm and about 4.0 mm, typically between about 2.5 mm and about 3.5 mm.

Typically, segments 430 and 440 are each shaped to define a lateral wall that has at least one flexible hollow lumen configured for sliding advancement of at least one control wire therethrough. As shown, a first control wire 480 and a second control wire 490 are disposed within both the first and second segments 430 and 440. Typically, wires 480 and 490 function to position and adjust a relative disposition and configuration of segments 430 and 440 with respect to a configuration of annulus 40 of valve 30. Such functions of wires 480 and 490 are described hereinbelow. As such, a diameter of control wires 480 and 490 (e.g., between about 0.2 mm and about 0.4 mm, typically, between 0.25 mm and 0.3 mm) provides the wires with the strength to control structure 408. Typically, control wires 480 and 490 provide a pulling and/or pushing force to segments 430 and 440.

Control wires 480 and 490 comprise a flexible, resilient, and superelastic material, e.g., nitinol, polyester, ePTFE, stainless steel, or cobalt chrome, and are configured to reside chronically within structure 100. In some embodiments, control wires 480 and 490 comprise a braided polyester suture (e.g., Ticron). In some embodiments, control wires 480 and 490 are coated with polytetrafluoroethylene (PTFE). In some embodiments, control wires 480 and 490 each comprise a plurality of wires that are intertwined to form a rope structure.

In some embodiments, first and second control tubes are disposed within both the first and second segments. Typically, the first and second control tubes are configured to function similarly to control wires 480 and 490 described herein.

Typically, each segment 430 and 440 comprises a plurality of compressible subunits 450 and a plurality of anchor mounts 461 which are disposed alternately with respect to one another. It is to be noted, however, that segments 430 and 440 may each comprise a single elongate structure comprising compressible material and do not comprise anchor mounts 461.

Typically, each anchor mount 461 is shaped to define a lateral wall that is shaped to provide a first portion 464 and a second portion 466 generally at opposite sites of mount 461 when viewed in cross-section (e.g., at 12 o'clock and 6 o'clock). Anchor mounts 461 of annuloplasty structure 408 each comprise at least one channel 460. Channel 460 is configured to extend from first portion 464, through the given segment, to second portion 466. A respective flexible and longitudinal guide member 470 is coupled, e.g., welded, looped through, or soldered, at a distal end thereof to a portion of lateral wall 462 of mount 461 and is used to facilitate anchoring of annuloplasty structure 408 to the annulus of the patient, as will be described hereinbelow.

It is to be noted that although anchor mount 461 is shaped to define channel 460 by way of illustration and not limitation. For example, anchor mount 461 may comprise any one of the anchor mounts described herein with reference to FIGS. 1, 3, 4, 5A, 5C, 8, 9, and 10. It is to be noted that a respective anchor channel 1200 described in FIG. 11 may be used in combination with one or more anchor mounts 461.

Typically, guide member 470 is configured to facilitate guiding of an anchoring system toward channel 460 (as will be described hereinbelow). Typically, guide member 470 comprises a flexible, superelastic metal wire, e.g., nitinol or PTFE. In some embodiments, guide member 470 comprises a fiber, e.g., nylon, polypropylene, Kevlar, Teflon, or polyester. Typically, each guide member 470 has a diameter of between about 0.05 mm and about 0.3 mm, e.g., 0.1 mm. Prior to advancing segments 430 and 440 into the left atrium of the patient, advancement catheter 410 is preloaded with segments 430 and 440, with control wires 480 and 490, with guide members 470, and with a multilumen catheter 420 which is disposed proximally to segments 430 and 440. Thus, segments 430 and 440 are simultaneously conveyed toward heart 20, during a single transcatheter advancement. Typically, advancement catheter 410 comprises a 12 F catheter, although other sizes may be appropriate depending on the size of catheter 404.

In some embodiments of the present invention, multilumen catheter 420 is shaped to provide a primary lumen and at least one secondary lumen. Typically, multilumen catheter 420 is configured to advance therethrough and into the left atrium an anchor coupled to an anchor-advancement structure, e.g., a tube or a rod. In some embodiments, the multilumen catheter is disposed proximally to the annuloplasty structure and is configured to push the segments through the advancement catheter.

Figure 17I:
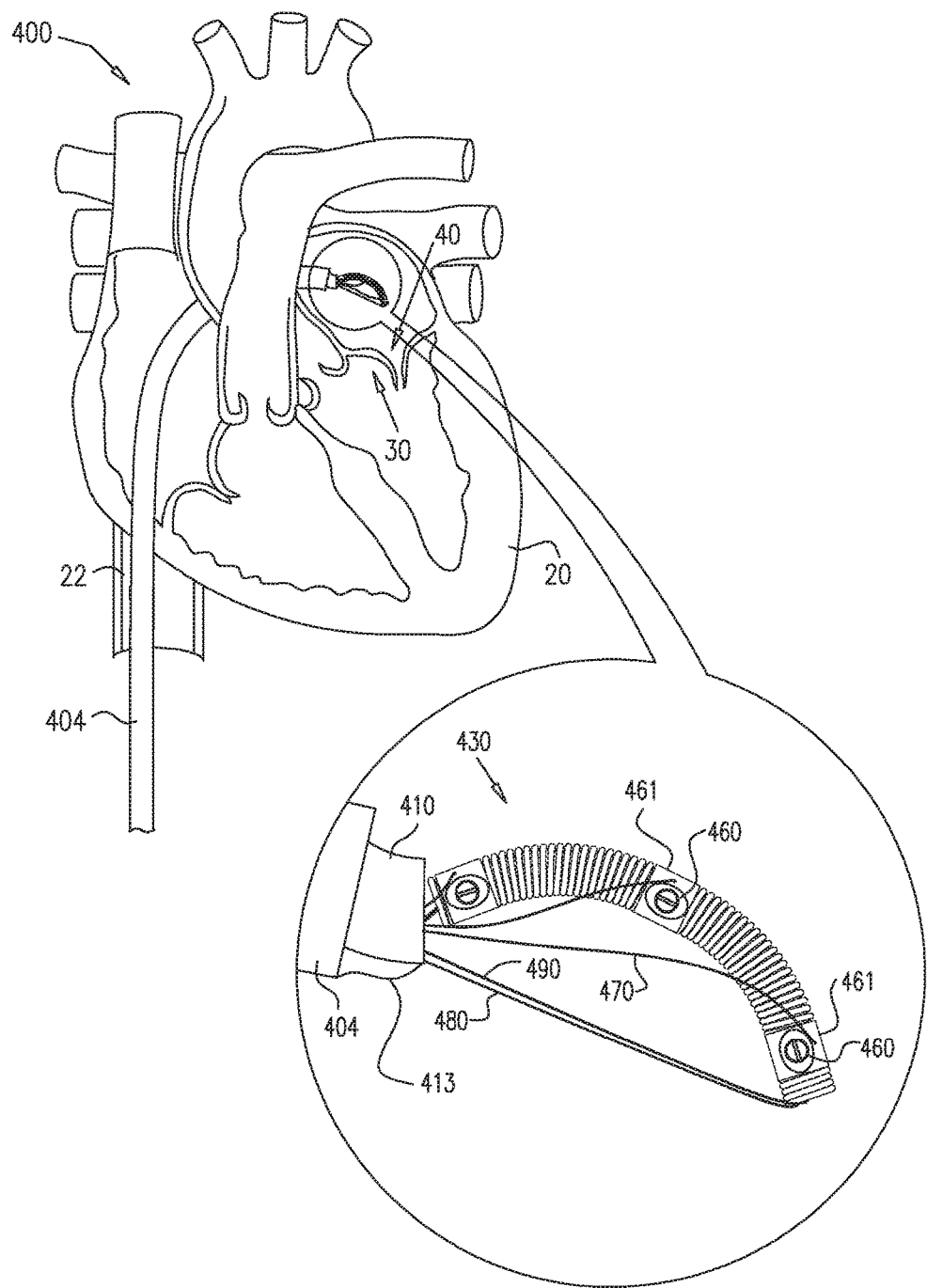

FIGS. 17H-I show deployment of first segment 430 of the segmented annuloplasty ring, in accordance with an embodiment of the present invention. Segments 430 and 440 are disposed in a linear configuration within advancement catheter 410 when catheter 410 is advanced within catheter 404 and initially enters the left atrium. As shown in FIG. 17H, a distal end of catheter 410 emerges from within catheter 404. Segment 430 maintains its linear configuration as it is initially pushed from within catheter 410.

Anchor mount 461 is coupled to a bar 710, as described hereinabove with reference to FIG. 11. It is to be noted that anchor mount 461 is coupled to bar 710 by way of illustration and not limitation. For example, anchor mount 461 may not be coupled to bar 710, as described hereinabove. Typically, bar 710 is disposed within channel 460 angularly, e.g., substantially perpendicular, with respect to an axis 477 (as shown in FIG. 17G) of channel 460, i.e., the axis that is transverse with respect to the longitudinal axis of structure 408, and substantially parallel to the longitudinal axis of annuloplasty structure 408.

Typically, first and second segments 430 and 440 of structure 408 are ultimately made to assume a somewhat round configuration that resembles an annuloplasty ring in structure and function.

As shown in FIG. 17I, control wires 480 and 490 are tightly pulled proximally, applying a force to segment 430 and compressing segment 430 so that it is made to assume a curved configuration. The curved configuration is thus achieved as compressible subunits 450 are compressed in response to the pulling of control wires 480 and 490. Typically, compressible subunits 450 are compressed generally in parallel with the longitudinal axis of segment 430. Such a curved configuration minimizes the possibility for segment 430 to prematurely contact walls of heart 20: (1) during deployment of system 400 within the left atrium, and (2) prior to positioning segments 430 and 440 along annulus 40.

It is to be noted that in some embodiments, segments 430 and 440 of annuloplasty structure 408 comprise a shape-memory alloy, e.g., nitinol. In some embodiments, segments 430 and 440 are introduced within catheter 410 in a straight configuration, and are each biased to assume a generally semi-circular configuration once expanded from within catheter 410. Annuloplasty structure 408 thus assumes a somewhat round configuration typically independently of the application of a proximal force to control wires 480 and 490. In such an embodiment, control wires 480 and 490 are used instead to expand the segments by separating at least a part of segment 430 from at least a part of segment 440.

FIG. 17J is a schematic illustration of system 400 comprising annuloplasty structure 408 and multilumen catheter 420, in accordance with an embodiment of the present invention. Each control wire 480 and 490 is coupled to a respective adjustment wire 482 and 492 by way of illustration and not limitation. Adjustment wires 482 and 492 are configured to contribute to adjusting a relative disposition of segments 430 and 440 once inside the left atrium of heart 20. The functions of wires 482 and 492 are described in more detail hereinbelow.

Typically, multilumen catheter 420 is shaped to define a primary lumen 426 and secondary lumens 422 and 424. The distal end of each guide member 470 is coupled to a respective anchor mount 461 and the proximal end of each guide member 470 is manipulated or controlled from outside the body of the patient proximally to catheter 410, while a majority of the remaining portion of guide member 470 (i.e., the portion of guide member 470 disposed between the proximal and distal ends thereof) is disposed within primary lumen 426.

In some embodiments, multilumen catheter 420 comprises a plurality of secondary lumens for passage of guide members 470 therethrough. In some embodiments, multilumen catheter 420 provides a respective lumen for each guide member 470. In such an embodiment, catheter 420 prevents tangling of guide members 470 as they are disposed therein. In some embodiments, two or more guide members 470 may be disposed within a single secondary lumen of multilumen catheter 420.

In some embodiments, a handle assembly (not shown) is coupled to a proximal end of catheter 410. The handle assembly may be disposable. Respective proximal ends of guide members 470 are accessible and controllable from the handle assembly. For example, a respective proximal end of each guide member 470 may be coupled to a respective switch which independently controls the guide member. Additionally, respective ends of control wires 480 and 490 are accessible and controllable from the handle assembly. Further additionally, a proximal end of lumen 426 and of catheter 421 disposed therein are accessible from the handle assembly in order to advance an anchor through catheter 421 and toward the annuloplasty structure (as will be described hereinbelow).

Each guide member 470 is reversibly coupled to a flexible, steerable catheter 421 which is disposed within primary lumen 426 of multilumen catheter 420. In some embodiments, a distal portion of each guide member 470 is disposed alongside an external surface of at least a portion, e.g., a distal portion, of catheter 421, e.g., typically, when catheter 421 is pushed distally from within multilumen catheter 420. Catheter 421 is steerable by guide members 470 in response to a pulling force applied to a respective one of guide members 470 (as will be described hereinbelow). Catheter 421 is shaped to define a lumen configured for passage therethrough of an anchor coupled to an anchor advancement system. Catheter 421 is typically steered toward a given anchor mount 461 in response to the pulling of a given guide member 470 attached thereto. Catheter 421 comprises a tapered distal end 429 which is positioned within channel 460 of anchor mount 461. Once end 429 is positioned within channel 460, the anchor disposed within catheter 421 is advanced therefrom distally toward the annulus. Since, a respective anchor or anchoring structure is advanced through the lumen of catheter 421, the lumen of catheter 421 typically has a diameter D7 of between about 1.0 mm to about 4.0 mm (e.g., 2.0 mm). Diameter D7 of catheter 421 allows passage therethrough of at least one anchor at a given time.

Typically, once segments 430 and 440 are initially pushed from within catheter 410, and prior to pushing of steerable catheter 421 from within multilumen catheter 420, one or more guide members 470 functions to position and adjust a relative disposition and configuration of segments 430 and 440 with respect to a configuration of annulus 40 of valve 30. For example, pulling on one or more guide members 470 may lift proximally from the annulus a portion of the segment to which it is coupled, while the remaining portions of the segment are disposed in a spatial orientation that is distal with respect to the portion of the segment being raised.

Typically, in order to accommodate for the combined diameters of catheter 421 and the plurality of guide members 470, primary lumen 426 of multilumen catheter 420 has a diameter D1 of between 1.2 mm and 4.5 mm, e.g., 2.5 mm.

Catheter 421 comprises an external ring 427 disposed proximally to distal end 429 and facilitates coupling of respective distal portions of guide members 470 to the external surface of catheter 421. As shown in the cross-section of ring 427, ring 427 is shaped to define a plurality of lumens 431 for passage therethrough of a respective one of guide members 470. In such an embodiment, guide members 470 are prevented from being tangled together. In some embodiments, two or more guide members 470 pass through a single lumen 431. In such an embodiment, lumen 431 may be circular, oval, or any other suitable shape. It is to be noted that the size and shape of lumen 431 are shown by way of illustration and not limitation and that the size and shape of lumens 431 may be larger than they appear in FIG. 17J. Typically, ring 427 is allowed to rotate with respect to the longitudinal axis of catheter 421. Such freedom of movement of ring 427 with respect to catheter 421 facilitates unobstructed steering of catheter 421 in response to pulling of a given longitudinal guide member 470. Additionally, the freedom of movement reduces any resistance in pulling of the given guide member 470.

First and second portions of control wire 490 and a portion of adjustment wire 482 are disposed within secondary lumen 422 (as shown) of multilumen catheter 420, while first and second portions of control wire 480 and a portion of adjustment wire 492 are disposed within secondary lumen 424 (as shown) of multilumen catheter 420. Multilumen catheter 420 separates and isolates control wire 480 from control wire 490 and separates and isolates adjustment wire 482 from adjustment wire 492, thereby enabling the physician to distinguish between each of control wires 480 and 490 and between adjustment wires 482 and 492. Thus, catheter 420 helps facilitate independent control by the physician of each of the wires which ultimately determine the relative positioning of structure 408 within the left atrium of heart 20.

In some embodiments, control wires 480 and 490 and adjustment wires 482 and 492 may be disposed within in the same secondary lumen of multilumen catheter 420 and are coupled to the handle (described hereinabove) in such a manner so as to prevent tangling and to allow proper control of each of the wires.

Typically, steerable catheter 421 pushes segments 430 and 440 distally within advancement catheter 410.

Figure 18A:
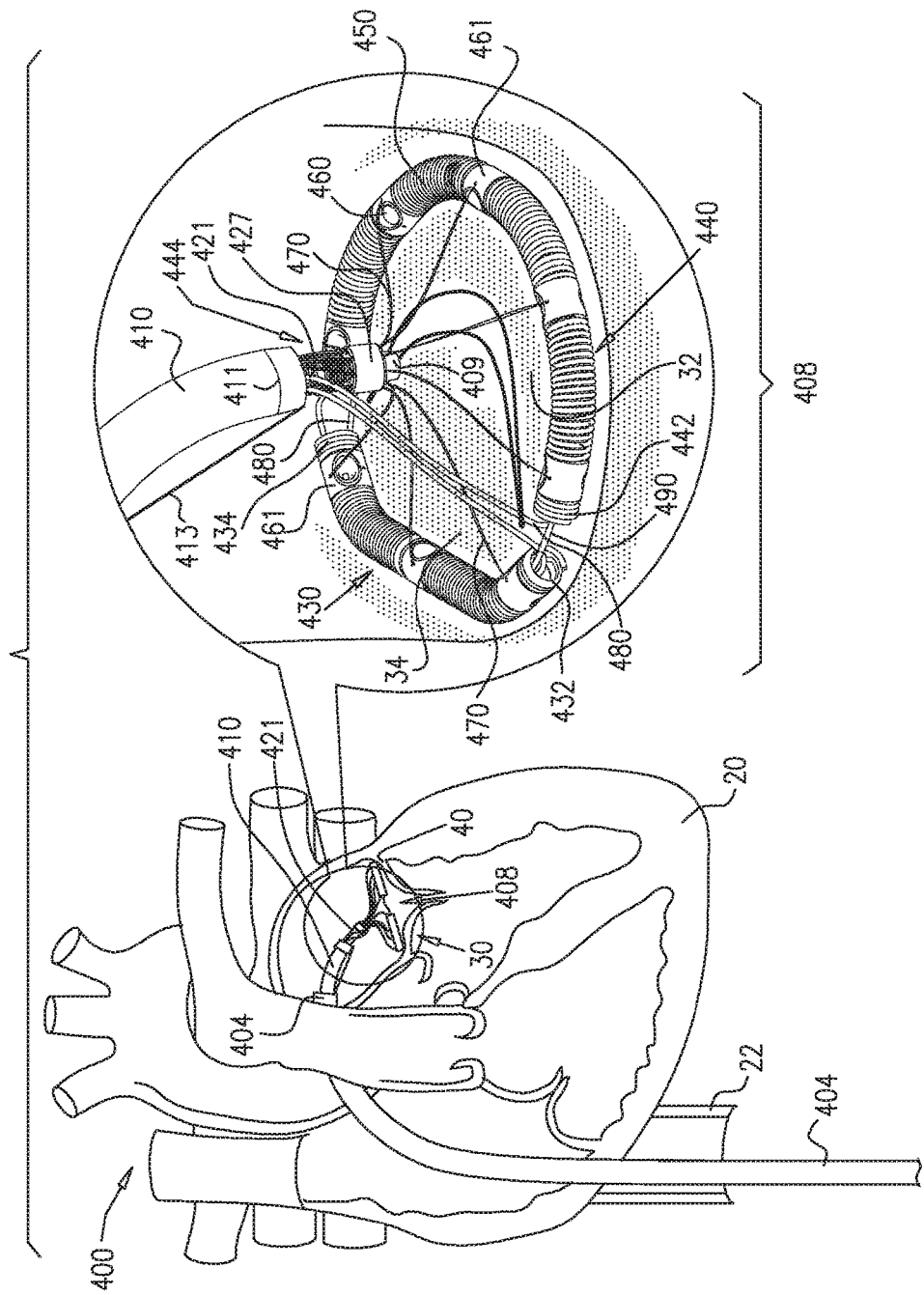
FIGS. 18A-B are schematic illustrations of the deployment of two annuloplasty ring segments of the system toward the annulus of the patient, in accordance with an embodiment of the present invention.
Figure 18B:
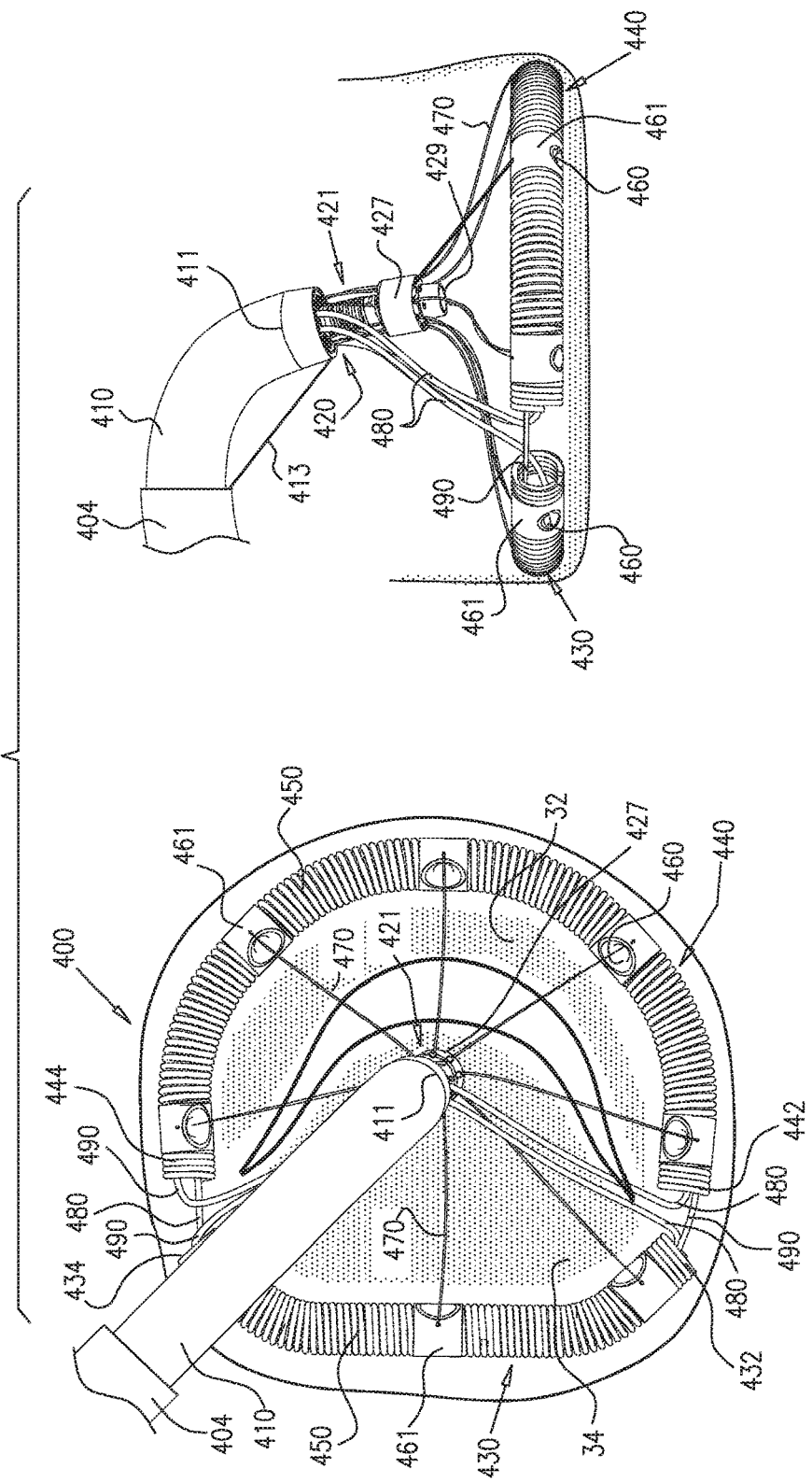

FIGS. 18A-B are schematic perspective views of system 400 comprising annuloplasty structure 408 which is coupled to annulus 40 of mitral valve 30, in accordance with an embodiment of the present invention. As shown, guide members 470 are coupled at respective distal ends thereof to respective anchor mounts 461 of annuloplasty structure 408. Respective portions of guide members 470 pass through ring 427 and alongside catheter 421, and ultimately through advancement catheter 410. As shown, advancement catheter 410 comprises a radiopaque marking 411 at a distal portion thereof, and marking 411 helps the physician locate the distal end of catheter 410 with respect to structure 408. In some embodiments, and during initial positioning of the distal end of advancement catheter 410 within the left atrium of heart 20, at least one steering wire 413, e.g., one as shown, is coupled at a distal end thereof to a distal portion of catheter 410. A proximal end of steering wire 413 is disposed at a site outside the body of the patient, enabling the physician to steer the distal end of catheter 410.

Control wires 480 and 490 are shown disposed within at least one hollow lumen of both first and second segments 430 and 440 of annuloplasty structure 408, thereby coupling the segments. In some embodiments, each of segments 430 and 440 is shaped to provide a first lumen configured for sliding advancement therethrough of wire 480, and a second lumen configured for sliding advancement of wire 490 (configuration not shown). First and second portions of control wire 480 emerge from within segments 430 and 440 at respective first ends 432 and 442 of segments 430 and 440. The first and second portions of control wire 480 are disposed within secondary lumen 424 of multilumen catheter 420 such that first and second ends of wire 480 are exposed and controllable from outside the body of the patient. Similarly, first and second portions of control wire 490 emerge from within segments 430 and 440 at respective second ends 434 and 444 of segment 430 and 440. The first and second portions of control wire 490 are disposed within secondary lumen 422 of multilumen catheter 420, such that first and second ends of wire 490 are exposed and controllable from outside the body of the patient.

In some embodiments, multilumen catheter 420 is shaped to provide additional secondary lumens (not shown for clarity of illustration). Typically, the additional secondary lumens are provided for passage of supplementary instruments, e.g., for suction and/or irrigation, therethrough and into the left atrium of the patient.

Following the deployment, segments 430 and 440 are expanded by being separated in accordance with the shape of the dilated annulus. In some embodiments, adjustment wires 482 and 492, shown in FIG. 17J, help facilitate the separation of segments 430 and 440. Techniques for use with annuloplasty structure 408 and adjustment wires (referred to hereinabove as 482 and 492) may be used in combination with techniques described in U.S. Provisional Application 61/001,013 to Gross et al., entitled, "Segmented ring placement," filed Oct. 29, 2007.

The separating of segments 430 and 440 occurs when the physician pushes control wires 480 and 490. In some embodiments, during the pushing of control wires 480 and 490, the physician simultaneously pushes while pushing the adjustment wires which provide an auxiliary pushing force which helps expand segments 430 and 440. Such pushing of the control wires feeds greater portions of control wires 480 and 490 into segments 430 and 440. The relaxed configuration of control wires 480 and 490 is shown in FIGS. 18A-B. Typically, segments 430 and 440 expand laterally as increasing lengths of control wires 480 and 490 are pushed and fed into segments 430 and 440.

Control wires 480 and 490 enable the physician to independently control a relative disposition of second ends 434 and 444 and first ends 432 and 442 of segments 430 and 440, respectively. For example, distal pushing of the first and second ends of control wire 480 distances second ends 434 and 444 of segments 430 and 440, respectively. Similarly, distal pushing of the first and second ends of control wire 490 distances first ends 432 and 442 of segments 430 and 440, respectively. It is to be noted that the use of two discrete control wires allows for independent control of the distance that separates first ends 432 and 442 and the distance that separates second ends 434 and 444 of segments 430 and 440.

Additionally, pulling on respective ends of control wires 480 and 490 shapes segments 430 and 440 in accordance with the curved structural conformation of annulus 40 at a given site destined for anchoring of a respective one of the segments thereto. For example, pulling on a first end of control wire 490 and on a first end of control wire 480 curves segment 430 by drawing together second end 432 and first end 434, respectively, of segment 430. Thus, segment 430 is compressed at least in part, and is made to assume a shape according to the curvature of the annulus at the base of the anteromedial leaflet.

In some embodiments of the present invention, structure 408 is optionally rotated as appropriate about an axis of annulus 40. Guided by fluoroscopy and/or echocardiography, the physician assesses the relative disposition of segments 430 and 440 with respect to annulus 40 of heart 20. Multilumen catheter 420 is configured to be rotatable 360 degrees about a longitudinal axis thereof. By rotating multilumen catheter 420, the segments are positioned properly with respect to the annulus. That is, segment 440 is positioned above a portion of annulus 40 at the base of the posterolateral leaflet, while segment 430 is positioned above a portion of annulus 40 at the base of the anteromedial leaflet.

Following the deployment and expansion of annuloplasty structure 408, catheter 421 is pushed distally from within advancement catheter 410, thereby exposing a distal end of steerable catheter 421. Additionally, in some embodiments, multilumen catheter 420 is retracted slightly within advancement catheter 410. Retracting multilumen catheter 420 frees the lumen of the distal end of catheter 410, thereby restoring flexibility to the distal end of catheter 410 and enabling proper steering thereof, e.g., in response to pulling steering wire 413. Structure 408 is pushed toward annulus 40 by pushing on both catheter 410 and on wires 480 and 490. Additionally, the structure is properly aligned with annulus 40 by steering and/or rotating the distal tip of catheter 410, and by steering and/or rotating the distal tip of multilumen catheter 420.

As shown, segment 440 is aligned against the base of posterolateral leaflet 32 at the annulus, and segment 430 is aligned against the base of anteromedial leaflet 34 at the annulus. Segments 430 and 440 are shown prior to anchoring thereof to annulus 40.

Figure 19A:
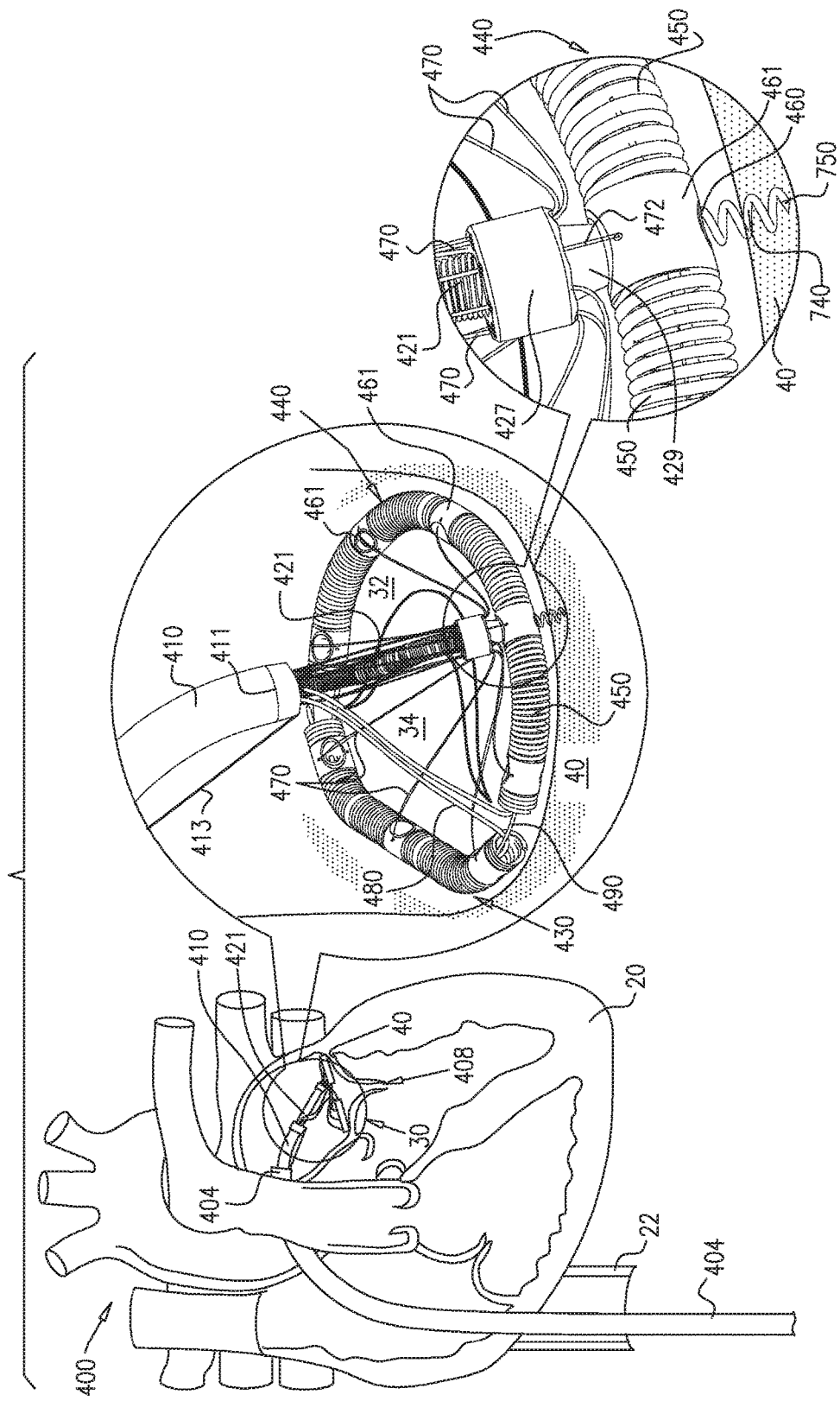

Reference is now made to FIG. 19A, which is a schematic illustration of catheter 421 of system 400 being steered toward a given anchor mount 461 of structure 408 and facilitating anchoring of structure 408 to annulus 40, in accordance with an embodiment of the present invention.

Once advancement catheter 410 and multilumen catheter 420 have positioned segments 430 and 440 in their proper orientation with respect to annulus 40, steerable catheter 421 is pushed from within advancement catheter 410, thereby exposing a distal portion of steerable catheter 421. The physician pulls on the proximal end of a first guide member 472 of the plurality of guide members 470. In response to the pulling, catheter 421 is steered toward the distal end of guide member 472, and thereby toward segment 440 and toward an anchor mount 461 which is coupled to the distal end of guide member 472. As the physician pulls the proximal end of guide member 472, he releases the respective proximal ends of guide members 470 not being pulled in order to provide slack to members 470 such that they do not resist movement of catheter 421 toward anchor mount 461. In conjunction with the steering of catheter 421, the physician pushes on a proximal end of catheter 421 so as to push catheter 421 distally toward the location along segment 440 to which it is being steered. As the distal end of catheter 421 is steered toward anchor mount 461, portions of members 470 that are coupled to ring 427 of catheter 421 are also drawn toward anchor mount 461. When the distal end of catheter 421 has been sufficiently steered toward anchor mount 461, catheter 421 is further pushed distally such that distal tapered end 429 of catheter 421 slides partially within channel 460 of anchor mount 461.

At a site proximal to catheter 404, and outside the body of the patient, the physician slides a first anchoring system through the lumen of catheter 421. The anchor is advanced via the anchoring system through the lumen of catheter 421 toward structure 408, through a lumen of distal tapered end 429, and subsequently inserted, in part, into channel 460 of anchor mount 461. For embodiments in which catheter 410 is coupled to the handle assembly, as described hereinabove, the anchor is introduced within the lumen of catheter 421 from a proximal opening within the handle which provides an access to the lumen of catheter 421. In some embodiments, the handle comprises a hemostatic valve at the opening. The anchor of the anchoring system is ultimately further advanced through tissue of annulus 40. As shown, the anchor of the anchoring system comprises a helical anchor 740 having a pointed distal tip 750 configured to puncture tissue of annulus 40. Anchor 740 is corkscrewed into tissue of annulus 40. It is to be noted that helical anchor 740 is shown by way of illustration and not limitation. For example, any anchor described herein as well as any suitable tissue anchor known in the art may be passed through the lumen of catheter 421 and used to anchor structure 408 to annulus 40 of mitral valve 30.

Figure 19C:
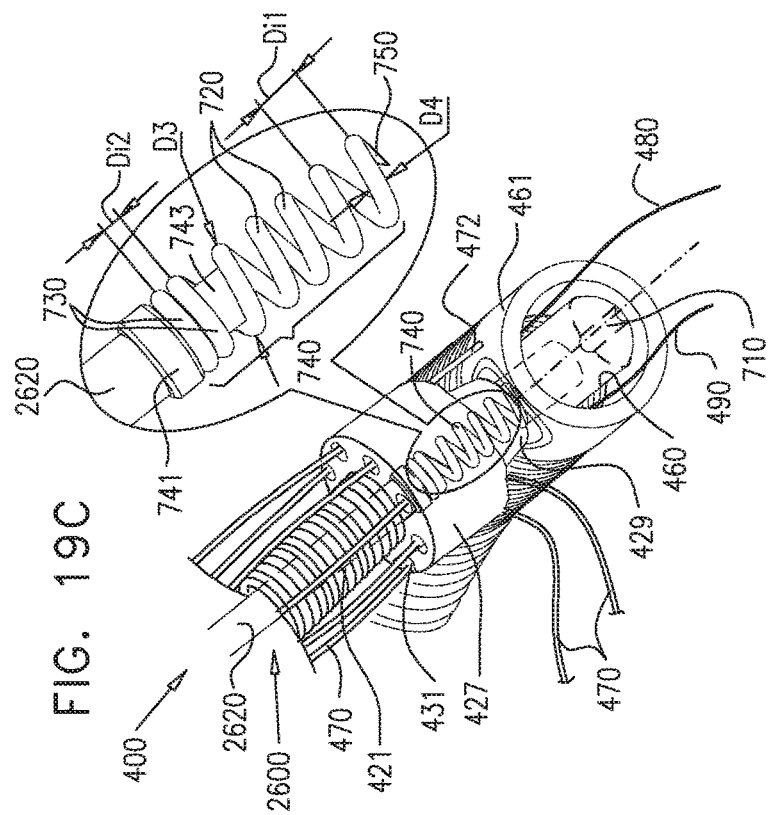
Figure 19B:
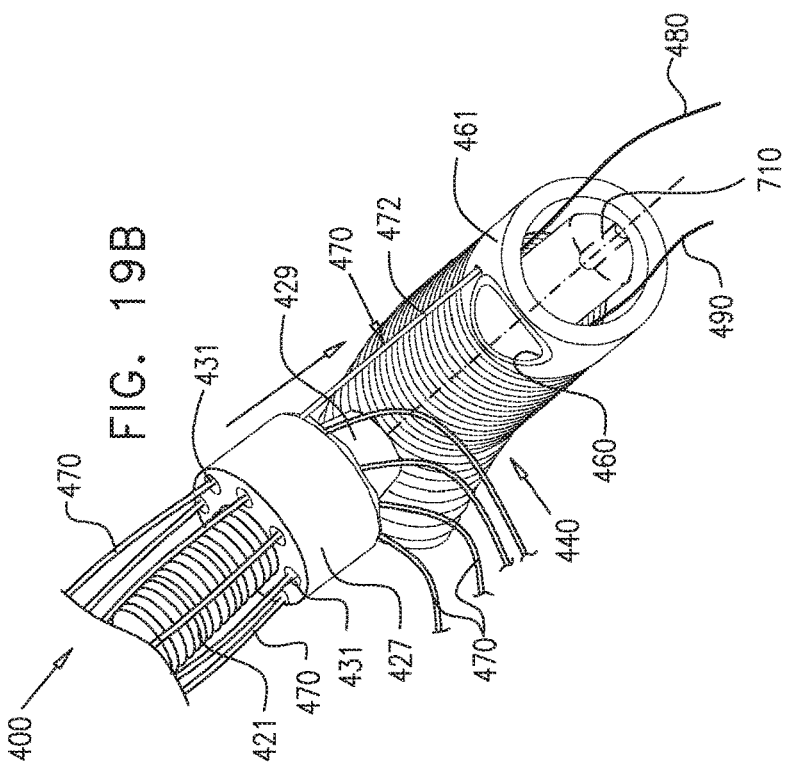

FIG. 19B shows catheter 421 being advanced toward anchor mount 461 of segment 440, in accordance with an embodiment of the present invention. Guide member 472 is pulled such that it is made taught and enables steering of catheter 421 toward anchor mount 461 to which guide member 472 is coupled. Guide members 470 that are not being pulled are shown as being in a relaxed, passive, slackened state. Typically, at least a distal portion of catheter 421 comprises a plurality of compressible subunits, e.g., accordion- or bellow-shaped structures, a braided mesh, or a plurality of coils, which enable steering and maneuvering of catheter 421 in the direction of the guide member 470 being pulled.

In some embodiments, once catheter 421 has been steered toward anchor mount 461 in response to pulling guide member 472, guide member 472 is further pulled and catheter 421 is pushed distally, in the direction as indicated by the arrow, in order to advance distal tapered end 429 of catheter 421 toward channel 460 of anchor mount 461.

Reference is now made to FIGS. 19C-E, which are schematic illustrations of an anchoring system 2600, in accordance with an embodiment of the present invention. FIG. 19C shows a bar 710 disposed within channel 460. Typically, bar 710 is disposed angularly with respect to an axis of channel 460, and at the base of the channel. It is to be noted that bar 710 is disposed substantially in parallel with the longitudinal axis of segment 440 (or segment 430) by way of illustration and not limitation. For example, bar 710 may be disposed perpendicularly to the axis of segment 440, i.e., the axis which runs from the first and second openings in the lateral wall of segment 440 between which channel 460 extends.

Anchoring system 2600 comprising an anchor advancement structure 2620, e.g., a rod or a tube, which is reversibly coupled to anchor 740 via an applicator 741. Typically, anchor 740 comprises a helical element whose proximal end is tightly wrapped around a distal projection 743 of applicator 741 coupled to a distal end of advancement structure 2620. In some embodiments, anchor 740 has a tendency to expand radially. By being advanced through the lumen of catheter 421, radial expansion of anchor 740 is inhibited as anchor 740 is advanced therein. Anchoring system 2600 is advanced partially within channel 460, as shown in FIG. 19C.

It is to be noted that applicator 741 is shown by way of illustration and not limitation, and that that scope of the present invention includes the use of anchor 740 independently of applicator 741. In such an embodiment, the proximal end of anchor 740 is tightly wrapped around a distal end of advancement structure 2620 and is decoupled therefrom in a manner as will be described hereinbelow with reference to the decoupling of anchor 740 from projection 743 of applicator 741.

Reference is now made to FIG. 19D. Anchoring of anchor 740 begins when the physician rotates advancement structure 2620 about a longitudinal axis thereof, as indicated by the arrow. Such rotation corkscrews a distal portion of the helical element around and beyond bar 710 and subsequently into annulus 40 of the patient.

Reference is again made to FIG. 19C. As described hereinabove, channel 460 has a diameter between about 0.8 mm and 2.5 mm, typically 1.8 mm. Diameter is thus sized in order to enable passage of anchor 740 through channel 460. Typically, anchor 740 configured for passage through channel 460 has a diameter D3 of between about 0.5 mm and 2.4 mm, e.g., 1.6 mm. Typically, each coil of the coiled, helical element has a diameter D4 of between about 0.2 mm and 0.6 mm, e.g., 0.3 mm.

Typically, the helical element of anchor 740 is shaped to define at least two adjacent distal rotational subunits 720 and at least two adjacent proximal rotational subunits 730. A distance Di1 (e.g., between about 0.3 mm and about 2.0 mm) between adjacent distal rotational subunits 720 is typically greater than a distance Di2 (e.g., between about 0 mm and about 0.6 mm) between adjacent proximal rotational subunits 730. Typically, a diameter of bar 710 is less than distance Di1 and greater than distance Di2. Distance Di1 enables distal rotational subunits 720 to be corkscrewed around and beyond bar 710 and subsequently into annulus 40 of the patient. Distance Di2 is typically less than a diameter of bar 710, and therefore restricts proximal rotational subunits 730 from being corkscrewed fully around bar 710 and into annulus 40.

During an attempt to corkscrew proximal rotational subunits 730 around bar 710, bar 710 restricts the rotation of subunits 730 therearound and applies a counterforce to a torque applied by rotation of structure 2620. The counterforce applied by bar 710 expands proximal subunits 730 radially such that subunits 730 are no longer wrapped tightly around the projection 743 of applicator 741. Following the expansion of subunits 730, anchor 740 is released from projection 743 of applicator 741, typically by pulling on structure 2620 while continuing to apply a rotational, helix-expanding force to proximal subunits 730. Structure 2620 and applicator 741 coupled thereto is then pulled proximally within the lumen of catheter 421 and extracted from within the body of the patient, as shown in FIG. 19E. During the removal of structure 2620 from heart 20, guide member 470 typically remains within system 400, and it is later decoupled from anchor mount 461.

In some embodiments of the present invention, a few coils of the helical element are wrapped around projection 743, while the remaining coils extend distally from a distal end of projection 743. Typically, a smaller number of coils are wrapped around projection 743 than the number of coils that extend distally from the distal end of projection 743 and are not wrapped around projection 743. As shown by way of illustration and not limitation, three coils are wrapped around projection 743, while four coils are disposed distally to the distal end of projection 743. The coils wrapped around projection 743 generally provide enough frictional force to maintain their position around projection 743 of applicator 741.

In some embodiments, a protrusion (not shown) is typically disposed along projection 743 adjacent to the proximal-most tip of the helical element of anchor 740. During initial implantation of the anchor within annulus 40 of the patient (i.e., as structure 2620 is rotated), the protrusion applies a circumferentially-directed pushing force to the proximal-most tip of the helical element. By pushing on the proximal-most tip of the helical element, the protrusion typically adds to the frictional force described above, in order to rotate anchor 740. One or both of these forces enable a distal end of anchor 740 to puncture annulus 40. As anchor 740 is advanced into tissue of annulus 40, a portion of proximal rotational subunits of anchor 740 slides distally along projection 743 and away from the protrusion.

Following implantation within annulus 40 of distal rotational subunits 720, the distal end of projection 743 is impeded by bar 710. The physician continues to rotate structure 2620 such that the proximal-most tip of anchor 740 continues to slide distally from the protrusion while the entire anchor 740 continues to be advanced distally within tissue of annulus 40.

During the continued rotation of structure 2620, fewer rotational subunits are wrapped around projection 743, thereby reducing friction between anchor 740 and projection 743. After a sufficient number of rotations, the minimal friction between anchor 740 and projection 743 enables the physician to pull on structure 2620 in order to applicator 741 from anchor 740.

As shown in FIG. 19E, once anchor 740 has been implanted within tissue of the annulus, catheter 421 is moved away from anchor mount 461 responsively to the pulling on a different guide member 470, as will be described hereinbelow, and to the proximal retracting of catheter 421.

Figure 20B:
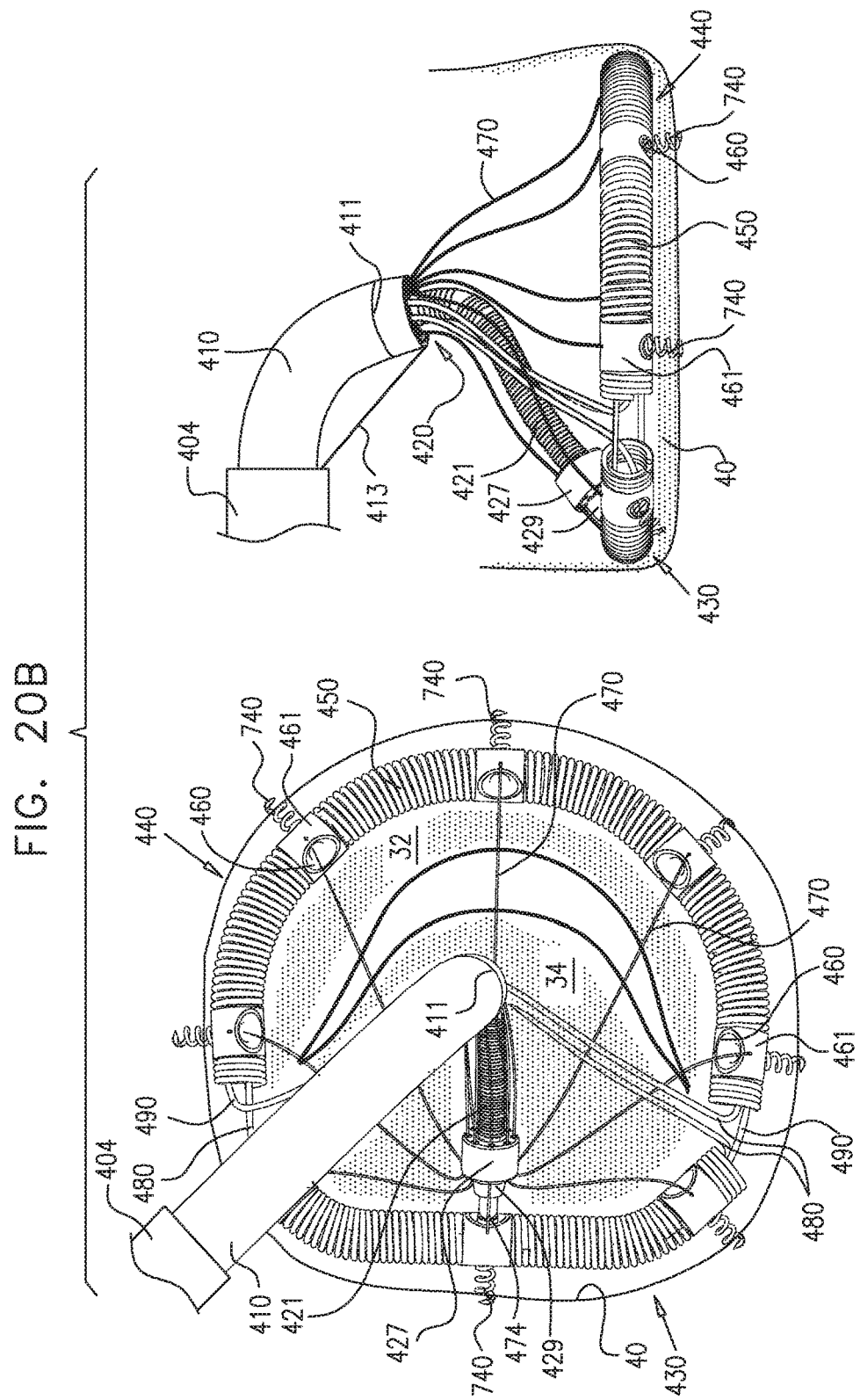

Reference is now made to FIGS. 20A-B, which are perspective schematic illustrations of catheter 421 of system 400 anchoring annuloplasty structure 408 to annulus 40, in accordance with respective embodiments of the present invention. Catheter 421 is advanced toward anchor mount 461 of segment 430 in order to anchor segment 430 to annulus 40 at the base of anteromedial leaflet 34. A second guide member 474 of the plurality of guide members 470 is pulled in order to steer catheter 421 toward anchor mount 461 coupled to guide member 474. Once distal tapered end 429 is advanced partially within channel 460 of anchor mount 461, an anchoring system advances an anchor through the lumen of catheter 421, through the lumen of distal tapered end 429, through channel 460, and subsequently into tissue of the annulus of the patient, as described hereinabove with reference to FIG. 19A-E.

As guide member 474 is pulled, the remaining guide members 470 that are not being pulled are released, in order to provide catheter 421 freedom to move toward guide member 474 and anchor mount 461 coupled thereto. As shown in FIG. 20A, portions of guide members 470 not being pulled and that are disposed distally to and in the vicinity of ring 427 are pulled toward anchor mount 461 coupled to guide member 470. In conjunction with the steering of catheter 421, catheter 421 is pushed distally in order to be advanced distally toward the anchor mount to which it is being steered.

FIG. 20B shows segments 430 and 440 anchored to annulus 40. A respective anchor 740 has been passed through each channel 460 of each anchor mount 461. In order to anchor structure 408 to annulus 40, catheter 421 is steered toward each anchor mount 461 by pulling on the respective guide member 470 coupled to each anchor mount. When distal end 429 of catheter 421 is positioned at a given anchor mount, an anchor is passed through the lumen of catheter 421 from a site outside the body of the patient and is advanced through catheter 421 by an anchor advancement system.

Catheter 421 may be steered toward the anchor mounts in any sequence thereof. For example, by pulling on a guide member coupled to an anchor mount of segment 440, catheter 421 may be steered first toward segment 440 in order to anchor structure 408 to annulus 40 at the base of posterolateral leaflet 32. The physician may then want to anchor structure 408 to annulus 40 at the base of anteromedial leaflet 34 by pulling on a guide wire coupled to an anchor mount of segment 430. In some embodiments, each guide member 470 is colorized in order to enable the physician to determine toward which anchor mount, and thus, to which location along annulus 40, catheter 421 is being steered in response to the pulling of a given guide member.

For some embodiments in which system 400 comprises a handle assembly coupled to advancement catheter 410, as described hereinabove, the proximal ends of each guide member 470 are pulled and released by at least one switch mechanism coupled to the handle. In some embodiments, each guide member 470 is controlled by a respective switch, and each switch is labeled with a suitable label indicating a position along structure 408 to which the guide member is coupled. For example, guide members 470 coupled to segment 440 may be labeled $P_1$ to $P_n$, and guide members 470 coupled to segment 430 may be labeled $A_1$ to $A_n$.

In some embodiments, catheter 421 is preloaded with a plurality of anchors, e.g., helical anchors or anchors as shown herein, or any other suitable anchor. When distal end 429 is steered toward each anchor mount 461, a pushing rod pushes on the proximal-most anchor in order to apply a force to the distal-most anchor disposed within the lumen of catheter 421 until the distal-most anchor is pushed through channel 460 of the respective anchor mount 461.

Typically, following anchoring of structure 408 to the annulus by implanting every anchor within the annulus, a cutting means is advanced through catheter 421. Catheter 421 is steered toward each anchor mount 461 (i.e., in a manner as described hereinabove) and the cutting means cuts the respective guide member coupled to each mount toward which catheter 421 is steered. As such, each guide member 470 is decoupled from the respective anchor mount 461.

In some embodiments, catheter 421 is extracted from within the body of the patient, and an overtube comprising a cutting means disposed therein is slid along each one of guide members 470 and toward the respective anchor mount to which the guide member is coupled. The cutting means then cuts the guide member, and the cutting means and the guide member are then extracted from within the body of the patient. Subsequently, the overtube is then reintroduced within the body of the patient by being slid along a second one of the guide members in order to decouple that guide member from the annuloplasty structure.

In some embodiments, once catheter 421 has been steered to a first location of the annuloplasty structure by pulling on a first one of guide members 470, and the anchor advancement structure (a) advances the anchor through catheter 421 and toward the annulus, (b) facilitates anchoring of the annuloplasty structure to the annulus, and (c) is decoupled from the anchor, the anchor advancement structure is extracted from within catheter 421. Subsequently, the cutting means is introduced within catheter 421 and is advanced through catheter 421 toward the anchor mount coupled to the first guide member. The cutting means cuts the guide member coupled to the anchor mount and is then extracted from within catheter 421 together with the cut guide member. Catheter 421 is then steered toward a second location of the annuloplasty structure by pulling on a second guide member 470. A second anchor is advanced to the second location and anchors the annuloplasty structure to the annulus at the second location. Following the anchoring, the second guide member is cut as described hereinabove. As such, each guide member 470 is systematically cut following implanting of the respective anchor in the vicinity of the location along the annuloplasty structure to which the respective guide member is coupled.

In some embodiments, a respective distal portion of each guide member 470 (i.e., a portion of guide member 470 that is proximal to the portion of guide member 470 that is coupled to anchor mount 461) comprises a material configured to dissolve after being exposed within heart 20 of the patient for a period of time, e.g., between 15 minutes and 90 minutes. In such an embodiment, following anchoring of anchors 740 to annulus 40 as described hereinabove, the respective distal portions of each guide member 470 dissolves, thereby decoupling guide member 470 from the respective anchor mount 461. Each guide member 470 is then pulled from its proximal end until its distal end is extracted from within the body of the patient.

In some embodiments, after anchoring annuloplasty structure 408 to annulus 40, one of control wires 480 or 490, e.g., control wire 480, is extracted from within segments 430 and 440 when the physician pulls on a first end of wire 480. Subsequently, the physician replaces control wire 490 with a contracting wire, e.g., a tensile suture, (not shown) by (a) tying a first end of the contracting wire to a first end of wire 490, and then (b) pulling on a second end of wire 490. The physician holds onto a second end of the contracting wire and pulls wire 490 until the first end of the contracting wire has replaced control wire 490 in segments 430 and 440, e.g., until the second end of the contracting wire is once again exposed outside the body of the patient. An intracorporeal portion of the contracting wire remains disposed within both segments 430 and 440. The contracting wire comprises a flexible and/or superelastic material, e.g., nitinol, polyester, ePTFE, PTFE, stainless steel, or cobalt chrome, and is configured to reside chronically within segments 430 and 440. In some embodiments, the contracting wire is coated with polytetrafluoroethylene (PTFE). In some embodiments, the contracting wire comprises a braided polyester suture (e.g., Ticron). Additionally, the contracting wire is configured to withstand cardiac forces and constant motion of segments 430 and 440 that result from the motion of annulus 40. As such, the contracting wire typically has a relatively thick diameter of between about 0.1 mm and about 1.0 mm, typically between about 0.2 mm and about 0.4 mm.

In some embodiments, two contracting wires reside chronically within segments 430 and 440. In such an embodiment, a first tensile suture replaces control wire 480, and a second tensile suture replaces control wire 490. Control wires 480 and 490 are replaced as described hereinabove.

In any embodiment, using tactile feedback, or echocardiography, and optionally in combination with fluoroscopic imaging, first and second ends of the contracting wire(s) are pulled to an extent that is based on (a) the level of dilation of the preoperative mitral valve, and/or (b) real-time monitoring of regurgitation minimization.

Typically, for embodiments in which a contracting wire is used, a lock is advanced around the first and second ends of the contracting wire and secures together the ends of the contracting wire, and thereby secures segments 430 and 440 of annuloplasty structure 408, thereby defining its final configuration within annulus 40 of mitral valve 30. The excess portions of the contracting wire are clipped proximally to the lock and are extracted from the body via catheter 404. Following clipping, first and second clipped ends of the contracting wire remain accessible for future tightening together of segments 430 and 440 upon need therefor. In some embodiments, the first and second ends of the contracting wire are located using fluoroscopy or any other method described herein.

Reference is now made to FIGS. 17G-J, 18A-B, 19A-E, and 20A-B. It is to be noted that two annuloplasty ring segments 430 and 440 are shown by way of illustration and not limitation. For example, annuloplasty structure 408 may comprise only one segment of segments 430 and 440. In some embodiments, annuloplasty structure 408 may comprise one elongate segment having a length of the combined lengths L1 and L2 (shown in FIG. 17H) of segments 430 and 440, respectively, or any other suitable length according to the needs of a given patient, e.g., according to the extent of dilation of the annulus of the mitral valve.

It is to be additionally noted that use of a helical anchor 740 is described herein by way of illustration and not limitation, and that the scope of the present invention includes the use of other apparatus for anchoring annuloplasty structure 408 to annulus 40. For example, anchor 740 may comprise a screw, harpoon, barb, or any other anchoring structure or anchor known in the art. In some embodiments, anchor 740 comprises a wire configured to penetrate annulus 40 in a generally straight configuration and to subsequently assume a curved configuration once inside tissue of annulus 40. It is to be noted that any anchoring structure, anchor and/or anchoring system described herein with reference to FIGS. 1, 4, 5A, 5C, 12, 13A-E, 14A-B, and 15 may be used to anchor structure 408 independently of or in combination with bar 710 shown in FIGS. 19B-E. It is to be noted that anchor mount 461 shown in FIGS. 19A-E may be used independently of or in combination with bar 710. In some embodiments, channel 1200 described hereinabove with reference to FIG. 11 may be used independently of or in combination with anchor mount 461 shown in FIGS. 19A-E. It is to be further noted that anchor mounts 461 shown in FIGS. 17G-J, 18A-B, 19A-E, and 20A-B may comprise any one of anchor mounts 461 shown in FIGS. 3-4, 5A-C, and 8-10.

It is to be further noted that segments 430 and 440 are shown as comprising mounts 461 by way of illustration and not limitation. For example, segments 430 and 440 may each comprise only one elongate compressible subunit 450, and each guide member 470 may be coupled to segments 430 and 440 at any respective suitable location along the compressible subunit 450.

By reducing a circumference of annulus 40, leaflets 32 and 34 are drawn toward one another to prevent recurring dilation of mitral valve 30, restore leaflet coaptation, and reduce mitral regurgitation.

It is to be noted that in some embodiments of the present invention, guide members 470 comprise a screw at a distal end thereof. In such an embodiment, each guide member 470 is screwed in to a respective anchor mount 461. Following the steering of catheter 421 toward the anchor mount and the anchoring of the annuloplasty structure to the annulus of the patient, the guide member is decoupled from the anchor mount by rotating the proximal end of the guide member from outside the body of the patient. The guide member is then extracted from the body of the patient via catheter 404.

It is to be noted that anchor mount 461 shown in FIGS. 1, 3, 4, 5A, 5C, and 8-10 may be used in combination with any of the annuloplasty structures described herein. In some embodiments, a given annuloplasty structure may comprise a plurality of identical anchor mounts 461. In some embodiments, a given annuloplasty structure may comprise a plurality of various types of anchor mounts 461 described herein.

It is to be noted that the scope of the present invention is not limited to minimally-invasive procedures (e.g., transcatheter procedures such as percutaneous or intercostal penetration procedures), and includes applications in which system 400 is applied in invasive procedures such as open-heart surgery.

It is to be noted that the annuloplasty structures described herein may be advanced toward the annulus using a percutaneous approach, a minimally-invasive approach and/or an open-heart approach.

Reference is again made to FIGS. 17A-J, 18A-B, 19A-E, and 20A-B. It is to be noted that system 400 is shown as being used in a percutaneous transcatheter access to the left atrium of the patient by way of illustration and not limitation. It is to be noted that system 400 may be used for anchoring annuloplasty structure 408 to annulus 40 during an open-heart procedure. For example, the left atrium may be exposed following an incision in a wall of heart 20. As mitral valve 30 is exposed, the patient is connected to a cardiopulmonary bypass pump which maintains the circulation of blood and the oxygen content of the patient's body during the exposing of valve 30. Catheter 404 is placed in the left atrium and segments 430 and 440 are pushed from within advancement catheter 410. In some embodiments, segments 430 and 440 are disposed externally to catheter 410 prior to placing catheter 404 in the left atrium. Segments 430 and 440 are then anchored to annulus 40 as described hereinabove. The wall of heart 20 is sutured around catheter 404, typically using a purse stitch, and the patient is disconnected from the cardiopulmonary bypass pump in order to restore function to heart 20. In such an embodiment, the physician is able to reduce the circumference of valve 30 in response to feedback from fluoroscopic and/or ultrasound real-time imaging of the function of valve 30 in a beating heart. Typically, the physician reduces the circumference while viewing the mitral regurgitation in real-time and tightens structure 408 responsively to the extent to which the regurgitation is reduced. For embodiments in which a minimally-invasive approach is used, system 400 may be introduced into the heart either through an intercostal access from the left side of the patient or through an intercostal access from the right side of the patient.

Reference is again made to FIGS. 17A-J, 18A-B, 19A-E, and 20A-B. In some embodiments, a distal end of each guide member 470 may be fixedly coupled to a distal portion of catheter 421, while a distal portion of each guide member 470 (i.e., a portion of guide member 470 proximal to the distal end thereof) is reversibly coupled to respective segments 430 and 440 by being looped within respective portions of segments 430 and 440 that are typically adjacent to channel 460 of each respective anchor mount 461. Such looping of the guide member creates a channel for slidable motion of the guide member. Remaining portions of the respective guide members 470 are disposed (a) within catheter 410 and run proximally alongside catheter 421, or in some embodiments, (b) within respective secondary lumens of multilumen catheter 420. In some embodiments, the remaining portions of guide members 470 are passed through respective channels within ring 427 of catheter 421. It is to be noted that in such an embodiment, catheter 421 may be used independently of ring 427.

In such an embodiment, catheter 421 is steered toward a first location along either segment in response to pulling of a guide member 470 coupled to the segment at the first location (as described hereinabove). As the guide member is pulled, the distal portion of guide member 470 slides within the channel thereby (a) allowing the remaining portions of guide member 470 to be fed proximally within catheter 410, and (b) pulling the distal end of guide member 470, and thereby catheter 421, toward the first location. An anchor is then passed through catheter 421, as described hereinabove, and catheter 421 facilitates anchoring of structure 408 to the annulus at the first location.

Once catheter 421 has facilitated anchoring of annuloplasty structure 408 to the annulus using a plurality of anchors, catheter 421 is extracted from within the body of the patient by being pulled proximally. As catheter 421 is pulled, the physician releases the proximal ends of guide members 470, and guide members 470, coupled at distal ends thereof to catheter 421, are pulled together with catheter 421. As catheter 421 is pulled, the proximal ends of guide members 470 are fed into advancement catheter 410 and toward the annuloplasty structure. The proximal ends of the guide members then trail the distal ends of the guide members as they are looped through the annuloplasty structure and then fed back through advancement catheter 410. As guide members 470 are pulled, they are slid from within their respective channels, and are thereby decoupled from structure 408.

FIGS. 21-22 are schematic illustrations of a handle assembly 2800 configured for use in an open-heart and/or a minimally-invasive procedure to deliver annuloplasty structure 100 as described hereinabove with reference to FIG. 1, in accordance with an embodiment of the present invention. Handle assembly 2800 comprises a handle 2802 and semi-flexible multitube portion 2808 coupled at a proximal end thereof to a distal end of handle 2802. Multitube portion 2808 comprises a plurality of tubes 2810 coupled and bound together by stabilizing rings 2812 and 2820. In some embodiments, a sheath surrounds tubes 2810 and is hermetically sealed at a distal end thereof to ring 2820 and at a proximal end thereof to a distal end of handle 2802. A respective distal end of each tube 2810 is coupled to structure 100 via a respective anchor mount 461. As such, the respective distal portions of tubes 2810 are flexible such that each tube 2810 branches radially. It is to be noted that a contracting wire is disposed within structure 100 (as described hereinabove with reference to FIG. 1), and is not shown for clarity of illustration. In some embodiments, handle assembly 2800 is disposable.

As shown in FIG. 21, a distal end 2840 of each tube 2810 is positioned against a first lateral surface of a respective anchor mount 461 in alignment with a proximal opening of channel 460 of anchor mount 461. Typically, a longitudinal axis of channel 460 is transverse with respect to the longitudinal axis of anchor mount 461. FIG. 22 shows contracting wire 110 of annuloplasty structure 100 coupled to tubes 2810. It is to be noted that compressible subunits 450 and anchor mounts 461 (shown in FIG. 21) are not shown for clarity of illustration. Each distal end 2840 of tubes 2810 is coupled to a contracting wire coupling element 2830, i.e., an extension or projection, at a proximal end thereof. Each contracting wire coupling element 2830 is shaped to define a hole at a distal portion thereof configured for slidable passage therethrough of at least a portion of contracting wire 110. As shown in FIG. 21, each contracting wire coupling element 2830 passes through an opening (e.g., a second channel, a hole, or a groove that is distinct from channel 460 and has a longitudinal axis that is transverse with respect to the longitudinal axis of anchor mount 461) in a respective anchor mount 461. Each contracting wire coupling element 2830 is configured to surround contracting wire 110 passing through mount 461 and enables slidable advancement therethrough of contracting wire 110.

As shown in FIG. 22, tubes 2810 and distal ends 2840 thereof are shaped to define a hollow lumen 2805 configured for passage of a respective anchor through each tube 2810, through distal end 2840, through channel 460 of anchor mount 461, and subsequently into tissue of the patient. FIG. 21 shows helical anchors 740 coupled to structure 100 via mounts 461. A cross-sectional illustration of proximal end 2801 of handle 2802 (FIG. 22) shows proximal end 2801 being shaped to define a plurality of proximal openings lumens 2803. Handle 2802 is shaped to define a plurality of lumens 2803 whose distal ends are accessed by respective proximal ends of tubes 2810. In some embodiments, each lumen 2803 is labeled at proximal end 2801 with a suitable label indicating to which portion of the annulus the anchor passed through a given lumen will be anchored. For example, lumens 2803 that are configured to deliver respective anchors to the annulus at the base of the anteromedial leaflet, are labeled $A_1$-$A_n$, in accordance with the number of desired anchoring sites along the annulus at the base of the anteromedial leaflet. Similarly, lumens 2803 that are configured to deliver respective anchors to the annulus at the base of the posterolateral leaflet, are labeled $P_1$-$P_n$, in accordance with the number of desired anchoring sites along the annulus at the base of the posterolateral leaflet.

An anchor is advanced into each lumen 2803 through a respective opening in proximal end 2801 of handle 2802. An anchor advancement system, e.g., a rod as described hereinabove, advances each anchor through a respective lumen 2803, through tube 2810 accessing lumen 2803, and toward anchor mount 461 coupled to that tube. In some embodiments, tubes 2810 are preloaded with a respective anchor, and once annuloplasty structure 100 is positioned at the annulus, an anchor advancement rod is advanced through each lumen in order to facilitate advancing of the anchor into tissue of the patient. In some embodiments, tubes 2810 are each preloaded with a respective anchor and a respective rod coupled at a distal end thereof to each anchor. A proximal end of each rod is accessible from proximal end 2801 of handle 2802 by a physician who is able to push and/or rotate the rod in order to facilitate advancing of the anchor into tissue of the patient.

A portion of contracting wire 110 is configured to be disposed within a lumen of structure 100, as described hereinabove. The remaining portions of contracting wire 110 are slidably disposed within (a) housing 610, (b) a tube 2811 of tubes 2810, and (c) handle 2802. Handle 2802 comprises first, second, and third rotating rings 2804, 2806, and 2807, respectively. Typically, a portion, e.g., an end, of a first end of contracting wire 110 is coupled to second rotating ring 2806, and a portion, e.g., an end, of a second end of contracting wire 110 is coupled to third rotating ring 2807. Once anchors 740 have been anchored to tissue of the patient, and structure 100 has been anchored thereby to the annulus, a portion of contracting wire 110 is pulled in order to reduce the perimeter/size of the portion of contracting wire 110 that is disposed within structure 100. Contracting wire 110 is pulled when the first and/or second ends thereof are drawn proximally in response to rotating rings 2806 and/or 2807. For example, as ring 2806 is rotated, a portion of the first end of contracting wire 110 is wrapped around a threaded element (not shown) disposed within handle 2802 and pulls contracting wire 110 proximally. As wire 110 is pulled proximally, the portion of wire 110 disposed within the lumen of structure 100 slides through the holes of contracting wire coupling elements 2830, and a portion of the portion of wire 110 that was originally disposed within the lumen of structure 100 slides proximally out of the lumen of structure 100 and toward handle 2802. In some embodiments, ring 2806 may be rotated as ring 2807 remains stationary, or vice versa. In some embodiments, rings 2806 and 2807 are rotated opposite directions.

Typically, ring 2804 locks rings 2806 and 2807 in place, thereby locking contracting wire 110 in a given perimeter as defined by the rotating of rings 2806 and 2807. It is to be noted that three rings 2804, 2806, and 2807 are shown by way of illustration and not limitation.

Using tactile feedback, or echocardiography, and optionally in combination with fluoroscopic imaging, the first and second ends of contracting wire 110 are pulled to an extent that is based on (a) the level of dilation of the preoperative mitral valve, and/or (b) real-time monitoring of regurgitation minimization. For embodiments in which structure 100 comprises a ratchet mechanism, as described hereinabove with reference to FIGS. 1, 2A-B, 3, 4, 5A-C, 6A-B, and 7, the ratchet mechanism maintains the ratcheted perimeter of structure 100 following the pulling of wire 110. Contracting wire 110 is then pulled from within the lumen of structure 100 by cutting a first portion of wire 110 and then pulling on a first end of contracting wire 110, e.g., by pulling proximally on assembly 2800.

In some embodiments, the first and second ends of contracting wire 110 are exposed proximally to rings 2806 and 2807, respectively. In such an embodiment, following the adjustment of annuloplasty structure 100 by rotating rings 2806 and 2807, ring 2804 is rotated in order to unlock rings 2806 and 2807 which are, in turn, allowed to rotate so as to unwind the portion of contracting wire 110 from the threaded element in handle 2802. One of the ends of the contracting wire is then pulled in order to remove contracting wire 110 from structure 100. A first end of contracting wire 110 is pulled such that the second end of the contracting wire is pulled (a) distally through tube 2811, (b) through housing 610, (c) through each hole of contracting wire coupling elements 2830, (d) back through housing 610, (e) pulled proximally back through tube 2811, until the second end of contracting wire 110 is exposed outside the body of the patient.

In some embodiments, the first and second ends of wire 110 are fixedly coupled to rings 2806 and 2807. In such an embodiment, in order to remove contracting wire 110 from within structure 100, tube 2811 is cut together with at least one portion of wire 110, and wire 110 is then pulled from within the lumen of structure 100. By pulling on wire 110 and freeing wire 110 from within structure 100 and from contracting wire coupling elements 2830, handle assembly 2800 is decoupled from structure 100.

Once contracting wire 110 is removed from within the holes of contracting wire coupling elements 2830, tubes 2810 are decoupled from structure 100 by pulling handle 2802 and/or tubes 2810 proximally such that contracting wire coupling elements 2830 are pulled from within anchor mounts 461. Handle assembly 2800 is pulled proximally leaving structure 100 coupled to the annulus of the patient.

In some embodiments, compressible subunits 450 comprise a coil, and the anchor used to anchor structure 100 to the annulus comprises a helical coil comprising coils which are coiled around a portion of coils of tubular, compressible subunits 450 of the annuloplasty structure and subsequently through the tissue of the annulus of the patient. In such an embodiment, the annuloplasty structure does not comprise anchor mounts 461, and the distal ends of tubes 2810 are positioned at a first lateral surface of compressible subunits 450 of the annuloplasty structure. During the manufacture of assembly 2800, the annuloplasty structure is coupled to each tube 2810 by passing a respective contracting wire coupling element 2830 between adjacent coils of compressible subunits 450. Contracting wire 110 is then fed through the respective holes defined by each contracting wire coupling element 2830. Following the coiling of the coils of the anchor around a portion of coils of compressible subunits 450, the contracting wire is pulled from within the lumen of the annuloplasty structure, and from within each hole of contracting wire coupling elements 2830. Handle assembly 2800 is thereby detached from the annuloplasty structure and can be pulled proximally therefrom.

It is to be noted that although helical anchors 740 are shown, the scope of the present invention includes the use of any anchor described herein.

In some embodiments, annuloplasty structure 100 does not comprise anchor mounts 461 but rather comprises a braided mesh. In either embodiment in which structure comprises or lacks anchor mounts 461, prior to advancement of structure 100 by handle assembly 2800, a plurality of sutures are sutured at respective locations along the annulus of the valve. Respective ends of each of the sutures are then threaded at respective locations through structure 100. Structure 100 is then slid along the sutures and toward the annulus of the valve by being pushed by handle assembly 2800. Once positioned at the annulus, the sutures are locked in place at the exposed lateral surface of structure 100. In some embodiments, a bead is slid distally along each suture, and is secured in place by crimping, an adhesive, or a ratcheting mechanism, thereby locking the suture in place proximal to structure 100. The remaining portions of the suture are then cut proximally to the bead. In some embodiments, respective portions of one suture or of two adjacent sutures are knotted together in order to lock the suture(s) in place. The remaining portions of the suture(s) are then cut proximally to the knot.

It is to be noted that although structure 100 is shown as being coupled to handle assembly 2800, the scope of the present invention includes the use of handle assembly 2800 to advance structure 408 as described hereinabove with reference to FIGS. 17G-J, 18A-B, 19A-E, and 20A-B. For example, handle assembly 2800 may advance segments 430 and/or 440.

For embodiments in which a minimally-invasive approach is used, assembly 2800 may be introduced into the heart either through an intercostal access from the left side of the patient or through an intercostal access from the right side of the patient.

It is to be noted that handle assembly 2800 (FIGS. 21 and 22) may be used for anchoring the annuloplasty structures described herein to the annulus during an open-heart procedure. For example, the left atrium may be exposed following an incision in a wall of the heart. As the mitral valve is exposed, the patient is connected to a cardiopulmonary bypass pump which maintains the circulation of blood and the oxygen content of the patient's body during the exposing of the valve. Once the annuloplasty structure is positioned along the annulus of the valve and anchored thereto, the wall of the heart is sutured around the tubular portions of handle assembly 2800 (i.e., multitube portion 2808 of assembly 2800), typically using a purse stitch, and the patient is disconnected from the cardiopulmonary bypass pump in order to restore function to the heart. The physician is able to reduce the perimeter of the annulus in response to feedback from fluoroscopic and/or ultrasound real-time imaging of the function of the valve in a beating heart. Typically, the physician reduces the perimeter while viewing the mitral regurgitation in real-time and tightens the annuloplasty structure responsively to the extent to which the regurgitation is reduced.

Figure 23A:
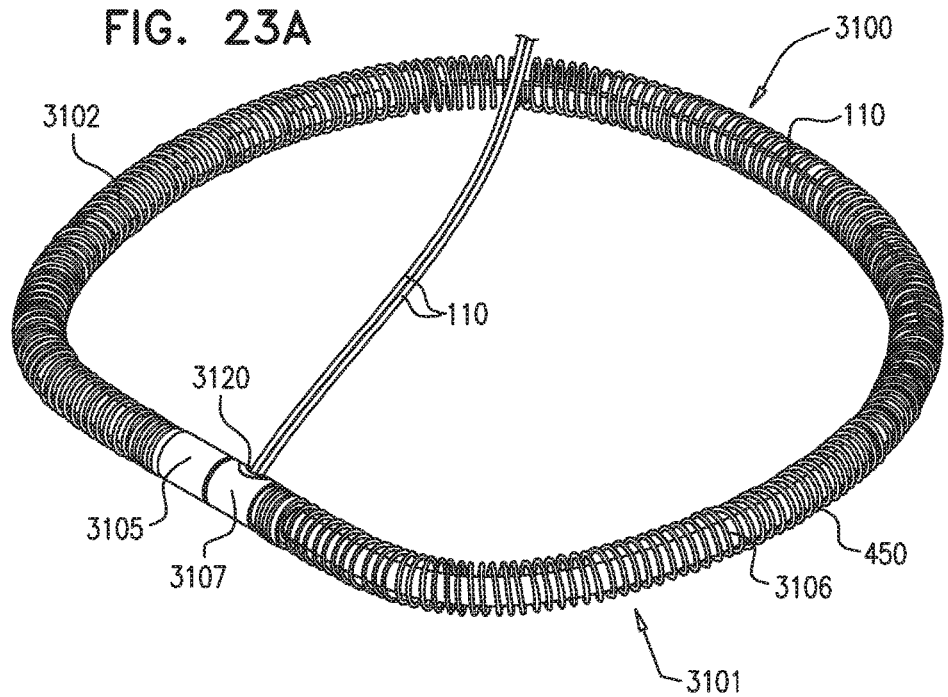
FIGS. 23A-B are schematic illustrations of an annuloplasty structure comprising a ratchet mechanism, in accordance with still yet another embodiment of the present invention.
Figure 23B:
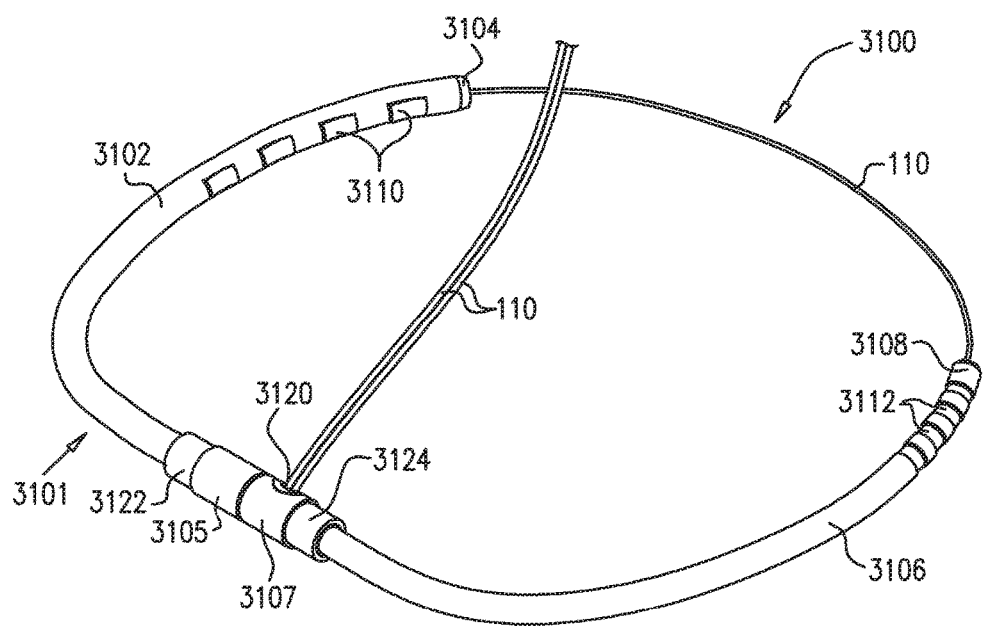

FIGS. 23A-B are schematic illustrations of an annuloplasty structure system 3100 comprising a tubular ratchet mechanism 3101, in accordance with an embodiment of the present invention. Typically, ratchet mechanism 3101 is surrounded by a compressible, tubular surrounding 450. Ratchet mechanism 3101 comprises a first tubular element 3102 and a second tubular element 3106 spaced apart from each other at first ends thereof. Tubular element 3102 is coupled at a second end thereof to a first tubular coupling member 3105, and tubular element 3106 is coupled at a second end thereof to a second tubular coupling member 3107. As shown in FIG. 23B, first tubular coupling member 3105 comprises a first coupling site 3122 configured for coupling thereto a first end of compressible, tubular surrounding 450 (FIG. 23A), and second tubular coupling member 3107 comprises a second coupling site 3124 configured for coupling thereto a second end of compressible, tubular surrounding 450 (FIG. 23A).

During the manufacture of system 3100, while holding a first end of contracting wire 110 in place outside system 3100, a second end of contracting wire 110 is fed through (a) a hole 3120 defined by second tubular coupling member 3107, (b) second tubular coupling member 3107, (c) tubular element 3106, (d) tubular element 3102, (e) first tubular coupling member 3105, (f) a portion of second tubular coupling member 3107, and finally back through hole 3120. Typically, contracting wire 110 is configured for slidable advancement within system 3100.

Typically, during open-heart and minimally-invasive procedures, system 3100 is advanced toward the annulus of the mitral valve of the patient in the configuration shown in FIG. 23A, i.e., first and second ratchet tubular coupling members 3105 and 3107, respectively, are coupled together. For embodiments in which system 3100 is used during a percutaneous procedure (and in some embodiments, during open-heart and minimally-invasive procedures), system 3100 is disposed within an advancement catheter in a linear configuration thereof. That is, (a) compressible, tubular surrounding 450 is disposed linearly, thereby defining a longitudinal axis thereof, (b) tubular elements 3102 and 3106 are disposed coaxially along the longitudinal axis, (c) first and second tubular coupling members 3105 and 3107, respectively, are not coupled together, but rather are disposed at opposite ends of system 3100 along the longitudinal axis, and (d) contracting wire 110 extends longitudinally within the advancement catheter between first and second tubular coupling members 3105 and 3107 while respective first and second ends of contracting wire 110 are disposed outside the body of the patient.

In such an embodiment, system 3100 is transcatheterally advanced toward the left atrium in a linear configuration thereof while first and second ends of contracting wire 110 are disposed outside the body of the patient. As system 3100 is pushed from within the advancement catheter and is disposed within the left atrium of the patient, the first and second ends of contracting wire 110 are pulled, thereby pulling first and second tubular coupling members 3105 and 3107 toward each other. In response to continued pulling of contracting wire 110, first and second tubular coupling members 3105 and 3107 are coupled and locked together, and system 3100 assumes a substantially circular configuration, as shown in FIG. 23A.

Typically, first tubular element 3102 has a diameter that is larger than a diameter of second tubular element 3106 such that second tubular element 3106 is allowed to slide through first tubular element 3102. First tubular element 3102 is shaped to define a plurality of first engaging elements (e.g., teeth) 3110 at a receiving portion 3104. Second tubular element 3106 is shaped to define a plurality of second engaging elements (e.g., indented portions 3112) at a feeding portion 3108 thereof. Typically, in response to continued pulling of contracting wire 110, as feeding portion 3108 (i.e., the first end, of second tubular element 3106) is initially fed through receiving portion 3104 (i.e., the first end, of first tubular element 3102), a first indented portion of indented portions 3112 is slid through receiving portion 3104 until it is aligned and locks in place with a first one of teeth 3110 of receiving portion 3104.

In response to additional force applied to tubular elements 3102 and 3106 by continued pulling of contracting wire 110, the first indented portion of indented portions 3112 is disengaged from the first tooth of teeth 3110 and is advanced toward the second tooth of teeth 3110. Typically, pulling on contracting wire 110 controls the spatial relationship between tubular elements 3102 and 3106 which, in turn, control the structural configuration of system 3100. Thus, a perimeter of system 3100 is modulated, i.e., reduced, in response to the compression of surrounding 450 by the inward, radial force applied due to the pulling of contracting wire 110.

It is to be noted that the plurality of teeth 3110 is provided such that tubular elements 3102 and 3106 of ratchet mechanism 3101, and thereby compressible, tubular surrounding 450, lock in place and maintain respective ratcheted perimeters thereof. Such a locking mechanism is applied so as to enable system 3100 to accommodate various sizes of dilated annuli of given patients. Additionally, ratchet mechanism 3101 facilitates: (1) positioning and anchoring of structure system 3100 to the dilated annulus while compressible surrounding 450 has a first perimeter thereof, (2) contracting of the dilated annulus in response to the contracting of ratchet mechanism 3101, and (3) maintaining of the contracted state of the annulus while tubular elements 3102 and 3106 (and thereby surrounding 450) have a second perimeter thereof that is typically smaller than the first perimeter.

Typically, compressible, tubular surrounding 450 comprises a coil, and the anchor used to anchor system 3100 to the annulus comprises a helical coil comprising coils which are coiled around a portion of coils of compressible, tubular surrounding 450 and subsequently through the tissue of the annulus of the patient, as described hereinabove.

In some embodiments, compressible, tubular surrounding 450 comprises a braided mesh, e.g., metal or fabric such as polyester. In such an embodiment, any anchor described herein may be passed through the braided mesh, and subsequently through the tissue of the annulus, thereby (a) anchoring system 3100 to the annulus, and (b) coupling system 3100 to the anchor. Alternatively, a plurality of sutures may be used to anchor system 3100 to the annulus of the patient.

Once system 3100 is anchored to the annulus of the patient, using real-time monitoring, tactile feedback, or echocardiography, and optionally in combination with fluoroscopic imaging, contracting wire 110 is pulled. Consequently, the leaflets are drawn toward one another in accordance with the level of dilation of the preoperative mitral valve. Thus, generally, the normal structural configuration is returned to the leaflets, effecting a reduction in mitral valve perimeter/size and regurgitation. As contracting wire 110 is pulled, ratchet mechanism 3101 locks system 3100 in place so that system 3100, and thereby the annulus of the patient, assumes and maintains a desired perimeter. While a first end of contracting wire 110 is freed, a second end of wire 110 is then pulled from a site outside the body of the patient until contracting wire 110 is removed from system 3100 and from the body of the patient.

It is to be noted that anchors described herein for passage through the braided mesh of the annuloplasty structure, or configured for coiling around a portion of coils of coiled compressible subunits 450, have a diameter of between 0.5 mm and 3.5 mm, e.g., 1.6 mm.

It is to be further noted that systems described herein for treatment of dilated mitral valves may be used to treat valves other than mitral valve 30, mutatis mutandis. For example, system 400 and structures 100 and 408 may be used to treat an aortic valve of the patient or a tricuspid valve. In some embodiments, systems described herein for use with a dilated annulus may be applied in order to treat dilated venous valves.

It is to be still further noted that systems described herein for treatment of mitral valves may be used to treat other annular muscles within the body of the patient. For example, the systems described herein may be used in order to treat a sphincter muscle within a stomach of the patient.

It is also to be noted that the scope of the present invention include the use of the anchors described herein in order to anchor intrabody apparatus other than annuloplasty structures.

Reference is now made to FIGS. 24A-F, which are schematic illustrations of a system 4400 for repairing a mitral valve 4030, being advanced into a left atrium of a patient, in accordance with an embodiment of the present invention. Typically, a catheter 4404 (FIG. 24B) is advanced into the left atrium of the patient using a percutaneous endovascular approach typically combined with continuous monitoring by electromagnetic and/or sound waves, e.g., fluoroscopy, transesophageal echo, and/or echocardiography, to maintain real-time orientation of a distal tip of the catheter within the heart of the patient. Typically, catheter 4404 is transseptally advanced into the left atrium.

Catheter 4404 typically comprises a 13 F catheter, although another size may be appropriate for a given patient. In some embodiments, catheter 4404 is advanced through vasculature of the patient and into the right atrium using a suitable point of origin typically determined for a given patient. For example:

(1) Catheter 4404 is introduced into the femoral vein of the patient, through the superior vena cava, into the right atrium of the heart, transseptally through the fossa ovalis, and finally into the left atrium;

(2) Catheter 4404 is introduced into the basilic vein, through the subclavian vein to the superior vena cava, into the right atrium, transseptally through the fossa ovalis, and finally into the left atrium; or (3) Catheter 4404 is introduced into the external jugular vein, through the subclavian vein to the superior vena cava, into the right atrium, transseptally through the fossa ovalis, and finally into the left atrium.

In some embodiments, catheter 4404 is advanced through an inferior vena cava 4022 of the patient (as shown) and into the right atrium using a suitable point of origin typically determined for a given patient.

Figure 24A:
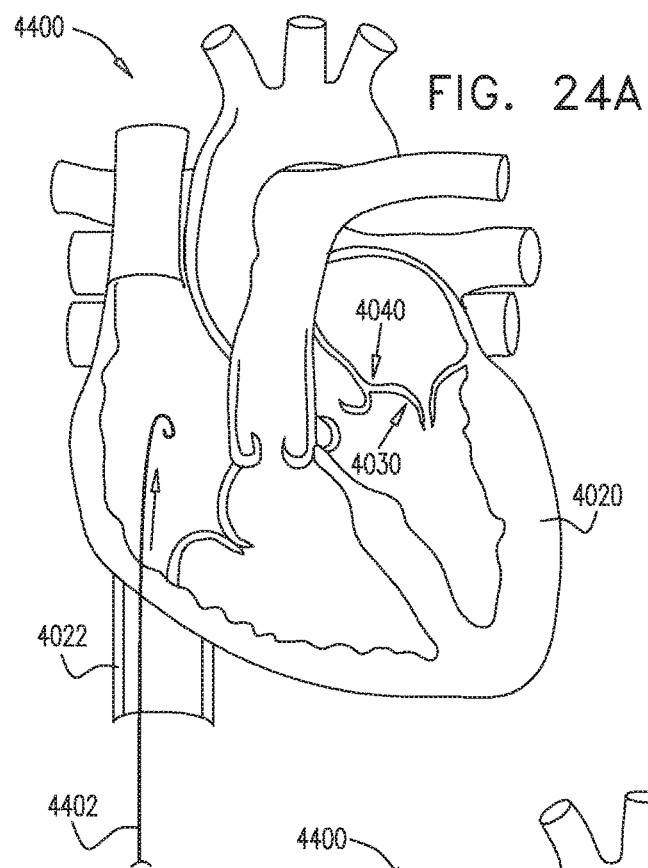
Figure 24B:
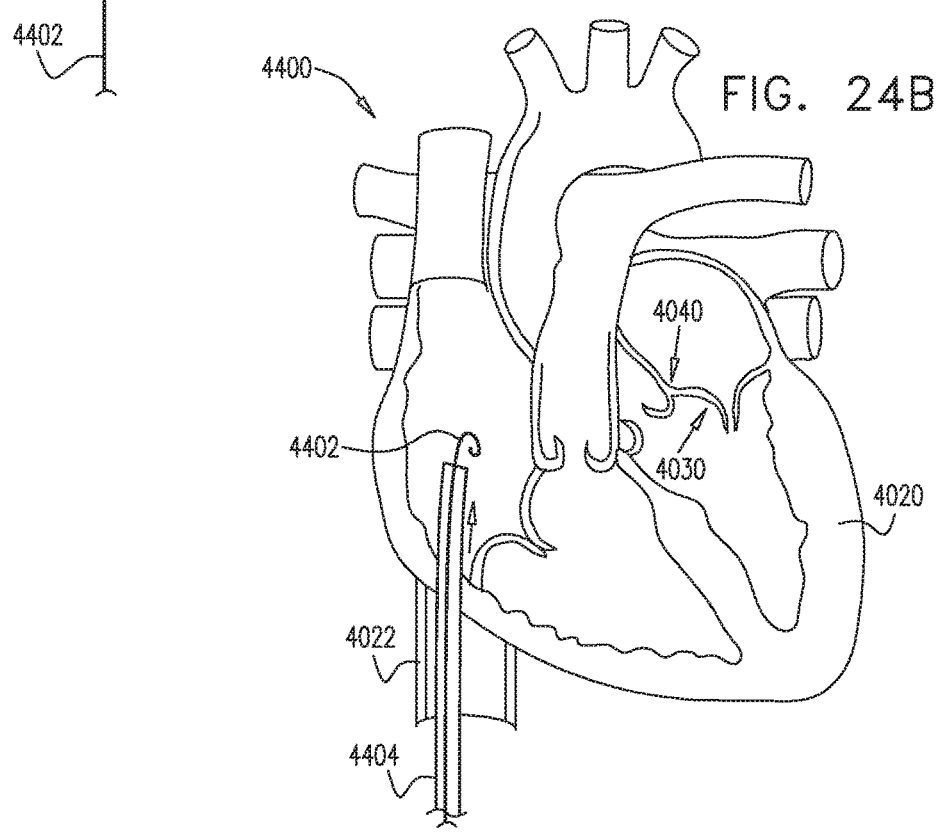
Figure 24C:
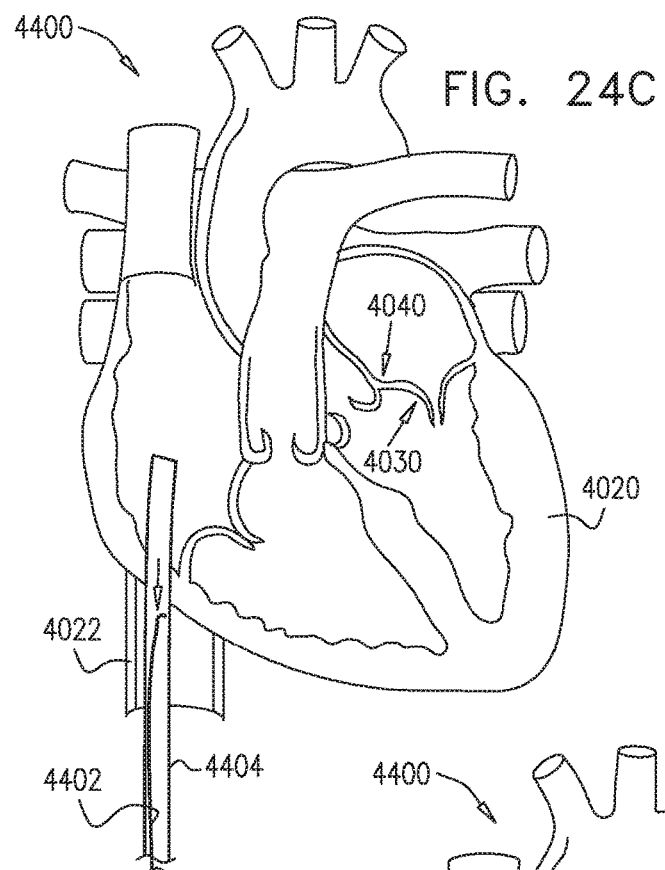
Figure 24D:
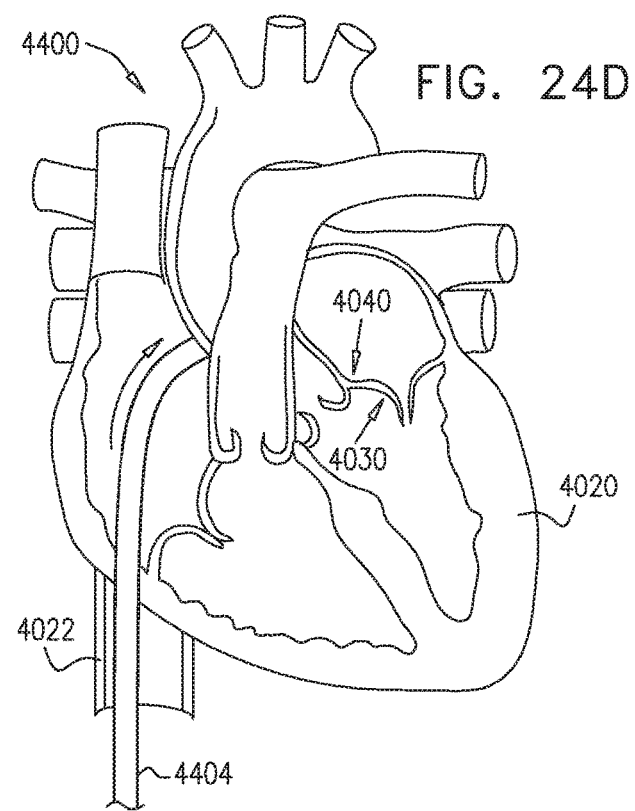

FIG. 24A shows a guide wire 4402 being advanced into the right atrium of the patient. Advancement of wire 4402 typically precedes advancement of catheter 4404 into the right atrium of the patient. Wire 4402 comprises a semi-rigid wire which provides a guide for the subsequent advancement of catheter 4404 therealong and into the right atrium of the patient, as shown in FIG. 24B. Once catheter 4404 has entered the right atrium, guide wire 4402 is retracted and extracted from within the body of the patient (FIG. 24C). In FIG. 24D, catheter 4404 is pushed distally until it reaches the interatrial septum of heart 4020 of the patient.

(In this context, in the specification and in the claims, "proximal" means closer to the orifice through which catheter 4404 is originally placed into the vasculature of the patient, and "distal" means further from this orifice.)

Figure 24E:
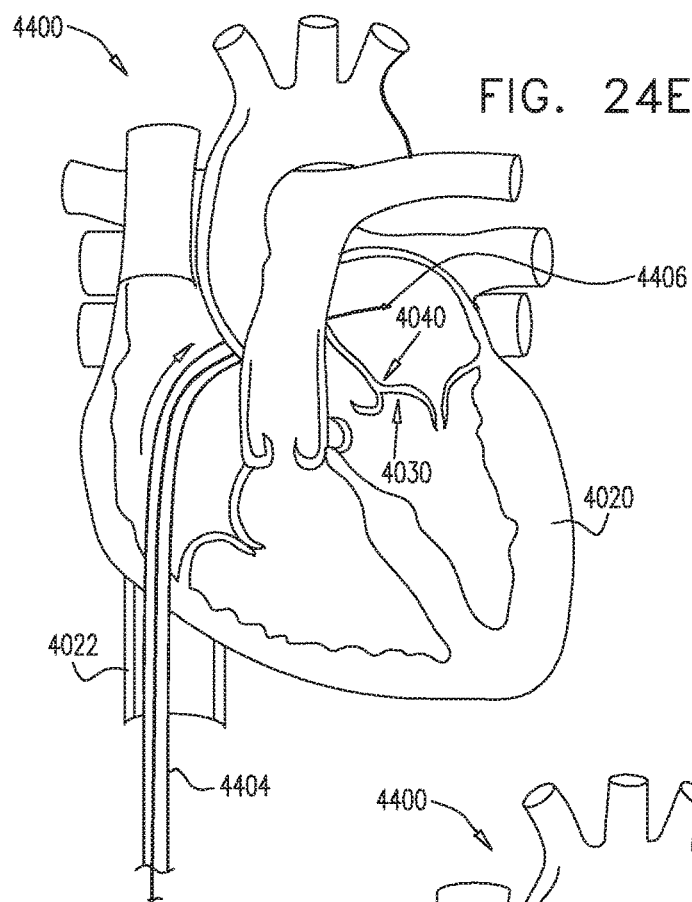
Figure 24F:
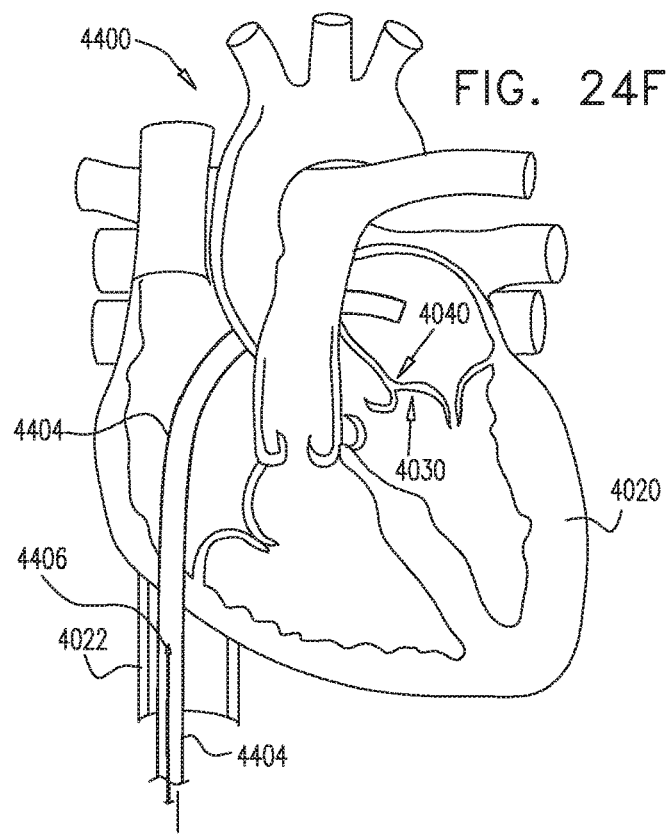

As shown in FIG. 24E, a resilient needle 4406 is advanced through catheter 4404 and into heart 4020 of the patient. In order to advance catheter 4404 transseptally into the left atrium, needle 4406 first punctures the septum of heart 4020 such that an opening is created which facilitates passage of catheter 4404 therethrough and into the left atrium. Subsequently, a dilator (not shown) is advanced along needle 4406 and toward the septum of heart 4020. Typically, the dilator is shaped to define a hollow shaft for passage along needle 4406, the hollow shaft being shaped to define a tapered distal end. This tapered distal end is first advanced through the hole created by needle 4406. The hole is enlarged when the gradually increasing diameter of the distal end of the dilator is pushed through the hole in the septum. The advancement of catheter 4404 through the septum and into the left atrium is followed by the extraction of the dilator from within catheter 4404 (FIG. 24F).

FIG. 24G is a schematic illustration of a first segment 4430 and a second segment 4440 of an annuloplasty structure 4408 being advanced along catheter 4404, in accordance with an embodiment of the present invention. Segments 4430 and 4440 are configured to be chronically implanted within heart 4020 along an annulus 4040 of mitral valve 4030. Typically, segments 4430 and 4440 comprise a biocompatible material, e.g., nitinol, titanium, silicone, polytetrafluoroethylene (PTFE), and/or polyester graft material. Additionally, segments 4430 and 4440 comprise accordion-like, compressible subunits 450 which facilitate bending of the segments into a suitable configuration and compressing of the segments when they are later drawn toward one another.

In some embodiments of the present invention, segments 4430 and 4440 comprise coils made of stainless steel, e.g., type 304 or type 316. Suitable coil shapes include round wire coils or flat wire coils.

Prior to advancing segments 4430 and 4440 into the left atrium of the patient, segments 4430 and 4440 are loaded into an advancement catheter 4410 in a substantially linear configuration, as shown in FIG. 24G. The linear configuration defines a longitudinal axis of segments 4430 and 4440 of structure 4408. Segments 4430 and 4440 are typically advanced into the left atrium of the patient during a single transcatheter advancement.

During advancement of segment 4430 within advancement catheter 4410, segment 4430 has a length L10 between about 10 mm and about 50 mm, e.g., 20 mm. Length L10 of segment 4430 typically corresponds with a portion of annulus 4040 at the junction between annulus 4040 and the base of the anteromedial leaflet of valve 4030. Similarly, second segment 4440 is designated to be anchored to annulus 4040 at the base of the posterolateral leaflet, and thus is sized in accordance therewith. For example, segment 4440 may have a length L20 of between about 20 mm and about 80 mm, e.g., 40 mm. The respective lengths of segments 4430 and 4440 enable the segments to dynamically support the mitral valve in accordance with the relative motion of the anteromedial and posterolateral leaflets. Typically, segments 4430 and 4440 each have a diameter L30 of between about 1 mm and about 5 mm, typically between about 2.5 mm and about 3.5 mm.

Typically, segments 4430 and 4440 are shaped to define a lateral wall 4462 that has at least one flexible hollow lumen configured for sliding advancement of at least one control wire therethrough. As shown, a first control wire 4480 and a second control wire 490 are disposed within both the first and second segments 4430 and 4440. Typically, wires 4480 and 4490 function to position and adjust a relative disposition and configuration of segments 4430 and 4440 with respect to a configuration of annulus 4040 of valve 4030. Additionally, the structural and spatial configurations of each segment are controlled independently by a respective one of the first and second control wires 4480 and 4490. Such functions of wires 4480 and 4490 are described hereinbelow. As such, a diameter of control wires 4480 and 4490 (e.g., between about 0.2 mm and about 0.4 mm, typically, between 0.25 mm and 0.3 mm) provides the wires with the strength to control structure 408. Typically, control wires 4480 and 4490 comprise a resilient material capable of providing a pulling force to segments 4430 and 4440, e.g., nitinol or Teflon. In some embodiments, control wires 4480 and 4490 are Teflon-coated.

In some embodiments, first and second control tubes are disposed within both the first and second segments. Typically, the first and second control tubes are configured to function similarly to control wires 4480 and 4490 described herein.

Typically, lateral wall 4462 of segments 4430 and 4440 is shaped to provide a first portion 4464 and a second portion 4466 generally at opposite sites of the segment when viewed in cross-section (e.g., at 12 o'clock and 6 o'clock). First and second segments 4430 and 4440 of annuloplasty structure 4408 each comprise at least one channel 4460. Channel 4460 is configured to extend from first portion 4464, through the given segment, to second portion 4466. A respective flexible and longitudinal guide member 4470 is partially disposed within each channel 4460 and is used to facilitate anchoring of annuloplasty structure 4408, as described hereinbelow.

Typically, guide member 4470 is configured to facilitate advancement therealong of a respective anchoring structure (described hereinbelow). The anchoring structure is typically advanced along guide member 4470, through channel 4460, and is ultimately anchored into annulus 4040 of mitral valve 4030, thereby anchoring the segment to annulus 4040. Typically, guide member 4470 comprises a flexible metal wire, e.g., nitinol or stainless steel. In some embodiments, guide member 4470 comprises a suture comprising an artificial fiber, e.g., nylon, polypropylene, Kevlar, Teflon, or polyester. Typically, each guide member 4470 has a diameter of between about 0.05 mm and about 0.2 mm, e.g., 0.1 mm.

Prior to advancing segments 4430 and 4440 into the left atrium of the patient, advancement catheter 4410 is preloaded with segments 4430 and 4440, with control wires 4480 and 4490, with guide members 4470, and with a multilumen catheter 420 which is disposed proximally to segments 4430 and 4440. Thus, segments 4430 and 4440 are simultaneously conveyed toward heart 20, during a single transcatheter advancement. Typically, advancement catheter 4410 comprises a 12 F catheter, although other sizes may be appropriate depending on the size of catheter 4404.

Figure 24H:
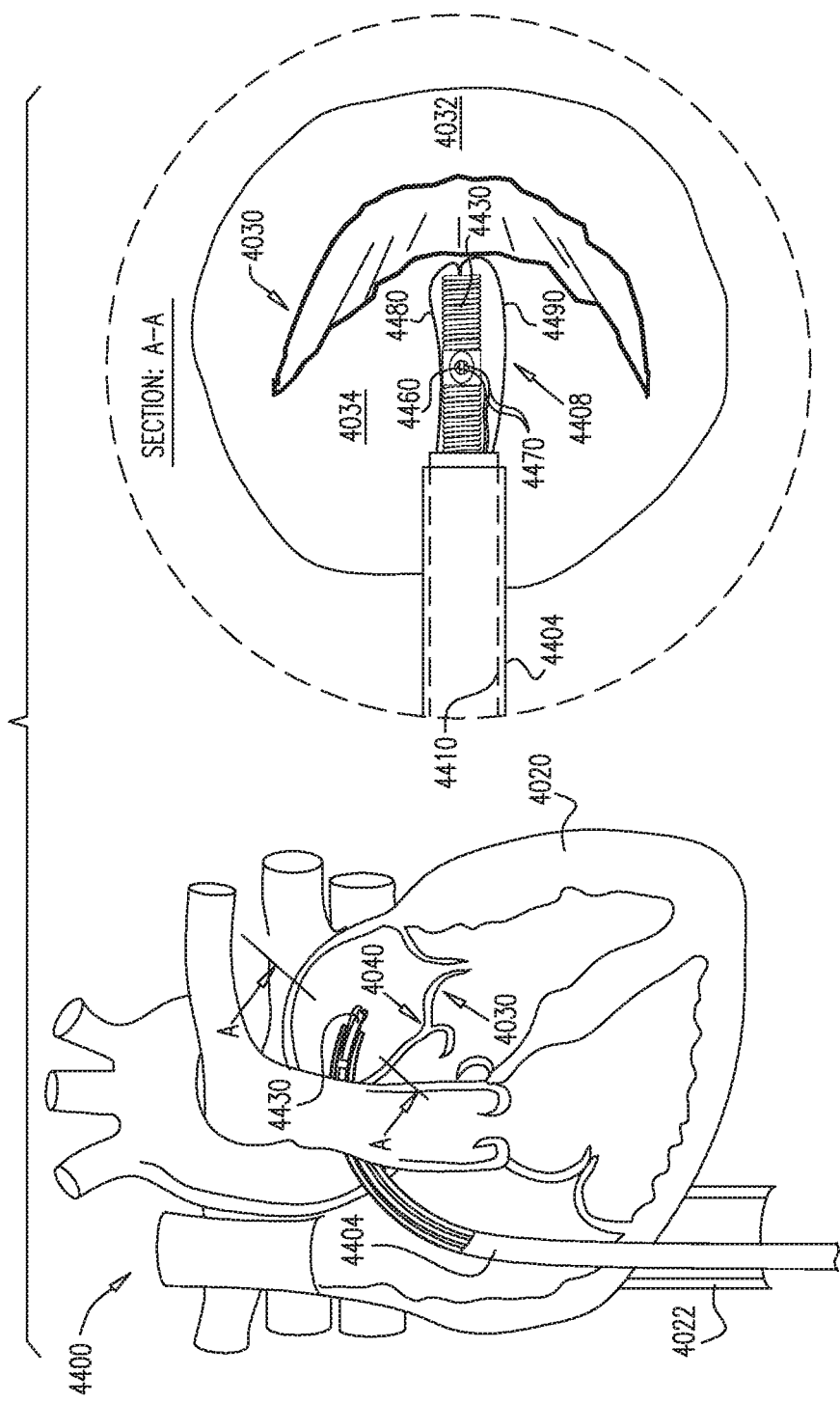
Figure 24I:
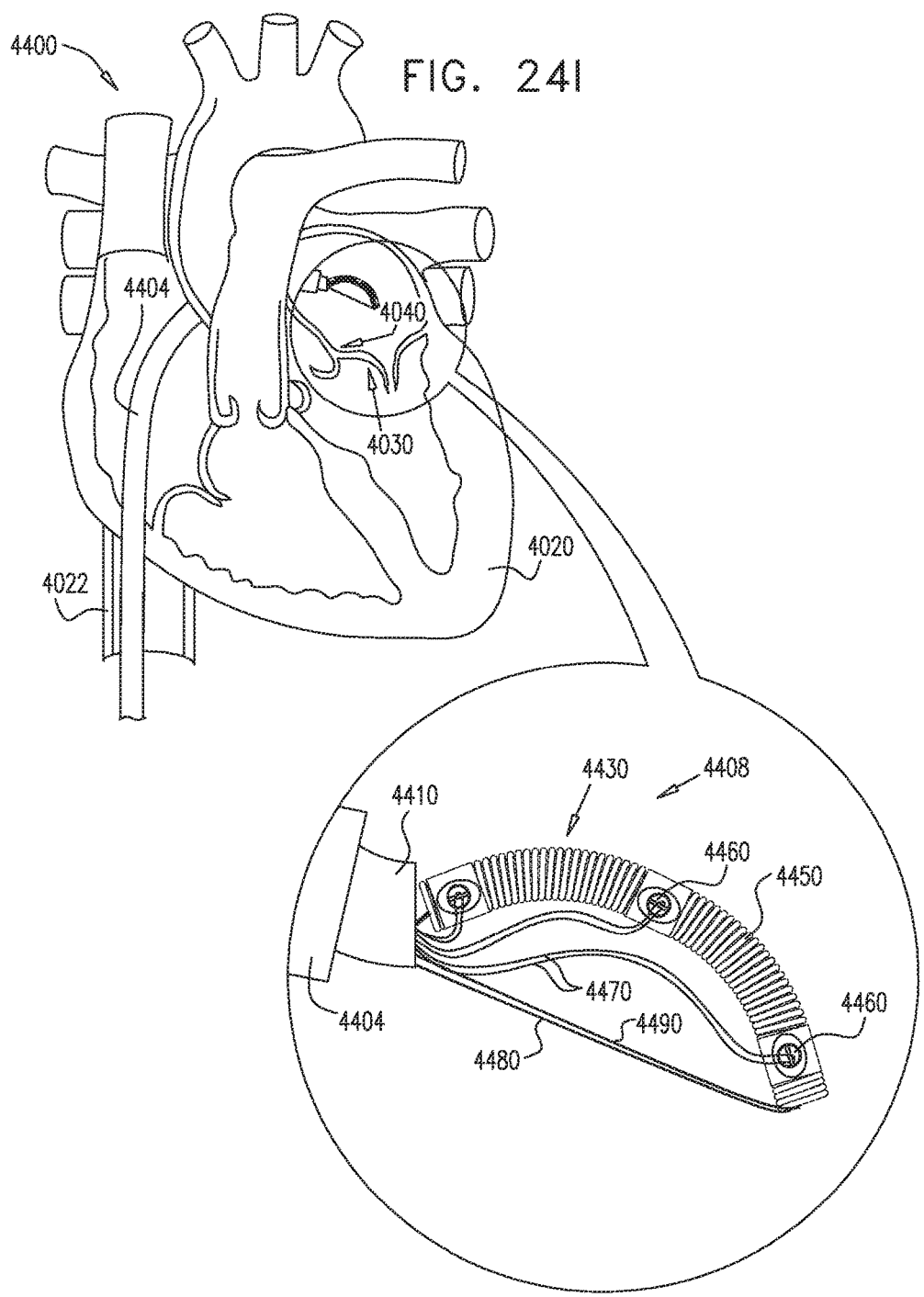

FIGS. 24H and 24I show deployment of first segment 4430 of the segmented annuloplasty ring, in accordance with an embodiment of the present invention. Segments 4430 and 4440 are in a linear configuration within advancement catheter 4410 when catheter 4410 is advanced within catheter 4404 and initially enters the left atrium. As shown in FIG. 24H, a distal end of catheter 4410 emerges from within catheter 4404. Segment 4430 maintains its linear configuration as it is initially pushed from within catheter 4410.

As shown by way of illustration and not limitation, each guide member 4470 is looped around a bar disposed within each channel 4460. The purpose of this bar is described hereinbelow.

Typically, first and second segments 4430 and 4440 of structure 4408 are ultimately made to assume a somewhat round configuration that resembles an annuloplasty ring in structure and function.

As shown in FIG. 24I, control wires 4480 and 4490 are tightly pulled proximally, applying a force to segment 4430 and compressing segment 4430 so that it is made to assume a curved configuration. The curved configuration is thus achieved as compressible subunits 4450 are compressed in response to the pulling of control wires 4480 and 4490. Typically, compressible subunits 450 are compressed generally in parallel with the longitudinal axis of segment 4430. Such a curved configuration minimizes the possibility for segment 4430 to prematurely contact walls of heart 4020: (1) during deployment of system 4400 within the left atrium, and (2) prior to positioning segments 4430 and 4440 along annulus 4040.

It is to be noted that in some embodiments, segments 4430 and 4440 of annuloplasty structure 4408 comprise a shape-memory alloy, e.g., nitinol. In these embodiments, segments 4430 and 4440 are introduced within catheter 4410 in a straight configuration, and are each biased to assume a generally semi-circular configuration once expanded from within catheter 4410. Annuloplasty structure 4408 thus assumes a somewhat round configuration typically independently of the application of a proximal force to control wires 4480 and 4490. In such an embodiment, control wires 4480 and 4490 are used instead to expand the segments by separating at least a part of segment 4430 from at least a part of segment 4440.

Reference is now made to FIG. 24J, which is a schematic illustration of system 4400 comprising annuloplasty structure 4408 and multilumen catheter 4420, in accordance with an embodiment of the present invention. As shown, each control wire 4480 and 4490 is coupled to a respective adjustment wire 4482 and 4492. Adjustment wires 4482 and 4492 are configured to contribute to adjusting a relative disposition of segments 4430 and 4440 once inside the left atrium of heart 4020. The functions of wires 4482 and 4492 are described in more detail hereinbelow.

Typically, multilumen catheter 4420 is shaped to define a primary lumen 4426 and secondary lumens 4422 and 4424. The flexible and longitudinal guide members 4470 are disposed within primary lumen 4426 and are exposed outside the body of the patient proximally to catheter 4404. Since, in some embodiments, a respective anchoring structure is advanced along each of guide members 4470, primary lumen 4426 typically has a diameter D10 of between about 1.0 mm to about 3.0 mm (e.g., 1.6 mm). The diameter D10 of lumen 4426 allows passage therethrough of at least one anchoring structure at a given time.

First and second portions of control wire 4490 and a portion of adjustment wire 4482 are disposed within secondary lumen 4422 (as shown), while first and second portions of control wire 4480 and a portion of adjustment wire 4492 are disposed within secondary lumen 4424 (as shown). Multilumen catheter 4420 separates and isolates control wire 4480 from control wire 4490 and separates and isolates adjustment wire 4482 from adjustment wire 4492, thereby enabling the physician to distinguish between each of control wires 4480 and 4490 and between adjustment wires 4482 and 4492. Thus, catheter 4420 helps facilitate independent control by the physician of each of the wires which ultimately determine the relative positioning of structure 4408 within the left atrium of heart 4020.

Reference is now made to FIGS. 25A and 25B, which are schematic illustrations of first segment 4430 of structure 4408 being advanced from within catheter 4410, as described hereinabove with reference to FIGS. 24H and 24I, in accordance with an embodiment of the present invention.

Reference is now made to FIG. 25C, which is a schematic illustration of the deployment and expansion of segments 4430 and 4440, in accordance with an embodiment of the present invention. Control wires 4480 and 4490 are shown disposed within at least one hollow lumen of both first and second segments 4430 and 4440 of annuloplasty structure 4408, thereby coupling the segments. In some embodiments, each of segments 4430 and 4440 is shaped to provide a first lumen configured for sliding advancement therethrough of wire 4480, and a second lumen configured for sliding advancement of wire 4490 (configuration not shown). First and second portions of control wire 4480 emerge from within segments 4430 and 4440 at respective first ends 432 and 442 of segments 4430 and 4440. The first and second portions of control wire 4480 are disposed within secondary lumen 4424 such that first and second ends of wire 4480 are exposed and controllable from outside the body of the patient. Similarly, first and second portions of control wire 4490 emerge from within segments 4430 and 4440 at respective second ends 4434 and 4444 of segment 4430 and 4440. The first and second portions of control wire 4490 are disposed within secondary lumen 4422, such that first and second ends of wire 4490 are exposed and controllable from outside the body of the patient.

In some embodiments, multilumen catheter 4420 is shaped to provide secondary lumens 4423 and 4425, as shown. Typically, lumens 4423 and 4425 are provided for passage of supplementary instruments, e.g., for suction and/or irrigation, therethrough and into the left atrium of the patient.

Following the deployment, segments 4430 and 4440 are expanded by being separated in accordance with the shape of the dilated annulus. Adjustment wire 4482 extends from secondary lumen 4422 and is coupled at a distal end thereof to control wire 4480. Typically, adjustment wire 4482 is coupled to a portion of wire 4480 that is disposed at a junction between respective second ends 4434 and 4444 of segments 4430 and 4440. Similarly, adjustment wire 4492 extends from secondary lumen 4424 and is coupled at a distal end thereof to control wire 4490. Typically, adjustment wire 4492 is coupled to a portion of control wire 4490 that is disposed at a junction between respective first ends 4432 and 4442 of segments 4430 and 4440. Typically, adjustment wires 4482 and 4492 are irreversibly coupled, e.g. knotted or otherwise fixed, to control wires 4480 and 4490, respectively. In some embodiments, adjustment wires 4482 and 4492 are looped around control wires 4480 and 4490, respectively.

The separating of segments 4430 and 4440 occurs when the physician pushes control wires 4480 and 4490 while pushing adjustment wires 4482 and 4492. Thus, adjustment wires 4482 and 4492 provide an auxiliary pushing force which helps expand segments 4430 and 4440. Such pushing of the control wires feeds greater portions of control wires 4480 and 4490 into segments 4430 and 4440. The relaxed configuration of control wires 4480 and 4490 is shown in FIG. 25C, while the taut configuration thereof is shown in FIG. 25B. Typically, segments 4430 and 4440 expand annularly as increasing lengths of control wires 4480 and 4490 are pushed and fed into segments 4430 and 4440.

In some embodiments of the present invention, adjustment wires 4482 and 4492 are pulled to elevate portions of segments 4430 and 4440, such that the segments conform to the shape of annulus 4040. For example, pulling adjustment wire 4482 elevates the portion of control wire 4480 which is disposed between segments 4430 and 4440. In response to the pulling, second ends 4434 and 4444 of segments 4430 and 4440, respectively, are elevated.

Control wires 4480 and 4490 enable the physician to control a relative disposition of second ends 4434 and 4444 and first ends 4432 and 4442 of segments 4430 and 4440, respectively. For example, distal pushing of the first and second ends of control wire 4480 distances second ends 4434 and 4444 of segments 4430 and 4440, respectively. Similarly, distal pushing of the first and second ends of control wire 4490 distances first ends 4432 and 4442 of segments 4430 and 4440, respectively. It is to be noted that the use of two discrete control wires allows for independent control of the distance that separates first ends 4432 and 4442 and the distance that separates second ends 4434 and 4444 of segments 4430 and 4440.

Additionally, pulling on respective ends of control wires 4480 and 4490 shapes segments 4430 and 4440 in accordance with the curved structural conformation of annulus 4040 at a given site destined for anchoring of a respective one of the segments thereto. For example, pulling on a first end of control wire 4490 and on a first end of control wire 4480 curves segment 4430 by drawing together second end 4434 and first end 4432, respectively, of segment 4430. Thus, segment 4430 is compressed at least in part, and is made to assume a shape according to the curvature of the annulus at the base of the anteromedial leaflet.

Reference is now made to FIG. 25D, which is a schematic illustration of the deployment and expansion of segments 4430 and 4440 as described hereinabove with reference to FIG. 25C, with the exception that structure 4408 is optionally rotated as appropriate about an axis of annulus 4040, in accordance with an embodiment of the present invention. Guided by echocardiography, the physician assesses the relative disposition of segments 4430 and 4440 with respect to annulus 4040 of heart 4020. Multilumen catheter 4420 is configured to be rotatable 360 degrees about a longitudinal axis thereof. By rotating multilumen catheter 4420, the segments are positioned properly with respect to the annulus. That is, segment 4440 is positioned above a portion of annulus 4040 at the base of the posterolateral leaflet, while segment 4430 is positioned above a portion of annulus 4040 at the base of the anteromedial leaflet.

FIG. 25E shows catheter 4410 comprising a steering wire 4500, in accordance with an embodiment of the present invention. Typically, a distal end of steering wire 4500 is coupled to a distal end of catheter 4410. A proximal end of wire 4500 is disposed at a site outside the body of the patient, enabling the physician to steer the distal end of catheter 4410. Following the deployment and expansion of annuloplasty structure 4408, multilumen catheter 4420 is retracted slightly within advancement catheter 4410. Retracting multilumen catheter 4420 frees the lumen of the distal end of catheter 4410, thereby restoring flexibility to the distal end of catheter 4410 and enabling proper steering thereof. Structure 4408 is pushed toward annulus 4040 by pushing on both catheter 4410 and on wires 4480 and 4490. Additionally, the structure is properly aligned with annulus 4040 by steering and/or rotating the distal tip of catheter 4410.

Figure 25F:
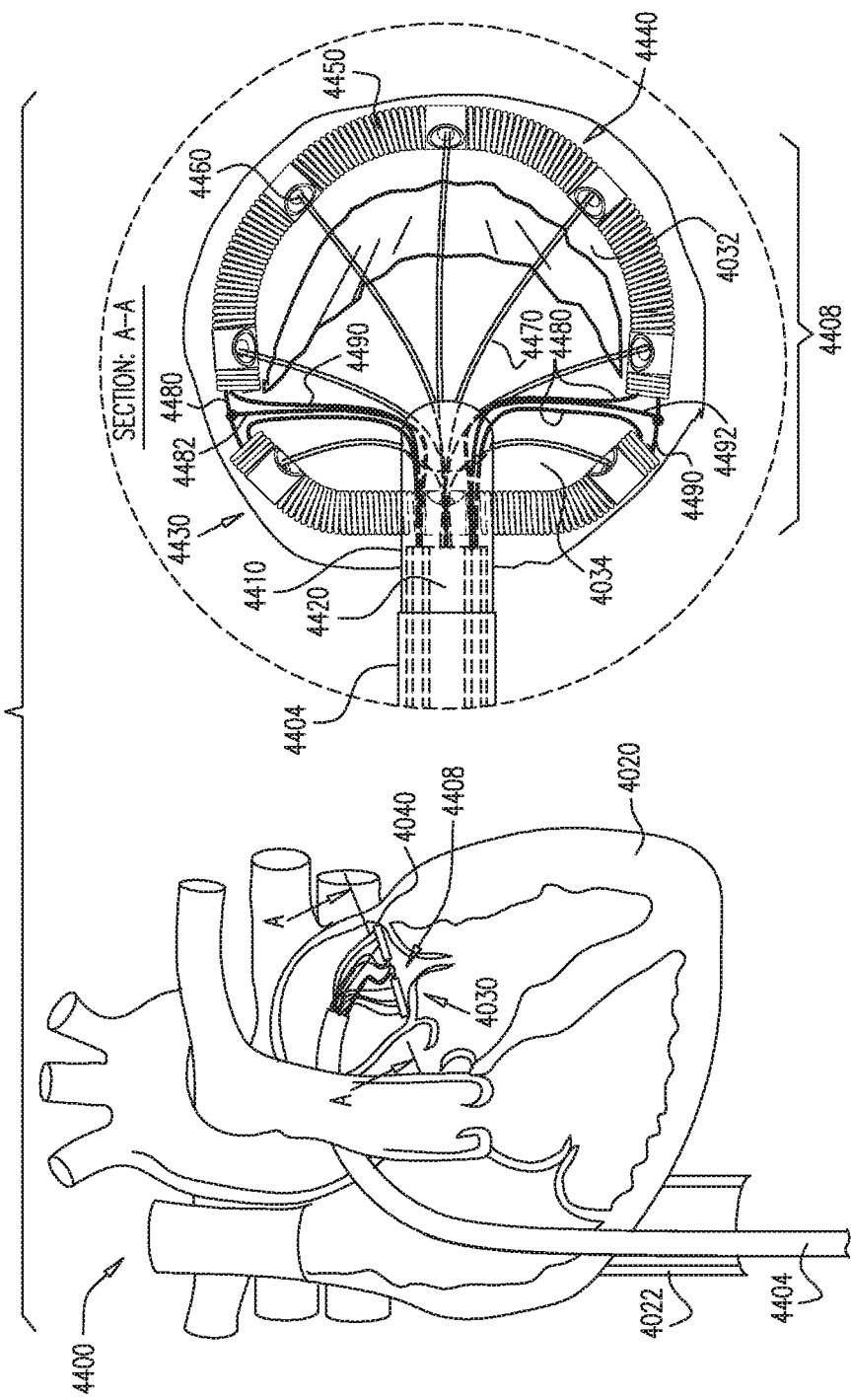

FIG. 25F shows system 4400 following the aligning of segments 4430 and 4440 with annulus 4040, in accordance with an embodiment of the present invention. Segment 4440 is aligned against the base of posterolateral leaflet 4032 at the annulus, and segment 4430 is aligned against the base of anteromedial leaflet 4034 at the annulus. Segments 4430 and 4440 are shown prior to anchoring thereof to annulus 4040. Multilumen catheter 4420 is shown in a slightly retracted state within catheter 4410.

Figure 26A:
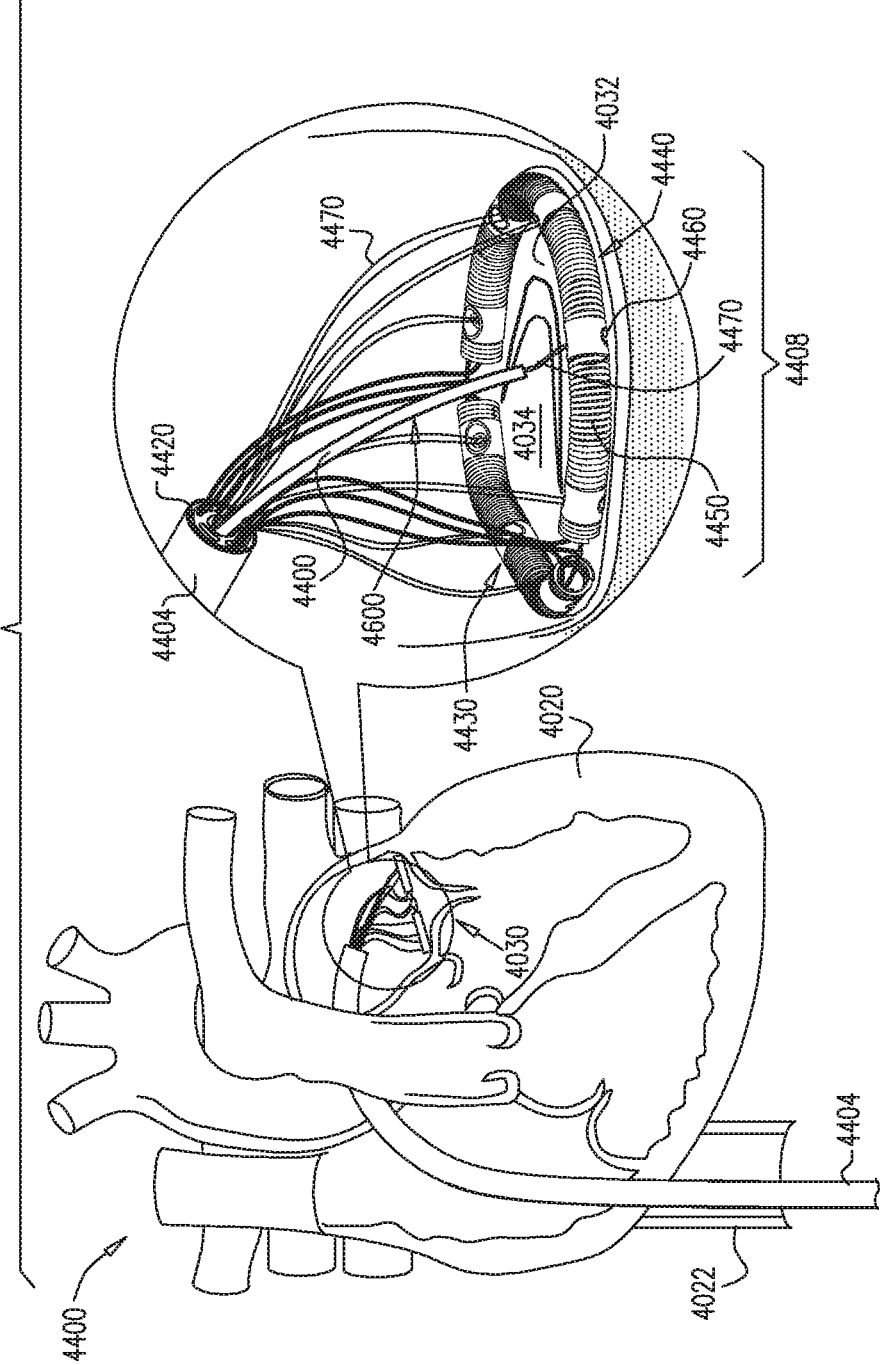

Reference is now made to FIGS. 26A and 26B, which are schematic illustrations of system 4400 comprising an anchoring system 4600, in accordance with an embodiment of the present invention. Once advancement catheter 4410 has positioned segments 4430 and 4440 in their proper orientation with respect to annulus 4040, catheter 4410 is retracted slightly within catheter 4404 and a distal end of multilumen catheter 4420 is exposed. At a site proximal to catheter 4404, and outside the body of the patient, the physician slides a first anchoring system 4600 around both ends of a first flexible and longitudinal guide member 4470. Anchoring system 4600 is advanced through primary lumen 426 of multilumen catheter 4420. Anchoring system 4600 is advanced along guide member 4470 and subsequently inserted, in part, into channel 4460, as shown in FIG. 26B.

Reference is now made to FIGS. 27A-E, which are schematic illustrations of anchoring system 4600, in accordance with an embodiment of the present invention. FIG. 4A shows a bar 4710 disposed within channel 4460. Typically, bar 4710 is disposed perpendicularly to an axis of channel 4460, and at the base of the channel. It is to be noted that bar 4710 is disposed parallel to the longitudinal axis of segment 4440 (or segment 4430) by way of illustration and not limitation. For example, bar 4710 may be disposed perpendicularly to the axis of segment 4440. Guide member 4470 is disposed within channel 4460 and is reversibly coupled to structure 4408 via bar 4710. Typically, guide member 4470 is looped around bar 4710 prior to the advancement of structure 4408 into the body of the patient. When structure 4408 is disposed within heart 4020, both ends of guide member 4470 are exposed outside the body of the patient, thus enabling the physician to slide anchoring system 4600 around both ends of member 4470 and therealong toward annulus 4040 of heart 4020.

FIG. 27B shows anchoring system 4600 comprising an outer tube 4610 housing an advancement tube 4620, which is reversibly coupled to an anchoring structure 4740. Typically, anchoring structure 4740 comprises a helical element whose proximal end is tightly wrapped around a distal end of advancement tube 4620. Outer tube 4610 typically prevents radial expansion of anchoring structure 4740 within primary lumen 4426 of multilumen catheter 4420 as structure 4740 is advanced therein. Anchoring system 4600 is advanced within channel 4460, as shown in FIG. 27C.

Reference is now made to FIG. 27D. Anchoring of anchoring structure 4740 begins when the physician rotates advancement tube 4620 about a longitudinal axis thereof. Such rotation corkscrews a distal portion of the helical element around and beyond bar 4710 and subsequently into annulus 4040 of the patient.

Reference is made to FIGS. 27A and 27B. Typically, channel 4460 has a diameter D20, e.g., between about 0.8 mm and 1.2 mm, typically 1.0 mm. Diameter D20 is thus sized in order to enable passage of anchoring structure 4740 through channel 4460. Typically, anchoring structure 4740 has a diameter D30 of between about 0.5 mm and 1.5 mm, e.g., 1 mm. Typically, each coil of the coiled, helical element has a diameter D40 of between about 0.05 mm and 0.5 mm, e.g., 0.2 mm.

Reference is again made to FIG. 27B. Typically, the helical element is shaped to define at least two adjacent distal rotational subunits 4720 and at least two adjacent proximal rotational subunits 4730. A distance Di10 (e.g., between about 0.3 mm and about 0.6 mm) between adjacent distal rotational subunits 4720 is typically greater than a distance Di20 (e.g., between about 0 mm and about 0.4 mm) between adjacent proximal rotational subunits 4730. Typically a diameter of bar 4710 is less than distance Di10 and greater than distance Di20. Distance Di10 enables distal rotational subunits 4720 to be corkscrewed around bar 4710 and subsequently into annulus 4040 of the patient. Distance Di20 is typically less than a diameter of bar 4710, and therefore restricts proximal rotational subunits 4730 from being corkscrewed fully around bar 4710 and into annulus 4040.

During an attempt to corkscrew proximal rotational subunits 4730 around bar 4710, bar 4710 restricts the rotation of subunits 4730 therearound and applies a counterforce to a torque applied by rotation of tube 4620. The counterforce applied by bar 4710 expands proximal subunits 4730 radially such that subunits 4730 are no longer wrapped tightly around the distal end of tube 4620. Following the expansion of subunits 4730, anchoring structure 4740 is released from tube 4620, typically by pulling on tube 4620 while continuing to apply a rotational, helix-expanding force to proximal subunits 4730. Tube 4620 is then pulled proximally along guide member 4470 and extracted from within the body of the patient, as shown in FIG. 27E. During the removal of tube 4620 from heart 4020, guide member 4470 typically remains within system 4400, although it is optionally removed at the same time as tube 4620.

In some embodiments of the present invention, a few rotational subunits of the helical element are wrapped around a distal end of tube 4620, while the remaining rotational subunits extend distally from the distal end of tube 4620. Typically, a smaller number of rotational subunits are wrapped around tube 4620 than the number of rotational subunits that extend distally from the distal end of tube 4620 and are not wrapped around the distal end of tube 4620. As shown by way of illustration and not limitation, three rotational subunits are wrapped around the distal end of tube 4620, while four rotational subunits are disposed distally to the distal end of tube 4620. The rotational subunits wrapped around the distal end of tube 4620 generally provide enough frictional force to maintain their position around the distal end of tube 4620.

A protrusion (not shown) is typically disposed along the distal end of tube 4620 adjacent to the proximal-most tip of the helical element of anchoring structure 4740. During initial implantation of the anchoring structure within annulus 4040 of the patient (i.e., as tube 4620 is rotated), the protrusion applies a circumferentially-directed pushing force to the proximal-most tip of the helical element. By pushing on the proximal-most tip of the helical element, the protrusion typically adds to the frictional force described above, in order to rotate anchoring structure 4740. One or both of these forces enable a distal end of structure 4740 to puncture annulus 4040. As anchoring structure 4740 is advanced into tissue of annulus 4040, the proximal end of anchoring structure 4740 slides distally along the distal end of tube 4620 and away from the protrusion.

Following implantation within annulus 4040 of distal rotational subunits 4720, the distal end of tube 4620 is impeded by bar 4710. The physician continues to rotate tube 4620 such that the proximal-most tip of anchoring structure 4740 continues to slide distally from the protrusion while the entire anchoring structure 4740 continues to be advanced distally within tissue of annulus 4040. During the continued rotation of tube 4620, fewer rotational subunits are wrapped around the distal end of tube 4620, thereby reducing friction between anchoring structure 4740 and the distal end of tube 4620. After a sufficient number of rotations, the minimal friction between structure 4740 and the distal end of tube 4620 enables the physician to pull on tube 4620 in order to detach tube 4620 from anchoring structure 4740.

It is to be understood that use of a helical anchoring structure 4740 is described herein by way of illustration and not limitation, and that the scope of the present invention includes the use of other apparatus for anchoring annuloplasty structure 4408 to annulus 4040. For example, anchoring structure 4740 may comprise a screw, harpoon, barb, or any other anchoring structure known in the art. In some embodiments, anchoring structure 4740 comprises a wire configured to penetrate annulus 4040 in a generally straight configuration and to subsequently assume a curved configuration once inside tissue of annulus 4040.

Figure 28B:
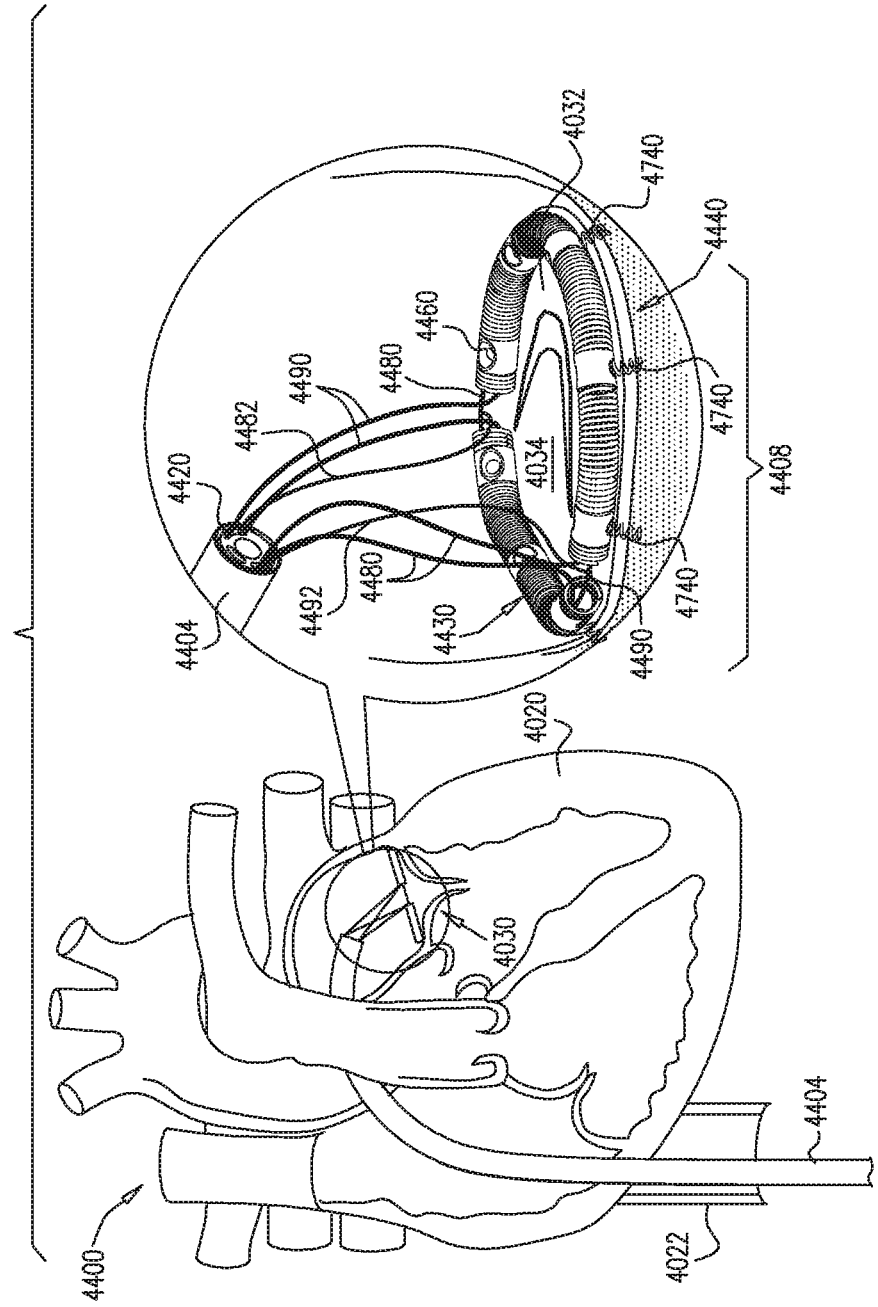

Reference is now made to FIGS. 28A-B, which are schematic illustrations of anchoring system 4600, which anchors segments 4430 and 4440 to annulus 4040 of heart 20, in accordance with an embodiment of the present invention. FIG. 28A shows segment 4440 being anchored, via anchoring system 4600, to annulus 4040 at the base of posterolateral leaflet 4032. A respective anchoring system 4600 is sequentially advanced along each guide member 4470 until both segments 4430 and 4440 are anchored to annulus 4040, and tubes 4620 and guide members 4470 are withdrawn.

As shown, the helical element of anchoring structure 4740 comprises a pointed distal tip 4750 configured to puncture tissue of annulus 4040 in order to enable screwing of structure 4740 within annulus 4040 of the patient. In some embodiments, distal tip 4750 comprises a barb or anchoring structure 4740 comprises a plurality of barbs, configured to provide a lock between structure 4740 and annulus 4040.

Following the anchoring of each structure 4740 within annulus 4040, each guide member 4470 is decoupled from the respective bar 4710. For embodiments in which guide member 4470 is looped around bar 4710, guide member 4470 is decoupled from bar 4710 when the physician pulls on a first end of guide member 4470 from a site outside the body of the patient. Guide member 4470 slides around bar 4710 until it is extracted from within the body of the patient.

In some embodiments, a first end of guide member 4470 comprises a material configured to dissolve when exposed within heart 4020 of the patient. In such an embodiment, guide member 4470 is typically not looped around bar 4710, rather, it is coupled at its first end to bar 4710 while a second end thereof is disposed outside the body of the patient. Following anchoring of structure 4740 to annulus 4040 as described hereinabove, the first end of guide member 4470 dissolves, thereby decoupling guide member 4470 from bar 4710. Guide member 4470 is then pulled from its second end until the first end is extracted from within the body of the patient.

In some embodiments, a first end of guide member 4470 is coupled to one of the segments, prior to placement in the patient's body, by, for example, passing through channel 4460 and being attached to an external surface of the segment. Alternatively, guide member 4470 comprises a "T"-shaped anchor at a distal end of guide member 4470, which passes through channel 4460 and inhibits proximal motion of the "T"-shaped anchor through the channel. In such an embodiment, guide member 4470 is typically not looped around bar 4710. Typically, a second end of guide member 4470 is disposed outside the body of the patient. Following anchoring of structure 4740 to annulus 4040 as described hereinabove, the physician pulls on the second end of guide member 4470 in order to tear the guide member at a pre-weakened point on the guide member, typically slightly proximal to the segment. Guide member 4470 is then extracted from within the body of the patient while the distal-most portion of guide member 4470 that is attached to the external surface of the segment, or the "T"-shaped anchor, remains disposed within structure 4408.

Reference is now made to FIG. 28C, which is a schematic illustration of system 4400, comprising a tensile suture 4800 configured for sliding advancement through segments 4430 and 4440, in accordance with an embodiment of the present invention. One of control wires 4480 or 4490, e.g., control wire 4480, is extracted from within segments 4430 and 4440 when the physician pulls on a first end of wire 4480. Subsequently, the physician replaces control wire 4490 with tensile suture 4800 by (a) tying a first end of suture 4800 to a first end of wire 4490, and then (b) pulling on a second end of wire 4490. The physician pulls wire 4490 until the first end of suture 4800 has replaced control wire 4490 in segments 4430 and 4440, e.g., until suture 4800 is once again exposed outside the body of the patient. As shown in FIG. 28C, a portion of suture 4800 remains disposed within both segments 4430 and 4440. Tensile suture 4800 comprises a flexible material, e.g., nitinol, Kevlar, titanium, or polytetrafluoroethylene (PTFE), and is configured to reside chronically within segments 4430 and 4440. For example, suture 4800 may comprise a braided polyester suture (e.g., Ticron). Additionally, suture 4800 is configured to withstand cardiac pressures and constant motion of segments 4430 and 4440 that result from the motion of annulus 4040. As such, suture 4800 typically has a relatively thick diameter of between about 0.1 mm and about 1.0 mm, typically between about 0.3 mm and about 0.6 mm.

In some embodiments, two tensile sutures 4800 reside chronically within segments 4430 and 4440. In such an embodiment, a first tensile suture replaces control wire 4480, and a second tensile suture replaces control wire 4490. Control wires 4480 and 4490 are replaced as described hereinabove.

In any embodiment, using tactile feedback and optionally in combination with fluoroscopic imaging, first and second ends of suture(s) 4800 are pulled to an extent that is based on (a) the level of dilation of the preoperative mitral valve, and/or (b) real-time monitoring of regurgitation minimization.

FIG. 28C shows a lock 4820 being advanced around first and second portions of suture 4800, in accordance with an embodiment of the present invention. Lock 4820 secures together segments 4430 and 4440 of annuloplasty structure 4408, thereby defining its final configuration within annulus 4040 of mitral valve 4030. The excess portions of tensile suture 4800 are clipped proximally to lock 4820 and are extracted from the body via catheter 4404. Following clipping, first and second ends of suture 4800 remain accessible for future tightening together of segments 4430 and 4440 upon need therefor. In some embodiments, the first and second ends of suture 4800 are located using fluoroscopy or any other method described herein.

FIG. 28D shows annuloplasty structure 4408 in a closed state, in accordance with an embodiment of the present invention. By reducing a circumference of annulus 4040, leaflets 4032 and 4034 are lifted and/or drawn toward one another to prevent recurring dilation of mitral valve 4030, restore leaflet coaptation, and reduce mitral regurgitation.

It is to be noted that in an embodiment of the present invention, guide members 4470 comprise a screw at a distal end thereof. Guide member 4470 in this embodiment is suitable for conveying torque, such that by rotating the proximal end of the guide member from outside the body of the patient, the screw at the distal end is screwed into the annulus. Following anchoring of the screw to the annulus of the patient, the guide member is clipped proximally to the screw and is extracted from within the body of the patient. In such an embodiment, guide member 4470 is configured to anchor structure 4408 to annulus 4040 independently of bar 4710 described hereinabove.

It is to be noted that the scope of the present invention is not limited to minimally-invasive procedures (e.g., transcatheter procedures such as percutaneous or intercostal penetration procedures), and includes applications in which system 4400 is applied in invasive procedures such as open heart surgery.

It is to be further noted that system 4400 may be used to treat valves other than mitral valve 4030. For example, system 4400 may be used to treat an aortic valve of the patient.

The scope of the present invention includes embodiments described in U.S. patent application Ser. No. 11/950,930 to Gross et al., filed Dec. 5, 2007, entitled, "Segmented ring placement," which published as US 2008/0262609, and which is assigned to the assignee of the present patent application and is incorporated herein by reference.

Additionally, the scope of the present invention includes embodiments described in one or more of the following:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007, which published as WO 08/068756;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008, which issued as U.S. Pat. No. 8,241,351;

U.S. Provisional Patent Application 61/207,908, to Miller et al., entitled, "Actively-engageable movement-restriction mechanism for use with an annuloplasty structure," filed on Feb. 17, 2009;

U.S. patent application Ser. No. 12/435,291 to Maisano et al., entitled: "Adjustable repair chords and spool mechanism therefor," filed May 4, 2009, which issued as U.S. Pat. No. 8,147,542; and U.S. patent application Ser. No. 12/437,103 to Zipory et al., entitled, "Annuloplasty ring with intra-ring anchoring," Filed on May 7, 2009, which issued as U.S. Pat. No. 8,715,342.

All of these applications are incorporated herein by reference. Techniques described herein can be practiced in combination with techniques described in one or more of these applications.

For some applications, techniques described herein are practiced in combination with techniques described in one or more of the references cited in the Background section and Cross-References section of the present patent application. All references cited herein, including patents, patent applications, and articles, are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
   a plurality of helical tissue anchors; and
   an annuloplasty structure for placement on an annulus of a heart valve, the annuloplasty structure comprising:
      a plurality of compressible subunits, and
      a plurality of anchor mounts alternately disposed with respect to the plurality of compressible subunits, each anchor mount defining a path for passage of a respective one of the plurality of helical tissue anchors;
   wherein the annuloplasty structure can be transitioned from a first configuration having a first diameter to a second configuration having a second diameter different from the first diameter.

2. The apparatus according to claim 1, further comprising a structural element in the path for corkscrewing a distal portion of the respective one of the plurality of helical tissue anchors therearound.

3. The apparatus according to claim 2, wherein the structural element comprises a bar that is disposed in parallel with a plane of the annuloplasty structure, the plane including a portion of each of the plurality of anchor mounts.

4. The apparatus according to claim 2, wherein the structural element is configured to restrict continued corkscrewing of the respective one of the plurality of helical tissue anchors into tissue beyond a limit.

5. The apparatus according to claim 1, wherein the path of a first anchor mount of the plurality of anchor mounts is non-parallel relative to the path of a second anchor mount of the plurality of anchor mounts.

6. The apparatus according to claim 1, further comprising a rotatable ring coupled to the annuloplasty structure, such that rotation of the rotatable ring contracts the annuloplasty structure.

7. The apparatus according to claim 6, further comprising a lock ring arranged to lock the rotatable ring.

8. The apparatus according to claim 1, wherein the annuloplasty structure comprises a contracting wire configured to control transitioning from the first configuration to the second configuration.

9. The apparatus according to claim 1, wherein the second diameter is smaller than the first diameter.

10. The apparatus according to claim 1, wherein the plurality of compressible subunits comprise struts.

11. The apparatus according to claim 1, further comprising first and second rotatable rings coupled to the annuloplasty structure, arranged such that (a) the first rotatable ring is rotatable about its axis of rotation to contract the annuloplasty structure while the second rotatable ring remains rotationally stationary about its axis of rotation, and (b) the second rotatable ring is rotatable about its axis of rotation to contract the annuloplasty structure while the first rotatable ring remains rotationally stationary about its axis of rotation.

12. The apparatus according to claim 1, further comprising a ratchet coupled to the annuloplasty structure, wherein the ratchet is configured to maintain a perimeter of the annuloplasty structure after transitioning the annuloplasty structure from the first configuration to the second configuration.

13. The apparatus according to claim 1, further comprising one or more longitudinal members reversibly coupled to the annuloplasty structure at respective locations of the annuloplasty structure, wherein the one or more longitudinal members are arranged such that the one or more longitudinal members are moveable to adjust a configuration of respective parts of the annuloplasty structure at the respective locations of the annuloplasty structure.

14. The apparatus according to claim 13, wherein the one or more longitudinal members comprise at least first and second longitudinal members coupled to the annuloplasty structure at respective first and second locations of the annuloplasty structure, and are configured such that movement of the first one of the longitudinal members moves a first part of the annuloplasty structure at the first location with respect to a second part of the annuloplasty structure at the second location.

15. The apparatus according to claim 1, wherein each anchor mount comprises first and second openings, and wherein each respective one of the plurality of helical tissue anchors is moveable through the first and second openings of each anchor mount.

16. The apparatus according to claim 15, wherein the distal portion of one of the plurality of helical tissue anchors is arranged to corkscrew around a structural element before moving through the second opening.

17. An system, comprising:
   a plurality of helical tissue anchors; and
   an annuloplasty structure for placement on an annulus of a heart valve, the annuloplasty structure comprising:
      a plurality of compressible subunits comprising struts, and
      a plurality of anchor mounts alternately disposed with respect to the plurality of compressible subunits, each anchor mount defining a path for passage of a respective helical tissue anchor of the plurality of helical tissue anchors;
   wherein the annuloplasty structure can be transitioned from a larger configuration to a smaller configuration to reduce a size of an annulus of a heart valve.

18. The system according to claim 17, wherein each of the plurality of compressible subunits is independently adjustable from an expanded configuration to a contracted configuration.

19. An annuloplasty system for reducing a size dimension of an annulus of a heart valve, comprising:
   an annuloplasty structure comprising a plurality of adjustable subunits and a plurality of anchor mounts alternately disposed with respect to the plurality of adjustable subunits;
   a first ring; and
   a second ring, wherein the first ring is rotatable about its axis of rotation to contract the annuloplasty structure while the second ring remains rotationally stationary about its axis of rotation, and the second ring is rotatable about its of rotation to contract the annuloplasty structure while the first ring remains rotationally stationary about its axis of rotation.

20. An annuloplasty system for reshaping an annulus of a native heart valve, comprising:

an annuloplasty structure comprising a plurality of adjustable segments and a plurality of anchor mounts connected to the plurality of adjustable segments;

a plurality of tissue anchors;

wherein each anchor mount of the plurality of anchor mounts is coupleable to a respective tissue anchor of the plurality of tissue anchors, such that the plurality of tissue anchors can be implanted in the annulus of the native heart valve to secure the annuloplasty structure to the annulus of the native heart valve at the plurality of anchor mounts; and wherein the annuloplasty structure is adjustable such that it can be used to treat a variety of different sizes of annuli of different patients, and a first segment of the annuloplasty structure is adjustable independently of a second segment of the annuloplasty structure.

* * * * *